US010191060B2

(12) United States Patent
Chiu et al.

(10) Patent No.: US 10,191,060 B2
(45) Date of Patent: Jan. 29, 2019

(54) FUNCTIONALIZED CHROMOPHORIC POLYMER DOTS AND BIOCONJUGATES THEREOF

(75) Inventors: Daniel T. Chiu, Seattle, WA (US); Changfeng Wu, Changchun (CN); Jason McNeill, Clemson, SC (US); Jiangbo Yu, Clemson, SC (US)

(73) Assignees: University of Washington, Seattle, WA (US); Clemson Univeristy, Clemson, SC (US)

( * ) Notice: Subject to any disclaimer, the term of this patent is extended or adjusted under 35 U.S.C. 154(b) by 448 days.

(21) Appl. No.: 13/508,981

(22) PCT Filed: Nov. 9, 2010

(86) PCT No.: PCT/US2010/056079
§ 371 (c)(1),
(2), (4) Date: Jul. 18, 2012

(87) PCT Pub. No.: WO2011/057295
PCT Pub. Date: May 12, 2011

(65) Prior Publication Data
US 2012/0282632 A1    Nov. 8, 2012

Related U.S. Application Data

(60) Provisional application No. 61/259,611, filed on Nov. 9, 2009.

(51) Int. Cl.
*G01N 33/58*    (2006.01)
*C09K 11/06*    (2006.01)

(52) U.S. Cl.
CPC ............ *G01N 33/587* (2013.01); *C09K 11/06* (2013.01); *G01N 33/582* (2013.01)

(58) Field of Classification Search
CPC .............................. G01N 33/587; C09K 11/06
(Continued)

(56) References Cited

U.S. PATENT DOCUMENTS 4,774,339 A    9/1988    Haugland et al.
4,946,778 A    8/1990    Ladner et al.
(Continued)

FOREIGN PATENT DOCUMENTS

CN    1541136 A    10/2004
CN    101302353 A    11/2008
(Continued)

OTHER PUBLICATIONS

Abbel, et al. Multicolour self-assembled particles of fluorene-based bolaamphiphiles. Chem Commun (Camb). Apr. 7, 2009;(13):1697-9. doi: 10.1039/b822943k. Epub Feb. 17, 2009.
Agard, et al. A comparative study of bioorthogonal reactions with azides. ACS Chem Biol. Nov. 21, 2006;1(10):644-8.
Baier, et al. Fluorescent conjugated polymer nanoparticles by polymerization in miniemulsion. J Am Chem Soc. Oct. 14, 2009;131(40):14267-73. doi: 10.1021/ja905077c.
Bernardin, et al. Copper-free click chemistry for highly luminescent quantum dot conjugates: application to in vivo metabolic imaging. Bioconjug Chem. Apr. 21, 2010;21(4):583-8. doi: 10.1021/bc900564w.
Best. Click chemistry and bioorthogonal reactions: unprecedented selectivity in the labeling of biological molecules. Biochemistry. Jul. 21, 2009;48(28):6571-84. doi: 10.1021/bi9007726.
(Continued)

*Primary Examiner* — Jezia Riley
(74) *Attorney, Agent, or Firm* — Wilson Sonsini Goodrich & Rosati

(57) ABSTRACT

The present invention provides, among other aspects, functionalized chromophoric polymer dots comprising a hydrophobic core and a hydrophilic cap, and bioconjugates thereof. Also provided are improved methods for preparing functionalized chromophoric polymer dots. Methods for in vivo imaging and molecular labeling are also disclosed.

70 Claims, 60 Drawing Sheets

(58) Field of Classification Search
USPC ............. 252/301.36; 525/54.1, 54.2, 55, 275
See application file for complete search history.

(56) References Cited

U.S. PATENT DOCUMENTS

| | | | |
|---|---|---|---|
| 5,723,218 | A | 3/1998 | Haugland et al. |
| 6,417,402 | B1 | 7/2002 | Das et al. |
| 7,432,298 | B2 | 10/2008 | Lam et al. |
| 7,462,325 | B2 | 12/2008 | Hancock et al. |
| 7,521,232 | B2 | 4/2009 | Moon |
| 7,985,426 | B1 | 7/2011 | Sung et al. |
| 8,367,042 | B2 | 2/2013 | Kim et al. |
| 9,382,473 | B2 | 7/2016 | Chiu et al. |
| 9,797,840 | B2 | 10/2017 | Chiu et al. |
| 9,810,693 | B2 | 11/2017 | Chiu et al. |
| 9,849,197 | B2 | 12/2017 | Saji et al. |
| 2002/0045045 | A1 | 4/2002 | Adams et al. |
| 2004/0018379 | A1 | 1/2004 | Kinlen |
| 2004/0101822 | A1 | 5/2004 | Wiesner et al. |
| 2004/0131886 | A1 | 7/2004 | Marrocco et al. |
| 2005/0019265 | A1 | 1/2005 | Hammer et al. |
| 2005/0171289 | A1 | 8/2005 | Kataoka et al. |
| 2005/0255044 | A1 | 11/2005 | Lomnes et al. |
| 2006/0127929 | A1 | 6/2006 | Swager et al. |
| 2007/0031490 | A1 | 2/2007 | Loebenberg et al. |
| 2007/0224345 | A1 | 9/2007 | Metz et al. |
| 2008/0081192 | A1 | 4/2008 | Goh et al. |
| 2008/0085566 | A1 | 4/2008 | Swager et al. |
| 2008/0178763 | A1 | 7/2008 | Schwartz et al. |
| 2008/0199700 | A1 | 8/2008 | Anderson et al. |
| 2008/0242806 | A1 | 10/2008 | Chen et al. |
| 2009/0075295 | A1 | 3/2009 | Lindsey |
| 2009/0130665 | A1 | 5/2009 | Sleiman et al. |
| 2009/0220434 | A1 | 9/2009 | Sharma |
| 2010/0016472 | A1 | 1/2010 | Wang et al. |
| 2010/0098902 | A1 | 4/2010 | Kotov et al. |
| 2010/0290999 | A1 | 11/2010 | Kim et al. |
| 2011/0159605 | A1 | 6/2011 | Whitten et al. |
| 2011/0278503 | A1* | 11/2011 | Janczewski et al. ..... 252/301.36 |
| 2011/0278536 | A1 | 11/2011 | Walker et al. |
| 2012/0015190 | A1 | 1/2012 | Goh et al. |
| 2012/0175571 | A1 | 7/2012 | Sarkar |
| 2013/0234067 | A1 | 9/2013 | Chiu et al. |
| 2013/0234068 | A1 | 9/2013 | Chiu et al. |
| 2013/0266957 | A1 | 10/2013 | Chiu et al. |
| 2014/0302516 | A1 | 10/2014 | Chiu et al. |
| 2014/0350183 | A1 | 11/2014 | Chiu et al. |
| 2015/0037259 | A1 | 2/2015 | Chiu et al. |
| 2016/0018395 | A1 | 1/2016 | Chiu et al. |
| 2016/0161475 | A1 | 6/2016 | Chiu et al. |
| 2016/0341737 | A1 | 11/2016 | Chiu et al. |

FOREIGN PATENT DOCUMENTS

| | | |
|---|---|---|
| CN | 102791827 A | 11/2012 |
| EP | 2251043 A2 | 11/2010 |
| JP | 2013168424 A | 8/2013 |
| WO | WO 2007/027159 A1 | 3/2007 |
| WO | WO 2007/095506 A1 | 8/2007 |
| WO | WO 2008/063378 A2 | 5/2008 |
| WO | WO 2009/051560 A1 | 4/2009 |
| WO | WO 2009/107859 A2 | 9/2009 |
| WO | WO 2010/006753 A2 | 1/2010 |
| WO | WO-2010075512 A1 | 7/2010 |
| WO | WO-2010075514 A1 | 7/2010 |
| WO | WO-2010099273 A1 | 9/2010 |
| WO | WO 2011/057295 A2 | 5/2011 |
| WO | WO-2012054525 A2 | 4/2012 |
| WO | WO-2012118136 A1 | 9/2012 |
| WO | WO 2013/101902 A2 | 7/2013 |
| WO | WO-2013116614 A1 | 8/2013 |
| WO | WO-2014153051 A1 | 9/2014 |

OTHER PUBLICATIONS

Breidenbach, et al. Targeted metabolic labeling of yeast N-glycans with unnatural sugars. Proc Natl Acad Sci U S A. Mar. 2, 2010;107(9):3988-93. doi: 10.1073/pnas.0911247107. Epub Feb. 8, 2010.

Bruchez, et al. Semiconductor nanocrystals as fluorescent biological labels. Science. Sep. 25, 1998;281(5385):2013-6.

Chan, et al. Quantum dot bioconjugates for ultrasensitive nonisotopic detection. Science. Sep. 25, 1998;281(5385):2016-8.

Chan, et al. Ultrasensitive copper(II) detection using plasmon-enhanced and photo-brightened luminescence of CdSe quantum dots. Anal Chem. May 1, 2010;82(9):3671-8. doi: 10.1021/ac902985p.

Chen, et al. Highly sensitive biological and chemical sensors based on reversible fluorescence quenching in a conjugated polymer. Proc Natl Acad Sci U S A. Oct. 26, 1999;96(22):12287-92.

Choi, et al. Design considerations for tumour-targeted nanoparticles. Nat Nanotechnol. Jan. 2010;5(1):42-7. doi: 10.1038/nnano.2009.314. Epub Nov. 1, 2009.

Choi, et al. Renal clearance of quantum dots. Nat Biotechnol. Oct. 2007;25(10):1165-70. Epub Sep. 23, 2007.

Collini, et al. Coherent intrachain energy migration in a conjugated polymer at room temperature. Science. Jan. 16, 2009;323(5912):369-73. doi: 10.1126/science.1164016.

Dieterich, et al. Selective identification of newly synthesized proteins in mammalian cells using bioorthogonal noncanonical amino acid tagging (BONCAT). Proc Natl Acad Sci U S A. Jun. 20, 2006;103(25):9482-7. Epub Jun. 12, 2006.

Dube, et al. Probing mucin-type O-linked glycosylation in living animals. Proc Natl Acad Sci U S A. Mar. 28, 2006;103(13):4819-24. Epub Mar. 20, 2006.

Fan, et al. Beyond superquenching: hyper-efficient energy transfer from conjugated polymers to gold nanoparticles. Proc Natl Acad Sci U S A. May 27, 2003;100(11):6297301. Epub May 15, 2003.

Fernandez-Suarez, et al. Fluorescent probes for super-resolution imaging in living cells. Nat Rev Mol Cell Biol. Dec. 2008;9(12):929-43. doi: 10.1038/nrm2531. Epub Nov. 12, 2008.

Friend, et al. Electroluminescence in conjugated polymers. Nature. 1999; 397:121-128.

Giepmans, et al. The fluorescent toolbox for assessing protein location and function. Science. Apr. 14, 2006;312(5771):217-24.

Gunes, et al. Conjugated polymer-based organic solar cells. Chem Rev. Apr. 2007;107(4):1324-38.

Han, et al. Development of a bioorthogonal and highly efficient conjugation method for quantum dots using tetrazine-norbornene cycloaddition. J Am Chem Soc. Jun. 16, 2010;132(23):7838-9. doi: 10.1021/ja101677r.

Hou, et al. Novelred-emitting fluorene-based copolymers. J Mater Chem. 2002; 12:2887-2892.

Hou, et al. Synthesis and electroluminescent properties of high-efficiency saturated red emitter based on copolymers from fluorene and 4,7-di(4-hexylthien-2-yl)-2,1,3-benzothiadiazole, Macromolecules. 2004; 37:6299-6305.

Howes, et al. Magnetic conjugated polymer nanoparticles as bimodal imaging agents. J Am Chem Soc. Jul. 21, 2010;132(28):9833-42. doi: 10.1021/ja1031634.

Howes, et al. Phospholipid encapsulated semiconducting polymer nanoparticles: their use in cell imaging and protein attachment. J Am Chem Soc. Mar. 24, 2010;132(11):3989-96. doi: 10.1021/ja1002179.

International search report and written opinion dated Jul. 28, 2011 for PCT/US2010/056079.

Kaeser, et al. Fluorescent nanoparticles based on self-assembled pi-conjugated systems. Adv Mater. Jul. 27, 2010;22(28):2985-97. doi: 10.1002/adma.201000427.

Kim, et al. Conjugated polymer nanoparticles for biomedical in vivo imaging. Chem Commun (Camb). Mar. 14, 2010;46(10):1617-9. doi: 10.1039/b923309a. Epub Jan. 12, 2010.

(56) References Cited

OTHER PUBLICATIONS

Kolb, et al. Click Chemistry: Diverse Chemical Function from a Few Good Reactions. w Chem Int Ed Engl. Jun. 1, 2001;40(11):2004-2021.
Kolb, et al. The growing impact of click chemistry on drug discovery. Drug Discov Today. Dec. 15, 2003;8(24):1128-37.
Laughlin, et al. Imaging the glycome. Proc Natl Acad Sci U S A. Jan. 6, 2009;106(1):12-7. doi: 10.1073/pnas.0811481106. Epub Dec. 22, 2008.
McCafferty, et al. Phage antibodies: filamentous phage displaying antibody variable domains. Nature. Dec. 6, 1990;348(6301):552-4.
Michalet, et al. Quantum dots for live cells, in vivo imaging, and diagnostics. Science. Jan. 28, 2005;307(5709):538-44.
Moon, et al. Live-cell-permeable poly(p-phenylene ethynylene). Angew Chem Int Ed Engl. 2007;46(43):8223-5.
Moses, et al. The growing applications of click chemistry. Chem Soc Rev. Aug. 2007;36(8):1249-62. Epub May 3, 2007.
Palacios, et al. Charging and discharging of single conjugated-polymer nanoparticles. Nat Mater. Sep. 2007;6(9):680-5. Epub Jul. 22, 2007.
Pepperkok, et al. High-throughput fluorescence microscopy for systems biology. Nat Rev Mol Cell Biol. Sep. 2006;7(9):690-6. Epub Jul. 19, 2006.
Prescher, et al. Chemical remodelling of cell surfaces in living animals. Nature. Aug. 19, 2004;430(7002):873-7.
Prescher, et al. Chemistry in living systems. Nat Chem Biol. Jun. 2005;1(1):13-21.
Pu, et al. Fluorescent single-molecular core—shell nanospheres of hyperbranched conjugated polyelectrolyte for live-cell imaging. Chem. Mater. 2009;21:3816-3822.
Que, et al. Metals in neurobiology: probing their chemistry and biology with molecular imaging. Chem Rev. May 2008;108(5):1517-49. doi: 10.1021/cr078203u. Epub Apr. 22, 2008.
Rahim, et al. Conjugated Polymer Nanoparticles for Two-Photon Imaging of Endothelial Cells in a Tissue Model. Adv. Mater. 2009; 21(34):3492-3496.
Resch-Genger, et al. Quantum dots versus organic dyes as fluorescent labels. Nat Methods. Sep. 2008;5(9):763-75. doi: 10.1038/nmeth.1248.
Sadtler, et al. Selective facet reactivity during cation exchange in cadmium sulfide nanorods. J Am Chem Soc. Apr. 15, 2009;131(14):5285-93. doi: 10.1021/ja809854q.
Sletten, et al. Bioorthogonal chemistry: fishing for selectivity in a sea of functionality. Angew Chem Int Ed Engl. 2009;48(38):6974-98. doi: 10.1002/anie.200900942.
Speers, et al. Activity-based protein profiling in vivo using a copper(i)-catalyzed azide-alkyne [3+2] cycloaddition. J Am Chem Soc. Apr. 23, 2003;125(16):4686-7.
Szymanski, et al. Single molecule nanoparticles of the conjugated polymer MEH-PPV, preparation and characterization by near-field scanning optical microscopy. J Phys Chem B. May 12, 2005;109(18):8543-6.
Thomas, et al. Chemical sensors based on amplifying fluorescent conjugated polymers. Chem Rev. Apr. 2007;107(4):1339-86. Epub Mar. 27, 2007.
Veiseh, et al. Specific targeting of brain tumors with an optical/magnetic resonance imaging nanoprobe across the blood-brain barrier. Cancer Res. Aug. 1, 2009;69(15):6200-7. doi: 10.1158/0008-5472.CAN-09-1157. Epub Jul. 28, 2009.
Wang, et al. Bioconjugation by copper(I)-catalyzed azide-alkyne [3+2] cycloaddition. J Am Chem Soc. Mar. 19, 2003;125(11):3192-3.
Wang, et al. Non-blinking semiconductor nanocrystals. Nature. Jun. 4, 2009;459(7247):686-9. doi: 10.1038/nature08072.
Wang, et al. Watching silica nanoparticles glow in the biological world. Anal. Chem. 2006;78(3):646-654.
Wu, et al. Conjugated polymer dots for multiphoton fluorescence imaging. J Am Chem Soc. Oct. 31, 2007;129(43):12904-5. Epub Oct. 6, 2007.
Wu, et al. Energy Transfer in a Nanoscale Multichromophoric System: Fluorescent Dye-Doped Conjugated Polymer Nanoparticles. Phys Chem C Nanomater Interfaces. Feb. 14, 2008;112(6):1772-1781.
Wu, et al. Energy transfer mediated fluorescence from blended conjugated polymer nanoparticles. J Phys Chem B. Jul. 27, 2006;110(29):14148-54.
Wu, et al. Immunofluorescent labeling of cancer marker Her2 and other cellular targets with semiconductor quantum dots. Nat Biotechnol. Jan. 2003;21(1):41-6. Epub Dec. 2, 2002.
Wu, et al. Multicolor conjugated polymer dots for biological fluorescence imaging. ACS Nano. Nov. 25, 2008;2(11):2415-23. doi: 10.1021/nn800590n.
Wu, et al. Preparation and encapsulation of highly fluorescent conjugated polymer nanoparticles. Langmuir. Mar. 28, 2006;22(7):2956-60.
Wu, et al. Ratiometric single-nanoparticle oxygen sensors for biological imaging. Angew Chem Int Ed Engl. 2009;48(15):2741-5. doi: 10.1002/anie.200805894.
Wu, et al. Ultrabright and bioorthogonal labeling of cellular targets using semiconducting polymer dots and click cAngew Chem Int Ed Engl. Dec. 3, 2010;49(49):9436-40. doi: 10.1002/anie.201004260. hemistry.
Xie, et al. Luminescent CdSe-ZnSe quantum dots as selective Cu2+ probe. Spectrochimica Acta Part A. 2004; 60:2527-2530.
Xing, et al. Bioconjugated quantum dots for multiplexed and quantitative immunohistochemistry. Nat Protoc. 2007;2(5):1152-65.
Yang, et al. Deep-red electroluminescent polymers: Synthesis and characterization of new low-band-gap conjugated copolymers for light-emitting diodes and photovoltaic devices. Macromolecules 2005; 38:244-253.
Yao, et al. Blinking and nonradiant dark fraction of water-soluble quantum dots in.aqueous solution. Proc Natl Acad Sci U S A. Oct. 4, 2005;102(40):14284-9. Epub Sep. 16, 2005.
Yu, et al. Nanoscale 3D tracking with conjugated polymer nanoparticles. J Am Chem Soc. Dec. 30, 2009;131(51):18410-4. doi: 10.1021/ja907228q.
Boyere, et al. Elaboration of drug nanocarriers based on a glucosamine labeled amphiphilic polymer. Polymer Chemistry. 2014; 5:3030-3037.
European search report and opinion dated Oct. 8, 2015 for EP Application No. 13743132.6.
Office action dated Feb. 2, 2016 for CN Application No. 201180068242.
Office action dated Feb. 4, 2015 for CN Application No. 201180068242.
Office action dated Apr. 28, 2014 for AU Application No. 2011317142.
Office action dated May 30, 2014 for CN Application No. 201180068242.
Office action dated Aug. 4, 2015 for CN Application No. 201180068242.
Office action dated Dec. 3, 2015 for JP Application No. 2013-535014.
Thivierge, et al. Brilliant BODIPY-fluorene Copolymers With Dispersed Absorption and Emission Maxima Macromolecules. May 24, 2011;44(10):4012-4015.
Hermanson. Bioconjugate techniques, Academic Press, San Diego, 1996; Ch 13, 570-591.
International search report and written opinion dated Aug. 22, 2014 for PCT/US2014/028846.
European search report and opinion dated Aug. 12, 2015 for EP Application No. 15175146.8.
Howes, et al. Synthesis, characterisation and intracellular imaging of PEG capped BEHP-PPV nanospheres. Chem Commun (Camb). May 14, 2009;(18):2490-2. doi: 10.1039/b903405f. Epub Apr. 2, 2009.
Kietzke, et al. Novel approaches to polymer blends based on polymer nanoparticles. Nat Mater. Jun. 2003;2(6):408-12.
Wu, et al. Corrigendum: Immunofluorescent labeling of cancer marker Her2 and other cellular targets with semiconductor quantum dots. Nat Biotechnol. Jan. 2003;21(1):41-6. Epub Dec. 2, 2002.

(56) References Cited

OTHER PUBLICATIONS

Wu, et al. Swelling-controlled polymer phase and fluorescence properties of polyfluorene nanoparticles. Langmuir. Jun. 3, 2003;24(11):5855-61. doi: 10.1021/la8000762. Epub May 7, 2008.
Achari, et al. 1.67-A X-ray structure of the B2 immunoglobulin-binding domain of streptococcal protein G and comparison to the NMR structure of the B1 domain. Biochemistry. Nov. 3, 1992;31(43):10449-57.
Akerstrom, et al. A physicochemical study of protein G, a molecule with unique immunoglobulin G-binding properties. J Biol Chem. Aug. 5, 1986;261(22):10240-7.
Alivistatos, et al. Quantum dots as cellular probes. Annu Rev Biomed Eng. 2005;7:55-76.
Ausborn, et al. The protective effect of free and membrane-bound cryoprotectants during freezing and freeze-drying of liposomes. Journal of Controlled Release. 1994; 30:105-116.
Berlier, et al. Quantitative comparison of long-wavelength Alexa Fluor dyes to Cy dyes: fluorescence of the dyes and their bioconjugates. J Histochem Cytochem. Dec. 2003;51(12):1699-712.
Bird, et al. Single-chain antigen-binding proteins. Science. Oct. 21, 1988;242(4877):423-6.
Caruso. Nanoengineering of Particle Surfaces. Adv. Mater. 2001; 13:11-22.
Chalfie, et al. Green fluorescent protein as a marker for gene expression. Science. Feb. 11, 1994;263(5148):802-5.
Chan, et al. Copper(II) and iron(II) ion sensing with semiconducting polymer dots. Chem Commun (Camb). Mar. 14, 2011;47(10):2820-2. doi: 10.1039/c0cc04929h. Epub Jan. 14, 2011.
Chan, et al. Development of ultrabright semiconducting polymer dots for ratiometric pH sensing. Anal Chem. Feb. 15, 2011;83(4):1448-55. doi: 10.1021/ac103140x. Epub Jan. 18, 2011.
Chan, et al. Hybrid semiconducting polymer dot-quantum dot with narrow-band emission, near-infrared fluorescence, and high brightness. J Am Chem Soc. May 2, 2012;134(17):7309-12. doi: 10.1021/ja3022973. Epub Apr. 23, 2012.
Clafton, et al. Chemical defects in the highly fluorescent conjugated polymer dots. Langmuir. Dec. 7, 2010;26(23):17785-9. doi: 10.1021/la103063p. Epub Nov. 11, 2010.
Derfus, et al. Probing the Cytotoxicity of Semiconductor Quantum Dots. Nano Letters. 2004; 4(1):11-18.
European search report and opinion dated Mar. 19, 2014 for EP Application No. 11835019.8.
Fernando, et al. Mechanism of cellular uptake of highly fluorescent conjugated polymer nanoparticles. Biomacromolecules. Oct. 11, 2010;11(10):2675-82. doi: 10.1021/bm1007103.
Green. Avidin and streptavidin. Methods Enzymol. Wilchek and Bayer. New York, Academic Press, Inc. 1990;184:51-67.
Hashim, et al. Luminescent quantum-dot-sized conjugated polymer nanoparticles—nanoparticle formation in miniemulsion system. Journal of Materials Chemistry. 2011; 21: 1797-1803.
Hermanson. Bioconjugate techniques, Academic Press, San Diego, 1996.
Howarth, et al. Monovalent, reduced-size quantum dots for imaging receptors on living cells. Nat Methods. May 2008;5(5):397-9. doi: 10.1038/nmeth.1206. Epub Apr. 20, 2008.
Howes, et al. Colloidal and optical stability of PEG-capped and phospholipid-encapsulated semiconducting polymer nanospheres in different aqueous media. Photochem Photobiol Sci. Aug. 2010;9(8):1159-66. doi: 10.1039/c0pp00106f. Epub Jun. 29, 2010.
International preliminary report on patentability dated Apr. 23, 2013 for PCT/US2011/056768.
International search report and written opinion dated Mar. 27, 2013 for PCT/US2012/071767.
International search report and written opinion dated Apr. 9, 2013 for PCT/US2013/024300.
International search report and written opinion dated Jun. 26, 2012 for PCT/US2011/056768.

Jin, et al. Generation of functionalized and robust semiconducting polymer dots with polyelectrolytes. Chem Commun (Camb). Mar. 28, 2012;48(26):3161-3. doi: 10.1039/c2cc17703j. Epub Feb. 20, 2012.
Jin, et al. Near-infrared fluorescent dye-doped semiconducting polymer dots. ACS Nano. Feb. 22, 2011;5(2):1468-75. doi: 10.1021/nn103304m. Epub Jan. 31, 2011.
Jin, et al. Silica Nanoparticles with Continuously Tunable Sizes: Synthesis and Size Effects on Cellular Imaging. Chem. Mater. 2008, 20:4411-4419.
Johnston, et al. Layer-by-layer engineered capsules and their applications. Curr. Opin. Colloid Interface Sci. 2006; 11:203-209.
Kumar, et al. Photon antibunching from oriented semiconducting polymer nanostructures. J Am Chem Soc. Mar. 24, 2004;126(11):3376-7.
Lee, et al. Recent advances in fluorescent and colorimetric conjugated polymer-based biosensors. Analyst. 2010 Sep;135(9):2179-89. doi: 10.1039/c0an00239a. Epub Jun. 11, 2010.
Li, et al. Polymer encapsulated conjugated polymer nanoparticles for fluorescence bioimaging. Journal of Materials Chemistry 2012; 22:1257-1264.
Moon, et al. Conjugated polymer nanoparticles for small interfering RNA delivery. Chem Commun (Camb). Aug. 7, 2011;47(29):8370-2. doi: 10.1039/c1cc10991j. Epub Jun. 22, 2011.
Nirmal, et al. Fluorescence intermittency in single cadmium selenide nanocrystals. Nature. 1996; 383:802-804. doi:10.1038/383802a0.
Pecher, et al. Nanoparticles of conjugated polymers. Chem Rev. Oct. 13, 2011;110(10):6260-79. doi: 10.1021/cr100132y.
Poon, et al. Controlling in vivo stability and biodistribution in electrostatically assembled nanoparticles for systemic delivery. Nano Lett. May 11, 2011;11(5):2096103. doi: 10.1021/n1200636r. Epub Apr. 27, 2011.
Poon, et al. Layer-by-layer nanoparticles with a pH-sheddable layer for in vivo targeting of tumor hypoxia. ACS Nano. Jun. 28, 2011;5(6):4284-92. doi: 10.1021/rm200876f Epub Apr. 29, 2011.
Pras, et al. Photoluminescence of 2,7-poly(9,9-dialkylfluorene-co-fluorenone) nanoparticles: effect of particle size and inert polymer addition. Langmuir. Sep. 21, 2010;26(18):14437-42. doi: 10.1021/la1011742.
Pu, et al. Fluorescent conjugated polyelectroltyes for bioimaging. Advanced Functional Materials. 2011; 21:3408-3423.
Sigma Aldrich. Product Information Triton X-1 00. Apr. 21, 1999. Retrieved at http://www.sigmaaldrich.com/content!dam/sigmaaldrich/docs/Sigma/Product_Information_Sheet/1/t8532pis.pdf on Mar. 14, 2014.
Smith, et al. Investigating lyophilization of lipid nanocapsules with fluorescence correlation spectroscopy. Langmuir. Jun. 15, 2010;26(12):10218-22. doi: 10.1021/la1003808.
Tian, et al. Amplified energy transfer in conjugated polymer nanoparticle tags and sensors. Nanoscale. Oct. 2010;2(10):1999-2011. doi: 10.1039/c0nr00322k. Epub Aug. 10, 2010.
Tsien. The green fluorescent protein. Annu Rev Biochem. 1998;67:509-44.
Tuncel, et al. Conjugated polymer nanoparticles. Nanoscale. Apr. 2010;2(4):484-94. doi: 10.1039/b9nr00374f. Epub Mar. 6, 2010.
Wu, et al. Bioconjugation of ultrabright semiconducting polymer dots for specific cellular targeting. J Am Chem Soc. Nov. 3, 2010;132(43):15410-7. doi: 10.1021/ja107196s.
Wu, et al. Design of highly emissive polymer dot bioconjugates for in vivo tumor targeting. Angew Chem Int Ed Engl. Apr. 4, 2011;50(15):3430-4. doi: 10.1002/anie.201007461. Epub Mar. 4, 2011.
Wu, et al. Highly fluorescent semiconducting polymer dots for biology and medicine. Angew Chem Int Ed Engl. Mar. 11, 2013;52(11):3086-109. doi: 10.1002/anie.201205133. Epub Jan. 10, 2013.
Ye, et al. A compact and highly fluorescent orange-emitting polymer dot for specific subcellular imaging. Chem Commun (Camb). Feb. 7, 20;48(12):1778-80. doi: 10.1039/c2cc16486h. Epub Jan. 4, 2012.
Ye, et al. Ratiometric temperature sensing with semiconducting polymer dots. J Am Chem Soc. Jun. 1, 2010;133(21):8146-9. doi: 10.1021/ja202945g. Epub May 11, 2011.

(56) References Cited

OTHER PUBLICATIONS

Yu, et al. Stable functionalization of small semiconducting polymer dots via covalent cross-linking and their application for specific cellular imaging. Adv Mater. Jul. 10, 2012;24(26):3498-504. doi: 10.1002/adma.201201245. Epub Jun. 11, 2012.
Zhang, et al. Importance of having low-density functional groups for generating high-performance semiconducting polymer dots. ACS Nano. Jun. 26, 2012;6(6):5429-39. doi: 10.1021/nn301308w. Epub May 24, 2012.
Zhang. Detection of the cancer marker CD146 expression in melanoma cells with semiconductor quantum dot label (Abstract). J Biomed Nanotechnol. Aug. 2010;6(4):303-11.
European search report and opinion dated Sep. 18, 2013 for EP Application No. 10829306.9.
Wu, Fluorescent conjugated polymer dots for single molecule imaging and sensing application A Dissertation presented to the Graduate School of Clemson University. Dec. 1, 2008. pp. 1-182. http://etd.lib.clemson.edu/documents/1239895063/Wu_clemson_005D_10023.pdf.
Abdelwahed, et al. Freeze-drying of nanoparticles: formulation, process and storage considerations. Adv Drug Deliv Rev. Dec. 30, 2006;58(15):1688-713.
Australian examination report dated Apr. 8, 2016 for AU Application 2015204342.
Benstead, et al. Addressing fluorescence and liquid crystal behaviour in multi-mesogenic Bodipy materials. New Journal of Chemistry. 2011; 35(7):1410-1417.
European office action dated Mar. 2, 2016 for EP Application No. 11835019.8.
European search report and opinion dated May 31, 2016 for EP Application No. 12861954.
European search report and opinion dated Sep. 8, 2016 for EP Application No. 14770843.2.
Greenham et al., Efficient light-emitting diodes based on polymers with high electron affinities, Nature, vol. 365:628-630, published Oct. 14, 1993, print retrieved on Oct. 10, 2016.
Greenham, et al., Measurement of Absolute Photoluminescence Quantum Efficiencies in Conjugated Polymers, Chemical Physics Letters, Jul. 14, 1995, 241(1995) 89-96.
Huyal, et al., White emitting polyfluorene functionalized with azide hybridized on near-UV light emitting diode for high color rendering index, Optics Express , Jan. 21, 2008, 16(2):1115-24.
Meng, et al. Color tuning of polyfluorene emission with BODIPY monomers, Macromolecules 2009, 42:1995-2001. 0.
Murcia, et al., Biofunctionalization of Fluorescent Nanoparticles, Nanotechnologies for the Life Sciences, 2005, vol. 1, 40 pages.
Nagai, et al. Highly luminescent BODIPY-based organoboron polymer exhibiting supramolecular self-assemble structure. J Am Chem Soc. Nov. 19, 2008;130(46):15276-8. doi: 10.1021/ja806939w.
Nagai, et al. Organoboron conjugated polymers. In Conjugated Polymer Synthesis: Methods and reactions. Ed. Yoshiki Chujo. Wiley-VCH Verlag GmbH & Co KGaA, Weinheim. 2010. 195-214.
Notice of allowance dated Jun. 16, 2017 for U.S. Appl. No. 13/687,813.
Notice of allowance dated Jun. 23, 2017 for U.S. Appl. No. 13/865,942.
Office action dated Jan. 29, 2016 for AU Application 2012362466.
Office action dated Feb. 11, 2016 for U.S. Appl. No. 13/865,942.
Office action dated Feb. 19, 2016 for CN Application 201280070923.3.
Office action dated Mar. 8, 2017 for AU Application No. 2015204342.
Office action dated Mar. 15, 2017 for JP Application No. 2013-535014.
Office action dated Mar. 29, 2016 for JP Application No. 2012-538915.
Office action dated Mar. 30, 2017 for U.S. Appl. No. 14/373,835.
Office action dated Apr. 5, 2017 for EP Application No. 15175146.8.
Office action dated Apr. 28, 2017 for U.S. Appl. No. 13/865,942.
Office action dated May 16, 2016 for U.S. Appl. No. 14/373,835.
Office action dated May 20, 2016 for EP Application No. 10829306.9.
Office action dated May 29, 2017 for CA Application No. 2,814,790.
Office action dated Jun. 6, 2017 for JP Application No. 2016-151438.
Office action dated Jun. 15, 2017 for CN Application No. 201180060824.2.
Office action dated Jun. 23, 2017 for CN Application No. 201480028351.1.
Office action dated Jul. 26, 2017 for CN Application No. 201280070923.3.
Office action dated Jul. 28, 2017 for EP Application No. 14770843.
Office action dated Sep. 26, 2016 for CN Application No. 201480028351.1.
Office action dated Sep. 27, 2016 for EP Application No. 11835019.8.
Office action dated Sep. 27, 2016 for JP Application 2014-550455.
Office action dated Sep. 29, 2016 for CN Application No. 201180060824.2.
Office action dated Oct. 20, 2016 for U.S. Appl. No. 13/687,813.
Office action dated Nov. 4, 2016 for CN Application No. 201280070923.3.
Office action dated Dec. 29, 2016 for U.S. Appl. No. 13/865,942.
Office action dated Jan. 30, 2017 for AU Application No. 2012362466.
Office action dated Mar. 1, 2017 for U.S. Appl. No. 14/366,863.
Office action dated Sep. 13, 2016 for U.S. Appl. No. 14/373,835.
Park, et al., White-Emitting Conjugated Polymer Nanoparticles with Cross-Linked Shell for Mechanical Stability and Controllable photometric Properties in Color-Conversion LED Applications, ACS Nano, 2011, 5(4):2483-92.
Riddle, et al. SignalLAmplifying Resonance Energy Transfer: A Dynamic Multichromophore Array for Allosteric Switching. Angewandte Chemie International Edition. 2007; 46(37):7019-7022.
Rong, et al. Multicolor fluorescent semiconducting polymer dots with narrow emissions and high brightness. ACS Nano. 2013; 7(1)L376-384.
Sun, et al. Lyophilization of semiconducting polymer dot bioconjugates. Anal Chem. May 7, 2013;85(9):4316-20. doi: 10.1021/ac4007123. Epub Apr. 19, 2013.
Yao, et al., Fluorescent Nanoparticles Comprising Amphiphilic Rod-Coil Graft Copolymers, Macromolecules, 2008, 41:1438-43.
Zhang, et al., Synthesis and characterization of a novel water-soluble block copolymer with a rod-coil structure, Materials Letters, 60, (2006), pp. 679-84.
Zhu, et al. Efficient tuning nonlinear optical properties: Synthesis and characterization of a series of novel poly (aryleneethynylene) s coLcontaining Bodipy. Journal of Polymer Science Part A: Polymer Chemistry. 2008; 46(22):7401-7410.
Office action dated Sep. 21, 2017 for EP Application No. 15175146.8.
Office action dated Sep. 22, 2017 for EP Application No. 11835019.8.
Office Action dated Oct. 10, 2017 for U.S. Appl. No. 14/366,863.
CN 201610969596.5 First Office Action dated Jan. 22, 2018.
JP 2016-502922Office Action dated Feb. 6, 2018.
Office Action dated Jan. 28, 2018 for EP Application No. 12861954.1.
U.S. Appl. No. 14/774,971 Office Action dated Feb. 16, 2018.
"AU 2017200592 Office Action dated Mar. 29, 2018".
"CN 201280070923.3 Forth Office Action dated Apr. 23, 2018 (w/ English translation)".
"CN 201480028351.1 Third Office Action dated Mar. 28, 2018 (w/ English translation)".
"EP 14770843.2 Office Action dated Apr. 13, 2018".
"JP 2016-235598 Office Action dated Mar. 28, 2018 (w/ English translation)".
Office Action dated Nov. 24, 2017 for CN Patent Application No. 201180060824.2.
Office Action dated Nov. 30, 2017 for U.S. Appl. No. 14/373,835.
European search report with written opinion dated Oct. 24, 2018 for EP Application No. 18193806.

(56) References Cited

OTHER PUBLICATIONS

Green, et al. Simple conjugated polymer nanoparticles as biological labels. Proc. R. Soc. A. 2009. 465. 2751-2759; DOI: 10.1098/rspa.2009.0181. Published Jul. 27, 2009.
JP 2016-235598 Office Action dated Oct. 3, 2018 (w/ English translation).

* cited by examiner

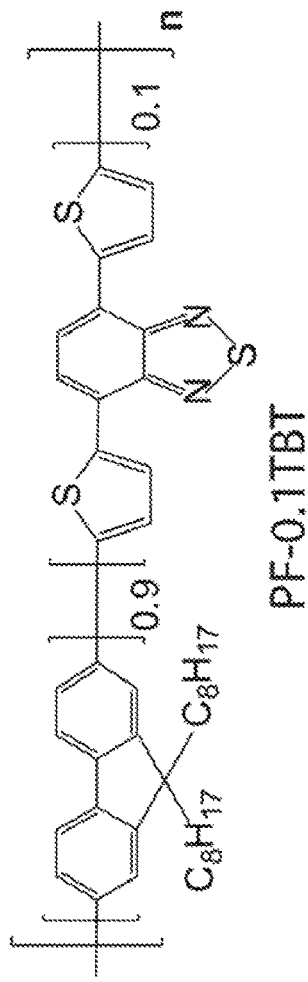
FIG. 25A
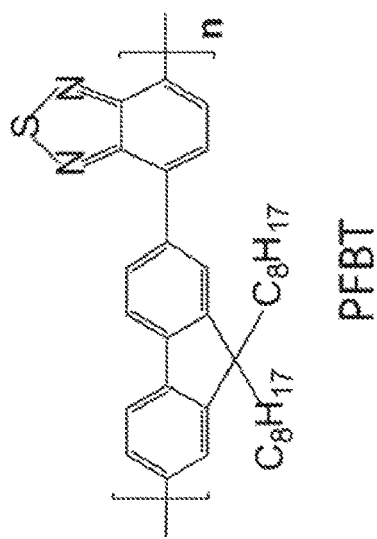

FUNCTIONALIZED CHROMOPHORIC POLYMER DOTS AND BIOCONJUGATES THEREOF

CROSS REFERENCES TO RELATED APPLICATIONS

The present application is a U.S. National Phase Application under 35 U.S.C. §371 of International Application No. PCT/US2010/056079, filed on Nov. 9, 2010, which claims the benefit of U.S. Provisional Application No. 61/259,611, filed Nov. 9, 2009, which are expressly incorporated herein by reference in their entirety for all purposes.

STATEMENT AS TO RIGHTS TO INVENTIONS MADE UNDER FEDERALLY SPONSORED RESEARCH OR DEVELOPMENT

This invention was made with US Government support under grant numbers R21AG029574, R21CA147831, and R01NS062725, awarded by the NIH. The US Government has certain rights in this invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Fluorescent probes have played a key role in modern cell biology and medical diagnostics. Organic small dye molecules are generally used in fluorescent based techniques such as fluorescence microscopy, flow cytometry, and versatile fluorescent assays and sensors. Historically, common fluorophores were derivatives of fluorescein, rhodamine, coumarin, and cyanine etc. Newer generations of fluorophores such as the Alexa Fluors are generally more photostable. However, for many imaging tasks and ultrasensitive assays, their brightness and photostability cannot provide sufficient signal to overcome the background associated with various autofluorescence and scattering processes within the cells. Other factors such as blinking and saturated emission rate may also pose difficulties in high-speed and high-throughout fluorescent assays.

Advances in understanding biological systems have relied on applications of fluorescence microscopy, flow cytometry, versatile biological assays, and biosensors (Pepperkok, R.; Ellenberg, J. Nat. Rev. Mol. Cell Biol. 2006, 7, 690-696; Giepmans, B. N. G.; Adams, S. R.; Ellisman, M. H.; Tsien, R. Y. Science 2006, 312, 217-224). These experimental approaches make extensive use of organic dye molecules as probes. But intrinsic limitations of the conventional dyes, such as low absorptivity and poor photostability, have posed great difficulties in further developments of high-sensitivity imaging techniques and high-throughout assays (Resch-Genger, U.; Grabolle, M.; Cavaliere-Jaricot, S.; Nitschke, R.; Nann, T. Nat. Methods 2008, 5, 763-775; Fernandez-Suarez, M.; Ting, A. Y. Nat. Rev. Mol. Cell Biol. 2008, 9, 929-943).

As a result, there has been considerable interest in developing brighter and more photostable fluorescent probes. For example, inorganic semiconducting quantum dots (Qdots) are under active development and now commercially available from Life Technologies (Invitrogen). Qdots are ideal probes for multiplexed target detection because of their broad excitation band and narrow, tunable emission peaks. They exhibit improved brightness and photostability over conventional organic dyes (Bruchez, M.; Moronne, M.; Gin, P.; Weiss, S.; Alivisatos, A. P. Science 1998, 281, 2013-2016; Chan, W. C. W.; Nie, S. M. Science 1998, 281, 2016-2018; Wu, X. Y.; Liu, H. J.; Liu, J. Q.; Haley, K. N.; Treadway, J. A.; Larson, J. P.; Ge, N. F.; Peale, F.; Bruchez, M. P. Nat. Biotechnol. 2003, 21, 452-452; and Michalet, X.; Pinaud, F. F.; Bentolila, L. A.; Tsay, J. M.; Doose, S.; Li, J. J.; Sundaresan, G.; Wu, A. M.; Gambhir, S. S.; Weiss, S. Science 2005, 307, 538-544). However, Qdots are not bright enough for many photon-starved applications because of their low emission rates, blinking, and a significant fraction of non-fluorescent dots (Yao, J.; Larson, D. R.; Vishwasrao, H. D.; Zipfel, W. R.; Webb, W. W. Proc. Natl. Acad. Sci. USA 2005, 102, 14284-14289). There has been recent work to develop non-blinking Qdots (Wang, X. Y.; Ren, X. F.; Kahen, K.; Hahn, M. A.; Rajeswaran, M.; Maccagnano-Zacher, S.; Silcox, J.; Cragg, G. E.; Efros, A. L.; Krauss, T. D. Nature 2009, 459, 686-689), but their toxicity, caused by the leaching of heavy metal ions, is still a critical concern for in vivo applications.

Quantum dots are inorganic semiconductor nanocrystals of the same material (for example CdSe/ZnS dot) with different size in the range of a few nanometers. They exhibit size tunable emission colors due to the quantum confinement effect. As compared to conventional dye, quantum dots are estimated to be 20 times brighter and 100 times more stable. However, these nanoparticles typically require a thick encapsulation layer to reach the required levels of water-solubility and biocompatibility, resulting in particle diameters on the order of 15-30 nm for an active fluorophore particle size of only 3-6 nm. The relatively large size of encapsulated quantum dots can significantly alter biological function and transport of the biomolecules. Quantum dots show broad band absorption and the major absorption part lies in the UV region, which is not appropriate for most laser based applications. Another critical issue with quantum dot probes is their toxicity due to the leaching of heavy metal $Cd^{2+}$ ions. The energy of UV irradiation is close to that of the covalent chemical bond energy of CdSe nanocrystals. As a result, the particles can be dissolved, in a process known as photolysis, to release toxic cadmium ions into the cellular or subcellular environment. The toxicity issue must be carefully examined before their applications in tumor or vascular imaging can be approved for human clinical purposes. Additionally, the low emission rates, blinking, and a significant fraction of nonfluorescent dots also raise potential problems, particularly for single molecule/particle imaging applications.

An alternative fluorescent nanoparticle is dye doped latex spheres, which exhibit improved brightness and photostability as compared to single fluorescent molecules because of multiple dye molecules per particle and the protective latex matrix. (Wang, L.; Wang, K. M.; Santra, S.; Zhao, X. J.; Hilliard, L. R.; Smith, J. E.; Wu, J. R.; Tan, W. H. Anal. Chem. 2006, 78, 646-654). However, there are also a number of limitations with the dye-loaded beads such as limited dye-loading concentration (a few percent) due to self-quenching, and the relatively large particle size (>30 nm) that would preclude sensing schemes involving the use of energy transfer to report analyte concentrations.

Light-emitting polymers have attracted an overwhelming interest since their discovery 20 years ago. These materials combine the easy processability and outstanding mechanical characteristics of polymers with the readily-tailored electrical and optical properties of semiconductors, therefore find extensive applications in light-emitting diodes, field-effect transistors, photovoltaic cells, and other optoelectronic devices. Fluorescent polymer dots exhibit extraordinarily high fluorescence brightness under both one-photon and two-photon excitation (Wu, C.; Szymanski, C.; Cain, Z.; McNeill, J. J. Am. Chem. Soc. 2007, 129, 12904-12905. C. Wu, B. Bull, C. Szymanski, K. Christensen, J. McNeill, ACS Nano 2008, 2, 2415-2423.). The fluorescent polymer dots possess arguably the highest fluorescence brightness/volume ratios of any nanoparticle to date, owing to a number of favorable characteristics of semiconducting polymer molecules, including their high absorption cross sections, high radiative rates, high effective chromophore density, and minimal levels of aggregation-induced fluorescence quenching. The use of fluorescent polymer dots as fluorescent probes also confers other useful advantages, such as the lack of heavy metal ions that could leach out into solution. However, for applying these probes in biological imaging or sensing applications, an important problem has yet to be solved, that is, the surface functionalization and bioconjugation.

Therefore, there remains a need to develop fluorescent polymer dots with functional groups on the surface that allow for probes to be used in biological systems. The surface functionalization should maintain or enhance the fluorescence brightness or photostability of the hydrophobic polymer dots, not change the size and the long-term monodispersity of the dots in aqueous environment, allow for further conjugation to biomolecules of a range of types, prevent or minimize non-specific binding to other biomoleucles, and allow for the polymer dots to be produced on a commercial scale in a cost-effective manner. The present invention meets these and other needs by providing, among other aspect, stable, functionalized chromophoric polymer dots (Pdots) and bioconjugates thereof.

BRIEF SUMMARY OF THE INVENTION

In one aspect of the present invention relates to a functionalized chromophoric polymer dot. The functionalized chromophoric polymer dot has a core of chromophoric polymer, and a cap of functionalization agent bearing one or more functional groups.

In one aspect, the present invention provides a functionalized chromophoric polymer dot having a hydrophobic core and a hydrophilic cap. In one embodiment, the functionalized Pdot comprises a chromophoric polymer and an amphiphilic molecule, having a hydrophobic moiety and a hydrophilic moiety attached to a reactive functional group, wherein the chromophoric polymer is embedded within the hydrophobic core of the Pdot and; wherein a portion of the amphiphilic molecule is embedded within the core of the Pdot and the reactive functional group is located in the hydrophilic cap. In a preferred embodiment, the chromophoric polymer is a semiconducting polymer.

In another aspect, a bioconjugate of the polymer dot is disclosed. The bioconjugate is formed by the attachment of a biomolecule to one or more functional groups of the chromophoric polymer dot. The attachment may be direct or indirect.

In yet another aspect a method of preparing functionalized chromophoric polymer dots is disclosed. The method involves the introduction of a protic solvent into an aprotic solution containing a mixture of a chromophoric polymer and a functionalization agent (bearing one or more functional groups).

In one aspect, the present invention provides a method for preparing a functionalized chromophoric polymer dot, the method comprising the steps of (a) preparing a mixture of a chromophoric polymer and an amphiphilic molecule attached to a reactive functional group in a non-protic solvent; (b) injecting all or a portion of the mixture into a solution comprising a protic solvent, thereby collapsing the chromophoric polymer and amphiphilic molecule into a nanoparticle; and (c) removing the non-protic solvent from the mixture formed in step (b), thereby forming a suspension of functionalized chromophoric polymer dots, wherein a portion of the amphiphilic molecule is embedded within the core of the nanoparticle and the reactive functional group is located on the surface of the nanoparticle.

In another aspect, the present invention provides a method for conjugating a biological molecule to a functionalized chromophoric polymer dot, the method comprising incubating a functionalized chromophoric polymer dot with the biological molecule in a solution containing polyethylene glycol under conditions suitable for conjugating the biological molecule to the functionalized chromophoric polymer dot, wherein the presence of polyethylene glycol in the solution reduces non-specific adsorption of the biological molecule to the surface of the polymer dot.

In yet another aspect, the present invention provides a method for labeling a target molecule in a biological sample, the method comprising contacting the biological sample with a chromophoric polymer dot conjugated to a targeting moiety that specifically binds the target molecule.

In another embodiment, the present invention provides a method for the bioorthogonal labeling of a cellular target, the method comprising contacting a cellular target having a first surface-exposed functional group capable of participating in a bioorthogonal chemistry reaction with a chromophoric polymer dot. In a particular embodiment, the bioorthogonal reaction is a click chemistry reaction that is performed with a Pdot carrying a reactive functional group capable of participating in such a reaction.

In yet another embodiment, the present invention provides chromophoric polymer dots having a red-shifted emission peak. In one embodiment, the red-shifted Pdots have a peak emission in the far-red region. In other embodiments, the red-shifted Pdots have a peak emission in the near-IR region. In one embodiment, the red-shifted Pdots comprise a PFTBT polymer. In certain embodiments, the polymer dots comprising a blend of two or more different chromophoric polymers. For example, in one embodiment, the Pdots comprise a blend of PFBT and PFTBT polymers.

DETAILED DESCRIPTION OF THE INVENTION

Introduction

Figure 1:
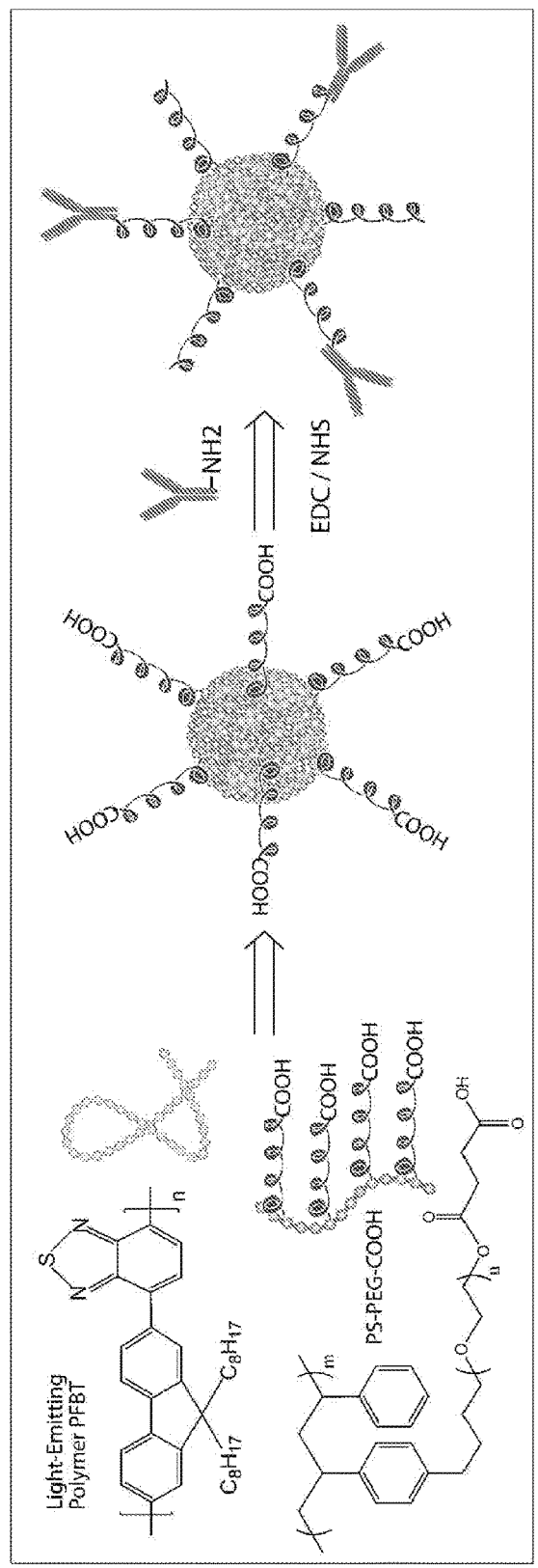
FIG. 1 shows a schematic diagram for preparing the functionalized chromophoric polymer dots and their biomolecular conjugates of the present invention. Chemical structures of a general chromophoric polymer PFBT and an amphiphilic functionalization polymer PS-PEG-COOH are sketched in the scheme.

Semiconducting polymers are attractive materials for various optoelectronic applications, including light-emitting diodes, field-effect transistors, and photovoltaic devices (See, for example, Friend, R. H.; Gymer, R. W.; Holmes, A. B.; Burroughes, J. H.; Marks, R. N.; Taliani, C.; Bradley, D. D. C.; Dos Santos, D. A.; Bredas, J. L.; Loglund, M.; Salaneck, W. R. Nature 1999, 397, 121; and Gunes, S.; Neugebauer, H.; Sariciftci, N. S. Chem. Rev. 2007, 107, 1324-1338, the disclosures of which are herein incorporated by reference in their entireties for all purposes). Their appeal is based on the readily-tailored electrical and optical properties of semiconductors combined with the easy processability of polymers. Water-soluble semiconducting polymers have also been demonstrated as highly sensitive biosensors and chemical sensors (see, for example, Chen, L.; McBranch, D. W.; Wang, H. L.; Helgeson, R.; Wudl, F.; Whitten, D. G. Proc. Natl. Acad. Sci. USA 1999, 96, 12287-12292; Fan, C. H.; Wang, S.; Hong, J. W.; Bazan, G. C.; Plaxco, K. W.; Heeger, A. J. Proc. Natl. Acad. Sci. USA USA 2003, 100, 6297-6301; and Thomas, S. W.; Joly, G. D.; Swager, T. M. Chem. Rev. 2007, 107, 1339-1386, the disclosures of which are herein incorporated by reference in their entireties for all purposes).

Since the early demonstration of semiconducting polymer nanoparticles (Szymanski, C.; Wu, C.; Hooper, J.; Salazar, M. A.; Perdomo, A.; Dukes, A.; McNeill, J. D. J. Phys. Chem. B 2005, 109, 8543-8546; and Wu, C.; Szymanski, C.; McNeill, J. Langmuir 2006, 22, 2956-2960, the disclosures of which are herein incorporated by reference in their entireties for all purposes), there has been rapid progress in the field, including the characterization of their complex photophysics (see, for example, Palacios, R. E.; Fan, F. R. F.; Grey, J. K.; Suk, J.; Bard, A. J.; Barbara, P. F. Nat. Mater. 2007, 6, 680-685; Wu, C.; Zheng, Y.; Szymanski, C.; McNeill, J. J. Phys. Chem. C 2008, 112, 1772-1781; Wu, C.; McNeill, J. Langmuir 2008, 24, 5855-5861; and Collini, E.; Scholes, G. D. Science 2009, 323, 369-373, the disclosures of which are herein incorporated by reference in their entireties for all purposes), and their development for biological imaging and high resolution single-particle tracking (see, for example, Wu, C. et al., J. J. Am. Chem. Soc. 2007, 129, 12904-12905; Wu, C. et al., J. ACS Nano 2008, 2, 2415-2423; Wu, C.; et al, Chem. Int. Ed. 2009, 48, 2741-2745; Moon, J. H. et al, Chem. Int. Ed. 2007, 46, 8223-8225; Baier, M. C. et al, Am. Chem. Soc. 2009, 131, 14267-14273; Abbel, R.; et al, J. Chem. Commun. 2009, 1697-1699; Pu, K. Y. et al, Chem. Mater. 2009, 21, 3816-3822; Yu, J. et al, J. Am. Chem. Soc. 2009, 131, 18410-18414; Howes, P. et al, J. Am. Chem. Soc. 2010, 132, 3989-3996; and Kim, S. et al. Chem. Commun. 46, 1617-1619 (2010), the disclosures of which are herein incorporated by reference in their entireties for all purposes).

Aspects of the present invention relate to a novel class of functionalized fluorescent probes, referred to as functionalized chromophoric polymer dots (functionalized CPdots or Pdots), and their biomolecular conjugates for a variety of applications, including but not limited to flow cytometry, fluorescence activated sorting, immunofluorescence, immunohistochemistry, fluorescence multiplexing, single molecule imaging, single particle tracking, protein folding, protein rotational dynamics, DNA and gene analysis, protein analysis, metabolite analysis, lipid analysis, FRET based sensors, high throughout screening, cellular imaging, in vivo imaging, fluorescence-based biological assays such as immunoassays and enzyme-based assays, and a variety of fluorescence techniques in biological assays and measurements.

The unique properties of the functionalized chromophoric polymer dot has basis in, but is not limited to, high per-particle fluorescence brightness, large absorption cross section, high fluorescence quantum yield, fast emissive rate, highly polarized fluorescence, excellent photostability, and ease of storage. Upon conjugating with appropriate biomolecules, the probe can be used in many areas, including but not limited to flow cytometry, fluorescence activated sorting, immunofluorescence, immunohistochemistry, fluorescence multiplexing, single molecule imaging, single particle tracking, protein folding, protein rotational dynamics, DNA and gene analysis, protein analysis, metabolite analysis, lipid analysis, FRET based sensors, high throughout screening, cellular imaging, in vivo imaging, fluorescence-based biological assays such as immunoassays and enzyme-based assays, and a variety of fluorescence techniques in biological assays and measurements.

Additional advantages and features of the invention will be set forth in part in the description which follows, and in part will be obvious from the description, or can be learned by practice of the invention. We perform experiments to demonstrate the present invention as illustrated in the following description and examples with reference to the accompanying figures.

Pdots exhibit extraordinarily high fluorescence brightness under both one-photon and two-photon excitations. Their brightness stems from a number of favorable characteristics of semiconducting polymer molecules, including their large absorption cross-sections, fast emission rates, and high fluorescence quantum yields. Recent studies have also shown that Pdots as fluorescent probes were photostable, and not cytotoxic in different cellular assays (see, for example, Wu, C.; Bull, B.; Szymanski, C.; Christensen, K.; McNeill, J. ACS Nano 2008, 2, 2415-2423; Pu, K. Y.; Li, K.; Shi, J. B.; Liu, B. Chem. Mater. 2009, 21, 3816-3822; and Rahim, N. A. A.; McDaniel, W.; Bardon, K.; Srinivasan, S.; Vickerman, V.; So, P. T. C.; Moon, J. H. Adv. Mater. 2009, 21, 3492-3496, the disclosures of which are herein incorporated by reference in their entireties for all purposes).

However, for a wide range of biological applications, a significant problem of Pdots has yet to be solved, namely how to control their surface chemistry and conjugation to biological molecules. Although research efforts involving silica or phospholipid encapsulation can result in composite particles with surface functional groups (see, for example, Wu, C.; Szymanski, C.; McNeill, J. Langmuir 2006, 22, 2956-2960 and Howes, P.; Green, M.; Levitt, J.; Suhling, K.; Hughes, M. J. Am. Chem. Soc. 2010, 132, 3989-3996), all the reported results until now on cellular labeling with Pdots are presumably based on endocytosis (see, for example, Wu, C.; Bull, B.; Szymanski, C.; Christensen, K.; McNeill, J. ACS Nano 2008, 2, 2415-2423; Pu, K. Y.; Li, K.; Shi, J. B.; Liu, B. Chem. Mater. 2009, 21, 3816-3822; Howes, P.; Green, M.; Levitt, J.; Suhling, K.; Hughes, M. J. Am. Chem. Soc. 2010, 132, 3989-3996; and Rahim, N. A. A.; McDaniel, W.; Bardon, K.; Srinivasan, S.; Vickerman, V.; So, P. T. C.; Moon, J. H. Adv. Mater. 2009, 21, 3492-3496), a far less effective and specific process compared to the established labeling methods for organic fluorophores and Qdots. It is still unclear whether Pdot probes could be made specific enough to recognize cellular targets for effective labeling. This challenge thus far has severely prevented the widespread use of Pdots in biological applications.

Advantageously, the present invention provides solutions for the challenges associated with Pdot bioconjugation and specific cellular targeting. In one aspect, the present invention provides a novel conjugation method that covalently links Pdots to biomolecules for labeling cellular targets by specific antigen-antibody or biotin-streptavidin interactions. This functionalization and bioconjugation strategy can be easily applied to any hydrophobic, fluorescent, semiconducting polymer. As shown in the examples provided herein, Pdot bioconjugates conjugated by the methods provided herein can be used for single-particle imaging, cellular imaging, and flow cytometry experiments and their advantages over conventional organic fluorophores and Qdot probes are demonstrated. This work, therefore, opens up a new and practical pathway for employing a variety of highly fluorescent, photostable, and non-toxic Pdot bioconjugates for biological applications.

In one aspect, the present invention is based on a novel strategy for the functionalization of Pdots, comprising entrapping heterogeneous polymer chains into a single dot, driven by hydrophobic interactions during nanoparticle formation. A small amount of amphiphilic polymer bearing functional groups is co-condensed with the semiconducting polymers to modify and functionalize the nanoparticle surface for subsequent covalent conjugation to biomolecules, such as streptavidin and immunoglobulin G (IgG). The Pdot bioconjugates can effectively and specifically label cellular targets, such as cell surface marker in human breast cancer cells, without any detectable non-specific binding. Single-particle imaging, cellular imaging, and flow cytometry experiments indicate a much higher fluorescence brightness of Pdots compared to those of Alexa dye and quantum dot probes. The successful bioconjugation of these ultrabright nanoparticles presents a novel opportunity to apply versatile semiconducting polymers to various fluorescence measurements in modern biology and biomedicine.

In one aspect, highly fluorescent semiconducting polymer dots with functional groups that allow for covalent conjugation to biomolecules are provided. The strategy for functionalization of these Pdots is based on entrapping heterogeneous polymer chains into a Pdot particle, driven by hydrophobic interactions during nanoparticle formation. It is shown herein that a small amount of amphiphilic polymer bearing functional groups can be co-condensed with the semiconducting polymers to modify and functionalize the nanoparticle surface. Subsequent covalent conjugation to biomolecules such as streptavidin and antibodies were performed using the standard carbodiimide coupling chemistry. These Pdot bioconjugates can effectively and specifically label cell-surface receptors and subcellular structures in both live and fixed cells, without any detectable non-specific binding. Single-particle imaging, cellular imaging, and flow cytometry were performed to experimentally evaluate the Pdot performance, and demonstrate their high cellular labeling brightness compared to those of Alexa-IgG and Qdot probes. These results bring forward a new class of highly fluorescent nanoparticle bioconjugates for a wide range of fluorescence-based biological detection.

Definitions

As used herein, the term "chromophoric nanoparticle" or "chromophoric polymer dot" refers to a structure comprising one or more chromophoric polymers that have been collapsed into a stable sub-micron sized particle. The chromophoric nanoparticles provided herein may be formed by any method known in the art for collapsing polymers, including without limitation, methods relying on precipitation, methods relying on the formation of emulsions (e.g. mini or micro emulsion), and methods relying on condensation. In a preferred embodiment, a chromophoric nanoparticle is formed by nanoprecipitation.

As used herein, "polymer" is a molecule composed of at least 2 repeating structural units typically connected by covalent chemical bonds. Polymers generally have extended molecular structures comprising backbones that optionally contain pendant side groups. It includes linear polymer and branched polymer such as star polymers, comb polymers, brush polymers, ladders, and dendrimers.

As used herein, the term "chromophoric polymer" is a polymer in which at least a portion of the polymer comprises chromophoric units. The term "chromophore" is given its ordinary meaning in the art. A chromophore absorbs certain wavelength of light from UV to near infrared region, and may be or may not be emissive.

A "chromophoric unit" in this invention includes, but not limited to, unit of structures with delocalized pi-electrons, unit of small organic dye molecules, and unit of metal complexes. Accordingly, examples of chromophoric polymers include polymers comprising units of structures with delocalized pi-electrons such as semiconducting polymers, polymers comprising units of small organic dye molecules, polymer comprising units of metal complexes, and polymers comprising unit of any combinations thereof.

As used herein, the term "functional group" refers to any chemical unit that can be attached, such as by any stable physical or chemical association, to the chromophoric polymer, thereby rendering the surface of the chromophoric polymer dot available for conjugation. Non-limiting examples of functional groups include, carboxylic acid, amino, mercapto, azido, alkyne, aldehyde, hydroxyl, carbonyl, sulfate, sulfonate, phosphate, cyanate, succinimidyl ester, alkyne, strained alkyne, azide, diene, alkene, cyclooctyne, and phosphine groups, substituted derivatives thereof, and combinations there of.

As used herein, the term "functionalization agent" refers to any molecule that can be attached, such as by any stable physical or chemical association, to the core of a chromophoric polymer dot, providing a functional group on the surface of the polymer dot.

As used herein the term "hydrophilic functional group" refers either to a functional group that is hydrophilic in nature or to a hydrophobic functional group that is attached to a hydrophilic side chain or hydrophilic moiety, which renders the hydrophobic functional group more hydrophilic in nature and which facilitate the arrangement of the hydrophobic functional groups on the chromophoric polymer dot particle surface rather than getting buried inside the hydrophobic core of the chromophoric polymer dot. Examples of hydrophobic functional groups that can be rendered more hydrophilic by attachment to hydrophilic side chains or moieties include but not limited to alkyne, strained alkyne, azide, diene, alkene, cyclooctyne, and phosphine groups (for click chemistry) attached to a hydrophilic side chain such as PEG (polyethylene glycol) or to any other hydrophilic side chains.

As used herein, the term "bioorthogonal reaction" refers to a conjugation between non-native, non-perturbing chemical handles that can be modified in living systems through highly selective reactions with exogenously delivered probes. The most well known of the bioorthogonal reaction schemes is known as click chemistry. For review of bioorthogonal reaction schemes, see, for example Best MD, Biochemistry. 2009 Jul. 21; 48(28):6571-84, the disclosure of which is herein incorporated by reference in its entirety for all purposes.

As used herein, the term "click reaction" is recognized in the art, which describe a collection of supremely reliable and self-directed organic reactions, such as the most recognized copper catalyzed azide-alkyne [3+2] cycloaddition. Non-limiting examples of click chemistry reactions can be found, for example, in H. C. Kolb, M. G. Finn, K. B. Sharpless, Angew. Chem. Int. Ed. 2001, 40, 2004 and E. M. Sletten, C. R. Bertozzi, Angew. Chem. Int. Ed. 2009, 48, 6974, the disclosures of which are herein incorporated by reference in their entireties for all purposes.

As used herein, the term "cross-linking agent" is used to describe a compound that is capable of forming a chemical bond between molecular groups on similar or dissimilar molecules so as to covalently bond together the molecules. Examples of common cross-linking agents are known in the art. See, for example, Bioconjugate Techniques (Academic Press, New York, 1996 or later versions) the content of which is herein incorporated by reference in its entirety for all purposes. Indirect attachment of the biomolecule to monovalent chromophoric polymer dots can occur through the use of "linker" molecule, for example, avidin, streptavidn, neutravidin, biotin or a like molecule.

As used herein, an "antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature*, 348:552-554 (1990)).

Functionalized Chromophoric Polymer Dots

The present invention provides, in one aspect, a functionalized chromophoric polymer dot, which comprises a core and a cap. The "core" contains at least one chromophoric polymer. The "cap" comprises a functionalization agent. The functionalization agent is attached to the core of chromophoric polymer by physical association or chemical bonding, and provides surface functional groups on chromophoric polymer dot for bioconjugation. In another embodiment, the functionalized chromophoric polymer dot comprises just the core attached covalently to functional groups which facilitate bioconjugation.

In one aspect, the present invention provides a functionalized chromophoric polymer dot (Pdot) comprising a core and a cap, wherein said core comprises a chromophoric polymer, and said cap comprises a functionalization agent bearing one or more functional groups, with the proviso that not all of the said cap is an organo silicate. In a specific embodiment, the cap does not comprise an organo silicate.

In one embodiment, the present invention provides a functionalized chromophoric polymer dot that comprises a core of chromophoric polymer ranging in size from about 1 nm to about 1000 nm, and an amphiphilic functionalization layer, wherein the hydrophobic moiety is permanently anchored to the core of polymer dot through hydrophobic interaction and the hydrophilic functional groups such as carboxylic acid extend in solution for further bioconjugation.

In a specific embodiment, the present invention provides a functionalized chromophoric polymer dot (Pdot) having a hydrophobic core and a hydrophilic cap, the Pdot comprising: (a) a chromophoric polymer; and (b) an amphiphilic molecule, having a hydrophobic moiety and a hydrophilic moiety attached to a reactive functional group, wherein the chromophoric polymer is embedded within the hydrophobic core of the Pdot and; wherein a portion of the amphiphilic molecule is embedded within the core of the Pdot and the reactive functional group is located in the hydrophilic cap. In a preferred embodiment, the chromophoric polymer is a semiconducting polymer.

In one embodiment of the chromophoric polymer dots provided herein, the reactive functional group is selected from the group consisting of a carboxyl, amino, mercapto, azido, alkyne, aldehyde, hydroxyl, carbonyl, sulfate, sulfonate, phosphate, cyanate, succinimidyl ester, and a derivative thereof. In a specific embodiment, the reactive functional group is an alkyne containing moiety, azido containing moiety, or other moiety capable of being conjugated to a molecule via a click chemistry reaction.

In one embodiment, the chromophoric polymer is a semiconducting homopolymer. Many semiconducting homopolymers are known in the art, including without limitation, fluorene polymers, phenylene vinylene polymers, phenylene polymers, phenylene ethynylene polymers, benzothiazole polymers, thiophen polymers, carbazole fluorene polymers, boron-dipyrromethene-based polymers, and derivatives thereof. A list of common semiconducting polymers and their abbreviations is given in Table 1.

TABLE 1

Non-limiting examples of semiconducting polymers

Fluorene Polymers:

Poly(9,9-dihexylfluorenyl-2,7-diyl) (PDHF),
Poly(9,9-dioctylfluorenyl-2,7-diyl) (PFO),
Fluorene based Copolymers:

Poly[{9,9-dioctyl-2,7-divinylene-fluorenylene}-alt-co-{2-methoxy-5-(2-ethylhexyloxy)-1,4-phenylene}] (PFPV),
Poly[(9,9-dioctylfluorenyl-2,7-diyl)-co-(1,4-benzo-{2,1,3}-thiadiazole)] (PFBT),
Poly[(9,9-dioctylfluorenyl-2,7-diyl)-co-(4,7-Di-2-thienyl-2,1,3-benzothiadiazole)] (PFTBT),
Poly[(9,9-dioctylfluorenyl-2,7-diyl)$_{0.9}$-co-(4,7-Di-2-thienyl-2,1,3-benzothiadiazole)$_{0.1}$] (PF-0.1TBT),
Phenylene Vinylene Polymers:

Poly[2-methoxy-5-(2-ethylhexyloxy)-1,4-phenylenevinylene] (MEH-PPV),
Phenylene Ethynylene Polynmers Poly(2,5-di(3',7'-dimethyloctyl)phenylene-1,4-ethynylene (PPE), In another embodiment, the chromophoric polymer is a semiconducting copolymer comprising at least two different chromophoric units. For example, a chromophoric copolymer may contain both fluorene and benzothiazole chromophoric units present at a given ratio. Typical chromophoric units used to synthesize semiconducting copolymers include, but are not limited to fluorene unit, phenylene vinylene unit, phenylene unit, phenylene ethynylene unit, benzothiazole unit, thiophen unit, carbazole fluorene unit, boron-dipyrromethene unit, and derivatives thereof. The different chromophoric units may be segregated, as in a block copolymer, or intermingled. As used herein, a chromophoric copolymer is represented by writing the identity of the major chromophoric species. For example, PFBT is a chromophoric polymer containing fluorene and benzothiazole units at a certain ratio. In some cases, a dash is used to indicate the percentage of the minor chromophoric species and then the identity of the minor chromophoric species. For example, PF-0.1BT is a chromophoric copolymer containing 90% PF and 10% BT.

In other embodiments, a chromophoric polymer dot comprises a blend of semiconducting polymers. The blends may include any combination of chromophoric homopolymers, copolymers, and oligomers. Chromophoric polymer blends used to form polymer dots may be selected in order to tune the properties of the resulting polymer dots, for example, to achieve a desired excitation or emission spectra for the polymer dot.

In one embodiment of the chromophoric polymer dots provided herein, the functionalization agent is an amphiphilic molecule. In certain embodiment, the amphiphilic molecule is a chromophoric polymer that has been modified with a functional group. For example, in one embodiment, the present invention provides a functionalized chromophoric polymer dot (Pdot) having a hydrophobic core and a hydrophilic cap, the Pdot comprising: (a) a first semiconducting polymer; and (b) a second semiconducting polymer attached to a reactive functional group, wherein the first semiconducting polymer is embedded within the hydrophobic core of the Pdot and; wherein a portion of the second semiconducting polymer is embedded within the core of the Pdot and the reactive functional group is located in the hydrophilic cap (i.e., on the surface of the Pdot).

In another embodiments, the amphiphilic molecule is a non-chromophoric molecule, for example a non-chromophoric polymer, lipid, carbohydrate, or other non-chromophoric molecule modified with a reactive functional group. For example, in one embodiment, the present invention provides a functionalized chromophoric polymer dot (Pdot) having a hydrophobic core and a hydrophilic cap, the Pdot comprising: (a) a semiconducting polymer; and (b) an amphiphilic molecule, having a hydrophobic moiety and a hydrophilic moiety attached to a reactive functional group, wherein the semiconducting polymer is embedded within the hydrophobic core of the Pdot and; wherein a portion of the amphiphilic molecule is embedded within the core of the Pdot and the reactive functional group is located in the hydrophilic cap (i.e., on the surface of the Pdot).

In a specific embodiment, the amphiphilic polymer is an amphiphilic comb-like polymer, for example, a polystyrene based comb-like amphiphilic polymer or a poly(methyl methacrylate) based comb-like polymers. In another specific embodiment, the amphiphilic polymer is poly(styrene-co-maleic anhydride) (PSMA).

In a specific embodiment, the amphiphilic polymer is a polystyrene based comb-like polymers. Non limiting examples of polystyrene based comb-like polymers include, polystyrene graft acrylic acid, polystyrene graft ethylene oxide functionalized with carboxy, polystyrene graft ethylene oxide functionalized with amine, polystyrene graft ethylene oxide functionalized with thiol, polystyrene graft ethylene oxide functionalized with succinimidyl ester, polystyrene graft ethylene oxide functionalized with azide, polystyrene graft ethylene oxide functionalized with alkyne, polystyrene graft ethylene oxide functionalized with cyclooctyne, polystyrene graft ethylene oxide functionalized with ester, phosphine, polystyrene graft butyl alcohol, and the like. In a specific embodiment, the amphiphilic polymer is a polyethylene glycol-grafted polystyrene. In a more specific embodiment, the polyethylene glycol moiety of the amphiphilic polymer is attached to one or more carboxyl groups. In another specific embodiment, the amphiphilic polymer is a poly(styrene-co-maleic anhydride).

In another embodiment, the amphiphilic polymer is a poly(methyl methacrylate) based comb-like polymers. Non-limiting examples of poly(methyl methacrylate) based comb-like polymers include, poly(methyl methacrylate) graft acrylic acid, poly(methyl methacrylate) graft ethylene oxide functionalized with carboxy, poly(methyl methacrylate) graft ethylene oxide functionalized with amine, poly(methyl methacrylate) graft ethylene oxide functionalized with thiol, poly(methyl methacrylate) graft ethylene oxide functionalized with succinimidyl ester, poly(methyl methacrylate) graft ethylene oxide functionalized with azide, poly(methyl methacrylate) graft ethylene oxide functionalized with alkyne, poly(methyl methacrylate) graft ethylene oxide functionalized with cyclooctyne, poly(methyl methacrylate) graft ethylene oxide functionalized with ester, poly(methyl methacrylate) graft ethylene oxide functionalized with phosphine, and the like.

In yet another embodiment, the amphiphilic polymer is a comb-like polymer comprising a carboxyl, amine, thiol, ester, succinimidyl ester, azide, alkyne, cyclooctyne, and/or phosphine group.

In some embodiments, the amphiphilic polymer is an amphiphilic copolymer, for example, (1) poly((meth)acrylic acid) based copolymers such as: poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), poly(t-butyl methacrylate-b-ethylene oxide), poly(2-acrylamido-2-methylpropanesulfonic acid-b-acrylic acid); (2) polydiene based copolymers such as: poly(butadiene(1,2 addition)-b-ethylene oxide), poly(butadiene(1,2 addition)-b-methylacrylic acid, poly(butadiene (1,4 addition)-b-acrylic acid), poly(butadiene(1,4 addition)-b-ethylene oxide, poly(butadiene(1,4 addition)-b-sodium acrylate), poly(butadiene(1,4 addition)-b-N-methyl 4-vinyl pyridinium iodide), poly(isoprene-b-ethylene oxide), poly (isoprene-b-ethylene oxide), and poly(isoprene-b-N-methyl 2-vinyl pyridinium iodide); (3) poly(ethylene oxide) based copolymers such as: poly(ethylene oxide-b-acrylic acid), poly(ethylene oxide-b-acrylamide), poly(ethylene oxide-b-butylene oxide), poly(ethylene oxide-b-ε-caprolactone), poly(ethylene oxide-b-lactide), poly(ethylene oxide-b-lactide), poly(ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide-b-t-butyl methacrylate), poly(ethylene oxide-b-tetrahydrofurfuryl methacrylate), poly(ethylene oxide-b-2-ethyl oxazoline), poly(ethylene oxide-b-2-hydroxyethyl methacrylate), poly(ethylene oxide-b-2-methyl oxazoline); (4) polyisobutylene based copolymers such as poly(isobutylene-b-acrylic acid), poly(isobutylene-b-ethylene oxide), poly(isobutylene-b-methacrylic acid); (5) polystyrene based copolymers such as poly(styrene-b-acrylamide), poly(styrene-b-acrylic acid), poly(styrene-b-cesium acrylate), poly (styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly(styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly(styrene-b-sodium acrylate) poly(styrene-b-sodium methacrylate), poly (p-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate); (6) polysiloxane based copolymers such as poly(dimethylsiloxane-b-acrylic acid), poly(dimethylsiloxane-b-ethylene oxide), poly(dimethylsiloxane-b-methacrylic acid); (7) poly(ferrocenyldimethylsilane) based copolymers such as poly(ferrocenyldimethylsilane-b-ethylene oxide); (8) poly(2-vinyl naphthalene) based copolymers such as poly(2-vinyl naphthalene-b-acrylic acid), (9) poly(vinyl pyridine and N-methyl vinyl pyridinium iodide) based copolymers such as poly(2-vinyl pyridine-b-ethylene oxide), poly(2-vinyl pyridine-b-methyl acrylic acid), poly(N-methyl 2-vinyl pyridinium iodide-b-ethylene oxide), poly(N-methyl 4-vinyl pyridinium iodide-b-methyl methacrylate), poly(4-vinyl pyridine-b-ethylene oxide) PEO end functional OH; (10) poly(vinyl pyrrolidone) based copolymers such as poly(vinyl pyrrolidone-b-D/L-lactide); and the like.

In one embodiment, the hydrophilic moiety of an amphiphilic polymer used to functionalize a chromophoric polymer dot is a water soluble polymer, such as a polyalkylene glycol (e.g., a PEG), a PEO, a polypropylene glycol, a polyoxyalkylene, a starch, a poly-carbohydrate, a polysialic acid, and the like. In one embodiment, the water soluble polymer is a polyalkylene glycol. In a more specific embodiment, the water soluble moiety is a polyethylene glycol (a PEG).

In one embodiment, the hydrophobic moiety of the amphiphilic polymer used to functionalize a chromophoric polymer dot is a hydrophobic polymer. Non-limiting examples of polymers that may be used include, without limitation, poly(meth)acrylate polymers, polyacrylamide polymers, polyisobutylene, polydiene, polyphenylene, polyethylene, poly(ethylene glycol), polylactide, polystyrene, polysiloxane, poly(vinyl pyridine), poly(vinylpyrrolidone), polyurethane, a block copolymer thereof, a random or alternating copolymer thereof, and the like.

Dependent upon many factors, such as, the desired level of functionalization, desired spectrophotometric properties, and intended use, the weight ratio of amphiphilic molecule to chromophoric polymer in a functionalized chromophoric polymer dot as provided herein, will range from about 0.01% to about 50%. In a preferred embodiment, the weight ratio of amphiphilic molecule to chromophoric polymer is between about 5% and about 20%. In yet other embodiment, the weight ratio of amphiphilic molecule to chromophoric polymer is no larger than about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or about 50%. In a specific embodiment, the weight ratio of amphiphilic molecule to chromophoric polymer is no larger than about 25%.

In one embodiment, the chromophoric polymer dots provided herein further comprise a component selected from the group consisting of a fluorescent dye, an inorganic luminescent material, a magnetic material, and a metal embedded within the core of the polymer dot.

In yet other embodiments, a chromophoric polymer dot, as provided herein, may be further conjugated to one or more non-reactive chemical groups. In this fashion, the presence of non-reactive chemical groups on the surface of the polymer dot will reduce and/or eliminate non-specific associations between the surface of the polymer dots and other molecules, e.g., proteins. In one embodiment, the non-reactive chemical group is a water soluble polymer, such as a polyalkylene glycol (e.g., a PEG), a PEO, a polypropylene glycol, a polyoxyalkylene, a starch, a polycarbohydrate, a polysialic acid, and the like. In one embodiment, the water soluble polymer is a polyalkylene glycol. In a more specific embodiment, the water soluble moiety is a polyethylene glycol (a PEG).

Utilizing the functionalization scheme described herein, successful conjugations of streptavidin and/or antibodies to different types of Pdots, including the five Pdots described in Wu et al. (Wu, C.; Bull, B.; Szymanski, C.; Christensen, K.; McNeill, J. ACS Nano 2008, 2, 2415-2423), have been achieved.

The present invention provides, among other aspects and embodiments, functionalized PFBT dots for single-particle imaging, cellular labeling, and flow cytometry applications. Functionalized PFBT dots exhibit a relatively broad absorption peak around 460 nm (FIG. 3), which is a convenient wavelength region for fluorescence microscopy and laser excitations. Analysis of the absorption and fluorescence spectra from ~10 nm-diameter PFBT dots indicated a peak extinction coefficient of $1.5 \times 10^7$ $M^{-1}cm^{-1}$ and a fluorescence quantum yield of 0.30. The photophysical properties of PFBT dots are summarized in Table 2, together with the properties of two widely used probes purchased from Invitrogen: Qdot 565 and fluorescent IgG-Alexa 488 (~6 dye molecules per IgG). These two commercial probes were selected because they have emissions in a similar wavelength region as that of PFBT dots. It is important to note that Pdots contain multiple emitters, thus, although the lifetimes of Pdots are ~50 times shorter than Qdots, the emission rates of Pdots can be three orders of magnitude faster than Qdots (see, Id.).

TABLE 2

Photophysical Properties of PFBT dots, IgG-Alexa 488, and Qdot 565.

| Probe (Size) | PFBT dot (~10 nm) | Alexa 488 (~1 nm) | Qdot 565 (~15 nm) |
|---|---|---|---|
| Abs./Fluores. Max | 460 nm/540 nm | 496 nm/519 nm | UV/565 nm |
| Extinction Coeffocient at 488 nm | $1.0 \times 10^7$ $M^{-1} cm^{-1}$ | $5.3 \times 10^4$ $M^{-1} cm^{-1}$ | $2.9 \times 10^5$ $M^{-1} cm^{-1}$ |
| Quantum Yield | 0.3 | 0.9 | 0.3~0.5 |
| Fluorescence Lifetime | 0.6 ns | 4.2 ns | ~20 ns |

The data for Alexa 488 and Qdot 565 given in Table 2 are according to the probe specification provided by Invitrogen. The parameters of Alexa 488 are for single-dye molecules. An IgG-Alexa 488 probe has a hydrodynamic diameter of 12 nm, contains an average of 6 dye molecules, but its brightness corresponds to ~2-4 dye molecules due to self-quenching. Fluorescence lifetime of PFBT dots was measured by a TCSPC setup. Also note that single PFBT dots contain multiple emitters, which results in photon emission rates that are higher than those predicted from fluorescence lifetime alone.

The "Core"

In one embodiment, the core of the chromophoric polymer dot comprises a luminescent semiconducting polymer with delocalized pi-electrons. The term "semiconducting polymer" is recognized in the art. Typical luminescent semiconducting polymers include, but are not limited to fluorene polymers, phenylene vinylene polymers, phenylene polymers, phenylene ethynylene polymers, benzothiazole polymers, thiophen polymers, carbazole fluorene polymers, boron-dipyrromethene-based polymers, polymer derivatives thereof, and copolymers comprising any combinations thereof. In some embodiments, the chromophoric polymers may be semiconducting polymers covalently linked with unit of small organic dyes, or metal complexes as emissive species. Such emissive units can tune the emission color, increase the quantum yield, and improve the photostability of the chromophoric polymer dot.

In a preferred embodiment, the small organic dyes, or metal complexes can have sensing functions, and therefore add additional functionalities to the chromophoric polymer dot, such as oxygen sensing capability, ion sensing capability, glucose sensing capability, neurotransmitter sensing capability, drug sensing capability, metabolite sensing capability, protein sensing capability, signaling molecule sensing capability, toxin sensing capability, DNA and RNA sensing capability, and the like. For example, platinum porphyrin can be linked covalently to semiconducting polymers, and the resulting chromophoric polymer dots can be used as an oxygen sensor. In another embodiment, the chromophoric polymers may be semiconducting polymers covalently linked with unit of photochromic dye. A photochromic unit can serve as energy transfer acceptor. Upon light illumination of appropriate wavelengths, the photochromic unit undergoes a reversible transformation between two structural forms with different absorption spectra. Accordingly, the luminescence of chromophoric polymer dot can be modulated with another wavelength of light, making the chromophoric polymer dot have a desirable photoswitching capability. The photoswitching probes are particularly useful for super-resolution imaging techniques such as PALM, STORM, etc as recognized in the art.

In some embodiments, the core of the chromophoric polymer dot contains polymers comprising unit of small organic dye molecules, metal complexes, photochromic dye, and any combinations thereof, for example, optically inactive polymer such as polystyrene covalently linked or grafted with small organic dye, metal complexes, photochromic dyes and any combination thereof. These dyes or metal complexes may have sensing functions, and therefore add additional functionalities to the chromophoric polymer dot, such as oxygen sensing capability, ion sensing capability, glucose sensing capability, neurotransmitter sensing capability, drug sensing capability, metabolite sensing capability, protein sensing capability, signaling molecule sensing capability, toxin sensing capability, DNA and RNA sensing capability, and the like.

In a related embodiment, a chromophoric polymer dot as provided herein may include one or more pH sensitive dyes. For example, fluorescein is a well known pH sensitive dye that may be conjugated to the surface of a polymer dot provided herein. Once fluorescein is conjugated to the polymer dot, it can participate in fluorescence resonance energy transfer (FRET) with the chromophoric polymers present in the core of the polymer dot. When present in solution, the FRET emission of a fluorescein-conjugated chromophoric polymer dot will be dependent upon the pH of the solution. This is demonstrated in Example 31 provided herein.

Likewise, in one embodiment, the present invention provides a method for determining the pH of a solution, the method comprising the steps of contacting the solution with a chromophoric polymer dot conjugated to a pH sensitive dye, or having a pH sensitive dye embedded within the core of the polymer dot, capable of participating in FRET with chromophoric units present in the core of the polymer dot, exciting chromophoric units in the core of the polymer dot, and detecting the FRET emission of the pH sensitive dye.

In another related embodiment, a chromophoric polymer dot as provided herein may include one or more temperature sensitive dyes. For example, Rhodamine B is a well known temperature sensitive dye that may be embedded within the core or functionalized to the surface of a chromophoric polymer dot. Once embedded within the hydrophobic core of the polymer dot, it can participate in fluorescence resonance energy transfer (FRET) with the chromophoric polymers present in the core of the polymer dot. When present in solution, the FRET emission of a Rhodamine B-conjugated chromophoric polymer dot will be dependent upon the temperature of the solution. This is demonstrated in Example 30 provided herein.

Likewise, in one embodiment, the present invention provides a method for determining the temperature of a solution, the method comprising the steps of contacting the solution with a chromophoric polymer dot conjugated to a temperature sensitive dye, or having a temperature sensitive dye embedded within the core of the polymer dot, capable of participating in FRET with chromophoric units present in the core of the polymer dot, exciting chromophoric units in the core of the polymer dot, and detecting the FRET emission of the temperature sensitive dye.

The core may be solely semiconducting homopolymer, semiconducting copolymer, or semiconducting oligomer composed of at least 2 repeating structural units. The core may also comprise simultaneously two or more of semiconducting homopolymer, semiconducting copolymer, and/or semiconducting oligomer. The semiconducting polymer or oligomer preferably has light-emitting properties. Typical light-emitting polymers include, but are not limited to fluorene polymers, phenylene vinylene polymers, phenylene polymers, phenylene ethynylene polymers, benzothiazole polymers, thiophen polymers, carbazole fluorene polymers, boron-dipyrromethene-based polymers, polymer derivatives thereof, and copolymers comprising any combinations thereof.

The core may also comprise a semiconducting polymer as active fluorophore, physically mixed or chemically cross-linked with other optically inactive polymers, for example polystyrene, to have desirable properties such as polarized emission. The optically inactive polymer may contain functional groups for conjugation to the desired biomolecule, and thus render the chromophoric polymer dots the ability to associate with a biomolecule of interest.

The core may also comprise semiconducting polymer, physically mixed or chemically cross-linked with other chromophoric polymer such as optically inactive polymer covalently linked or grafted with small organic dye, metal complexes, photochromic dyes and any combination thereof, to have additional functionalities such as oxygen sensing capability, ion sensing capability, glucose sensing capability, neurotransmitter sensing capability, drug sensing capability, metabolite sensing capability, protein sensing capability, signaling molecule sensing capability, toxin sensing capability, DNA and RNA sensing capability, and the like. The core may also comprise a semiconducting polymer, physically mixed or chemically cross-linked with other components consisting of fluorescent dye, inorganic luminescent materials, magnetic materials, metal materials, to tune emission color, improve quantum yield and photostability, and have additional functionalities such as magnetic functions, plasmon resonance functions, and the like. The size of the core of a chromophoric polymer dot ranges and can be tuned in size from about 1 nm to about 1000 nm. FIG. 1 shows a chemical structure of chromophoric copolymer PFBT derived from fluorene and benzothiazole.

The "Cap"

The cap of a chromophoric polymer dot comprises a functionalization agent attached to the core of chromophoric polymer by physical association or chemical bonding, and provides surface functional groups on chromophoric polymer dot for bioconjugation. Preferably, the functionalization agent is a polymer, which may or may not be chromophoric. For example, functionalization can be provided by an amphiphilic polymer that comprises a hydrophobic moiety and a hydrophilic moiety containing one or more functional groups. In one embodiment, the hydrophobic moiety is physically embedded in the core of the chromophoric polymer dot by hydrophobic interaction, while the hydrophilic moiety containing functional groups extends into the solution for bioconjugation. In another embodiment, it may be preferred to chemically associate the polymer containing the functional groups with a preformed chromophoric polymer to form the functionalized chromophoric polymer dot. Chemical association can be any number of chemical bonding interactions, such as a covalent bond, an ionic bond, a polar covalent bond, a hydrogen bond, or metal-ligand bond.

Preferably, the functionalization agent will help maintain the water solubility and stability of the chromophoric polymer dot without causing aggregation for at least about one week, and more preferably stable in solution for over 1 month, 3 months, 6 months, 1 year, 3 years, and 5 years.

In one embodiment, the functionalization agent is attached to the core of chromophoric polymer by chemical association such as covalent bond, ionic bond, hydrogen bond and the like. Functionalization agent may be chemically linked to reactive sites in the backbone or side chain of the chromophoric polymer.

In another embodiment, the functionalization agent is anchored to the core of chromophoric polymer dot by physical association. Physical association can arise from a range of forces, including but not limited to van de Waals, electrostatic, pi-stacking, hydrophobic, entropic forces and combinations thereof. In a preferable embodiment, the functionalization agent may comprise a hydrophobic moiety and a hydrophilic moiety containing one or more functional groups. The hydrophobic moiety is physically embedded in the chromophoric polymer dots by hydrophobic interaction, while the hydrophilic moiety containing functional groups extends into the solution for bioconjugation. In a particular embodiment, the functionalization agent can be any molecule that comprises biotin, folic acid, folate, phalloidin, or a peptide, a nucleic acid, a carbohydrate, and the like, which can directly or indirectly bind to biological entities.

In some embodiments, the functionalization agent is a small organic molecule, a surfactant, or a lipid molecules that comprise functional groups such as carboxylic acid or salts thereof, amino, mercapto, azido, alkyne, aldehyde, hydroxyl, carbonyl, sulfate, sulfonate, phosphate, cyanate, succinimidyl ester, substituted derivatives thereof, or combinations there of. In general, any functional groups that allow bioconjugation may be used. Such groups could be found by one of ordinary skill in the art, for example in Bioconjugate Techniques (Academic Press, New York, 1996 or later versions). These molecules can be attached chemically or physically to the core of chromophoric polymer dot, and provide surface functional groups on the chromophoric polymer dot for bioconjugation.

In another embodiment, the functionalization agent is a polymer that comprises functional groups such as carboxylic acid or salts thereof, amino, mercapto, azido, alkyne, aldehyde, hydroxyl, carbonyl, sulfate, sulfonate, phosphate, cyanate, succinimidyl ester substituted derivatives thereof, or combinations there of. In general, any functional groups that allow bioconjugation may be used. Such groups could be found by one of ordinary skill in the art, for example in Bioconjugate Techniques (Academic Press, New York, 1996 or later versions). The functionalization polymer is associated with the core of chromophoric polymer dot by any chemical bonding or physical forces, and provide surface functional groups on the chromophoric polymer dot for bioconjugation.

In a preferred embodiment, the functionalization agent is an amphiphilic polymer that comprises a hydrophobic moiety and a hydrophilic moiety containing one or more functional groups. The hydrophobic moiety is physically embedded in the chromophoric polymer dots by hydrophobic interaction, while the hydrophilic moiety containing functional groups extends into the solution for bioconjugation.

In certain embodiment, the amphiphilic polymer is a hydrophobic chromophoric polymer that has been modified with hydrophilic functional groups. For example, in one embodiment, the functionalized chromophoric polymer dot (Pdot) having a hydrophobic core and a hydrophilic cap, the Pdot comprising: (a) a first hydrophobic semiconducting polymer; and (b) a second amphiphlic semiconducting polymer attached to a reactive functional group, wherein the first hydrophobic semiconducting polymer is embedded within the hydrophobic core of the Pdot and; wherein a portion of the second semiconducting polymer is embedded within the core of the Pdot and the reactive functional group is located in the hydrophilic cap (i.e., on the surface of the Pdot).

In another embodiment, the functionalization agent is a comb-like amphiphilic polymer comprising multiple repeating units of hydrophobic moiety and multiple repeating units of hydrophilic moiety so that the functionalization agent is permanently anchored to the core of polymer dot by strong hydrophobic force and the hydrophilic moieties comprise functional groups that extend into the solution for bioconjugation.

The hydrophobic moiety of an amphiphilic polymer may be an alkyl group, more preferably an aryl group to strengthen the hydrophobic attachment to the core of polymer dot that consist of many aromatic rings. Suitable hydrophilic moieties may be polyalkylene glycol which may be functionalized by carboxylic acid or salts thereof, amino, mercapto, azido, alkyne, aldehyde, hydroxyl, carbonyl, sulfate, sulfonate, phosphate, cyanate, succinimidyl ester, substituted derivatives thereof, or combinations there of. In general, any functional groups that allow bioconjugation may be used. Such groups could be found by one of ordinary skill in the art, for example in Bioconjugate Techniques (Academic Press, New York, 1996 or later versions). Desirably, the functionalization agent of the present invention is an amphiphilic polymer that comprises multiple units of an aryl group and multiple units of carboxylic acid, amino, mercapto, azido, alkyne, aldehyde, succinimidyl ester, or hydroxyl attached to the polyalkylene glycol. FIG. 1 shows the chemical structure of such a functionalization agent, polystyrene graft ethylene oxide terminated with carboxylic acid (PS-PEG-COOH).

Bioorthogonal or Clickable Chromophoric Polymer Dots

Click chemistry describes a powerful set of chemical reactions that are rapid, selective, and produce high yields (H. C. Kolb, M. G. Finn, K. B. Sharpless, Angew. Chem. Int. Ed. 2001, 40, 2004). The most recognized of these reactions is the copper (I)-catalyzed azide-alkyne cycloaddition, which has been applied to diverse areas, ranging from materials science (J. E. Moses, A. D. Moorhouse, Chem. Soc. Rev. 2007, 36, 1249) to drug discovery (H. C. Kolb, K. B. Sharpless, Drug Discov. Today 2003, 8, 1128) and chemical biology (Q. Wang, T. R. Chan, R. Hilgraf, V. V. Fokin, K. B. Sharpless, M. G. Finn, J. Am. Chem. Soc. 2003, 125, 3192; A. E. Speers, G. C. Adam, B. F. Cravatt, J. Am. Chem. Soc. 2003, 125, 4686; J. A. Prescher, C. R. Bertozzi, Nat. Chem. Biol. 2005, 1, 13; N. J. Agard, J. M. Baskin, J. A. Prescher, A. Lo, C. R. Bertozzi, ACS Chem. Biol. 2006, 1, 644; and E. M. Sletten, C. R. Bertozzi, Angew. Chem. Int. Ed. 2009, 48, 6974).

For biological applications, both azido and alkyne groups are considered to be bioorthogonal chemical reporters because they do not interact with any native biological functional groups. As a result, these bioorthogonal reporters can be incorporated into a target biomolecule using the cell's biosynthetic machinery to provide chemical handles that can be subsequently tagged with exogenous probes. The bioorthogonal chemical reporters are complementary to genetically encoded tags, such as green fluorescent protein (GFP), and provide a means to tag biomolecules without the need of direct genetic encoding. These reporters offer a powerful approach for visualizing multiple classes of biomolecules, not just proteins but also glycans, lipids, and nucleic acids (Prescher et al., supra). Furthermore, unlike GFP, the bioorthogonal chemical reporters are based on small molecules, which are less likely to perturb the functioning of the cell.

Bioorthogonal reactions via click chemistry are highly sensitive with low background noise despite the complexities of the cellular environment. In practice, however, the sensitivity is constrained by the abundance of the target molecules, the labeling efficiency of the chemical reporters, and the performance of the exogenous probes. In almost all cases, bright and photostable probes are highly desirable, particularly for long-term tracking and sensitive detection of low-abundance biomolecules.

Fluorescent nanoparticles have attracted much attention in recent years. The popular quantum dots (Qdots) exhibit improved brightness and photostability over traditional fluorescent dyes. In the context of click chemistry, however, the copper catalyst irreversibly quenches Qdot fluorescence and prevents their usage in the various applications based on copper-catalyzed click chemistry (S. Han, N. K. Devaraj, J. Lee, S. A. Hilderbrand, R. Weissleder, M. G. Bawendi, J. Am. Chem. Soc. 2010, 132, 7838). Because of copper's cytotoxicity, copper-free bioorthogonal approaches, such as the Staudinger ligation and the strain-promoted azide-alkyne cycloaddition, have been developed for live cell and in vivo applications (Agard et al., supra), although these reactions can sometimes be more difficult to implement due to tedious syntheses (Han et al., supra). Qdots can be employed in the copper-free methods (A. Bernardin, A. Cazet, L. Guyon, P. Delannoy, F. Vinet, D. Bonnaffe, I. Texier, Bioconjug. Chem. 2010, 21, 583), where their instability caused by copper is not an issue. However, Qdots' intrinsic toxicity, caused by the leaching of heavy metal ions, is still a critical concern.

Semiconducting polymer dots (Pdots) represent a new class of ultrabright fluorescent probes, which can overcome both issues for click chemistry-based applications. Previous studies showed that Pdots were not cytotoxic in different cellular assays, making them appealing for studies in living system. In one aspect, the present invention is focused on Pdot biological applications involving click chemistry. Pdots are much brighter fluorescent probes than Qdots; have a thousand-fold faster emission rates than Qdots; and are photostable and do not "blink". For biological applications, however, a significant problem of Pdots is the control over their surface chemistry and conjugation to biological molecules. This is a significant challenge that has prevented the widespread adoption of Pdots in biological studies.

Figure 14:
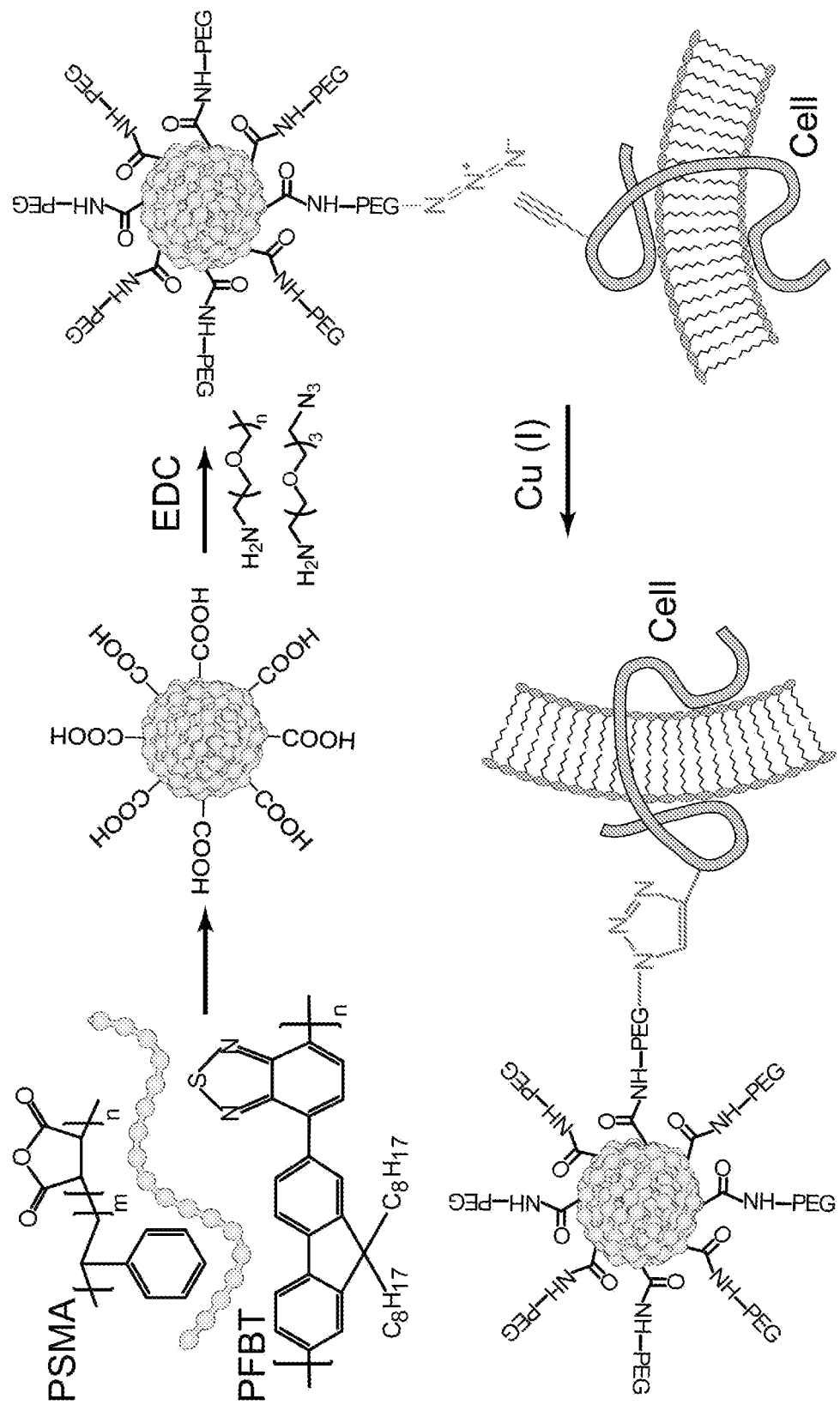
FIG. 14 Functionalization and conjugation of fluorescent semiconducting polymer dots for bioorthogonal labeling via click chemistry. A copolymer PSMA was co-condensed with a fluorescent semiconducting polymer, such as PFBT (depicted as green string), thereby forming Pdots with surface carboxyl groups. The carboxyl groups enabled further surface conjugations to functional molecules for copper (I)-catalyzed click reaction. The functionalized Pdots were selectively targeted against newly synthesized proteins or glycoproteins (blue string) in mammalian cells that were metabolically labeled with bioorthogonal chemical reporters.

In one aspect, the present invention provides a general method that overcomes this challenge by creating functional groups on the Pdot surface. Because the formation of Pdot is driven by hydrophobic interaction, some amphiphilic polymer with hydrophilic functional groups may be co-condensed into a single dot during nanoparticle formation. The hydrophilic groups on the amphiphilic polymer can be used as handles for functionalizing the Pdots for conjugation to biomolecules. It was found that a general copolymer, poly(styrene-co-maleic anhydride) (PSMA), successfully functionalized the Pdots for further surface conjugations (FIG. 14). PSMA provides excellent options for Pdot functionalization because it is commercially available in a broad range of molecular weights and maleic anhydride contents.

As shown in Example 17, PSMA was employed to functionalize Pdots made from a highly fluorescent semiconducting polymer Poly[9,9-dioctylfluorenyl-2,7-diyl)-co-1,4-benzo-[2,1'-3]-thiadiazole)] (PFBT), but the method can be applied to any hydrophobic, fluorescent, semiconducting polymers. During Pdot formation, the hydrophobic polystyrene units of PSMA molecules were likely anchored inside the Pdot particles while the maleic anhydride units localized to the Pdot surface and hydrolyzed in the aqueous environment to generate carboxyl groups on the Pdot surface. As shown herein, the carboxyl groups enable further surface conjugations.

As shown in Example 21, very low Pdot concentrations (~50 nM), which was orders of magnitude less than the general concentration used for small dye molecules (typically in the µM range) can be used for biological labeling applications. These results also shown that Pdot tagging via click chemistry is highly specific, with virtually no background labeling in all the control samples. Additionally, the Pdot probes were also used to detect glycoproteins and newly synthesized proteins detect in a different cell line, 3T3 fibroblast. In all these cases, the Pdots also specifically and effectively labeled the targets, demonstrating the strategy was equally efficient and successful in different cell lines.

Accordingly, in one embodiment, the present invention provides a method for conjugation that covalently links functional molecules to Pdots for click chemistry-based bioorthogonal labeling of cellular targets. These functionalized Pdots can selectively target, for example, newly synthesized proteins and glycoproteins in mammalian cells that were metabolically labeled with bioorthogonal chemical reporters. The highly efficient, specific, and bright protein labeling using Pdots and click chemistry demonstrate the potential of this method for visualizing various cellular processes. The methods and compositions described here will enable Pdots to be used in a wide range of cellular studies and fluorescence applications.

In one embodiment, the present invention provides chromophoric polymer dot conjugates in which a molecule, preferably a biomolecule, is attached to the polymer dot by chemical bonding via a click reaction. In order to achieve this, a first functional group capable of participating in a click chemistry reaction is engineered into the molecule (e.g., a biomolecule). For example, an attractive approach for installing azides into biomolecules is based on metabolic labeling, whereby an azide-containing biosynthetic precursor is incorporated into biomolecules by using the cells' biosynthetic machinery. Then, a second, complementary functional group capable of participating in a click chemistry reaction with the first functional group is attached to a chromophoric polymer dot, as provided herein. Reactions between the first functional group in the biomolecule and the complementary functional group on the polymer dot via click chemistry result in the formation of a polymer dot bioconjugate.

Figure 22:
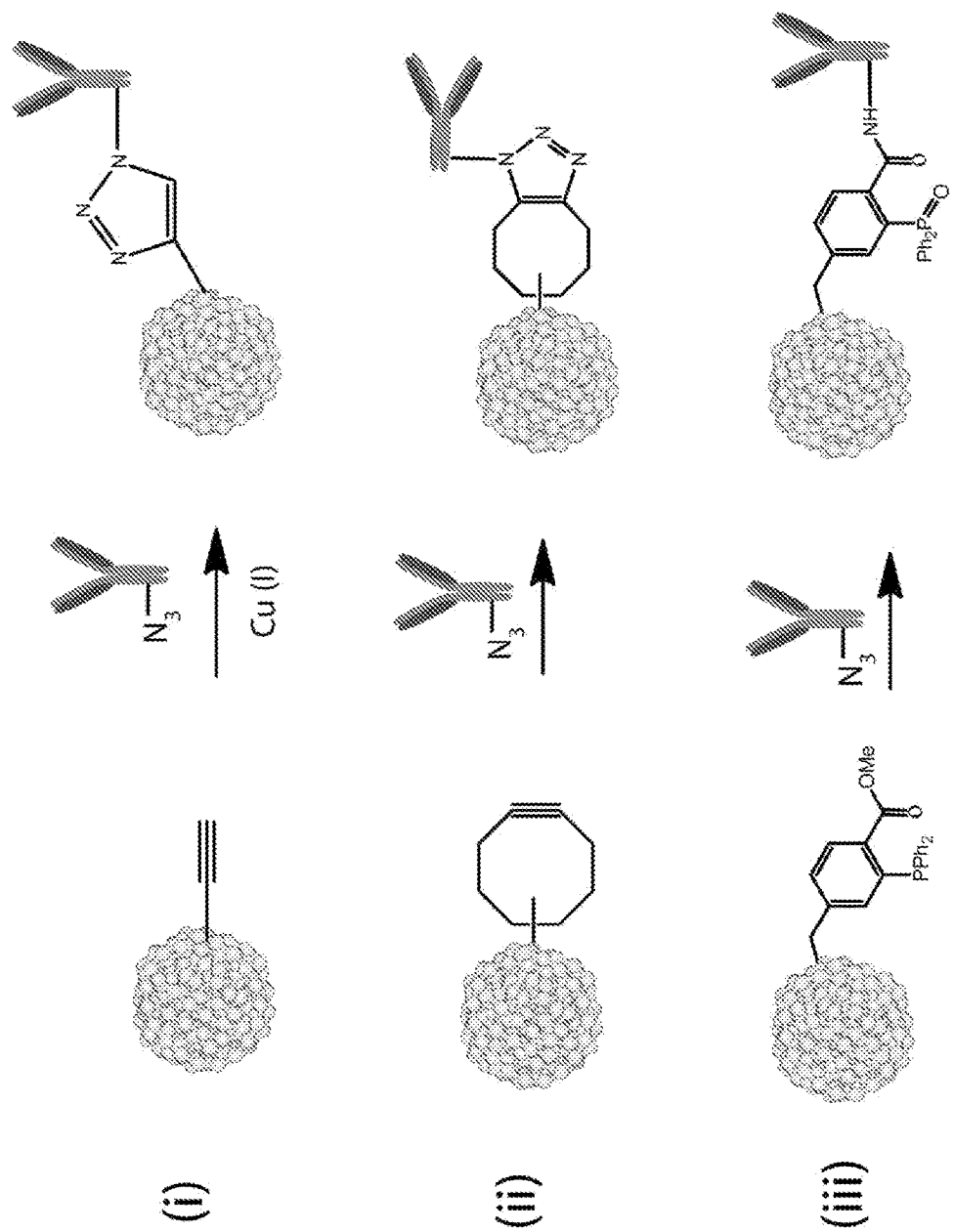
FIG. 22 Three schemes for bioconjugation via click chemistry.

In one embodiment, an organic azide is used as functional group linked or enriched in the biomolecule. A terminal alkyne as complementary functional group is associated with polymer dot. As shown in FIG. 22 (reaction i), the [3+2] cycloaddition between azide and alkyne groups with copper (I) as a catalyst lead to the formation of stable triazole linkage between the polymer dot and the biomolecule. Alternatively, alkynes can be activated by ring strain. For example, cyclooctynes and their derivatives can react with azides at room temperature without the need for a catalyst. The bioconjugation via the strain-promoted [3+2] cycloaddition (FIG. 22, reaction ii) removes the requirement for cytotoxic copper, which is particularly suitable for live cell and in vivo applications. In another embodiment, biomolecule can be conjugated to polymer dot via Staudinger ligation (FIG. 22, reaction iii). The term of "Staudinger ligation" is recognized in the art, which describes the selective reaction between phosphines and azides to form an amide bond. A functional phosphine group is associated with or covalently attached to polymer dot. Reaction of the phosphine group with the azide group in the biomolecule also results in formation of polymer dot bioconjugate without the need of catalyst. Click chemistry and Staudinger ligation can be employed to conjugate free biomolecules to polymer dot. The azide-, cyclooctyne-, and phosphine-functionalized polymer dots can also be used to specifically targeting the azide-containing biomolecules in vitro or in vivo.

Accordingly, in one embodiment, the present invention provides a functionalized chromophoric polymer dot (Pdot) comprising a core and a cap, wherein said core comprises a chromophoric polymer, and said cap comprises a functionalization agent bearing one or more functional groups capable of being conjugated to a molecule via a click chemistry reaction, with the proviso that not all of the said cap is an organo silicate. In a specific embodiment, the functional group is selected from an alkyne, strained alkyne, azide, diene, alkene, tetrazine, strained alkene, cyclooctyne, phosphine groups, and other groups for click reaction and other bioorthogonal reactions.

In a related embodiment, the present invention provides a functionalized chromophoric polymer dot (Pdot) having a hydrophobic core and a hydrophilic cap, the Pdot comprising: (a) a semiconducting polymer; and (b) an amphiphilic molecule, having a hydrophilic moiety and a hydrophobic moiety, attached to a reactive functional group capable of being conjugated to a molecule via a click chemistry reaction, wherein the semiconducting polymer is embedded within the hydrophobic core of the Pdot and; wherein a portion of the amphiphilic molecule is embedded within the core of the Pdot and the reactive functional group is located in the hydrophilic cap. In a specific embodiment, the functional group is selected from an alkyne, strained alkyne, azide, diene, alkene, tetrazine, strained alkene, cyclooctyne, phosphine groups, and other groups for click reaction and other bioorthogonal reactions.

Bioconjugated Chromophoric Polymer Dots

In another aspect, the present invention provides a bioconjugate comprising a functionalized chromophoric polymer dot as described herein and a biomolecule, wherein the biomolecule is attached to the polymer dot either directly or indirectly by any suitable means. The bioconjugates also comprise functionalized chromophoric polymer dot as described above, physically or chemically associated with biological particle such as virus, cells, biological or synthetic vesicles such as liposomes.

The term "biomolecule" is used to describe a synthetic or naturally occurring protein, glycoprotein, peptide, amino acid, metabolite, drug, toxin, nuclear acid, nucleotide, carbohydrate, sugar, lipid, fatty acid and the like. The biomolecule may be attached to the polymer dot directly or indirectly by any suitable means, such as by any stable physical or chemical association. Desirably, the biomolecule is attached to the hydrophilic functional groups of the functionalized polymer dot via one or more covalent bonds. For example, if the functional group of the polymer dot is carboxyl group, a protein biomolecule can be directly attached to the polymer dot by cross-linking the carboxyl group with amine group of the protein biomolecule.

The term "cross-linking agent" is used to describe a compound that is capable of forming a chemical bond between molecular groups on similar or dissimilar molecules so as to covalently bond together the molecules. In the present invention, a suitable cross-linking agent is one that couple carboxyl to amine groups, for example 1-Ethyl-3-[3-dimethylaminopropyl]carbodiimide hydrochloride (EDC). Other examples of common cross-linking agents are known in the art. See, for example, Bioconjugate Techniques (Academic Press, New York, 1996 or later versions). Indirect attachment of the biomolecule to the chromophoric polymer dots can occur through the use of "linker" molecule, for example, avidin, streptavidn, neutravidin, biotin or a like molecule.

Accordingly, in one embodiment, the present invention provides a functionalized chromophoric polymer dot having a hydrophobic core and a hydrophilic cap, as provided herein, wherein a biological molecule is conjugated to a reactive functional group present in the hydrophilic cap structure (i.e., on the surface of the polymer dot).

Generally, any biological molecule of interest may be conjugated to a chromophoric polymer dot provided herein, including without limitation targeting molecules, effector molecules, inhibitor molecules, imaging molecules, and the like. Exemplary biological molecules that may be conjugated to a chromophoric polymer dot provided by the invention include, synthetic or naturally occurring proteins, glycoproteins, polypeptides, amino acids, nucleic acids, carbohydrates, lipids, fatty acids, and combinations thereof.

In a specific embodiment, the present invention provides a functionalized chromophoric polymer dot (Pdot) comprising a core and a cap, wherein said core comprises a chromophoric polymer, and said cap comprises a functionalization agent bearing one or more functional groups conjugated to a biological molecule, with the proviso that not all of the said cap is an organo silicate. In one embodiment, the biological molecule is selected from a synthetic protein, a naturally occurring protein, a glycoprotein, a polypeptide, an amino acid, a nucleic acid, a carbohydrate, a lipid, a fatty acid, and a combination thereof. In a specific embodiment the biological molecule is a polypeptide. In one embodiment, the polypeptide is an antibody or fragment thereof. In another specific embodiment, the biological molecule is a nucleic acid. In one embodiment, the biological molecule is an aptamer.

In a related aspect, the present invention provides a functionalized chromophoric polymer dot (Pdot) having a hydrophobic core and a hydrophilic cap, the Pdot comprising: (a) a semiconducting polymer; and (b) an amphiphilic molecule bearing a reactive functional group conjugated to a biological molecule, wherein the semiconducting polymer is embedded within the hydrophobic core of the Pdot and; wherein a portion of the amphiphilic molecule is embedded within the core of the Pdot and the reactive functional group and conjugated biological molecule is located in the hydrophilic cap (i.e., on the surface of the polymer dot).

In one embodiment, the reactive functional group used to conjugate a biological molecule to a chromophoric polymer dot, is a chemical moiety capable of participating in a click chemistry reaction and other bioorthogonal reactions. In a specific embodiment, the functional group is selected from an alkyne containing moiety, an azido containing moiety, and a phosphine containing moiety.

In some embodiments, the chromophoric polymer dot is conjugated to an "effector moiety". The effector moiety can be any number of molecules, including labeling moieties such as radioactive labels or fluorescent labels; targeting moieties such as antibodies, aptamers, proteins, peptides; or can be a therapeutic moiety. Such therapeutic moieties include, but are not limited to, an anti-tumor drug, a toxin, a radioactive agent, a cytokine, an antibody or an enzyme. Further, the invention provides an embodiment wherein the chromophoric polymer dot of the invention is linked to an enzyme that converts a prodrug into a cytotoxic agent.

In yet other embodiments, a functionalized chromophoric polymer dot, as provided herein, is conjugated to more than one type of effector molecule. For example, in one embodiment, a chromophoric polymer dot is conjugated to both a targeting moiety (e.g., an antibody or aptamer) and a therapeutic moiety (e.g., an anti-tumor drug, a toxin, a radioactive agent, a cytokine, an antibody or an enzyme). As such, the functionalized chromophoric polymer dots provided herein may serve as a both a diagnostic/imaging tool, through the fluorescence of the polymer dot itself, and a therapeutic moiety.

Chromophoric Polymer Dots for In Vivo Applications

Nanoparticle-based diagnostic and therapeutic agents have attracted considerable interest because of their potential for clinical oncology and other biomedical research. Versatile nanostructures have been demonstrated for in vivo applications, such as lipid and polymeric nanocapsules for drug delivery, iron oxide nanoparticles for magnetic resonance imaging, gold nanoparticles for X-ray computed tomography, and quantum dots (Qdots) for fluorescence imaging. Among those, the organic molecule based nanocapsules provide flexible vehicles for drug encapsulation and delivery. However, they rarely provide imaging contrast, and generally require a molecular tag to enable in vivo monitoring by fluorescence. Conversely, inorganic nanoparticles are primarily used as imaging contrast agents owing to their unique properties. Qdots represent one of the exciting nanotechnologies translated to biology in the past decade. The size-tunable luminescence make them appealing as multicolor fluorophores for extensive biological labeling, imaging, and sensing. For in vivo applications, however, the intrinsic toxicity of Qdots is of critical concern, which may impede their final clinical translation.

In a recent landmark paper (Choi, H. S. et al. Nature Biotechnol. 25, 1165-1170 (2007)), three criteria were proposed for distinguishing a nanoparticle that has potential clinical utility: (i) a final hydrodynamic diameter (HD) <5.5 nm to permit fast renal clearance and/or (ii) a formulation with completely nontoxic components and/or (iii) biodegradability to clearable components. Although small HD (<5.5 nm) could result in efficient renal clearance to mitigate toxic effect (Id.), such a size limit poses great challenges for most nanoparticle systems, particularly the quantum dots (Choi, H. S. et al. Nature Nanotechnol. 5, 42-47 (2010)), where the luminescence is size-dependent and an encapsulation layer is required for water solubility. Therefore, design of bright fluorescent probes with biologically benign materials is highly desirable for many in vivo applications related to diagnosis and treatment of human disease.

Semiconducting polymers combine the organic polymeric nature with the unique optical properties of semiconductors. The motivation of adapting semiconducting polymers as fluorescent nanoparticle labels stems from a number of favorable characteristics such as the high per-particle brightness, fast emission rates, and excellent photostability. Furthermore, semiconducting polymer dots (Pdots) are intrinsically benign and biocompatible: cytotoxicity was not observed in different cell lines incubated with highly concentrated nanoparticles for days (Moon, J. H. et al., Angew. Chem. Int. Ed. 46, 8223-8225 (2007); and Pu, K. Y. et al., Chemistry of Materials 21, 3816-3822 (2009)). While still at the early stage of development, Pdots have been attracting intensive interest (see, for example, Pecher, J. & Mecking, S. Chem. Rev. Article ASAP (2010); and Kaeser, A. & Schenning, A. P. H. J. Adv. Mater. 22, 2985-2997 (2010)).

Researchers including synthetic chemists have developed various methods to improve the nanoparticle's versatility and functions for biomedical studies, such as tuning the emission color (Abbel, R., et al., Chem. Commun., 1697-1699 (2009), the disclosure of which is herein incorporated by reference in its entirety for all purposes), exploring new preparation methods (Baier, M. C. et al., J. Am. Chem. Soc. 131, 14267-14273 (2009), the disclosure of which is herein incorporated by reference in its entirety for all purposes), engineering the particle surface (Howes, P. et al., J. Am. Chem. Soc. 132, 3989-3996 (2010), the disclosure of which is herein incorporated by reference in its entirety for all purposes), encapsulating magnetic materials (Howes, P. et al. J. Am. Chem. Soc. 132, 9833-9842 (2010), the disclosure of which is herein incorporated by reference in its entirety for all purposes), and the first in vivo experiment for sentinel lymph node mapping (Kim, S. et al. Chem. Commun. 46, 1617-1619 (2010), the disclosure of which is herein incorporated by reference in its entirety for all purposes). Despite all the efforts, it is still unclear whether these polymer based novel probes can be specifically targeted to malignant tumors in vivo. Specific tumor targeting is the first prerequisite for any further clinical considerations. In one aspect, the present invention overcomes several challenges related to ligand conjugation and probe performance of chromophoric nanoparticles useful for in vivo application.

Figure 23:
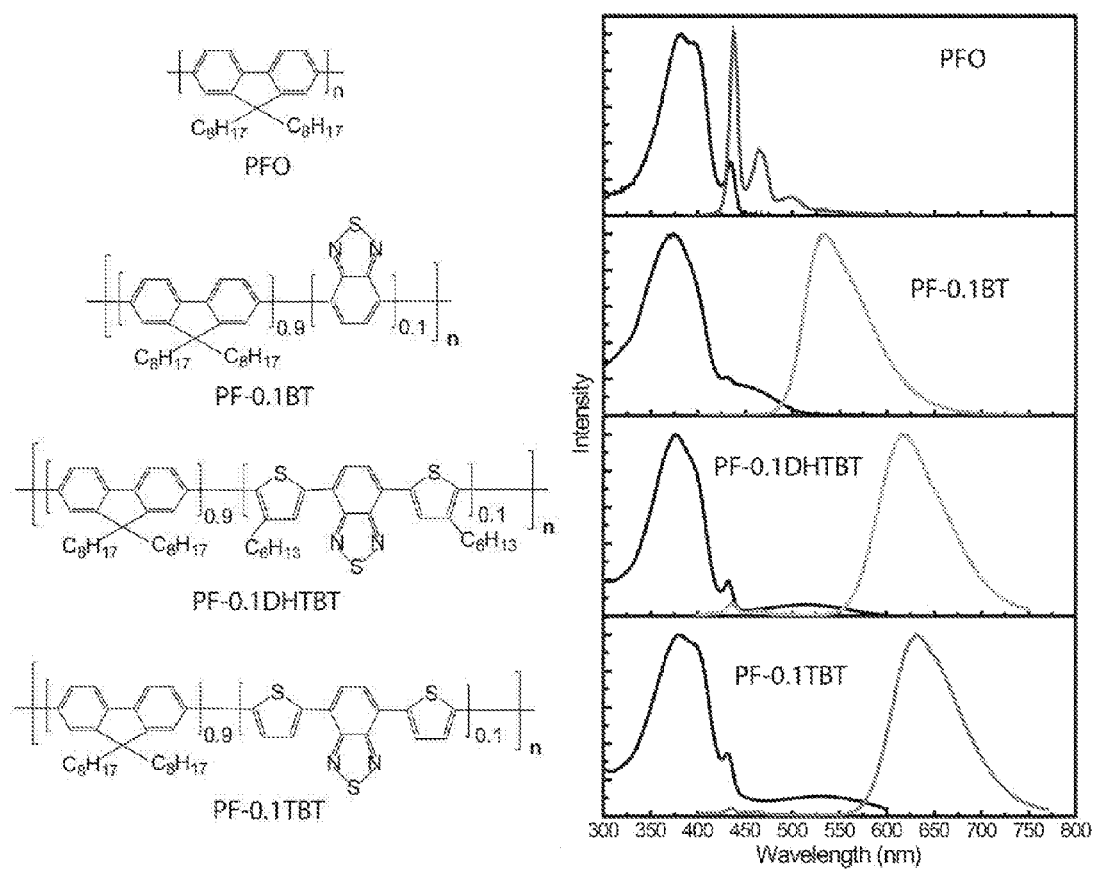
FIG. 23 Multicolor semiconducting polymer dots based on polyfluorene polymers. While the emission color can be tuned to deep-red region, the dominant absorption is in the UV region to maintain high fluorescence quantum yields. The dominant UV absorption is due to the majority of fluorene unit. The left shows chemical structures of these polymers.

As described herein, various semiconducting polymers can be used for preparing small Pdots as fluorescent labels. Particularly, polyflourenes (PF) and their derivatives exhibit high fluorescence quantum yields and excellent thermal and chemical stability. Significant success has been made to tune their emission color from blue to deep-red region by introducing narrow-band-gap monomers into the polymer backbone (see, Hou, Q. et al. Macromol. 37, 6299-6305 (2004); and Yang, R. Q. et al. Macromol. 38, 244-253 (2005), the disclosures of which are herein incorporated by reference in their entireties for all purposes), exhibiting great flexibility for designing fluorescent probes. However, the fluorescence quantum yield, particularly in the deep-red region, drops significantly as the concentration of narrow-band-gap monomers is increased (see, Id.). As a trade off, only a small amount of narrow-band-gap monomers were incorporated in the PF copolymer to maintain a high fluorescent quantum yield, which resulted in the dominant absorption of relative Pdots in the ultraviolet (UV) region (FIG. 23). This is a severe drawback for in vivo applications.

Figure 24:
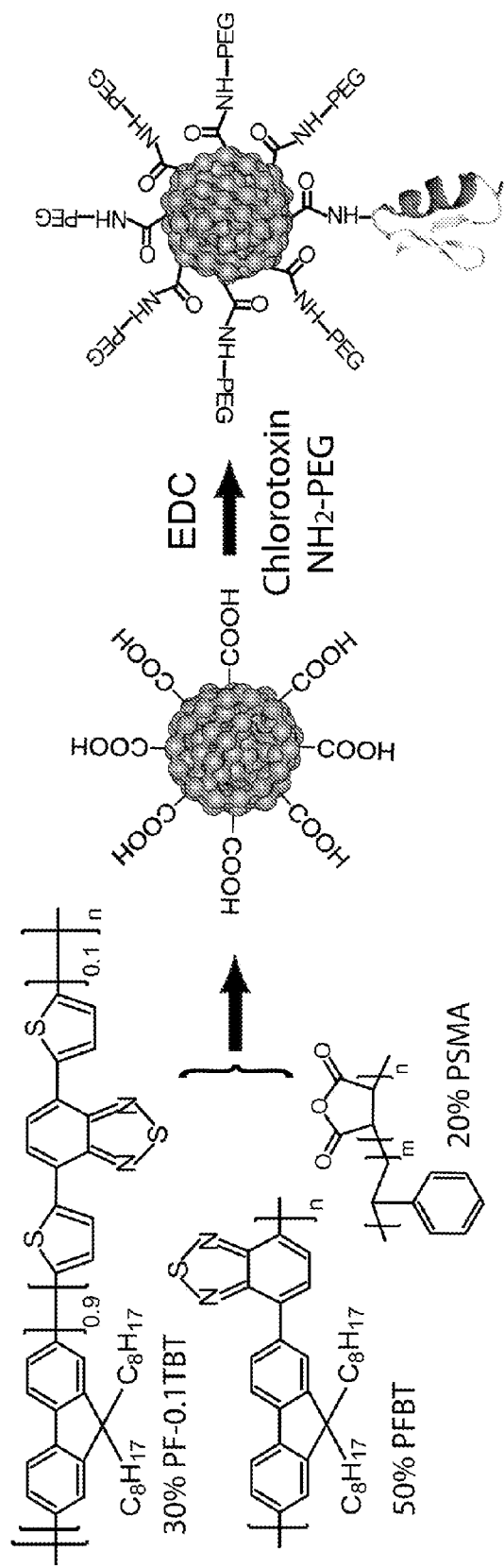
FIG. 24 A light-harvesting polymer PFBT, and a red-emitting polymer PF-0.1TBT, and a functional copolymer PSMA was co-condensed to form highly fluorescent PBdots with surface carboxyl groups. The carboxyl groups enabled further surface conjugations to a tumor-specific peptide ligand CTX.
Figure 25B:
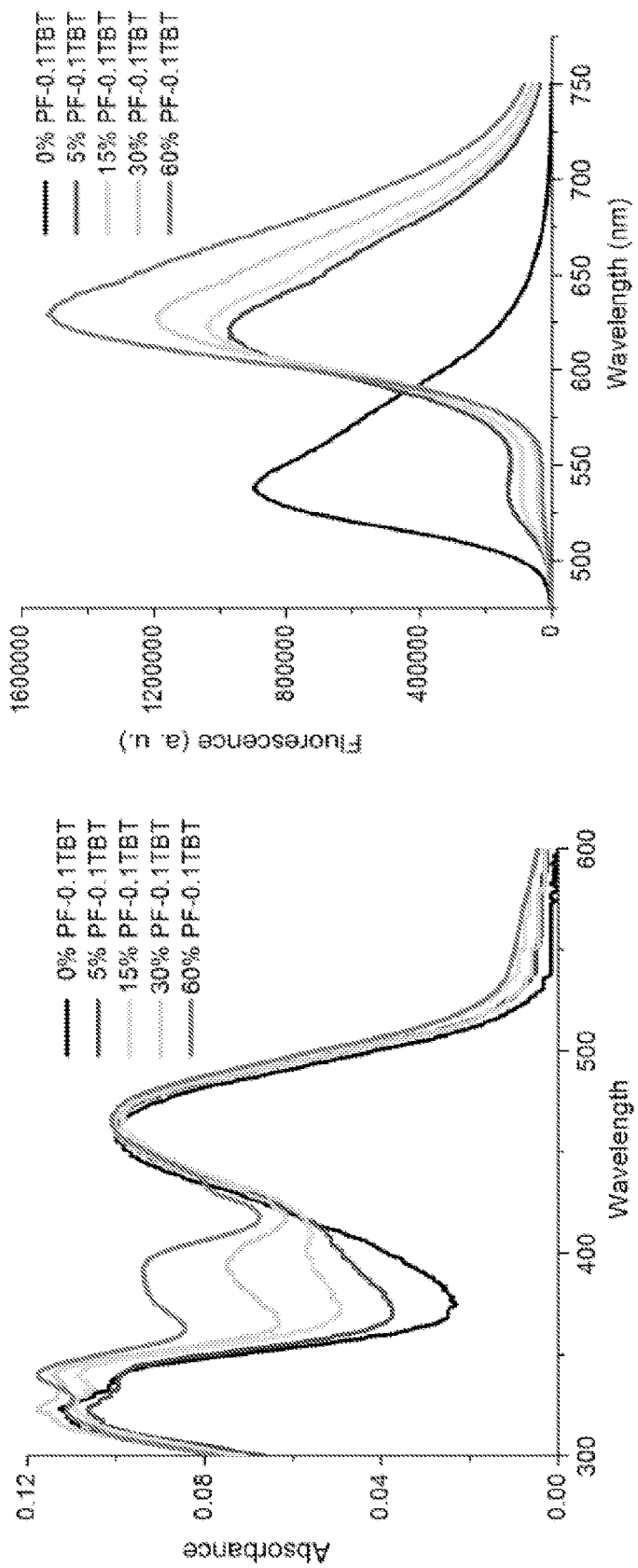
FIG. 25(A) Chemical structures of PFBT and PF-0.1TBT polymers. (B) Concentration dependent absorption spectra (left) and emission spectra (right) of PBdots containing a light-harvesting PFBT donor polymer and a red-emitting PF-0.1TBT acceptor polymer. At a blending ratio of 0.6 (PF-0.1TBT to PFBT), the PBdots show broad absorption in visible region and efficient deep-red emission from PFTBT. The top shows chemical structures of PFBT and PF-0.1TBT. (C) Absorbance spectra (left) and fluorescence emission spectra (right) of the quantum yield (QY) standard DCM dye and PBdots. The absorbance of both PBdots in water and DCM in methanol was adjusted to be 0.1. Fluorescence spectra were taken under identical spectrometer conditions.
Figure 25C:
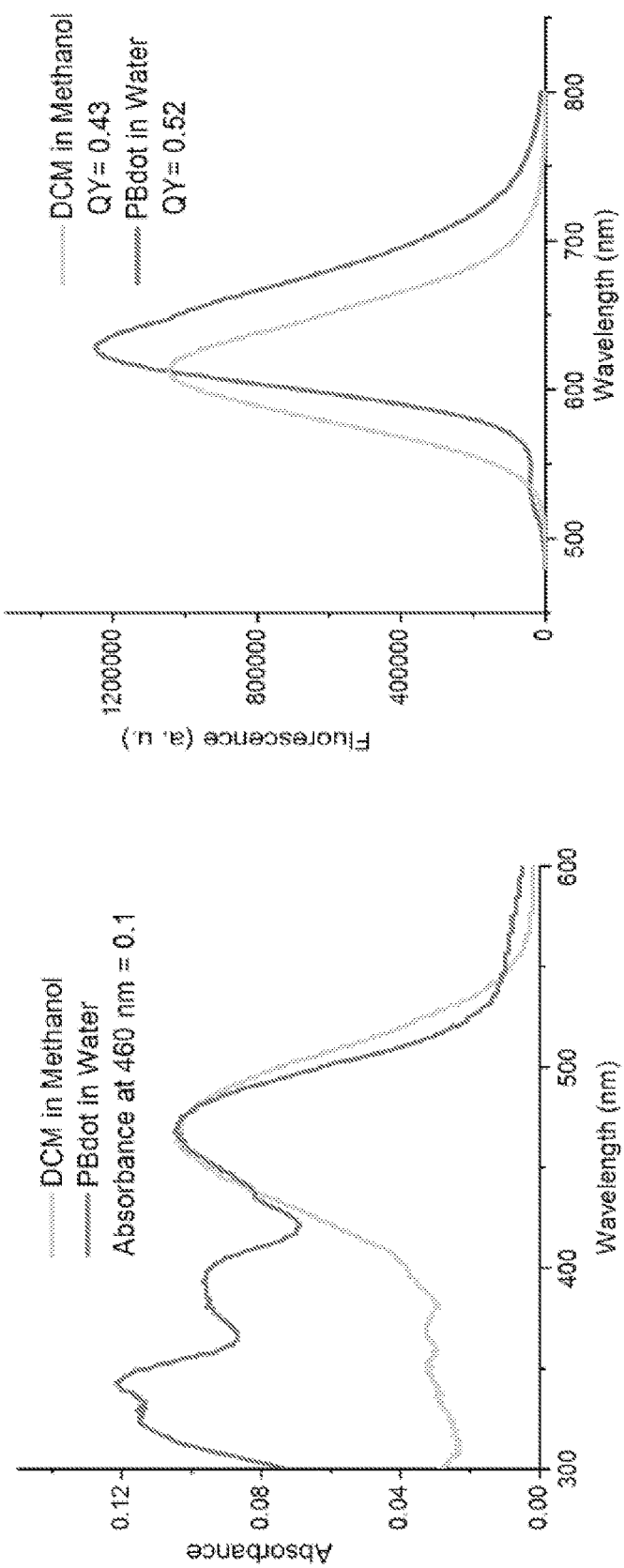
Figure 26:
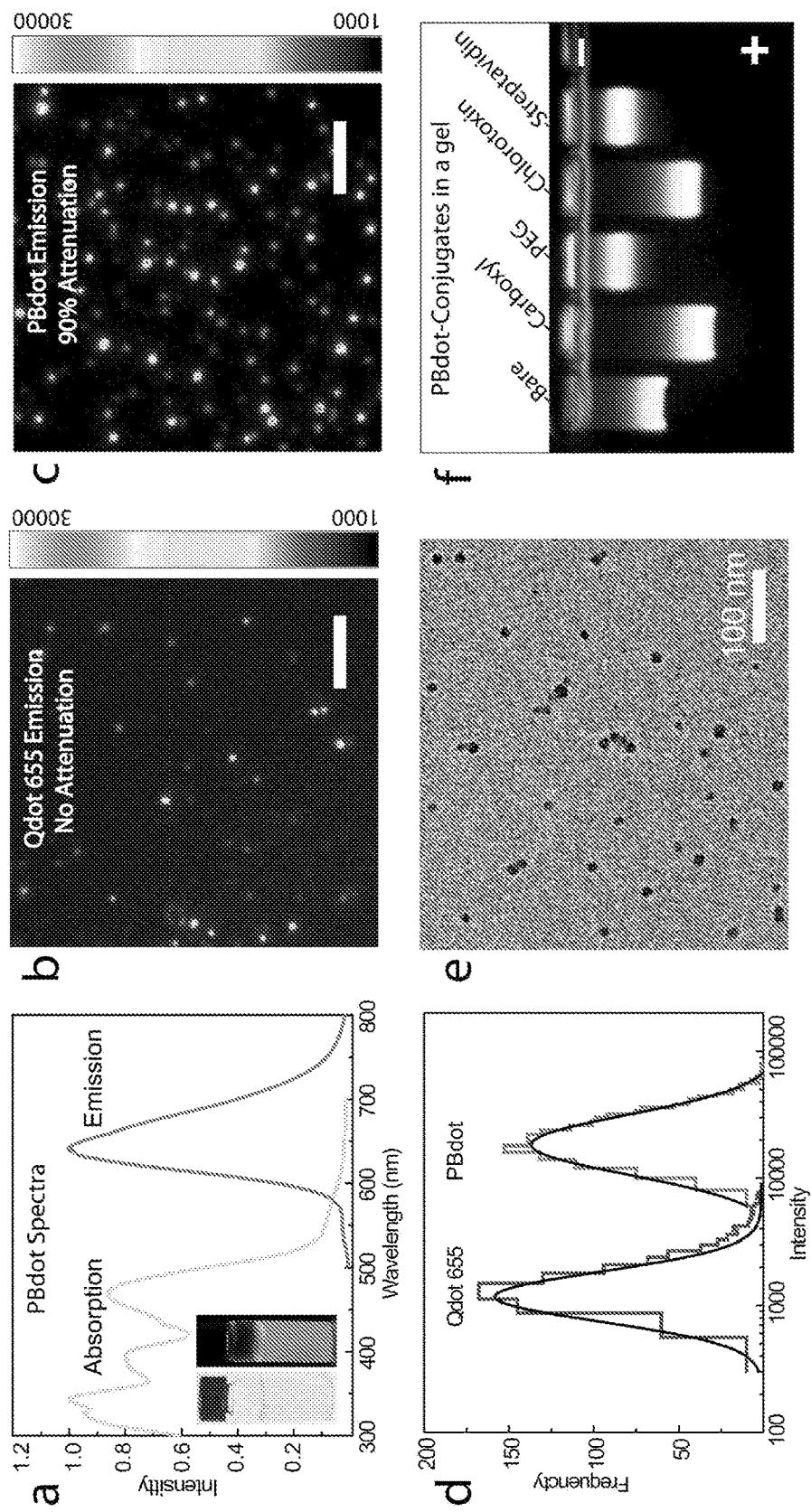
FIG. 26(a) Absorption and emission spectra of PBdot. The inset shows photographs of aqueous PBdot solution under room light (left) and UV light (right) illumination. (b) Single-particle fluorescence image of Qdot 655 nanocrystals. Scale bar, 4 µm. (c) Single-particle fluorescence image of PBdot. Images were obtained under the same excitation conditions as those for Qdot 655, but the 90% of the emitted light was blocked by a neutral density filter (OD=1) to avoid detector saturation. Scale bar, 4 µm. (d) Intensity distributions of single particle fluorescence. PBdots are ~15 times brighter than Qdot 655 probes. (e) TEM image of carboxyl functionalized PBdots. Scale bar, 100 nm. (f) Gel electrophoresis of functionalized and bioconjugated PBdots. PBdots conjugated with different biomolecules showed shifted migration bands in an agarose gel, indicating successful functionalization and biomolecular conjugation.

In order to overcome the above limitation, the present invention provides nanoparticles consisting of donor-acceptor polymer blends, which take advantage of the efficient intra-particle energy transfer that occurs in Pdots (see, for example, Wu, C. et al., J. Phys. Chem. C 112, 1772-1781 (2008); and Wu, C. et al., J. Phys. Chem. B 110, 14148-14154 (2006)). The polymer blend dots ("PBdots") were prepared by using a visible-light-harvesting polymer (PFBT) as donor and an efficient deep-red emitting polymer (PF-0.1TBT) as acceptor (polymer structures shown in FIG. 24). Because the donor and acceptor polymers were closely packed into single dots, intra-particle energy transfer resulted in complete quenching of the PFBT donor, accompanied by an effective fluorescence from the acceptor polymer alone (FIG. 25B). At a given blending ratio of 0.6 (PF-0.1TBT to PFBT in weight), the PBdots exhibit a broad visible absorption band extending to 600 nm, and an efficient 650 nm emission with a quantum yield of 0.52 (FIGS. 25C and 26A).

Figure 27:
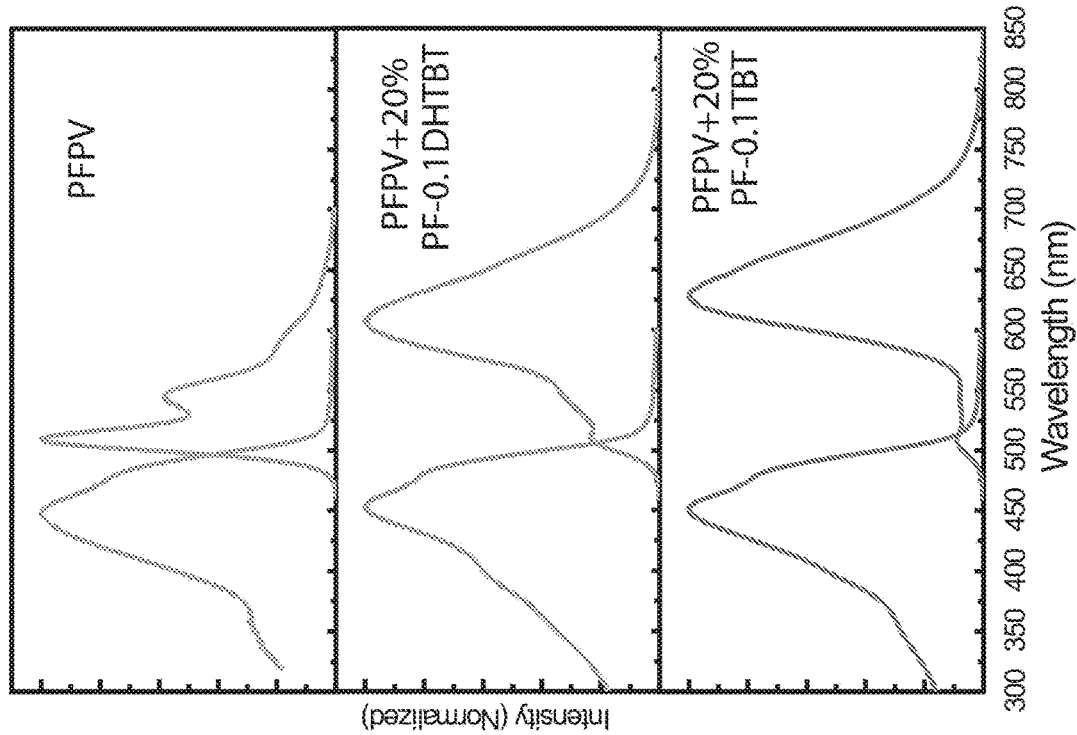
FIG. 27 Absorption spectra (left) and emission spectra (right) of PBdots containing a light-harvesting PFPV donor polymer, and two red-emitting polymers PF-0.1DHTBT, PF-0.1 TBT, respectively. The left shows the chemical structures of the polymers.
Figure 27:
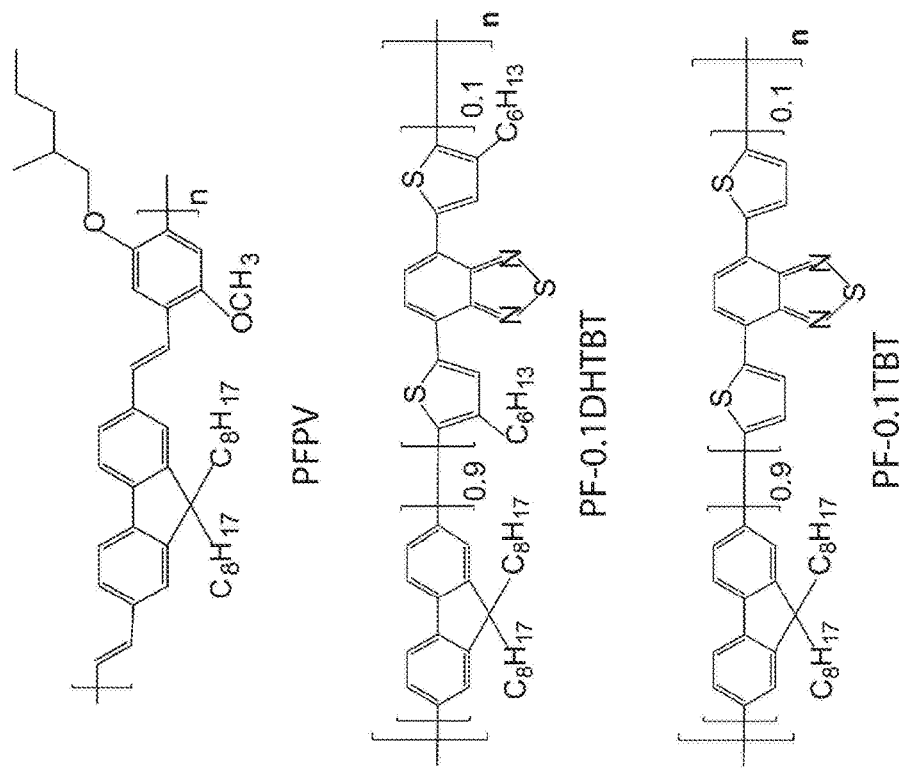
Figure 28:
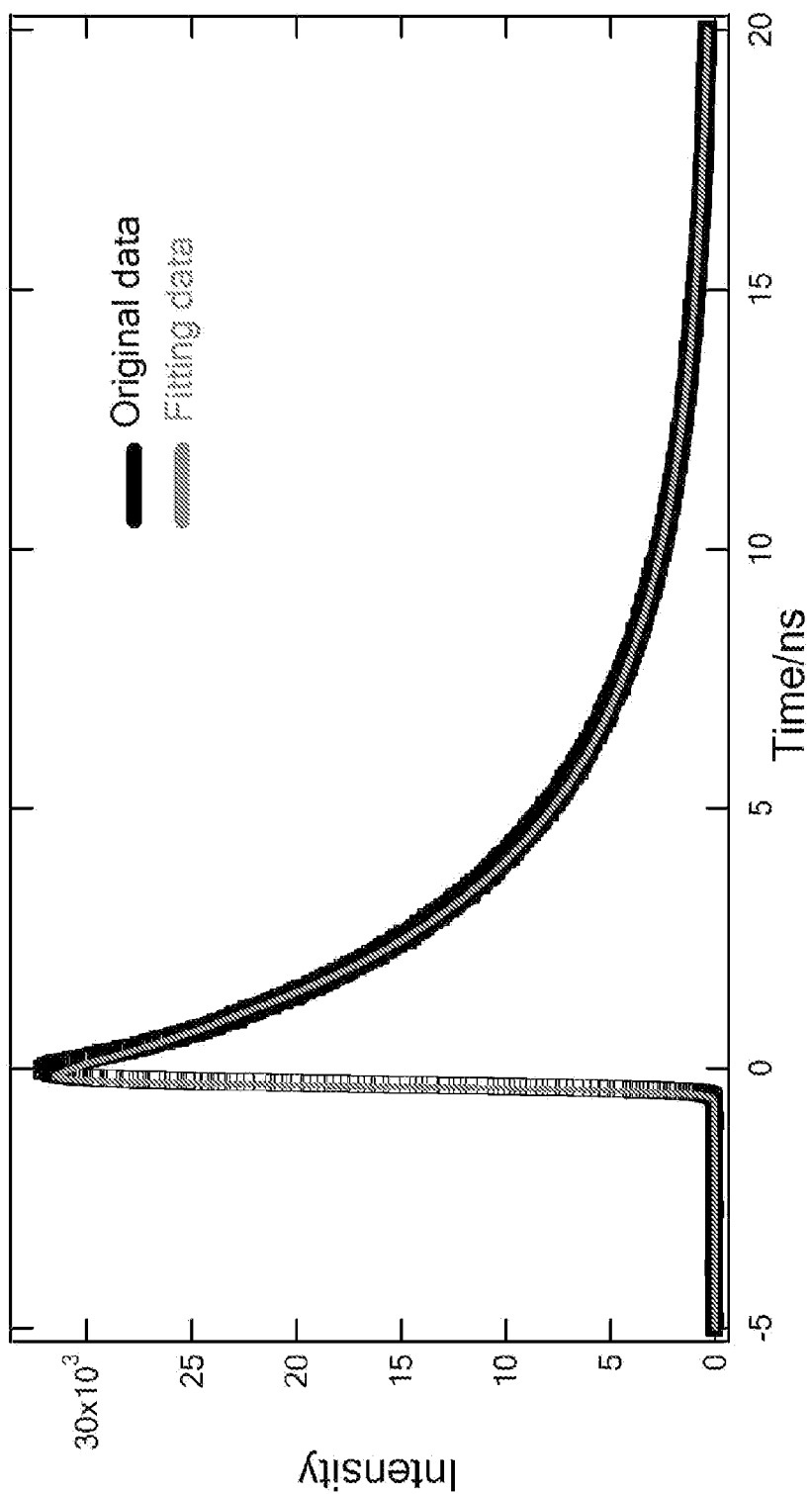
FIG. 28 Fluorescence decay lifetime (3.5 ns) of PBdots measured by a time correlated single photon counting instrument (TCSPC). The black line represents experimental data, and the red line is the fitting curve.

The blending strategy was also successfully applied to other polymer donor-acceptor systems consisting of light-harvesting polymer PFPV and different red-emitting polymers (FIG. 27), indicating its general application for tuning Pdot properties. Although Pdots emitting in near infrared (NIR) region are more preferable for in vivo imaging, as shown in Example 29, the current PBdots represent the brightest probe in deep-red region among various nanoparticles of similar size (~15 nm diameter), which may significantly overcome background autofluorescence and scattering in biological tissues.

Accordingly, in one embodiment, the present invention provides a chromophoric polymer dot having a deep-red-shifted emission. In one embodiment, the chromophoric polymer dot comprises a blend of a polyflourene polymer (PF) and fluorene-benzothiadiazole-thiophen copolymer (PF-0.1TBT). The narrow-band-gap TBT monomers were introduced into polyfluorene backbone in order to tune the emission color from blue to deep-red region. (see, Hou, Q. et al. Macromol. 37, 6299-6305 (2004); and Yang, R. Q. et al. Macromol. 38, 244-253 (2005)). The concentration of TBT monomers can be varied from 0.01 to 0.5. Advantageously, these polymer blends comprising PFBT and PF-0.1TBT result in dominant absorption in the visible region and deep-red fluorescence without significant loss of quantum yield. Generally, the blend will contain between about 2% and about 75% PF-0.1TBT copolymer. In certain embodiment, the ratio of PF to PF-0.1TBT is no greater than about 50:1 or no greater than about 45:1, 40:1, 35:1, 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 3:2, 1:1, 2:3, 1:2, or 1:3. In one specific embodiment, the polymer blends comprise PFBT and PF-0.1TBT. In another specific embodiment, the polymer blends comprise PFPV and PF-0.1TBT. In a preferred embodiment, the polymer dot comprises a functional group on its surface.

In a specific embodiment, the deep-red shifted polymer dot, having a hydrophobic core and a hydrophilic cap, comprises: (a) a blend of a PFBT and PF-0.1TBT semiconducting polymers; and (b) an amphiphilic molecule, having a hydrophilic moiety and a hydrophobic moiety, attached to a reactive functional group, wherein the semiconducting polymers are embedded within the hydrophobic core of the Pdot and; wherein a portion of the amphiphilic molecule is embedded within the core of the Pdot and the reactive functional group is located in the hydrophilic cap (i.e., on the surface of the polymer dot). In some embodiments, the polymer dot is further conjugated to an effector molecule (e.g., a targeting agent). In one embodiment, the red shifted polymer dot has a peak emission between about 600 nm and about 700 nm (i.e., in the deep red region).

In another embodiment, the deep-red shifted polymer dot, having a hydrophobic core and a hydrophilic cap, comprises: (a) a PFBT polymer; and (b) a PF-0.1TBT semiconducting polymer, wherein a sub-population of the semiconducting polymers harbors a reactive functional group, wherein the semiconducting polymers not harboring reactive functional groups are embedded within the hydrophobic core of the Pdot and; wherein a portion of the semiconducting polymers harboring reactive functional groups are embedded within the core of the Pdot and the reactive functional group is located in the hydrophilic cap (i.e., on the surface of the polymer dot). In some embodiments, the polymer dot is further conjugated to an effector molecule (e.g., a targeting agent).

In a related embodiment, deep-red shifted polymer dots are provided which are conjugated to an effector molecule, for example, a targeting moiety. In one embodiment, the bioconjugated chromophoric polymer dot comprises a blend of a semiconducting polymer (e.g., PF, PFBT, PFPV, etc.) and PF-0.1TBT semiconducting polymer. Generally, the blend will contain between about 2% and about 75% PF-0.1TBT copolymer. In certain embodiment, the ratio of PF to PF-0.1TBT is no greater than about 50:1 or no greater than about 45:1, 40:1, 35:1, 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 3:2, 1:1, 2:3, 1:2, or 1:3. In one specific embodiment the polymer blends comprise PFBT and PF-0.1TBT. In another specific embodiment, the polymer blends comprise PFPV and PF-0.1TBT.

In another aspect, the present invention provides chromophoric polymer dots having near-infrared (NIR) fluorescent emission. As used herein, "near-infrared emission" refers to electromagnetic radiation having a wavelength between about 700 nm and about 1500 nm. As shown in Example 29, NIR fluorescent emission can be achieved by embedding a NIR dye into the hydrophobic core of a chromophoric polymer dot provided herein. Many NIR fluorescent dyes are known in the art, for example cyanine dyes are the most commonly used near-IR fluorescent dyes. Other NIR dye families include oxazine, rhodamine, and phthalocyanine dyes. To achieve NIR emission after excitation, the NIR Pdot takes advantage of efficient intermolecular FRET between the chromophoric polymer comprising the Pdot and the NIR dye embedded within the hydrophobic core of the molecule. Accordingly, when selecting a NIR dye to be used for the preparation of a NIR Pdot, care must be taken to select chromophores having overlapping emission and excitation spectras (i.e., an appropriate chromophoric polymer FRET donator and NIR dye FRET acceptor). In a preferred embodiment, the NIR polymer dot is further functionalized on its surface.

Accordingly, in one embodiment, a NIR polymer dot comprises a core and a cap, wherein said core comprises a chromophoric polymer and a NIR dye, and said cap comprises a functionalization agent bearing one or more functional groups, with the proviso that not all of said cap is an organo silicate. In one embodiment, the polymer dot is further conjugated to an effector molecule (e.g., a targeting agent).

In a related embodiment, a NIR polymer dot, having a hydrophobic core and a hydrophilic cap, comprises: (a) a semiconducting polymer; (b) an NIR dye; and (c) an amphiphilic molecule, having a hydrophobic moiety and a hydrophilic moiety attached to a reactive functional group, wherein the semiconducting polymer and NIR dye are embedded within the hydrophobic core of the Pdot and; wherein a portion of the amphiphilic molecule is embedded within the core of the Pdot and the reactive functional group is located in the hydrophilic cap. In one embodiment, the polymer dot is further conjugated to an effector molecule (e.g., a targeting agent).

Methods for Preparing Chromophoric Polymer Dots

In one aspect, the present invention provides novel methods for functionalizing the surface of chromophoric nanoparticles (i.e., chromophoric polymer dots or "Pdots"). In one embodiment, the method is based on a concept in which heterogeneous polymer chains are entrapped into a single Pdot by hydrophobic interactions established during nanoparticle formation. A small amount of amphiphilic polymers is co-condensed with the semiconducting polymers of the Pdots to modify and functionalize the nanoparticle surface.

FIG. 1 illustrates an example of this, by using a functional, amphiphilic, comb-like, polystyrene polymer PS-PEG-COOH, however, other amphiphilic polymers with different functional groups can also be used. PS-PEG-COOH consists of a hydrophobic polystyrene backbone and several hydrophilic side chains of ethylene oxide terminated with carboxylic acid. During nanoparticle formation, the hydrophobic polystyrene backbones are embedded inside the Pdot particles while the hydrophilic PEG chains and functional groups extend outside into the aqueous environment. Unlike physical adsorption, therefore, this method should permanently anchors the PEG and functional groups to the Pdot surface. The PEG chains provide a biocompatible layer that minimizes non-specific absorption. The PEG chains also act as a steric barrier against nanoparticle aggregation, while the functional carboxyl group can be easily covalently-linked to biomolecules using established protocols (see, for example, Xing, Y.; Chaudry, Q.; Shen, C.; Kong, K. Y.; Zhau, H. E.; WChung, L.; Petros, J. A.; O'Regan, R. M.; Yezhelyev, M. V.; Simons, J. W.; Wang, M. D.; Nie, S. Nature Protoc. 2007, 2, 1152-1165, the contents of which is herein incorporated by reference in its entirety for all purposes).

In a preferred embodiment, chromophoric polymer dots are prepared by precipitation. This technique involves the rapid addition (e.g., facilitated by sonication or vigorous stirring) of a dilute chromophoric polymer solution (e.g., chromophoric polymer dissolved in an organic solvent) into an excess volume of non-solvent (but miscible with the organic solvent), such as water or another physiologically relevant aqueous solution. For example, in some embodiments, the hydrophobic chromophoric polymer is first dissolved into an organic solvent where the solubility is good (good solvent), such as THF (tetrahydrofuran), after which the dissolved polymer in THF is added to an excess volume of water or buffer solution, which is a poor solvent for the hydrophobic chromophoric polymers but which is miscible with the good solvent (THF). The resulting mixture is sonicated or vigorously stirred to assist the formation of chromophoric polymer dots, then the organic solvent is removed to leave behind well dispersed chromophoric nanoparticles. In using this procedure, the chromophoric polymer must be sufficiently hydrophobic to dissolve into the organic solvent (e.g. THF).

However, other methods of forming chromophoric polymer dots are also possible, including but not limited to various methods based on emulsions (e.g., mini or micro emulsion) or precipitations or condensations. In one embodiment, hydrophobic functional groups may be localized to the surface of the polymer dot such that they will be available for conjugation, for example, to a biomolecule. In one scheme, hydrophobic reactive functional groups are localized to the surface of the Pdot by attaching the functional group to a hydrophilic linker that carries the functional group to the hydrophilic exterior of the polymer dot. This latter approach may work particularly well using functional groups that are both hydrophobic and clickable (i.e., chemical reactions that fall within the framework of click chemistry), including but not limited to alkyne, strained alkyne, azide, diene, alkene, cyclooctyne, and phosphine groups.

Accordingly, in a preferred embodiment, the present invention provides a method for preparing a functionalized chromophoric polymer dot by introducing a mixture of a semiconducting polymer and an amphiphilic molecule attached to a reactive functional group solvated in a non-protic solvent into a solution comprising a protic solvent. In one embodiment, the method further comprises filtering the suspension to isolate a population of polymer dots of a particular size.

In a specific embodiment, the method for preparing a functionalized chromophoric polymer dot comprises the steps of (a) preparing a mixture of a semiconducting polymer and an amphiphilic molecule attached to a reactive functional group in a non-protic solvent; (b) introducing (e.g., by injecting) all or a portion of the mixture into a solution comprising a protic solvent, thereby collapsing the semiconducting polymer and amphiphilic molecule into a nanoparticle; and (c) removing the aprotic solvent from the mixture formed in step (b), thereby forming a suspension of functionalized chromophoric polymer dots, wherein a portion of the amphiphilic molecule is embedded within the core of the nanoparticle and the reactive functional group is located on the surface of the nanoparticle. In one embodiment, the method further comprises filtering the suspension to isolate a population of polymer dots of a particular size.

In one specific embodiment, the amphiphilic polymer is further conjugated to an effector molecule through a reactive functional group prior to introducing the mixture into the solution somprising a protic solvent. This approach will work for molecules that tolerate non-protic solvents, but won't work well with other molecules (e.g., proteins) that do not. As a demonstration of the feasibility of this strategy, Example 31 provides a case wherein an amphiphilic polymer containing a reactive functional group was first conjugated to a pH sensitive fluorescein isothiocyanate dye and then blended with a semiconducting polyer to form a conjugated polymer dot.

Many techniques are know in the art for removing an aprotic solvent from a mixture comprising an aprotic and a protic solvent, including without limitation, distillation, nitrogen stripping, and various chromatographic techniques (e.g., buffer exchange chromatography). In a preferred embodiment, wherein the boiling point of the aprotic solvent is lower than the boiling point of the protic solvent, the aprotic solvent is removed from the mixture formed in step (b) by nitrogen stripping. In a preferred embodiment, the protic solvent is water.

Methods for Preparing Chromophoric Polymer Dot Bioconjugates

As described herein, the functionalized chromophoric polymer dots provided by the present invention allow for the facile conjugation of biological molecules to stable, non-toxic fluorescent probes (i.e., Pdots) that can be used in a wide array of diagnostic and experimental assays. In this fashion, a molecule, preferably a biomolecule, may be attached to a chromophoric polymer dot through adsorption to the surface of the polymer dot (e.g., mediated through electrostatic or hydrophobic interactions) or by direct chemical attachment.

As used herein, a "bioconjugated CPdot" or "bioconjugated Pdot" refers to a chromophoric polymer dot with any biomolecule stably attached through any stable physical or chemical association. "Bioconjugation" in this application refers to a process that conjugates biomolecules to the chromophoric polymer dot by any stable physical or chemical association.

1. Bioconjugation Through Physical Adsorption

A biomolecule is stably associated with the chromophoric polymer dots by physical adsorption. Physical adsorption can arise from a range of forces, including but not limited to van de Waals, electrostatic, pi-stacking, hydrophobic, entropic forces and combinations thereof. Physical adsorption will be mediated by the physical and chemical properties of the cap structure on the chromophoric polymer dot and the target molecule (e.g., biomolecule) being adsorbed. As such, the functional group attached to the polymer dot through the hydrophilic cap structure, will determine the type of molecules that may be adsorbed on to the polymer dot.

Accordingly, in one embodiment, the present invention provides a bioconjugated chromophoric polymer dot comprising a hydrophobic core and a hydrophilic cap, wherein said core comprises a chromophoric polymer, and said cap comprises a functionalization agent bearing one or more functional groups to which a biological molecule is adsorbed.

In one embodiment, a bioconjugated chromophoric polymer dot is prepared by introducing a mixture of a semiconducting polymer and an amphiphilic molecule attached to a reactive functional group solvated in a non-protic solvent into a solution comprising a protic solvent to prepare a functionalized chromophoric polymer dot and then adsorbing a biological molecule onto the surface of the polymer dot. In one embodiment, the method further comprises filtering the suspension to isolate a population of polymer dots of a particular size prior to adsorbing the biological molecule onto the polymer dot.

In a specific embodiment, the method for preparing a bioconjugated chromophoric polymer dot comprises the steps of (a) preparing a mixture of a semiconducting polymer and an amphiphilic molecule attached to a reactive functional group in a non-protic solvent; (b) introducing (e.g., by injecting) all or a portion of the mixture into a solution comprising a protic solvent, thereby collapsing the semiconducting polymer and amphiphilic molecule into a nanoparticle; (c) removing the aprotic solvent from the mixture formed in step (b), thereby forming a suspension of functionalized chromophoric polymer dots, wherein a portion of the amphiphilic molecule is embedded within the core of the nanoparticle and the reactive functional group is located on the surface of the nanoparticles; and (d) adsorbing a biomolecule of interest onto the surface. In one embodiment, the method further comprises filtering the suspension to isolate a population of polymer dots of a particular size.

2. Bioconjugation Through Chemical Bonding

In a preferred embodiment, a molecule (e.g., a biomolecule) is attached to the polymer dot by chemical bonding, which requires that functional groups be available on the polymer dot, such as carboxylic acid, amino, mercapto, azido, alkyne, aldehyde, hydroxyl, carbonyl, sulfate, sulfonate, phosphate, cyanate, succinimidyl ester, substituted derivatives thereof, or combinations there of. In general, any functional groups that allow bioconjugation may be used. Such groups could be found by one of ordinary skill in the art, for example in Bioconjugate Techniques (Academic Press, New York, 1996 or second edition, 2008; the disclosures of which are herein incorporated by reference in their entireties for all purposes). Then the bioconjugation can be done by standard bioconjugation techniques. (Id.)

Accordingly, in one embodiment, the present invention provides a bioconjugated chromophoric polymer dot comprising a core and a cap, wherein said core comprises a chromophoric polymer, and said cap comprises a functionalization agent bearing one or more functional groups to which a biological molecule is covalently attached.

In a specific embodiment, the present invention provides a bioconjugated chromophoric polymer dot having a hydrophobic core and a hydrophilic cap, the polymer dot comprising: (a) a chromophoric polymer; and (b) an amphiphilic molecule conjugated to a biological molecule via a reactive functional group, wherein the chromophoric polymer is embedded within the hydrophobic core of the Pdot and; wherein a portion of the amphiphilic molecule is embedded within the core of the Pdot and the conjugated biological molecule is located in the hydrophilic cap (i.e., on the surface of the polymer dot). In a preferred embodiment, the chromophoric polymer is a semiconducting polymer.

2a. Covalent Modification of Chromophoric Polymers

One synthetic strategy for making functionalized CPdot is a two-step process: the first step is to synthesize a chromophoric polymer bearing functional groups such as carboxylic acid, amino, mercapto, azido, alkyne, aldehyde, hydroxyl, carbonyl, sulfate, sulfonate, phosphate, cyanate, succinimidyl ester, substituted derivatives thereof, or combinations there of. In general, any functional groups that allow bioconjugation may be used. Such groups could be found by one of ordinary skill in the art, for example in Bioconjugate Techniques (Academic Press, New York, 1996 or second edition, 2008). Functional groups can be created with covalent bonding to the backbone or a side chain of the chromophoric polymer. Such chemical modification is known to one of skill in the art. In the second step, the functionalized chromophoric polymer is used as a precursor for preparing CPdots (that would have functional groups available for bioconjugation). The CPdot preparation from the functionalized chromophoric polymer can use the method provided in this application (Example 1), based on mixing two miscible solvents. The CPdot preparation from the functionalized chromophoric polymer can also be achieved by a emulsion or miniemulsion method, based on shearing a mixture comprising two immiscible liquid phases (such as water and another immiscible organic solvent) in the presence of a surfactant. A shearing process such as ultrasonication makes stable droplets that contain the functionalized chromophoric polymers in the suspension. After removing the organic solvent, functionalized CPdots are obtained, which typically have a size from a few nanometer to sub-microns.

Accordingly, in one embodiment, the present invention provides a method for preparing a bioconjugated chromophoric polymer dot, the method comprising forming a chromophoric polymer dot having a hydrophobic core and a hydrophilic cap with a chromophoric polymer bearing one or more reactive functional groups, wherein the reactive functional groups are localized in the hydrophilic cap (i.e., on the surface of the polymer dot) and covalently attaching a biomolecule to the polymer dot via a linkage to the reactive functional group.

Another synthetic strategy of making functionalized CPdots may be demonstrated in a process combining the synthesis of chromophoric polymer with nanoparticle formation. A portion of the monomer units and/or the terminating units for synthesizing the chromophoric polymer have functional groups such as carboxylic acid, amino, mercapto, azido, alkyne, aldehyde, hydroxyl, carbonyl, sulfate, sulfonate, phosphate, cyanate, succinimidyl ester, substituted derivatives thereof, or combinations there of. In general, any functional groups that allow bioconjugation may be used. Such groups could be found by one of ordinary skill in the art, for example in Bioconjugate Techniques (Academic Press, New York, 1996 or later versions). Formed by emulsion or other methods, droplets may serve as micro or nano-reactors that contain the monomers, functional monomers and catalyst for synthesizing the chromophoric polymer dot. Chromophoric polymer dot obtained by this method are expect to show well controlled size from nanometer to micron size and have surface functional groups such as carboxylic acid, amino, mercapto, azido, alkyne, aldehyde, hydroxyl, carbonyl, sulfate, sulfonate, phosphate, cyanate, succinimidyl ester, substituted derivatives thereof, or combinations there of. Then the bioconjugation can be done by standard bioconjugation techniques. [Bioconjugate Techniques, Academic Press, New York, 1996]

2b. Blending of Functionalization Agents

Alternatively, the functionalized CPdots can be prepared by collapsing one or more chromophoric polymers (many of which are commercially available) in the presence of one or more amphiphilic functionalization agents harboring a functional group. The amphiphilic nature of the functionalization agents allow the hydrophobic portion of the molecule to be anchored in the hydrophobic core of the collapsed polymer dot, while the hydrophilic portion of the molecule, containing one or more functional groups, is localized to the hydrophilic cap of the polymer dot. In certain embodiments, the functionalization agent may be a chromophoric polymer that has been functionalized. In other embodiments, the functionalization agent may be a non-chromophoric molecule.

Non-limiting examples of functionalization agents that may be used to functionalize the chromophoric polymer dots of the present invention include, small organic molecules, lipid molecules, and polymer molecules that comprise functional groups such as carboxylic acid or salts thereof, amino, mercapto, azido, alkyne, aldehyde, hydroxyl, carbonyl, sulfate, sulfonate, phosphate, cyanate, succinimidyl ester, substituted derivatives thereof, or combinations there of. In general, any functional groups that allow bioconjugation may be used. Such groups could be found by one of ordinary skill in the art, for example in Bioconjugate Techniques (Academic Press, New York, 1996 or second edition, 2008). These molecules can be associated with the core of chromophoric polymer dot by any chemical bonding and/or physical forces, and provide surface functional groups on the chromophoric polymer dot for bioconjugation.

Preferably, the functionalization agent is an amphiphilic polymer that comprises a hydrophobic moiety and a hydrophilic moiety containing functional groups. The hydrophobic moiety is physically embedded in the polymer dots by hydrophobic interactions, while the hydrophilic moiety extends into the solution. This physical embedding of the hydrophobic moiety in the polymer dots may be further facilitated if desired by the use of chemical association between the hydrophobic moiety of the functionalization agent and the polymer dot. More preferably, the functionalization agent is a comb-like amphiphilic polymer comprising multiple repeating units of the hydrophobic moiety and multiple repeating units of the hydrophilic moiety so that the functionalization agent is permanently anchored to the polymer dot by strong hydrophobic forces, and the hydrophilic moieties comprise functional groups extending into the solution for bioconjugation.

The hydrophobic moiety of an amphiphilic functionalization molecule may be, for example, an alkyl group, more preferably an aryl group to strengthen the hydrophobic attachment to the chromophoric polymer dot that consists of many aromatic rings. The hydrophilic moiety may be, for example, a polyalkalene glycol or preferably polyethylene glycol, which may further be substituted by groups such as carboxylic acid, amino, mercapto, azido, alkyne, aldehyde, hydroxyl, carbonyl, sulfate, sulfonate, phosphate, cyanate, succinimidyl ester, substituted derivatives thereof, or combinations there of. In general, any functional groups that allow bioconjugation may be used. Such groups could be found by one of ordinary skill in the art, for example in Bioconjugate Techniques (Academic Press, New York, 1996 or second edition, 2008).

The functionalized CPdots from the chromophoric polymer and a functionalization agent can be prepared by the method provided in this application (Example 1), based on mixing two miscible solvents. The functionalized CPdots by the chromophoric polymer and a functionalization agent can also be prepared by a emulsion or miniemulsion method, based on shearing a mixture comprising two immiscible liquid phases (such as water and another immiscible organic solvent) with the presence of a surfactant. A shearing process such as ultrasonication makes stable droplets that contain the chromophoric polymer and functionalization agent. After removing the organic solvent, functionalized CPdots are obtained, which typically have a size from few nanometer to sub-microns. These functionalized CPdots can be further bioconjugated.

Accordingly, in one embodiment, the present invention provides a method for preparing a bioconjugated chromophoric polymer dot by (i) forming a functionalized chromophoric dot having a hydrophobic core and a hydrophilic cap, the Pdot comprising: (a) a chromophoric polymer; and (b) an amphiphilic molecule, having a hydrophobic moiety and a hydrophilic moiety attached to a reactive functional group, wherein the chromophoric polymer is embedded within the hydrophobic core of the Pdot and; wherein a portion of the amphiphilic molecule is embedded within the core of the Pdot and the reactive functional group is located in the hydrophilic cap; and (ii) covalently attaching a biomolecule to the polymer dot via a linkage to the reactive functional group. In a preferred embodiment, the chromophoric polymer is a semiconducting polymer.

2c. Reduction of Non-Specific Binding

As demonstrated in Example 11, significant non-specific adsorption of biomolecules can occur on the surface of functionalized Pdots. This non-specific adsorption interferes with the covalent attachment of targeted molecules, rendering the product of conjugation reactions unusable. Advantageously, it was found that the addition of free polyethylene glycol to the conjugation reaction eliminated non-specific binding between the biological molecule of interest and the functionalized Pdots, allowing for completion of the conjugation reaction. This finding is demonstrated in Example 11 provided herein.

Accordingly, in one embodiment, the present invention provides a method for conjugating a biological molecule to a functionalized chromophoric polymer dot, the method comprising incubating a functionalized chromophoric polymer dot with the biological molecule in a solution containing water soluble polymer under conditions suitable for conjugating the biological molecule to the functionalized chromophoric polymer dot, wherein the presence of the water soluble polymer in the solution reduces non-specific adsorption of the biological molecule to the surface of the polymer dot. Generally, any water soluble polymer that reduces the non-specific binding of a target biological molecule and the surface of the polymer dot may be used. Non-limiting examples of water soluble polymers include, a polyalkylene glycol (e.g., a PEG), a PEO, a polypropylene glycol, a polyoxyalkylene, a starch, a poly-carbohydrate, a polysialic acid, and the like. In a preferred embodiment, the water soluble polymer is a polyalkylene glycol. In a specific embodiment, the water soluble polymer is polyethylene glycol.

In one embodiment, the functionalized chromophoric polymer dot comprises: (a) a semiconducting polymer; and (b) an amphiphilic molecule attached to a reactive functional group, wherein a portion of the amphiphilic molecule is embedded within the core of the polymer dot and the reactive functional group is located on the surface of the polymer dot.

In one embodiment, the present invention provides a method for conjugating a biological molecule to a functionalized chromophoric polymer dot, the method comprising incubating a functionalized chromophoric polymer dot with the biological molecule in a solution containing a blocking agent under conditions suitable for conjugating the biological molecule to the functionalized chromophoric polymer dot, wherein the presence of the blocking agent in the solution reduces non-specific adsorption of the biological molecule to the surface of the polymer dot.

Generally, the blocking agent may be any molecule that reduces or effectively eliminates non-specific binding of the target biological molecule and polymer dot, therefore allowing proper conjugation to proceed. In one embodiment, the blocking agent is a water soluble polymers, for example, a polyalkylene glycol (e.g., a PEG), a PEO, a polypropylene glycol, a polyoxyalkylene, a starch, a poly-carbohydrate, a polysialic acid, and the like. In another embodiment, the blocking agent is a detergent, such as a non-ionic detergent or surfactant. Non-limiting examples of detergents that may be used include Triton X-100, Tween 20, Tween 80, a Brij detergent, and the like. In yet another embodiment, the blocking agent is a carbohydrate, for example, dextran, amylose, glycogen, and the like.

Methods for Imaging and Molecular Labeling

As described above, the use of fluorescent polymers for in vivo imaging and molecular labeling has several advantages over the materials currently in use, including Qdots and doped latex particles. For example, fluorescent polymer dots possess high fluorescence brightness/volume ratios, have high absorption cross sections, high radiative rates, high effective chromophore density, and minimal levels of aggregation-induced fluorescence quenching. The use of fluorescent polymer dots as fluorescent probes also confers other useful advantages, such as the lack of heavy metal ions that could leach out into solution. However, for applying these probes in biological imaging or sensing applications several important problems have yet to be solved, in particular, the surface chemistry and bioconjugation.

As described herein, the present invention provides numerous solutions for providing useful chromophoric polymer dot surface chemistry, functionalization and bio conjugation. Accordingly, the present invention provides improved methods for in vivo imaging and molecular labeling comprising the use of functionalized chromophoric polymer dots provided herein.

In one embodiment, the present invention provides a method for labeling a target molecule in a biological sample, the method comprising contacting the biological sample with a bioconjugated chromophoric polymer dot, wherein the bioconjugated chromophoric polymer dot comprises a core and a cap, wherein said core comprises a chromophoric polymer, and said cap comprises a functionalization agent attached to a targeting moiety via a reactive functional group, with the proviso that not all of the said cap is an organo silicate. The targeting agent may be any molecule capable of specifically binding to the target molecule of interest. In a preferred embodiment, the targeting agent is an antibody or a fragment thereof. In another related embodiment, the targeting agent is an aptamer.

In a related embodiment, a method is provided for labeling a target molecule in a biological sample, the method comprising contacting the biological sample with a bioconjugated chromophoric polymer dot, wherein the bioconjugated chromophoric polymer dot comprises: (a) a semiconducting polymer; and (b) an amphiphilic molecule attached to a targeting moiety via a reactive functional group, wherein a portion of the amphiphilic molecule is embedded within the core of the polymer dot and the targeting moiety is located on the surface of the polymer dot. The targeting agent may be any molecule capable of specifically binding to the target molecule of interest. In a preferred embodiment, the targeting agent is an antibody or a fragment thereof. In another related embodiment, the targeting agent is an aptamer.

The targeted molecule of interest may be any molecule found inside an organism, for example, a specific cell, protein, nucleic acid, carbohydrate, lipid, metabolite, and the like. In one specific embodiment, the target molecule is a molecule present on the surface of a cell, for example a cancer cell. In a specific embodiment, the functional groups are selected from an alkyne, strained alkyne, azide, diene, alkene, cyclooctyne, and phosphine groups.

In another embodiment, the present invention provides a method for the bioorthogonal labeling of a cellular target, the method comprising contacting a cellular target having a first surface-exposed functional group capable of participating in a click chemistry reaction with a clickable chromophoric polymer dot, wherein the clickable chromophoric polymer dot comprises a core and a cap, wherein said core comprises a chromophoric polymer, and said cap comprises a functionalization agent attached to a second functional group capable of reacting with the first functional group in a click chemistry reaction, with the proviso that not all of the said cap is an organo silicate. In a specific embodiment, the functional groups are selected from an alkyne, strained alkyne, azide, diene, alkene, cyclooctyne, and phosphine groups.

In a related embodiment, the present invention provides a method for the bioorthogonal labeling of a cellular target, the method comprising contacting a cellular target having a first surface-exposed functional group capable of participating in a click chemistry reaction with a clickable chromophoric polymer dot, wherein the clickable chromophoric polymer dot comprises: (a) a semiconducting polymer; and (b) an amphiphilic molecule attached to a second functional group capable of reacting with the first functional group in a click chemistry reaction, wherein a portion of the amphiphilic molecule is embedded within the core of the polymer dot and the second functional group is located on the surface of the polymer dot.

As described above, methods of incorporating a first functional group capable of participating in a click chemistry reaction into a molecule of interest are known in the art. For example, an attractive approach for installing azides into biomolecules is based on metabolic labeling, whereby an azide-containing biosynthetic precursor is incorporated into biomolecules by using the cells' biosynthetic machinery.

Methods for the Detection of $Cu^{2+}$ and $Fe^{2+}$ Ions Using Chromophoric Polymer Dots Copper and iron ions are two of the three most abundant transition metal ions (including zinc) in the human body. The recommended intakes of copper and iron range from 0.8-0.9 mg/day and 8-18 mg/day for normal adults, respectively. The overdose of copper or iron, however, is known to cause Cirrhosis of the liver, acute toxicity, acidosis, coagulopathy, and acute respiratory distress syndrome. According to the drinking water standards and health advisories revised by U.S. Environmental Protection Agency (EPA), the amount of copper and iron is limited to 1.0 mg/L and 0.3 mg/L, respectively. As a result, there has been ongoing efforts to develop better sensors for the detection of copper and iron, due to their significance in the environment and in biological systems (Que E. L., et al., Chem. Rev., 2008, 108, 1517-1549). In the past decade, nanoparticle-based ion sensors have attracted intense interest because of their simplicity, good sensitivity and selectivity, high reliability, and relatively low cost. However, exploitation of semiconducting polymer nanoparticles (Pdots) based fluorescence ion sensors remains unexplored.

Accordingly, in one aspect, the present invention provides a strategy for the quantitative detection of copper and iron ion. This strategy is based on fluorescence quenching induced by the aggregation of carboxyl functionalized Pdots. A demonstration of this method can be found in Example 27.

In one aspect, the present invention provides a sensitive and ratiometric approach for $Cu^{2+}$ and $Fe^{2+}$ ion detection based on chelation-mediated Pdot sensors. The linear detection range for both $Cu^{2+}$ and $Fe^{2+}$ fall within the physiologically relevant concentration range. However, this linear range can be further extended, if needed, by modulating the PS-COOH density and/or the size of the Pdots. This simple, sensitive, and economical technique takes advantage of the high brightness and optical tunability of semiconducting polymer nanoparticles, and affords a means of rapid determination of $Cu^{2+}$ and $Fe^{2+}$ for physiological or environmental analysis.

Accordingly, in one embodiment a method is provided for detecting copper (II) and/or iron (II) in a solution, the method comprising the steps of: (a) contacting a solution with a carboxyl functionalized semiconducting polymer dot; and (b) detecting the level of fluorescence from the polymer dot in the solution, wherein a reduction of fluorescence in the solution, as compared to the fluorescence of the polymer dot in a solution not containing copper (II) or iron (II), is indicative that the solution contains copper (II) and/or iron (II).

In one embodiment, the method further comprises the step of quantitating the level of copper (II) in the solution by: (c) adding a divalent cation chelating agent to the solution; (d) detecting the level of fluorescence in the solution after the addition of the divalent cation chelating agent; and (e) determining the difference in the fluorescence of the polymer dots in solution before and after the addition of the divalent chelating agent, wherein the level of copper (II) in the solution is determined by comparing the difference in the fluorescence with a standard.

In another embodiment, the method further comprises the step of quantitating the level of iron (II) in the solution by: (c) adding a divalent cation chelating agent to the solution; (d) detecting the level of fluorescence in the solution after the addition of the divalent cation chelating agent; and (e) determining the difference between the fluorescence of the polymer dots in solution after the addition of the divalent chelating agent and the fluorescence of the polymer dots in a solution not containing copper (II) or iron (II), wherein the level of iron (II) in the solution is determined by comparing the difference in the fluorescence with a standard.

EXAMPLES

The following examples are included to further describe the present invention, and should not be used to limit the scope of the invention.

A method for preparing the functionalized chromophoric polymer dot is demonstrated, a process comprising the step of mixing a protic solvent with a mixture of chromophoric polymer and functionalization agent in an aprotic solution. The present invention also provides a bioconjugate, and its composition, which comprises the functionalized chromophoric polymer dot and a biomolecule, wherein the biomolecule is attached directly or indirectly to the functional group.

Example 1: Method for Preparing Functionalized Chromophoric Polymer Dots

The present example provides a method for obtaining a quantity of functionalized chromophoric polymer dots for subsequent characterization and biomolecular conjugation. FIG. 1 shows a schematic diagram for preparing the functionalized chromophoric polymer dots and their biomolecular conjugates.

Functionalized chromophoric polymer dots in aqueous solution were prepared as follows. First, a chromophoric polymer, for example PFBT, was dissolved in tetrahydrofuran (THF) by stirring under inert atmosphere to make a stock solution with a concentration of 1 mg/mL. Certain amount of functionalization agent, for example PS-PEG-COOH in THF solution, was mixed with a diluted solution of PFBT to produce a solution mixture with a PFBT concentration of 40 µg/mL and a PS-PEG-COOH concentration of 4 µg/mL. The mixture was stirred to form homogeneous solutions. A 5 mL quantity of the solution mixture was added quickly to 10 mL of deionized water while sonicating the mixture. The THF was removed by nitrogen stripping, and the solution was concentrated by continuous nitrogen stripping to 4 mL on a 90° C. hotplate, followed by filtration through a 0.2 micron filter. The resulting nanoparticle dispersions are clear and stable for months with no signs of aggregation.

Example 2: AFM Characterization of Functionalized Chromophoric Polymer Dots

Figure 2A:
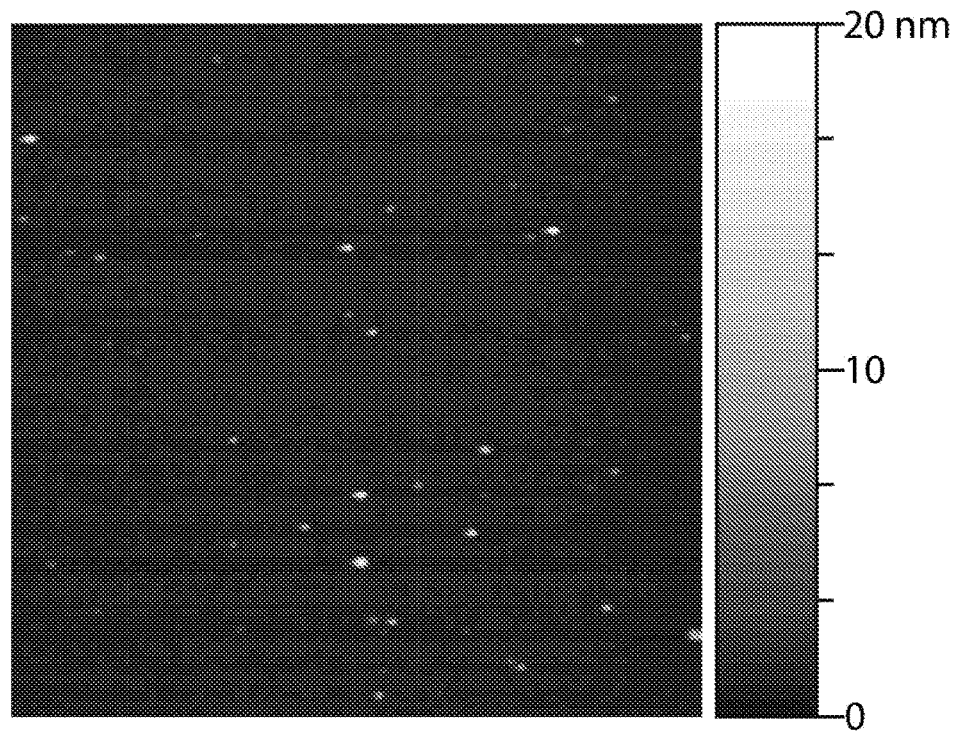
FIG. 2(A) Shows atomic force microscope (AFM) image of functionalized chromophoric PFBT dots prepared in accordance with the method of the present invention. (B) Shows a particle height histogram taken from an AFM image.
Figure 2B:
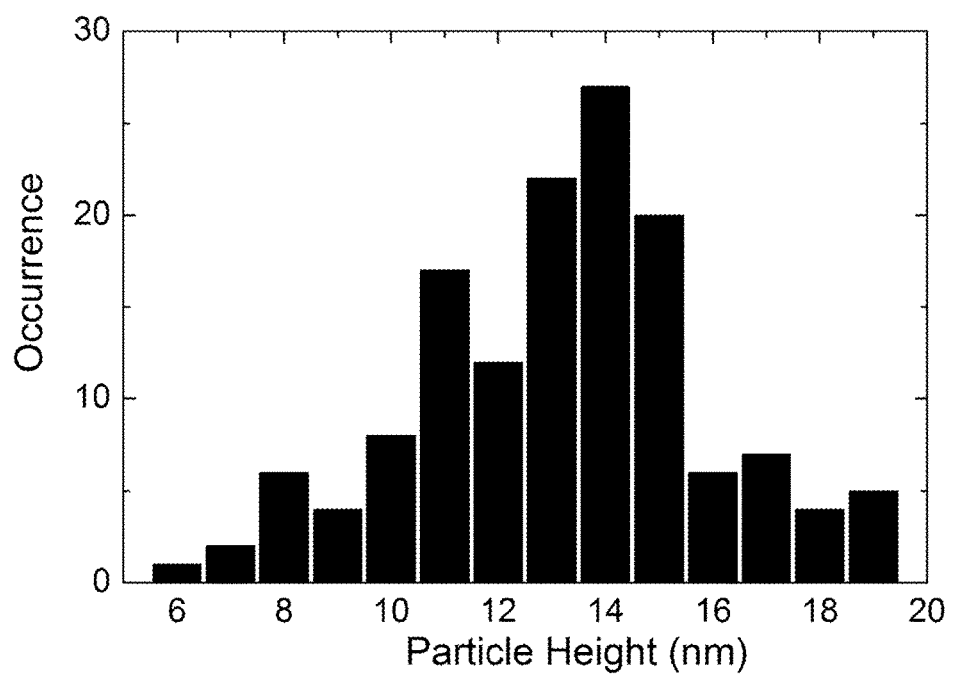

The functionalized chromophoric polymer dots prepared according to the method provided in Example 1 were assessed by AFM for their size, morphology and monodispersity. For the AFM measurements, one drop of the nanoparticle dispersion was placed on freshly cleaved mica substrate. After evaporation of the water, the surface was scanned with a Digital Instruments multimode AFM in tapping mode. FIG. 2A shows a representative AFM image of the functionalized chromophoric polymer dots. A particle height histogram taken from the AFM image indicates that most particles possess diameters in the range of 10-20 nm (FIG. 2B). The lateral dimensions are also in the range of 10-20 nm after the tip width is taken into account. The morphology and size are consistent with those of the polymer dots prepared without functionalization polymer, indicating the presence of a small amount of amphiphilic polymer has no apparent effect on particle size and morphology. In accordance with the preparation method in Example 1, the functionalized chromophoric polymer dots can be prepared with their size ranging from 2 nm to 1000 nm by adjusting the injection concentration of the chromophoric polymer.

Example 3: Optical Characterization of Functionalized Chromophoric Polymer Dots

Figure 3:
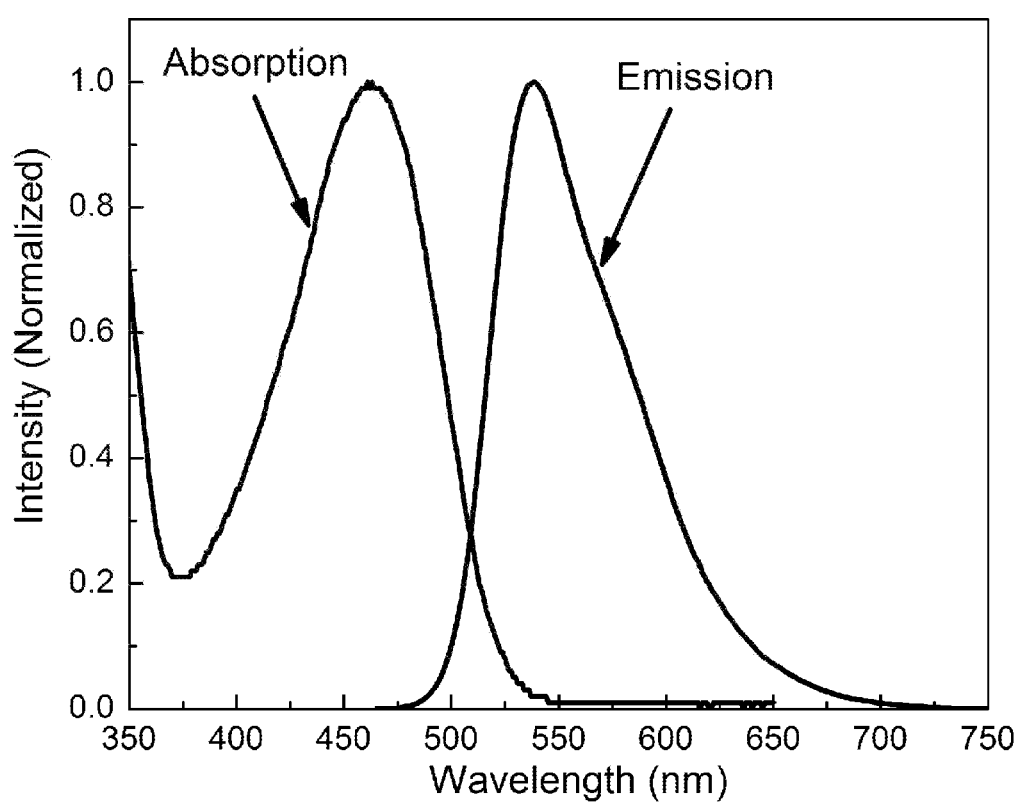
FIG. 3 shows the absorption and emission spectra of functionalized chromophoric PFBT dots prepared in accordance with the method of the present invention.

The functionalized chromophoric polymer dots prepared according to the method provided in Example 1 were assessed for their fluorescence properties. UV-Vis absorption spectra were recorded with a DU 720 spectrophotometer using 1 cm quartz cuvettes. Fluorescence spectra were collected with a Fluorolog-3 fluorometer using a 1 cm quartz cuvette. The functionalized chromophoric polymer dots exhibit similar absorption and emission spectra to those of bare chromophoric polymer dots (FIG. 3), indicating the surface functionalization does not effect the optical properties of the polymer dots. Depending on the chromophoric polymer species, the chromophoric polymer dots exhibit absorption bands ranging from 350 nm to 550 nm, a wavelength range that is convenient for fluorescence microscopy and laser excitation. FIG. 3 shows the absorption and emission spectra of functionalized chromophoric polymer PFBT. Analysis of the UV-Vis absorption spectra at a known particle concentration indicated that the peak absorption cross section of single particles (~15 nm diameter) were about $2 \times 10^{-13}$ cm$^2$, roughly ten to one hundred times larger than that of CdSe quantum dots in the visible and near-UV range, and roughly three orders of magnitude larger than typical organic fluorescent dyes.

Fluorescence quantum yield of the PFBT dots was determined to be 30% using a diluted solution of Coumarin 6 in ethanol as standard. The fluorescence brightness is defined as the product of absorption cross section and quantum yield results. To the best of our knowledge, the fluorescence brightness of the chromophoric polymer dots exceeds that of any other nanoparticle of the same size under typical conditions. The size of the particle does not appear to have an appreciable effect on the shape of the absorption and fluorescence spectra—the principal effect of increased particle size is an increase in the absorption cross-section and brightness. This property facilitates adjustment of particle size and brightness to meet the demands of a particular application, and is in contrast with colloidal semiconductor quantum dots.

Example 4: Conjugation of Biomolecules to Functionalized Chromophoric Polymer Dots This example demonstrates that functionalized chromophoric polymer dots can be conjugated to biomolecules for subsequent imaging of cellular structure, or any other fluorescence based biological detection. The functionalized chromophoric polymer dots prepared in accordance with the method of the present invention can be conjugated to any biomolecules, such as protein and antibodies, which contain primary amino functional groups. Carboxyl groups can be reacted to N-hydroxysuccinimide (NHS) in the presence of a carbodiimide such as EDC to produce amine-reactive esters of carboxylate groups for crosslinking with primary amine groups. In a typical bioconjugation reaction, 20 μL of EDC (5 mg/mL in MilliQ water) and 10 μL of NHS (5 mg/mL in MilliQ water) were added to 1 mL of functionalized chromophoric polymer dots (40 μg/mL in MilliQ water). The above mixture was left on a rotary shaker for 30 minutes for activation. Then 20 μL of polyethylene glycol (5% w/v PEG) and 20 μL of concentrated HEPES buffer (1 M) were added, resulting in a solution of the activated polymer dots in 20 mM HEPES buffer with a pH of 7.3. Finally, 40 μL of Streptavidin or IgG antibody (1 mg/mL) was added to the solution, and the reaction last for 4 hours at room temperature. The resulting chromophoric polymer dot bioconjugates were separated from free biomolecules by gel filtration using Sephacryl HR-300 as the media.

Example 5: Use of Chromophoric Polymer Dot-IgG Conjugates for Cancer Marker Detection in Live Cells This example provides a demonstration using the chromophoric polymer dot bioconjugates to detect cancer markers in human breast cancer cells. The breast cancer cell line SK-BR-3 was cultured in McCoy's 5A medium supplemented with 10% Fetal Bovine Serum and 1% penicillin/streptamycin. A million cells were harvested from the culture flask, washed, and resuspended in 100 μL labeling buffer (1×PBS, 2 mM EDTA, 0.5% BSA). The cell suspension was incubated with primary anti-human CD326 (EpCAM) antibody on a shaker for 30 minutes at dark and room temperature, followed by two washing steps using labeling buffer. Then the cells were incubated with the chromophoric polymer dot secondary IgG conjugates for 30 min on a shaker at dark and room temperature, followed by another two washing steps. A drop of cell suspension was placed on a coverslip, covered with a glass slide, and imaged immediately under a fluorescence confocal microscope (Zeiss LSM 510).

Figure 4A:
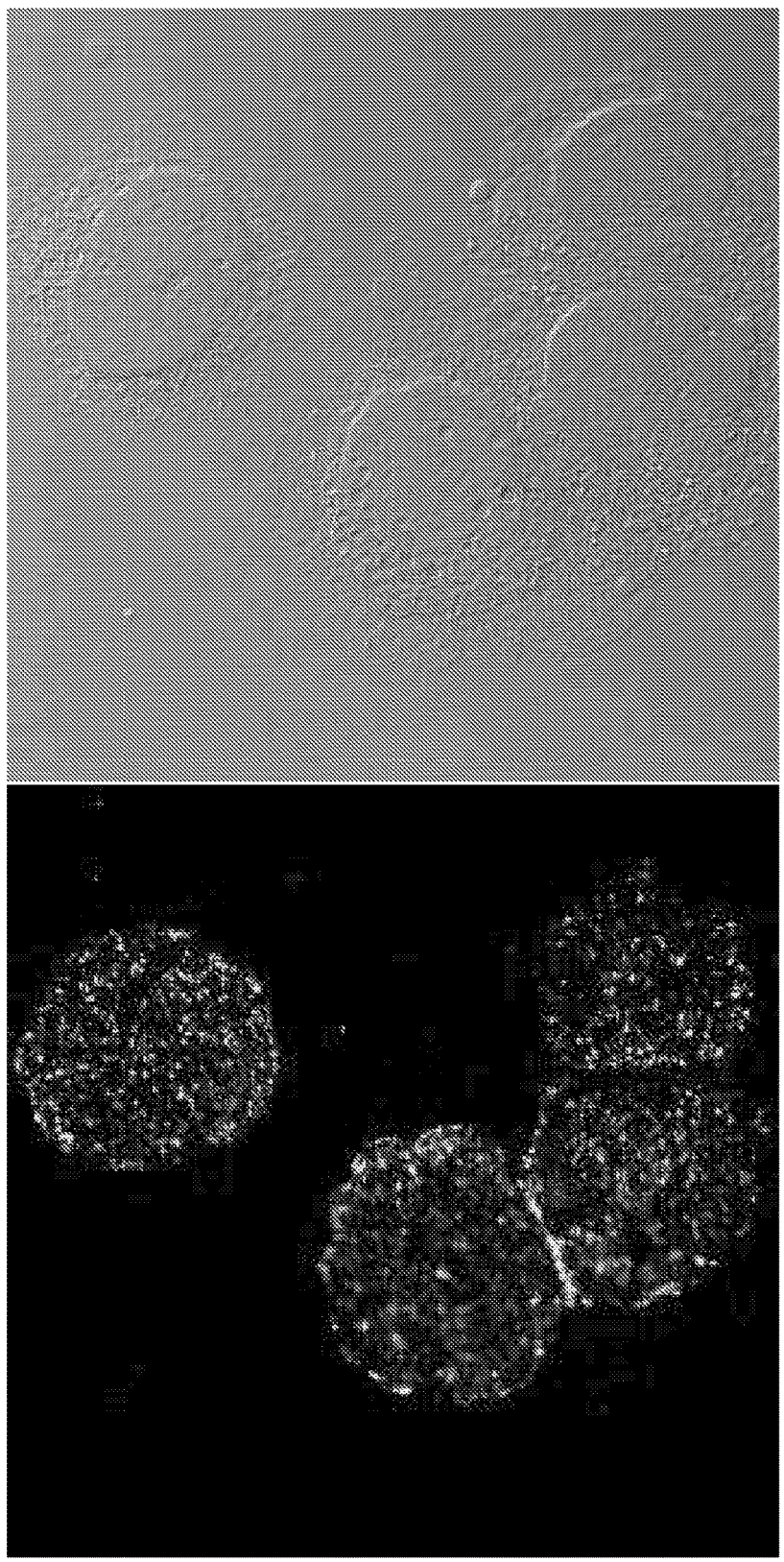
FIG. 4(A) Shows fluorescence confocal image of SK-BR-3 cancer cells incubated with primary anti-EpCAM, and then chromophoric PFBT dots conjugated with secondary anti-mouse IgG antibody. (B) Shows fluorescence confocal image of SK-BR-3 cancer cells incubated with chromophoric PFBT dots conjugated with secondary anti-mouse IgG antibody. No primary antibody is used in the control (B).
Figure 4B:
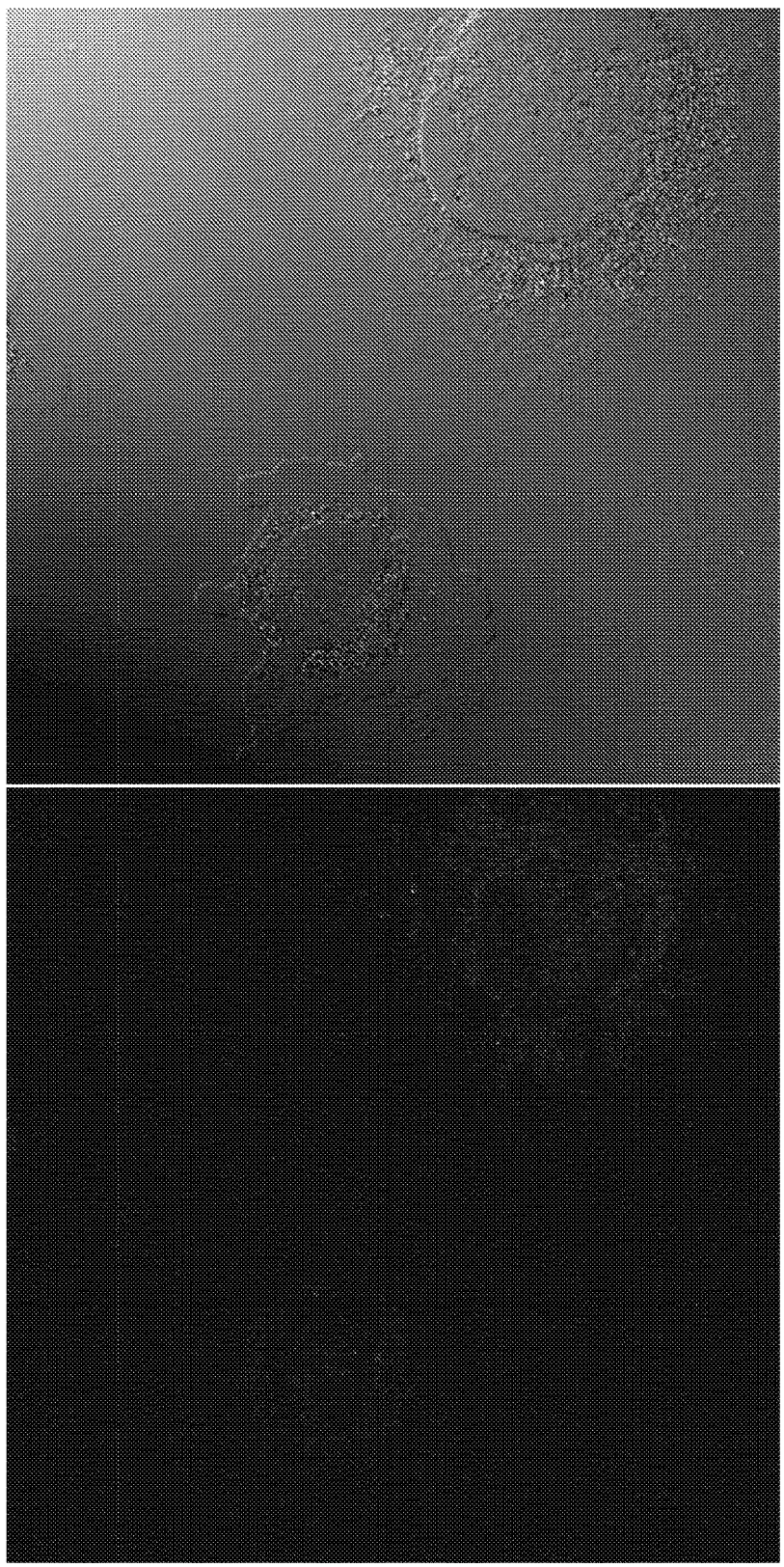

As shown in FIG. 4A, the chromophoric polymer dot-IgG probe successfully labeled EpCAM receptors on the surface of human SK-BR-3 breast cancer cells after the cells were incubated with a primary anti-EpCAM antibody. When the primary antibody is absent, i.e., the cells were incubated with the polymer dot-IgG alone, little or no signal was detected (FIG. 4B), indicating that the polymer dot-IgG conjugates are specific for the target.

Figure 5A:
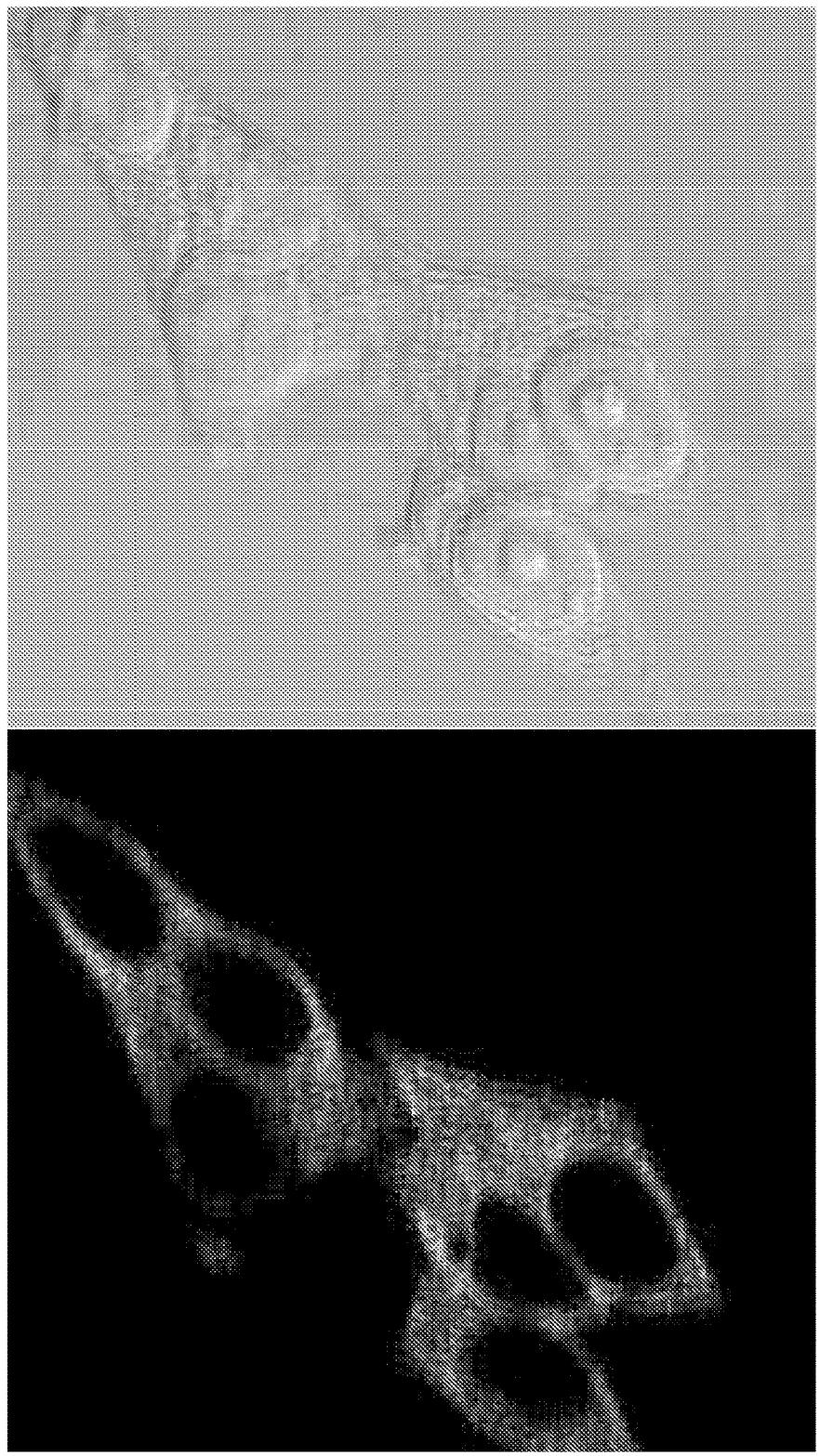
FIG. 5(A) Shows fluorescence confocal image of MCF-7 cancer cells incubated with anti-tubulin biotin primary antibody, and then chromophoric PFBT dots conjugated with streptavidin. (B) Show fluorescence confocal image of MCF-7 cancer cells incubated with biotin anti-tubulin primary antibody, and then bare PFBT dots. The PFBT dots without streptavidin conjugation are used as a control.
Figure 5B:
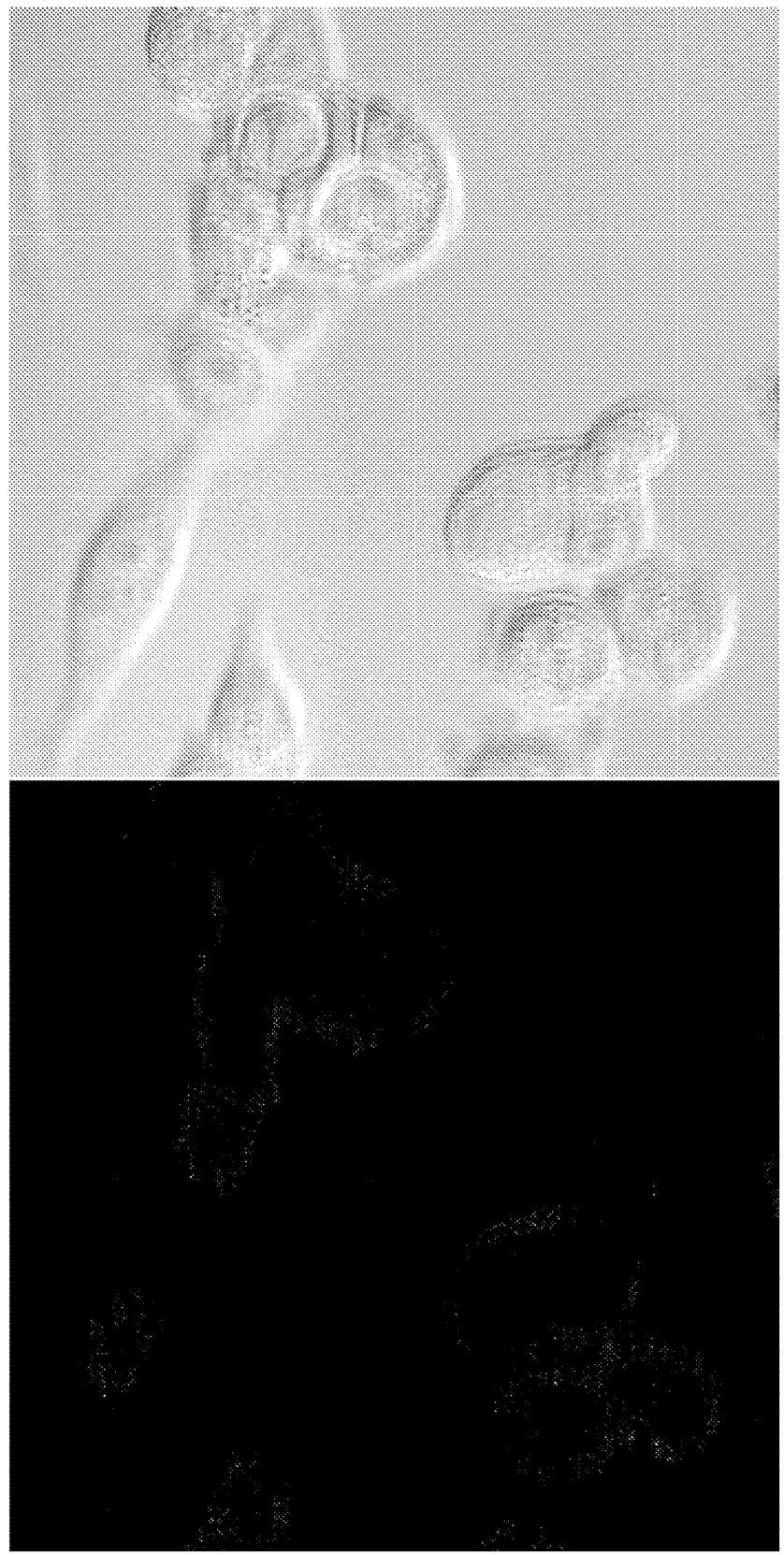
Figure 6A:
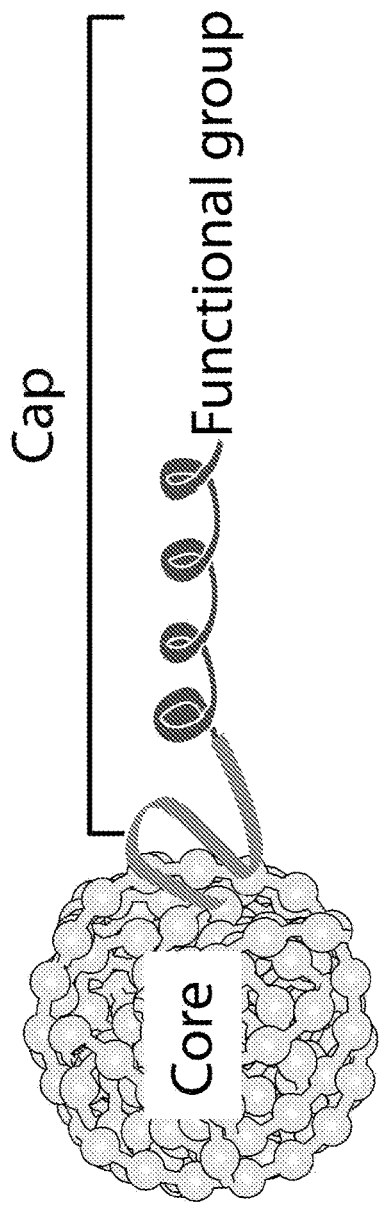
FIG. 6(A) Shows a generalized CPdot of the invention, the core could be a semiconducting polymer, a non-semiconducting chromophore-containing polymer (such as dyes, metal complexes, and the like), a semiconducting polymer with optical inert polymer or inorganic functional materials, or their combinations; the cap could be a small molecule bearing functional groups, a surfactant bearing functional groups, a lipid bearing functional groups, or a polymer bearing functional groups. The cap and the core could be held together by chemical bonding or by physical association. (B) Shows a preferred CPdot of the invention the core could be a semiconducting polymer, a non-semiconducting chromophore-containing polymer (such as dyes, metal complexes, and the like), a semiconducting polymer with optical inert polymer or inorganic functional materials, or their combinations; the cap comprises an amphiphilic polymer which has a hydrophobic moiety and a hydrophilic moiety. The hydrophobic moiety is embedded in the core by physical association or by chemical bonding and the hydrophilic moiety, which possess functional groups for bioconjugation, extends out for bioconjugation.
Figure 6B:
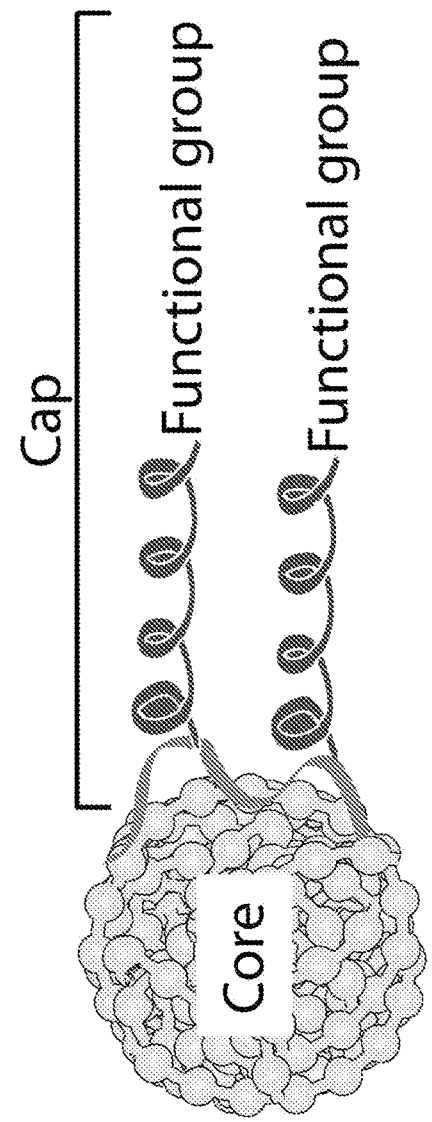

Example 6: Use of Chromophoric Polymer Dot-Streptavidin Conjugates for Subcellular Imaging This example provides a demonstration using the chromophoric polymer dot bioconjugates to detect subcellular structures. The breast cancer cell line MCF-7 was cultured in Eagles minimum essential medium supplemented with 10% Fetal Bovine Serum and 1% penicillin/streptamycin. Ten thousand cells were plated on a 22×22 mm glass coverslip, cultured using the above medium in a 6-well plates until the density reach 50-70% confluence. The cells were fixed with 4% paraformaldehyde for 15 minutes, permeabilized with 0.25% Triton-X 100 in PBS for 15 minutes, and blocked in 2% BSA (w/v) for 30 minutes. To label microtubules, the fixed and BSA-blocked MCF-7 cells were incubated sequentially with biotinylated monoclonal anti-α-tubulin antibody for one hour, and chromophoric polymer dot-streptavidin conjugates for 30 minutes. The coverslip with the stained cells were mounted on a glass slide and imaged with the fluorescence confocal microscope (Zeiss LSM 510). As shown in FIG. 5A, microtubules were clearly labeled with the chromophoric polymer dot-streptavidin. When the cells were incubated with the chromophoric polymer dot-streptavidin alone, very weak or no apparent signal was detected (FIG. 5B), indicating that the polymer dot-streptavidin conjugates are specific for the labeling.

Example 7: Functionalization of Semiconducting Polymer Dots

Fluorescent semiconducting polymer Poly[(9,9-dioctylfluorenyl-2,7-diyl)-co-(1,4-benzo-[2,1',3]-thiadiazole)] (PFBT, MW 157,000, polydispersity 3.0) was purchased from ADS Dyes, Inc. (Quebec, Canada). A comb-like polymer, polystyrene grafted with ethylene oxide functionalized with carboxyl groups (PS-PEG-COOH, main chain MW 8,500, graft chain MW 1,200, total chain MW 21,700, polydispersity 1.25), was purchased from Polymer Source Inc. (Quebec, Canada). All other reagents were purchased from Sigma-Aldrich (St. Louis, Mo., USA), and all experiments were performed at room temperature unless indicated otherwise.

Functionalized Pdots in aqueous solution are prepared by using a modified nano-precipitation method. First, PFBT was dissolved in tetrahydrofuran (THF) to make a stock solution with a concentration of 1 mg/mL. PS-PEG-COOH was also dissolved in THF and mixed with a diluted solution of PFBT to produce a solution mixture with a PFBT concentration of 50 µg/mL and a PS-PEG-COOH concentration ranging from 0 to 10 µg/mL. The mixture was sonicated to form homogeneous solutions. A 5 mL quantity of the solution mixture was added quickly to 10 mL of MilliQ water in a bath sonicator. The THF was removed by nitrogen stripping, and the solution was concentrated by continuous nitrogen stripping to 5 mL on a 90° C. hotplate, followed by filtration through a 0.2 micron filter. The resulting functionalized Pdot dispersions are clear and stable for months without signs of aggregation.

Figure 7:
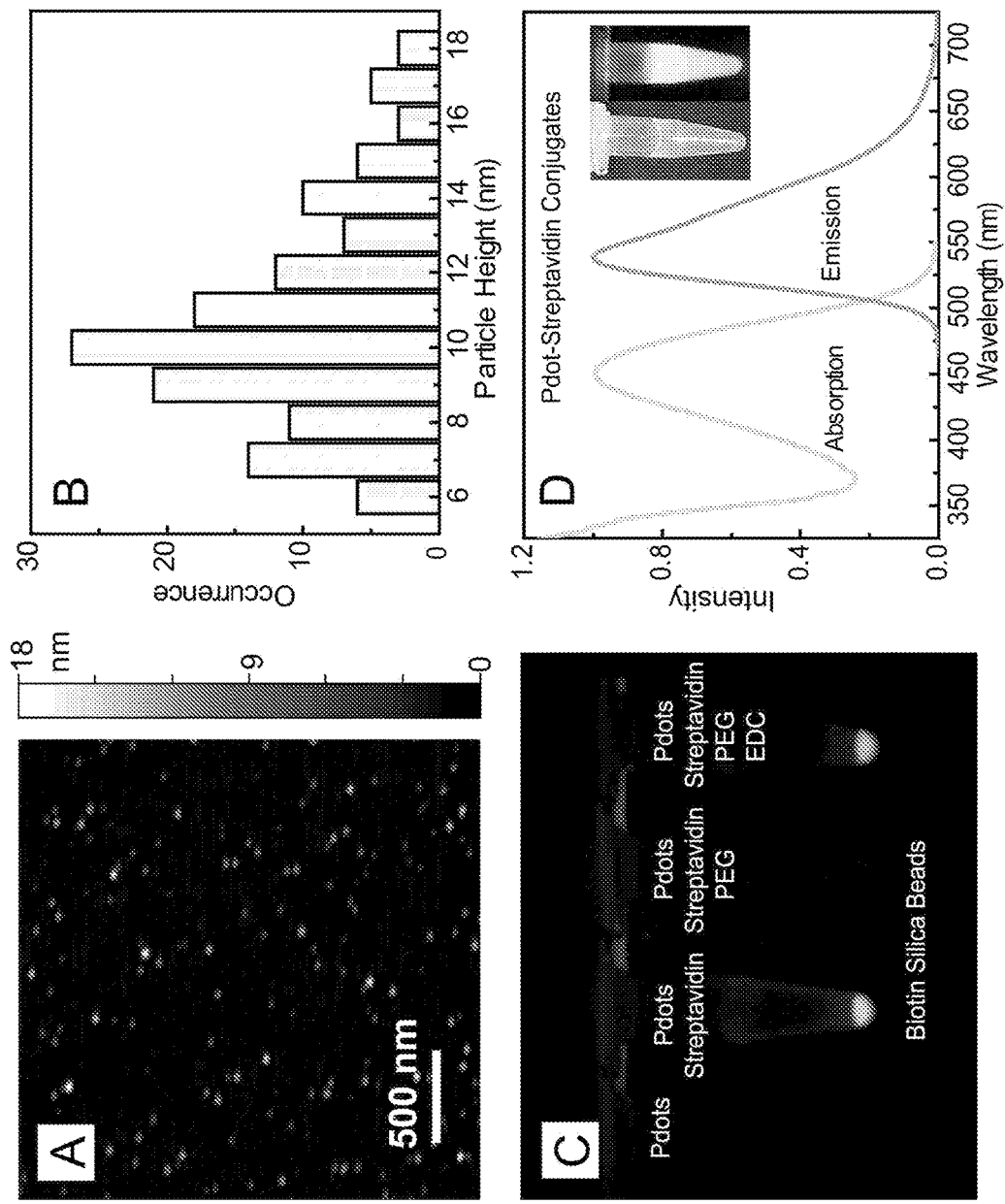
FIG. 7(A) Typical AFM image of functionalized PFBT dots. (B) Histogram of particle height taken on AFM images of functionalized PFBT dots. (C) An assay using biotin silica beads to verify bioconjugation through EDC-catalyzed covalent coupling. (D) Absorption and fluorescence spectra of PFBT dot-streptavidin bioconjugates in 1×PBS buffer solution after 6 months of storage, the inset shows photographs of the Pdot-bioconjugate solution under room (left picture) and UV (right picture) illumination.

Example 8: Physical Characterization of Functionalized Semiconducting Polymer Dots Functionalized PFBT dots were prepared using a precursor solution mixture with a constant PFBT concentration and PS-PEG-COOH/PFBT fractions ranging from 0 to 20 weight percent. The size and morphology of the functionalized PFBT dots were characterized by atomic force microscopy (AFM, FIG. 7A). Particle height histogram obtained from AFM images indicated that the majority of PFBT dots possessed diameters in the range of 10±3 nm (FIG. 7B). In comparison with the unfunctionalized Pdots, the presence of a small amount of PS-PEG-COOH polymer (<20 wt %) did not cause any noticeable effects on particle size and morphology. Absorption and emission spectra of Pdots do not change with size (Wu, C.; Bull, B.; Szymanski, C.; Christensen, K.; McNeill, J. ACS Nano 2008, 2, 2415-2423), and thus this size-independent feature of Pdot significantly relaxes the constraint on size control in nanoparticle preparation. Moreover, this size-independence feature may be advantageous to obtain brighter probes for certain applications because a larger size merely increases the brightness of the probe. It should be noted that this functionalization strategy led to effective nanoparticle probes in terms of fluorophore density; for example, more than 80 percent of the semiconducting polymer nanoparticles can be effective fluorophores. In contrast, for Qdots and dye-loaded spheres, the effective fluorophores are limited to a few percent of the particle volume or weight due to the presence of a thick encapsulation layer (for Qdots) or self-quenching of dyes (for dye-doped spheres).

Example 9: Optical Characterization of Bioconjugated Semiconducting Polymer Dots The cell-labeling brightness of Pdot bioconjugates with those of commercially available Qdot 565-streptavidin and Alexa-IgG probes was first quantified using a microfluidic flow cytometer. The flow-through experiments were conducted with a microfluidic chip with 200 µm wide and 50 µm high straight channels on an inverted light microscope equipped with a 20× NA 0.4 objective (Nikon Eclipse TE 2000-U, Melville, N.Y., USA). The as-labeled cell suspensions (10,000 per ml) were introduced into the rectangular channel using a syringe pump at 50 µl min-1 for up to 5 minutes. A 488 nm sapphire laser (Coherent, Santa Clara, Calif.) was guided into the microscope to excite the sample. Before each sample acquisition, the laser power was measured in the path of light before entering the microscope using a power meter. Fluorescence signal was filtered by a 500 nm long pass filter (HQ500LP; Chroma, Rockingham, Vt., USA), and collected by a Single Photon Counting Module (APD, PerkinElmer SPCM-QC9-QTY2, Salem, Mass., USA). A personal computer and a LabView coded program (National Instruments Corporation, Austin, Tex., USA) were used to read out the signals of the SPCM at a sampling frequency of 10 kHz. The raw APD counts for each sample were stored in text files and converted in to frequency plots using a custom-coded Maple 5.1 program (MapleSoft, Waterloo, ON, Canada).

Figure 12A:
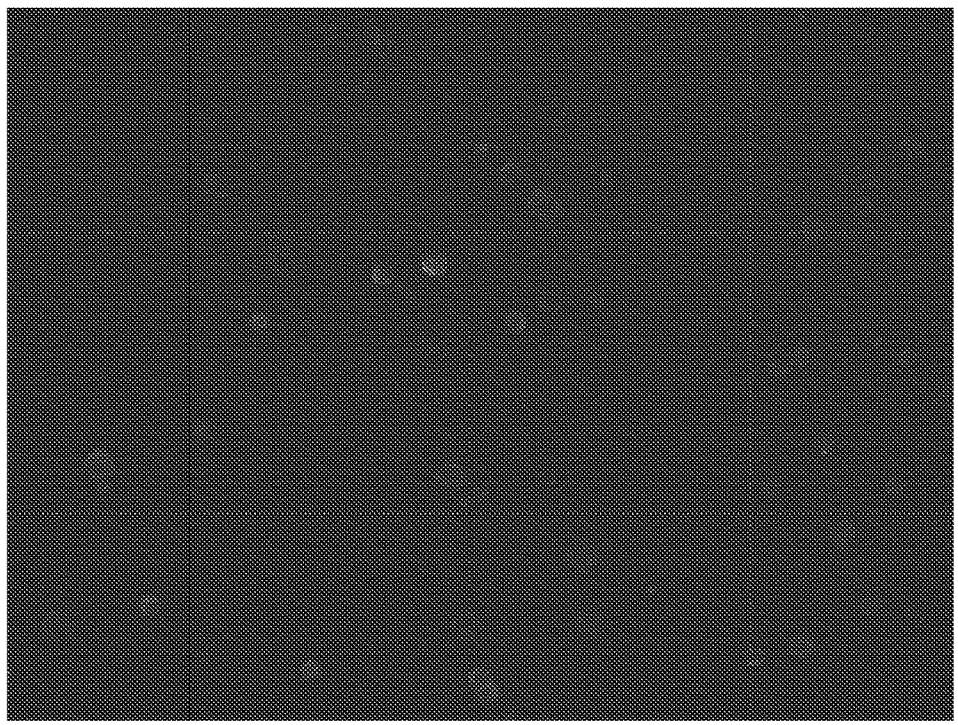
FIG. 12(A) Fluorescence images for Qdot 565-streptavidin-labeled MCF-7 cells obtained on a low numerical aperture wide-field microscope. (B) Fluorescence images for Pdot-streptavidin-labeled MCF-7 cells obtained under identical conditions as those used in (A). (C) Fluorescence intensity distributions of Pdot-labeled cells compared to Qdot-labeled ones.
Figure 12B:
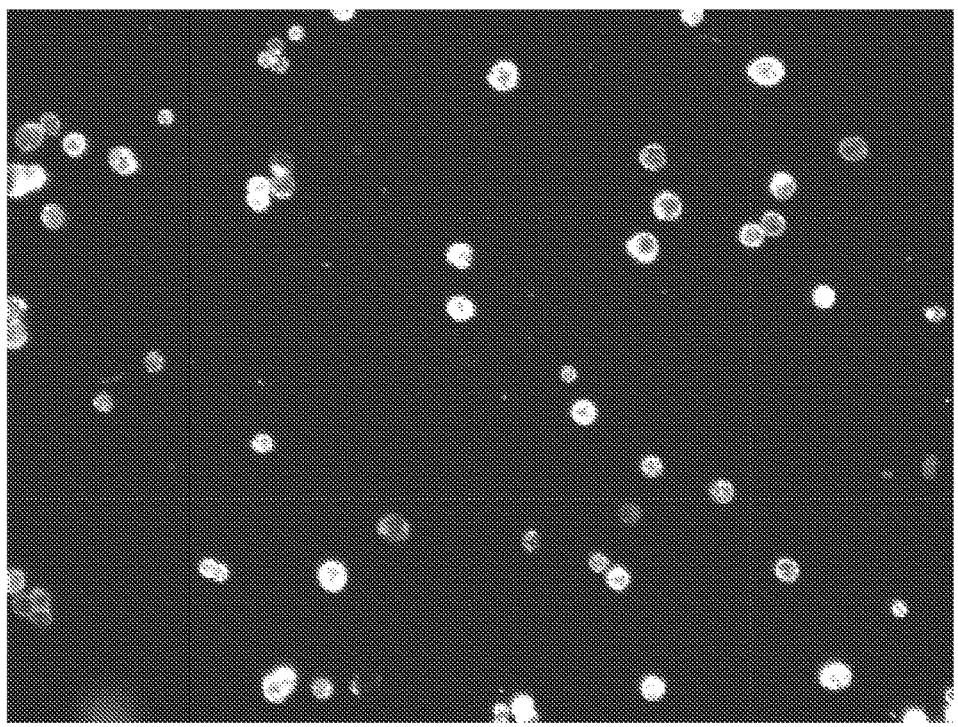
Figure 12C:
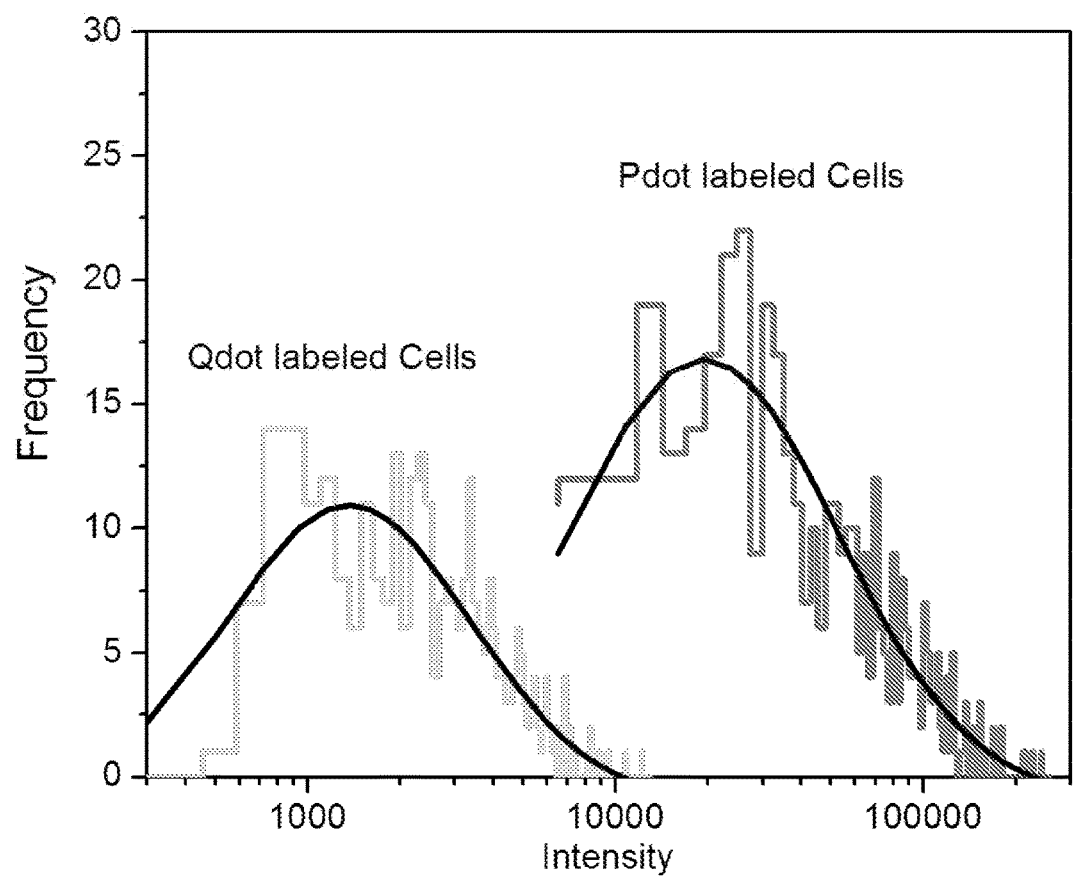
Figure 13:
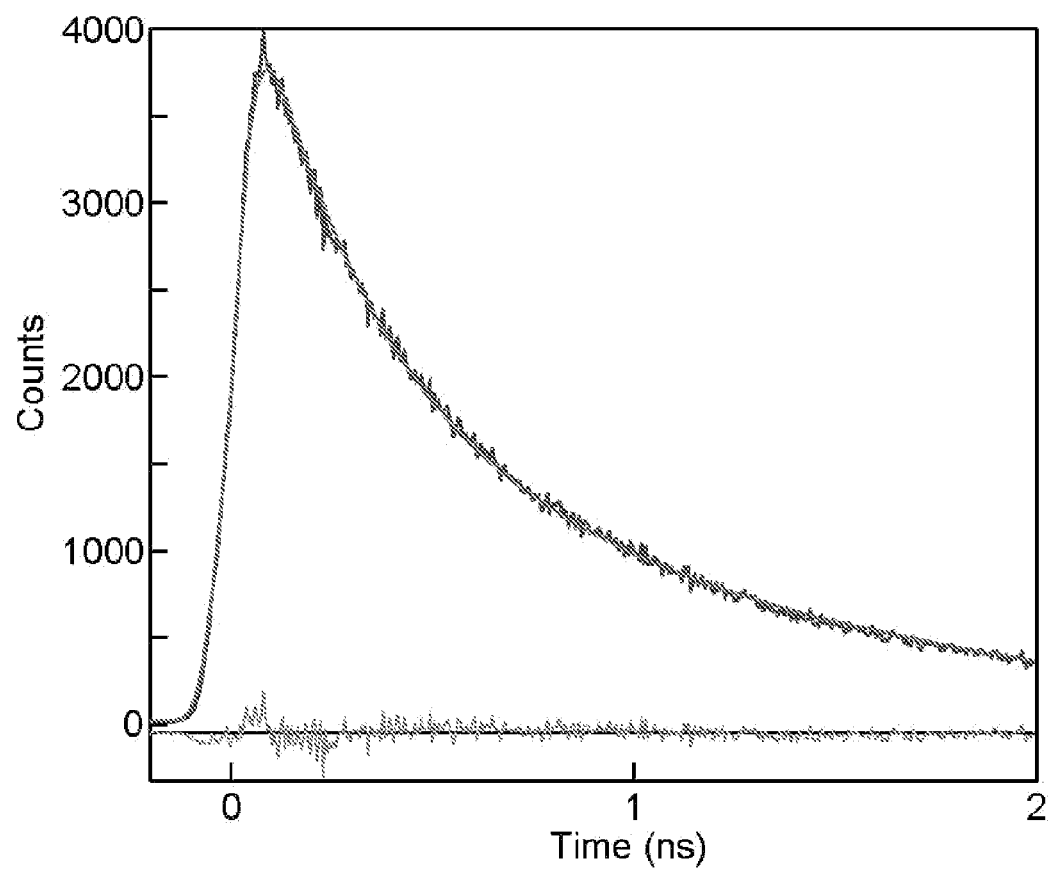
FIG. 13 Fluorescence decay lifetime (0.6 ns) of PFBT dots measured by a TCSPC setup. The blue line represents experimental data, and the green line is fitting curve obtained employing an iterative deconvolution method. Residual is shown below the curves (red line).

The cell-labeling brightness of Pdot-streptavidin and Qdot 565-streptavidin probes was also quantified by analyzing fluorescence images of the labeled MCF-7 cells. A drop of cell suspension was placed on a coverslip, covered with a glass slide, and viewed on an upright microscope with an AZ-Plan Apo 4× NA 0.4 objective (Nikon AZ100, Melville, N.Y., USA). The excitation light was provided with a fiber illuminator (130 W mercury lamp), and filtered by a band pass filter (Semrock FF01-482/35-25, Rochester, N.Y. USA). Fluorescence signal was filtered by a 520 nm long pass filter (HQ520LP; Chroma, Rockingham, Vt., USA), and imaged on a CCD camera (Prosilica GC1380, Newburyport, Mass.). Fluorescence images were processed with a custom-coded Labview program, and intensity distributions of single-cell labeling brightness were obtained (FIG. 12).

Example 10: Single Particle Imaging of PFBT Pdots

A useful estimate of fluorescence brightness is given by the product of the peak absorption cross section and the fluorescence quantum yield. Photophysical data indicate that PFBT dots of ~10 nm diameter are about 30 times brighter than IgG-Alexa 488, and Qdot 565 probes under a typical laser excitation (488 nm). A side-by-side brightness comparison would provide further evidence of the extraordinary brightness of Pdots. We carried out single-particle imaging to experimentally evaluate and compare the brightness and photostability of the three probes.

Figure 8:
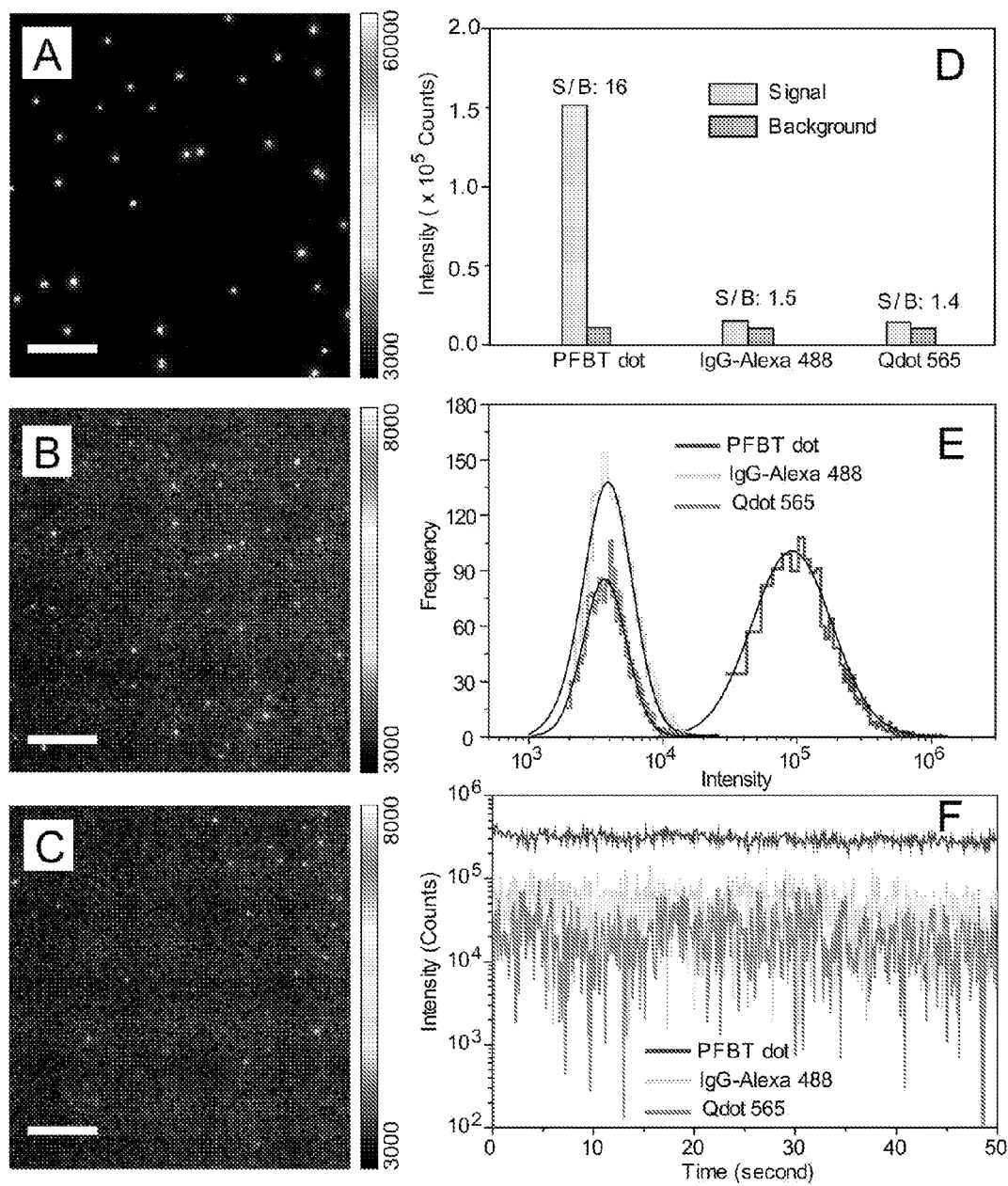
FIG. 8 Single-particle fluorescence images of (A) PFBT dot, (B) IgG-Alexa 488, and (C) Qdot 565, obtained under identical excitation conditions. Note the color bar for IgG-Alexa and Qdot 565 has to be set to a lower value (8000 counts rather than 60,000 counts) because they are significantly dimmer than PFBT dots. Scale bar represents 5 μm. (D) Signal and background for single Pdots as compared to single IgG-Alexa 488 and single Qdots, observed under identical excitation power of 1 mW. (E) Intensity distributions of single particle fluorescence for the three probes under the excitation power of 4 mW. Pdots are ~30 brighter than either IgG-Alexa 488 or Qdots. (F) Single-particle photobleaching trajectories. Blinking was not observed for PFBT dots (blue), while frequent blinking was observed for Qdots (red).

Briefly, fluorescent samples were diluted in Milli-Q water, dried under vacuum on cleaned glass coverslips, and imaged on a fluorescence microscope. The 488-nm laser beam from a sapphire laser (Coherent, Santa Clara, Calif. USA) was directed into an inverted microscope (Nikon TE2000U, Melville, N.Y., USA) using lab-built steering optics. Laser excitation power was measured at the nosepiece before the objective. The objective used for illumination and light collection was a 1.45 NA 60×TIRF objective (Nikon, Melville, N.Y., USA). Fluorescence signal was filtered by a 500 nm long pass filter (HQ500LP; Chroma, Rockingham, Vt., USA) and imaged on an EMCCD camera (Photometrics Cascade: 512B, Tucson, Ariz. USA). Because saturation of the detector was observed for some Pdot particles in FIG. 8, a neutral density filter (optical density of 1.5) was placed together with the emission filter when imaging Pdot samples. Fluorescence intensity of Pdot particles was back-calculated according to the attenuation factor. Single-particle photobleaching measurements were obtained by acquiring a series of consecutive frames. Fluorescence intensity emitted per frame for a given particle was estimated by integrating the CCD signal over the fluorescence spot.

FIGS. 8A, 8B, and 8C show typical single-particle epifluorescence images of PFBT dots, IgG-Alexa 488, and Qdot 565, respectively, obtained under identical acquisition and laser excitation conditions. With a relative low excitation power (1 mW) from a 488 nm laser, very bright, near-diffraction-limited spots were clearly observed for individual PFBT dots. Some Pdots actually saturated the detector (FIG. 8A), whereas the IgG-Alexa 488 and Qdots exhibited much lower intensity levels, barely detected by the camera at the low excitation power we used (FIGS. 8B, 8C). The PFBT dots exhibited an order-of-magnitude improvement in signal-to-background ratio compared to those of Qdot 565 and IgG-Alexa 488 (FIG. 8D). Such a prominent contrast is primarily due to the high per-particle absorption cross section of Pdots, which would be particularly suitable for fluorescence detection requiring low excitation conditions. For further comparing the probe performance, we increased laser excitation power to 4 mW so that Qdot 565 and IgG-488 probes can be sufficiently detected by the camera. Because saturation of the detector was observed for Pdot particles, a neutral density filter (optical density of 1.5, which blocks 97% of the emitted fluorescence) was placed together with the emission filter when imaging Pdot samples, and their fluorescence intensities were back-calculated according to the attenuation factor. For all the three probes, background was subtracted. Fluorescence intensity distribution of several thousands particles indicated that PFBT dots were ~30 times brighter than IgG-Alexa 488 and Qdot 565 (FIG. 8E), consistent with the brightness comparison based on the photophysical parameters.

Single-particle photobleaching measurements indicated excellent photostability of PFBT dots (FIG. 8F). Statistical analyses of multiple photobleaching trajectories showed that over $10^9$ photons per Pdot were emitted prior to photobleaching, two or three orders of magnitude larger than those emitted by individual Qdot 565 and IgG-Alexa 488 particles. Furthermore, a large number of photons could be obtained from individual Pdots at high acquisition rates (~200,000 photons detected per Pdot per 20 ms exposure) because of their high brightness, short fluorescence lifetime, and the presence of multiple emitters per particle. This feature was recently exploited to yield a particle tracking uncertainty of ~1 nm (Yu, J.; Wu, C.; Sahu, S.; Fernando, L.; Szymanski, C.; McNeill, J. J. Am. Chem. Soc. 2009, 131, 18410-18414), which makes Pdots far superior in high-speed single-particle tracking experiments than conventional fluorescent dyes and Qdots. It is worth noting that most PFBT dots exhibit continuous emission behavior without any obvious fluorescence blinking while most Qdots exhibit pronounced blinking (FIG. 8F). This non-blinking feature of Pdots is particularly valuable in single-molecule applications.

Example 11: Elimination of Non-Specific Binding to the Surface of Functionalized Pdots In a first attempt to functionalize Pdots, streptavidin was selected because most biological labeling molecules, such as antibodies, can be easily derivatized with biotin. However, because the relatively large surface area of Pdots is intrinsically hydrophobic, although surface modification tends to make it more hydrophilic, there is a concern that biomolecules will be non-specifically adsorbed onto the Pdot surface. This concern was verified for carboxyl functionalized Pdots. Briefly, carboxyl functionalized Pdots were mixed with and without streptavidin in a buffered solution, in the absence of a coupling reagent that links carboxyl groups to amine groups on biological molecules, and then incubated with biotin silica beads. After centrifugation, the Pdots that had been incubated with streptavidin were clearly retained in the pellet of the biotin silica beads, and those incubated without streptavidin showed no binding to the beads (FIG. 7C), thus indicating severe non-specific adsorption of streptavidin onto the Pdot surface.

To overcome this non-specific adsorption, Pdots were mixed with streptavidin in a buffer solution containing 0.1 wt % polyethylene glycol (PEG). The resulting Pdots showed no detectable binding to biotin silica beads, suggesting that the presence of PEG significantly reduced non-specific adsorption (FIG. 7C). Accordingly, covalent bioconjugation was successfully performed in a PEG-containing buffer. The peptide bond formation between the carboxyl groups on Pdots and the amine groups of streptavidin was catalyzed by a carbodiimide such as 1-ethyl-3-[3-dimethylaminopropyl]carbodiimide hydrochloride (EDC). The EDC-catalyzed, Pdot-streptavidin conjugates showed clear binding to biotin silica beads; while binding was not observed for the products obtained in the absence of EDC (FIG. 7C). In a separate control, identical bioconjugation conditions (i.e. streptavidin and EDC in PEG-containing buffer) were employed with bare, non-functionalized Pdots. Binding was not detectable on biotin beads, further confirming that the bioconjugation of streptavidin to Pdots was covalent and that labeling of strepadvidin-Pdots to biotin beads was specific and without any detectable non-specific binding.

The Pdots may be further passivated with additives such as bovine serum albumin (BSA), which can maintain long-term colloidal stability, block hydrophobic surfaces, and reduce non-specific binding in labeling experiments. We found BSA-passivated Pdot bioconjugates are stable for months at physiological pH in HEPES, PBS, Tris, and borate buffers. FIG. 7D inset shows two photographs of PFBT-streptavidin conjugates in 1×PBS buffer after 6 months of storage. The suspension of PFBT conjugates was stable, clear (not turbid), and exhibited strong fluorescence under UV lamp illumination (365 nm).

Example 12: Biomolecular Conjugation to Functionalized Pdots

Streptavidin and goat anti-mouse IgG antibodies were purchased from Invitrogen (Eugene, Oreg., USA). Bioconjugation was performed by utilizing the EDC-catalyzed reaction between carboxyl groups on Pdots and amine groups on biomolecules. In a typical bioconjugation reaction, 20 μL of polyethylene glycol (5% w/v PEG, MW 3350) and 20 μL of concentrated HEPES buffer (1 M) were added to 1 mL of functionalized Pdot solution (50 μg/mL in MilliQ water), resulting in a Pdot solution in 20 mM HEPES buffer with a pH of 7.3. Then, 40 μL of streptavidin or IgG antibody (1 mg/mL) was added to the solution and mixed well on a vortex. Last, 20 μL of freshly-prepared 1-ethyl-3-[3-dimethylaminopropyl]carbodiimide hydrochloride (EDC) solution (5 mg/mL in MilliQ water) was added to the solution, and the above mixture was left on a rotary shaker for 4 hours at room temperature. Finally, the resulting Pdot bioconjugates were separated from free biomolecules by gel filtration using Sephacryl HR-300 gel media.

Example 13: Cell Culture

The breast cancer cell lines MCF-7 and SK-BR-3 were ordered from American Type Culture Collection (ATCC, Manassas, Va., USA). Cells were cultured at 37° C., 5% $CO_2$ in Eagles minimum essential medium (for MCF-7) or McCoy's 5A medium (for SK-BR-3) supplemented with 10% Fetal Bovine Serum (FBS), 50 U/mL penicillin, and 50 µg/mL streptomycin. The cells were pre-cultured prior to experiments until confluence was reached. The cells were harvested from the culture flask by briefly rinsing with culture media followed by incubation with 5 mL of Trypsin-EDTA solution (0.25 w/v % Trypsin, 0.53 mM EDTA) at 37° C. for 5-15 minutes. After complete detachment, the cells were rinsed, centrifuged, and resuspended in labeling buffer (1×PBS, 2 mM EDTA, 1% BSA). The cell concentration was determined by microscopy using a hemacytometer.

Example 14: Use of Chromophoric Polymer Dot-IgG Conjugates for Detection of CD326 and CD340 Cell Markers It was previously demonstrated that bare Pdots could be delivered into cultured cells, presumably by endocytosis. However, when Pdots non-specifically bound to the cell surface; specific cellular targets were not labeled (see, for example, Wu, C.; Bull, B.; Szymanski, C.; Christensen, K.; McNeill, J. ACS Nano 2008, 2, 2415-2423; Pu, K. Y.; Li, K.; Shi, J. B.; Liu, B. Chem. Mater. 2009, 21, 3816-3822; Howes, P.; Green, M.; Levitt, J.; Suhling, K.; Hughes, M. J. Am. Chem. Soc. 2010, 132, 3989-3996; and Rahim, N. A. A.; McDaniel, W.; Bardon, K.; Srinivasan, S.; Vickerman, V.; So, P. T. C.; Moon, J. H. Adv. Mater. 2009, 21, 3492-3496). Therefore, it was unclear from these studies whether Pdot probes could be made specific enough to recognize cellular targets for effective labeling in real applications.

For a cell labeling experiment, Qdot 565-streptavidin, Alexa 488-IgG, and BlockAid™ blocking buffer were purchased from Invitrogen (Eugene, Oreg., USA). Pdot bioconjugates were synthesized using the methods as described above.

For labeling a cell-surface marker with IgG conjugates, a million cells in 100 µL labeling buffer was incubated with 5 µg/mL primary anti-human CD326 antibody (anti-EpCAM, Biolegend, San Diego, Calif., USA) for MCF-7 cells, or 5 µg/mL primary anti-human CD340 (anti-Her2, Biolegend, San Diego, Calif., USA) on a rotary shaker for 30 minutes in the dark and at room temperature, followed by a washing step using labeling buffer. Then the cells were incubated with 5 nM Pdot-IgG or Alexa 488-IgG conjugates for 30 minutes on a shaker in the dark and at room temperature, followed by another two washing steps. For labeling cell-surface marker with streptavidin conjugates, a million MCF-7 cells in 100 µL labeling buffer was incubated sequentially with 5 µg/mL primary anti-human CD326 antibody, 5 µg/mL biotinylated secondary anti-mouse IgG (Biolegend, San Diego, Calif., USA), and 5 nM Pdot-streptavidin or Qdot 565-steptavidin (Invitrogen, Eugene, Oreg., USA) for 30 minutes each, followed by another two washing steps. A drop of cell suspension was placed on a coverslip, covered with a glass slide, and imaged immediately under a fluorescence confocal microscope (Zeiss LSM 510).

Figure 9:
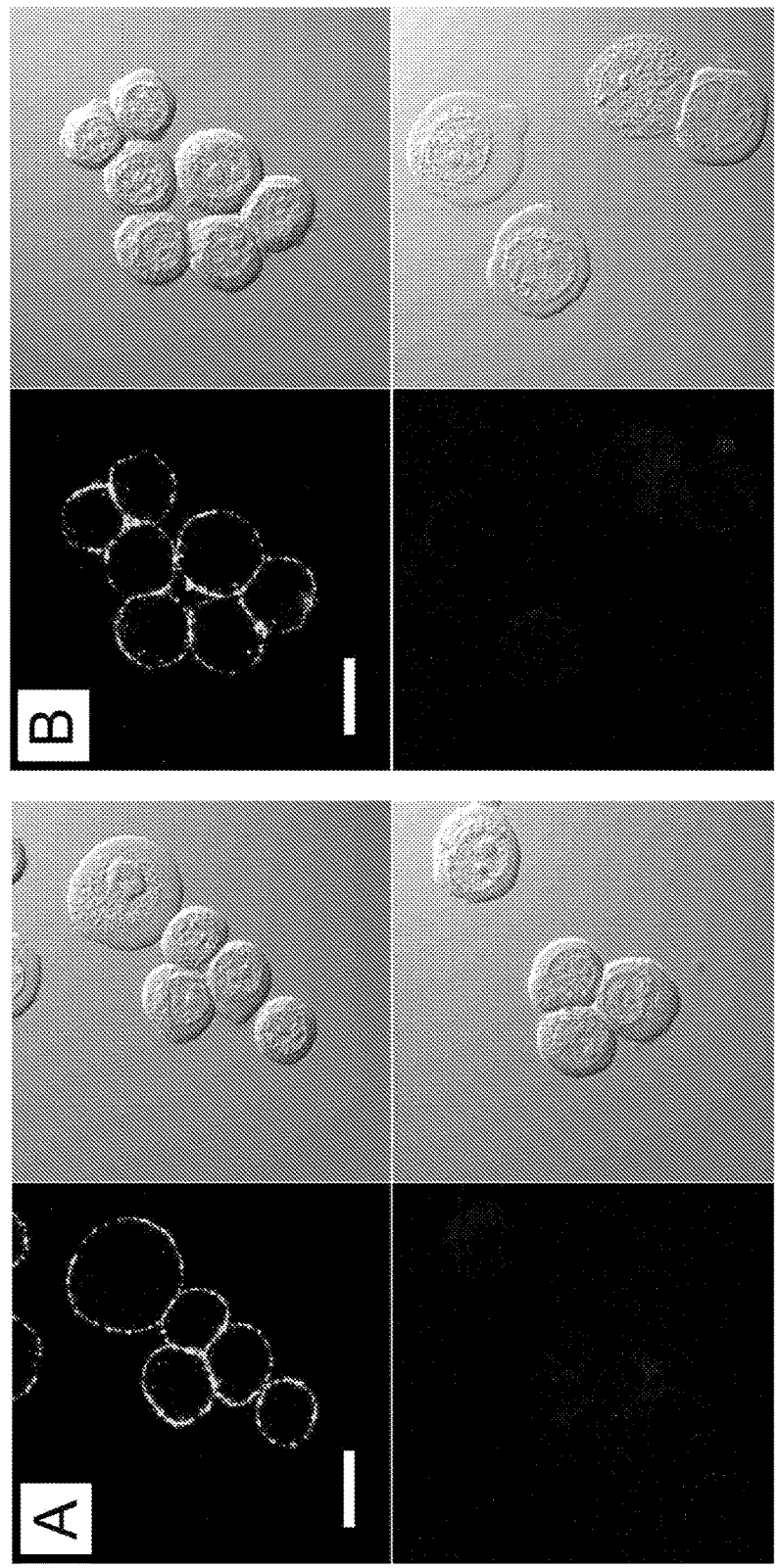
FIG. 9 Fluorescence imaging of cell-surface marker (EpCAM) in human breast cancer cells labeled with Pdot bioconjugates. (A) Imaging of live MCF-7 cells incubated sequentially with anti-EpCAM primary antibody and Pdot-IgG conjugates. The bottom panels show control samples in which the cells were incubated with Pdot-IgG alone (no primary antibody). The Nomarski (DIC) images are shown to the right of the confocal fluorescence images. Scale bar represents 20 μm. (B) Imaging of live MCF-7 cells incubated sequentially with anti-EpCAM primary antibody, biotinylated goat anti-mouse IgG secondary antibody, and Pdot-streptavidin conjugates. The bottom panels show control samples where the cells were incubated with anti-EpCAM antibody and Pdot-strepavidin (no secondary antibody). The Nomarski (DIC) images are shown to the right of the confocal fluorescence images. Scale bar represents 20 μm.

Streptavidin and IgGs are widely used in bioconjugation for immunofluorescent labeling of cellular targets. We created Pdot-IgG and Pdot-streptavidin probes and investigated their ability to label a specific cellular target, EpCAM/CD326, an epithelial cell-surface marker currently used for the detection of circulating tumor cells. FIG. 9A shows the Pdot-IgG probes successfully labeled EpCAM receptors on the surface of live MCF-7 human breast cancer cells after the cells were incubated with a monoclonal primary anti-Ep-CAM antibody. When the cells were incubated with just the Pdot-IgG alone, in the absence of the primary antibody, cell-labeling was not detected (FIG. 9A, bottom), indicating that the Pdot-IgG conjugates are highly specific for the target.

Next, Pdot-streptavidin conjugates were used as an alternative probe to detect EpCAM. The Pdot-streptavidin probes, together with the primary anti-EpCAM antibody and biotinylated goat anti-mouse IgG secondary antibody, also effectively labeled EpCAM on the surface of live MCF-7 cells (FIG. 9B). When the cells were incubated with primary antibody and Pdot-streptavidin in the absence of biotin anti-mouse IgG, no fluorescence was observed on the cell surface (FIG. 9B, bottom), thus again demonstrating the highly specific binding of Pdot-strepavidin. The lack of signal also indicated the absence of nonspecific binding in this biotin-streptavidin labeling system.

Pdot bioconjugates were then used to label another cell-surface marker, Her2 (target of the anti breast cancer drug, Heceptin), on a different cell line SK-BR-3, as well as subcellular structures such as microtubules in fixed MCF-7 cells (FIG. 5). Pdot bioconjugates in both cases labeled the targets specifically and effectively, demonstrating their comprehensive application to cell labeling.

Example 15: Use of Chromophoric Polymer Dot-IgG Conjugates for the Labeling of Microtubules For microtubule labeling, ten thousands of MCF-7 cells were plated on a 22×22 mm glass coverslip, cultured until the density reach 60-70% confluence. The cells were fixed with 4% paraformaldehyde for 15 minutes, permeabilized with 0.25% Triton-X 100 in PBS for 15 minutes, and blocked in 2% BSA (w/v) for 30 minutes. The fixed and BSA-blocked MCF-7 cells were incubated sequentially with 5 µg/mL biotinylated monoclonal anti-α-tubulin antibody (Biolegend, San Diego, Calif., USA) for 60 minutes, and 10 nM Pdot-streptavidin conjugates for 30 minutes. The stained cells were mounted on a glass slide and imaged with the fluorescence confocal microscope (Zeiss LSM 510).

Example 16: Use of Chromophoric Polymer Dot Conjugates in Flow Cytometry

Figure 10:
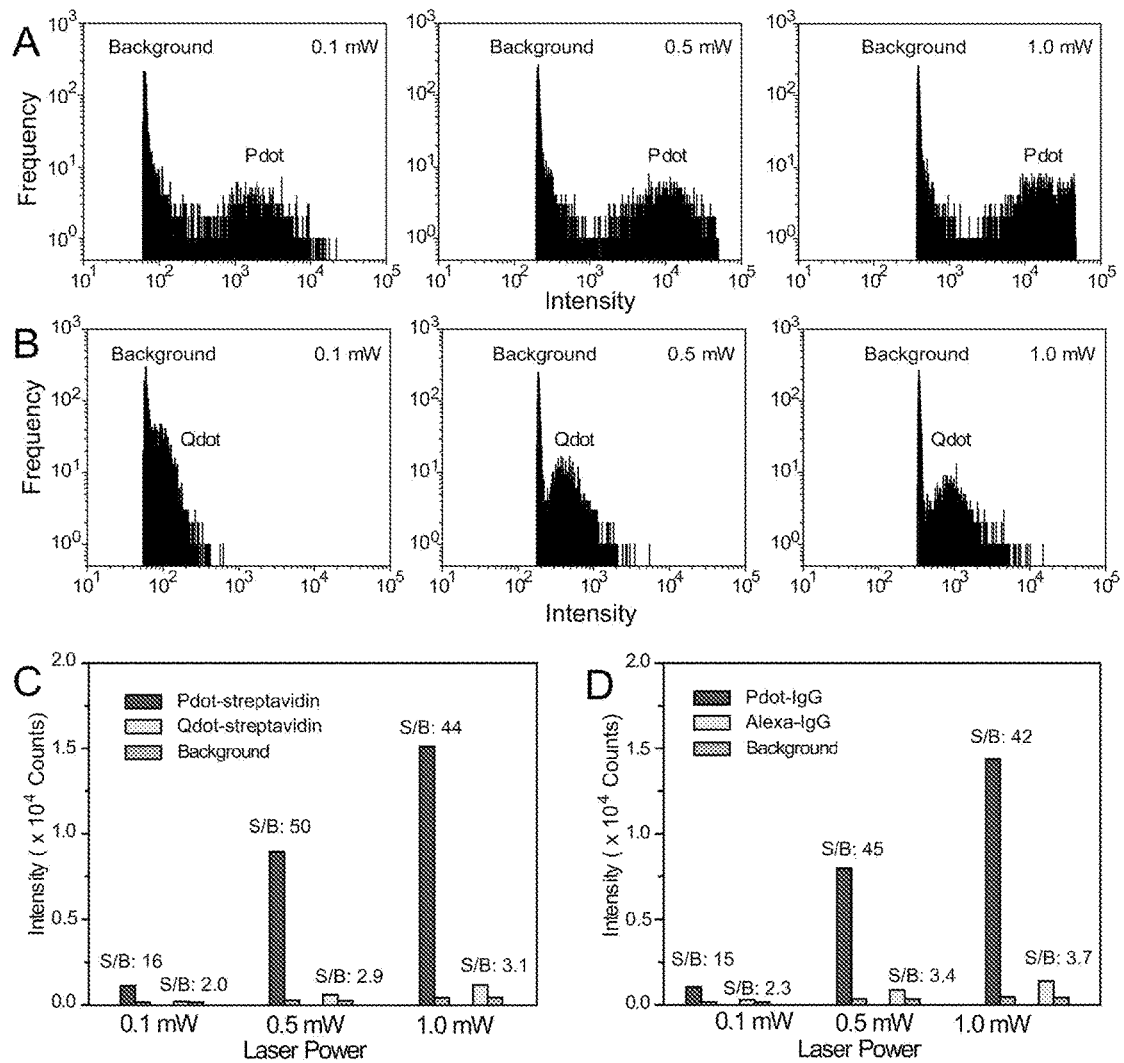
FIG. 10 Flow-through detection of fluorescently labeled cancer cells. (A) Fluorescence intensity distributions obtained by flowing Pdot-streptavidin labeled MCF-7 cells through a microfluidic flow cytometer; laser excitation was varied from 0.1 to 0.5 to 1 mW. (B) Fluorescence intensity distributions for Qdot 565-streptavidin labeled MCF-7 cells obtained under identical experimental conditions as those used in (A). (C) Comparison of average fluorescence brightness obtained using the microfluidic flow cytometer for cells labeled with Pdot-streptavidin and Qdot-streptavidin. (D) The same experiment and comparison as described in (A-C) was carried using Pdot-IgG and Alexa 488-IgG.

Besides fluorescence imaging, flow cytometry is another area where the brightness of probes is important. The labeling brightness of Pdot bioconjugates was compared to that of commercially available Qdot-streptavidin and Alexa-IgG probes using a microfluidic flow cytometer. FIG. 10A shows the flow-through detection of MCF-7 cells labeled with Pdot-streptavidin. At the lowest excitation intensity used (0.1 mW), a well-defined intensity peak for the Pdot-labeled cells appeared far above the background. In contrast, the peak for Qdot-labeled cells was not clearly separated from the background (FIG. 10B). The Pdot peak moved to higher intensity with increasing excitation intensity and started to saturate the detector at a laser power of 0.5 mW. In all excitation conditions, MCF-7 cells labeled with Pdot-streptavidin exhibited much higher intensity levels compared to the results of Qdot-labeled cells using the same labeling concentration as Pdot-streptavidin. The Pdot probes could provide significantly higher signal level at low excitation conditions, a very useful benefit for biological detection in optically turbid media such as blood or thick tissues.

Figure 11:
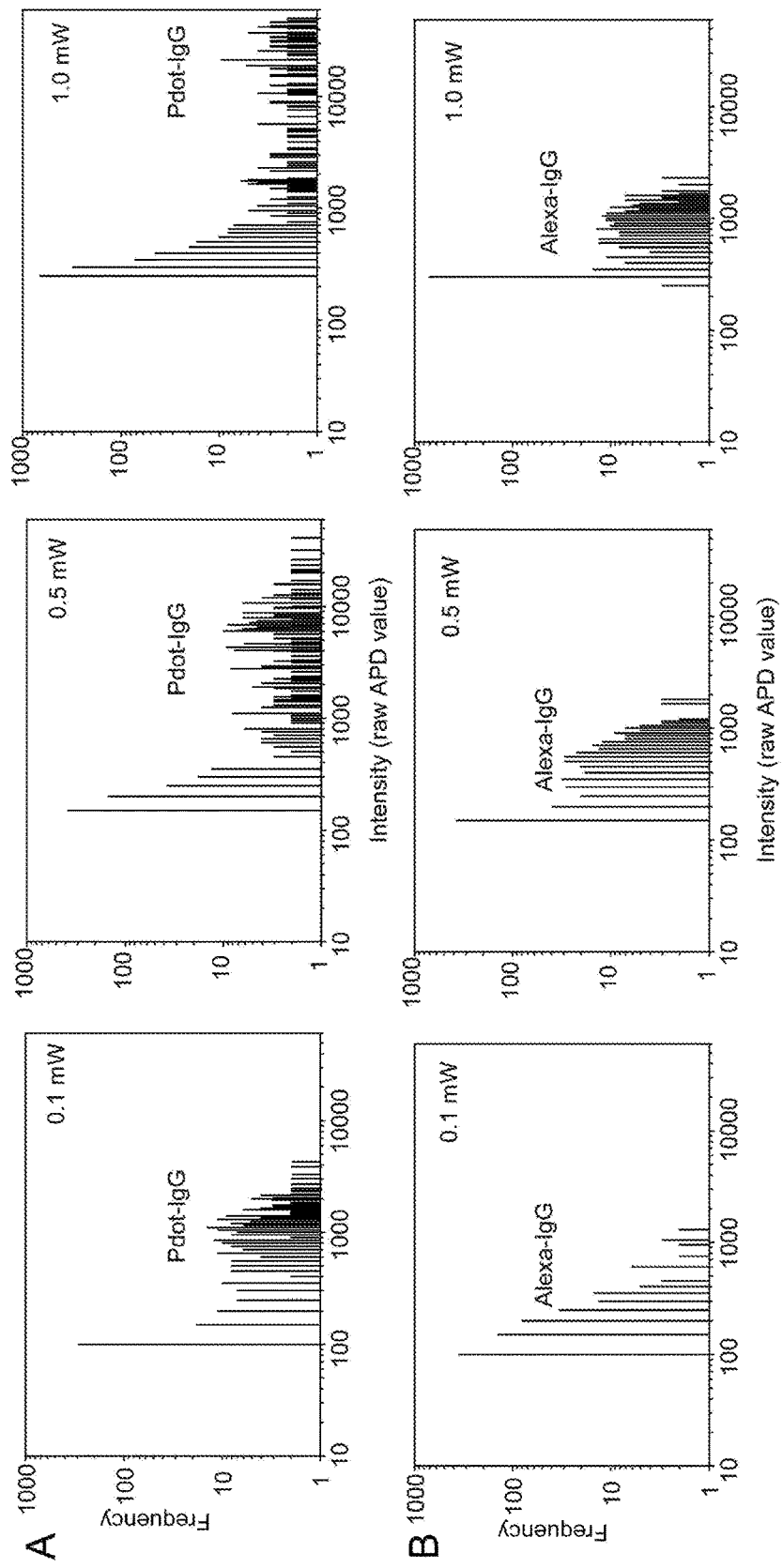
FIG. 11(A) Fluorescence intensity distributions obtained by flowing Pdot-IgG-labeled MCF-7 cells through a microfluidic flow cytometer; laser excitation was varied from 0.1 to 0.5 to 1 mW. (B) Fluorescence intensity distributions for Alexa 488-IgG-labeled MCF-7 cells obtained under identical experimental conditions as those used in (A).

Similar intensity comparisons were performed using Pdot-IgG and Alexa 488-IgG probes using the microfluidic flow cytometer (FIG. 11). Quantitative analyses of the flow cytometry data showed that the average intensity of Pdot-labeled cells is ~25 times brighter than the Qdot-labeled ones (FIG. 10C), and ~18 times brighter than Alexa-IgG labeled cells (FIG. 10D). We further quantified the labeling brightness by analyzing fluorescence images of MCF-7 cells labeled with either Pdot-streptavidin or Qdot-streptavidin. The Pdot-labeled cells were ~20 times brighter than the Qdot-labeled ones, consistent with the flow cytometry data (FIG. 12).

These cell-labeling comparison values are slightly lower than those obtained from single-particle imaging. The lower values may be attributed to several factors, such as discrepancies in collective emission behavior of probe assemblies compared to individual particles; change in binding constants of antibody or streptavidin upon bioconjugation; or variation in emission rate with excitation intensity (saturation). It is also worth noting that cell labeling was performed according to the optimized concentrations for Qdot-streptavidin and Alexa-IgG probes which may not be optimal for Pdot probes. Therefore, the present comparison is a conservative estimate of the advantages provided by Pdot bioconjugates over traditional dye and Qdot bioconjugates. More detailed work is needed for optimizing the bioconjugation reactions, as well as the labeling conditions, for this new class of Pdot-based probes. Nevertheless, the current cell imaging and flow cytometry results clearly indicate that Pdot labeling provides significant improvements in signal level compared to commercially available Alexa-IgG and Qdot probes.

Example 17: Preparation and Azido- and Alkyne-Pdots Compatible with Click Chemistry Applications The fluorescent semiconducting polymer poly[(9,9-dioctylfluorenyl-2,7-diyl)-co-(1,4-benzo-[2,1',3]-thiadiazole)] (PFBT, MW 157,000, polydispersity 3.0) was purchased from ADS Dyes, Inc. (Quebec, Canada). The copolymer poly(styrene-co-maleic anhydride) (PSMA, cumene terminated, average Mw ~1,700, styrene content 68%) was purchased from Sigma-Aldrich (St. Louis, Mo., USA)). All other reagents for nanoparticle preparation were purchased from Sigma-Aldrich (St. Louis, Mo., USA).

Functionalized Pdots in aqueous solution were prepared by using a modified nano-precipitation method. All experiments were performed at room temperature unless indicated otherwise. In a typical preparation, the fluorescent semiconducting polymer PFBT was first dissolved in tetrahydrofuran (THF) to make a 1 mg/mL stock solution. The copolymer PSMA was also dissolved in THF and mixed with a diluted solution of PFBT to produce a solution mixture with a PFBT concentration of 50 μg/mL and a PSMA concentration of 20 μg/mL. The mixture was sonicated to form a homogeneous solution. A 5 mL quantity of the solution mixture was quickly added to 10 mL of MilliQ water in a bath sonicator. The THF was removed by nitrogen stripping. The solution was concentrated by continuous nitrogen stripping to 5 mL on a 90° C. hotplate followed by filtration through a 0.2 micron filter. During nanoparticle formation, the maleic anhydride units of PSMA molecules were hydrolyzed in the aqueous environment, generating carboxyl groups on Pdots. The Pdot dispersions were clear and stable for months without signs of aggregation.

Surface conjugation was performed by utilizing the EDC-catalyzed reaction between carboxyl Pdots and the respective amine-containing molecules. 11-Azido-3,6,9-trioxaundecan-1-amine was used to form azido-Pdots. Propargylamine was used to produce alkyne-Pdots. Amine-terminated poly(ethylene glycol) was used to form PEG-Pdots. In a typical conjugation reaction, 60 μL of polyethylene glycol (5% w/v PEG, MW 3350) and 60 μL of concentrated HEPES buffer (1 M) were added to 3 mL of carboxyl Pdot solution (50 μg/mL in MilliQ water), resulting in a Pdot solution in 20 mM HEPES buffer with a pH of 7.3. Then, 30 μL of amine-containing molecules (1 mg/mL) was added to the solution and mixed well on a vortex. Last, 60 μL of freshly-prepared EDC solution (5 mg/mL in MilliQ water) was added to the solution, and the above mixture was magnetically stirred for 4 hours at room temperature. Finally, the resulting Pdot conjugates were separated from free molecules by Bio-Rad Econo-Pac® 10DG columns (Hercules, Calif., USA).

Example 18: Characterization of Clickable Pdots

Figure 15:
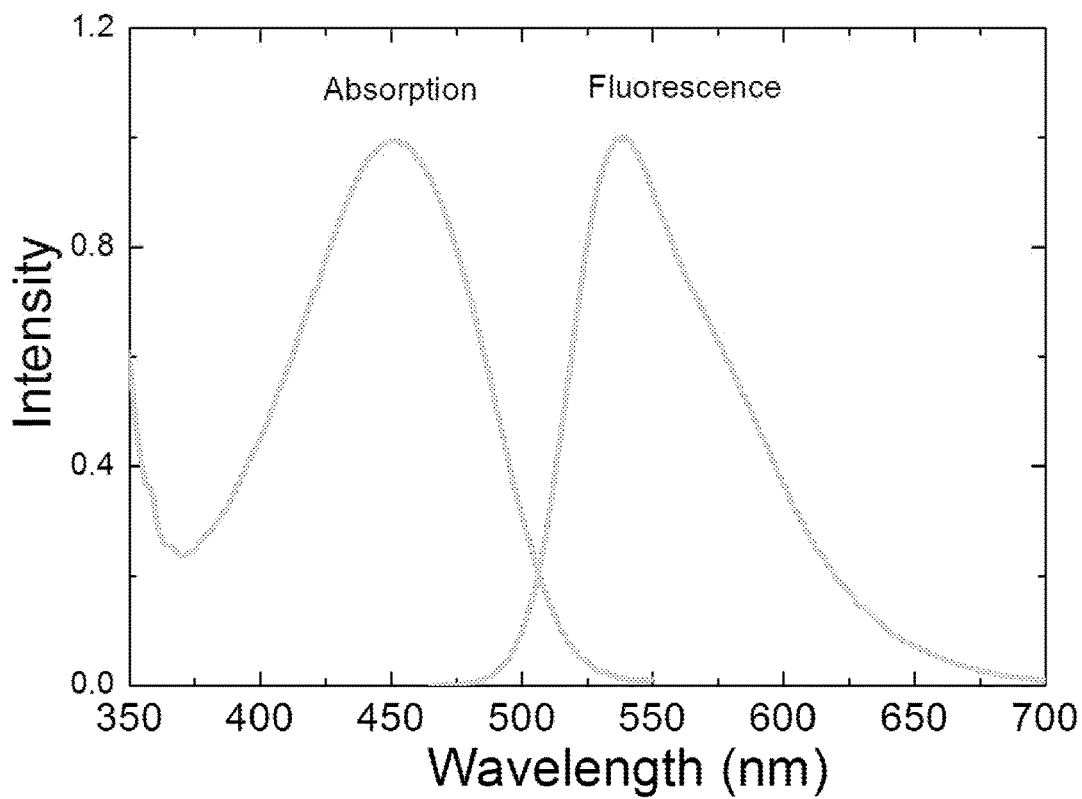
FIG. 15 Absorption and fluorescence spectra of carboxyl functionalized PFBT dots.

Fluorescence spectra were obtained using a commercial Fluorolog-3 fluorometer (HORIBA Jobin Yvon, N.J. USA). Analysis of the absorption spectrum for ~15 nm-diameter PFBT dots indicated a peak extinction coefficient of $5.0 \times 10^7$ $M^{-1}cm^{-1}$ (FIG. 15). Fluorescence quantum yield of the functionalized Pdots was determined to be 0.28 using a dilute solution of Coumarin 6 in ethanol as standard. The large extinction coefficient and high quantum yield indicate much higher per-particle brightness as compared to other fluorescent nanoparticles. Single-particle photobleaching studies of the functionalized Pdots showed that over $10^9$ photons per Pdot were emitted prior to photobleaching, consistent with their excellent photostability (C. Wu, B. Bull, C. Szymanski, K. Christensen, J. McNeill, ACS Nano 2008, 2, 2415).

Figure 17:
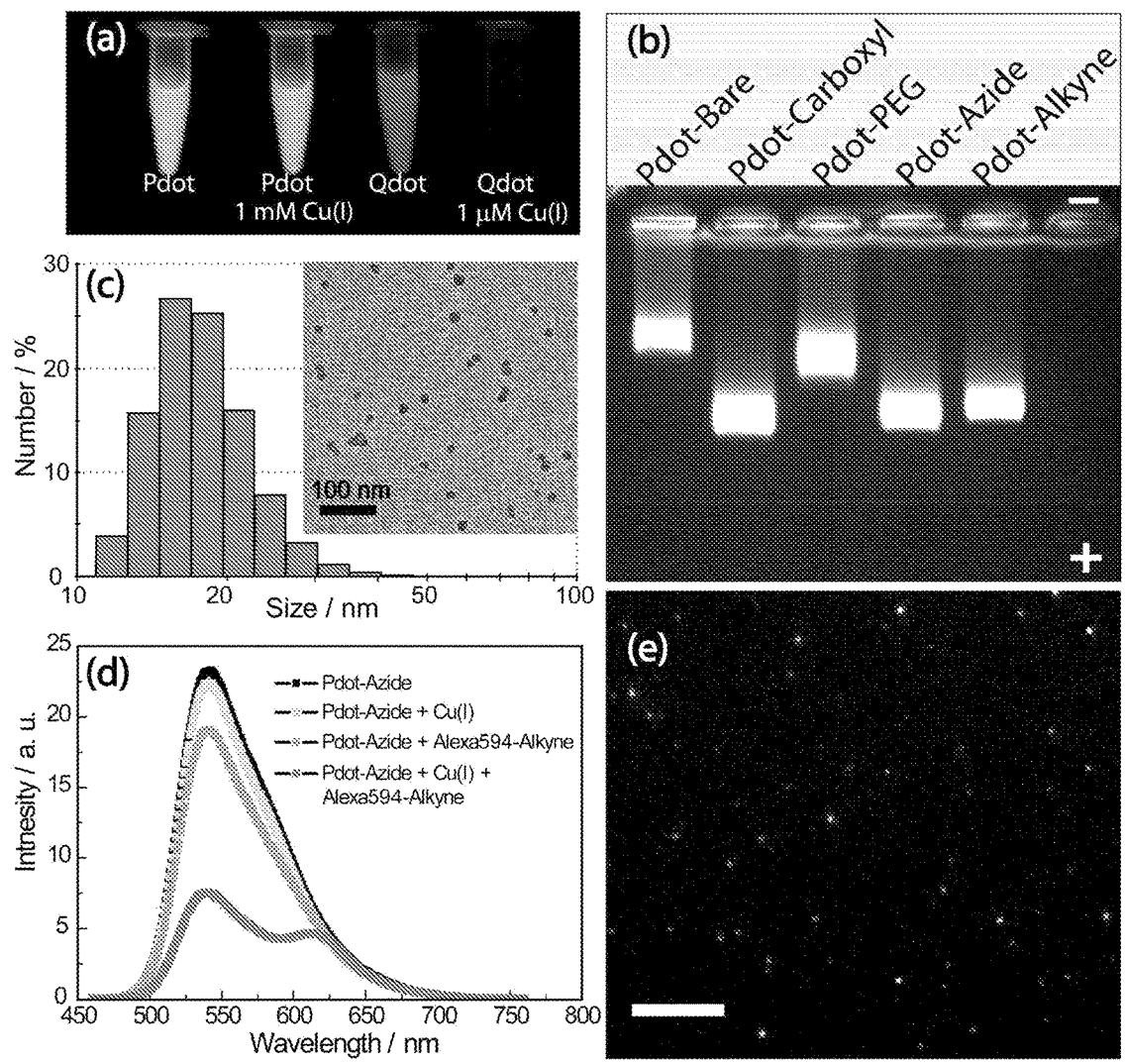
FIG. 17 Characterization of functionalized Pdots. (a) Fluorescence photographs of Pdots versus Qdots in the presence of copper (I) under UV illumination. (b) Migration bands of Pdots with different surface functional groups. (c) Hydrodynamic diameter of carboxyl functionalized Pdots measured by dynamic light scattering; inset shows a typical TEM image of functionalized Pdots. (d) A fluorescent assay using alkyne-Alexa 594 dye to verify successful functionalization of Pdots with azido groups. (e) Single-particle fluorescence images of alkyne-silica nanoparticles coupled to azido-Pdots by click reaction. Scale bar represents 50 μm.

Gel electrophoresis was performed to characterize the formation of different functional groups on the Pdot surface using a 0.7% agarose gel (FIG. 17b). Compared with unfunctionalized, bare Pdots, the carboxyl-functionalized Pdots exhibited an apparent increase in mobility in the gel. Briefly, agarose gel electrophoresis of the functionalized Pdots was carried out using a Mupid®-exU submarine electrophoresis system. Pdots (in 30% glycerol) were loaded onto a 0.7% agarose gel containing 0.1% PEG. The Pdot-loaded gel was run for 20 min at 135 V in tris-borate-EDTA (TBE) buffer, and then imaged on Kodak image station 440CF system.

Dynamic light scattering and transmission electron microscopy (TEM) measurements showed that both the bare and the functionalized Pdots had comparable particle sizes, with an average of ~15 nm in diameter (FIG. 17c). Therefore, the high mobility of PSMA-functionalized Pdots indicated the formation of negatively charged carboxyl groups on the Pdot surface. For the TEM measurements, one drop of the Pdot dispersion was placed on a carbon-coated copper grid. After evaporation of the water, the nanoparticles were imaged with a transmission electron microscope (FEI Tecnai F20). UV-V is absorption spectra were recorded with a DU 720 scanning spectrophotometer (Beckman Coulter, Inc., Calif. USA) using 1 cm quartz cuvettes.

Surface conjugation was performed with different amine-containing molecules (amine-terminated polyethylene glycol (PEG), azide, and alkyne). Dynamic light scattering of the conjugated Pdots showed no obvious change in particle size because the conjugation was with small molecules. However, they exhibited shifted migration bands in the gel as anticipated, due to the reduced charges of the Pdot conjugates compared to the carboxyl-functionalized Pdots.

These results clearly indicate successful carboxyl functionalization of the Pdots as well as all the subsequent surface modifications.

Example 19: Stability of Functionalized Pdots

Figure 16:
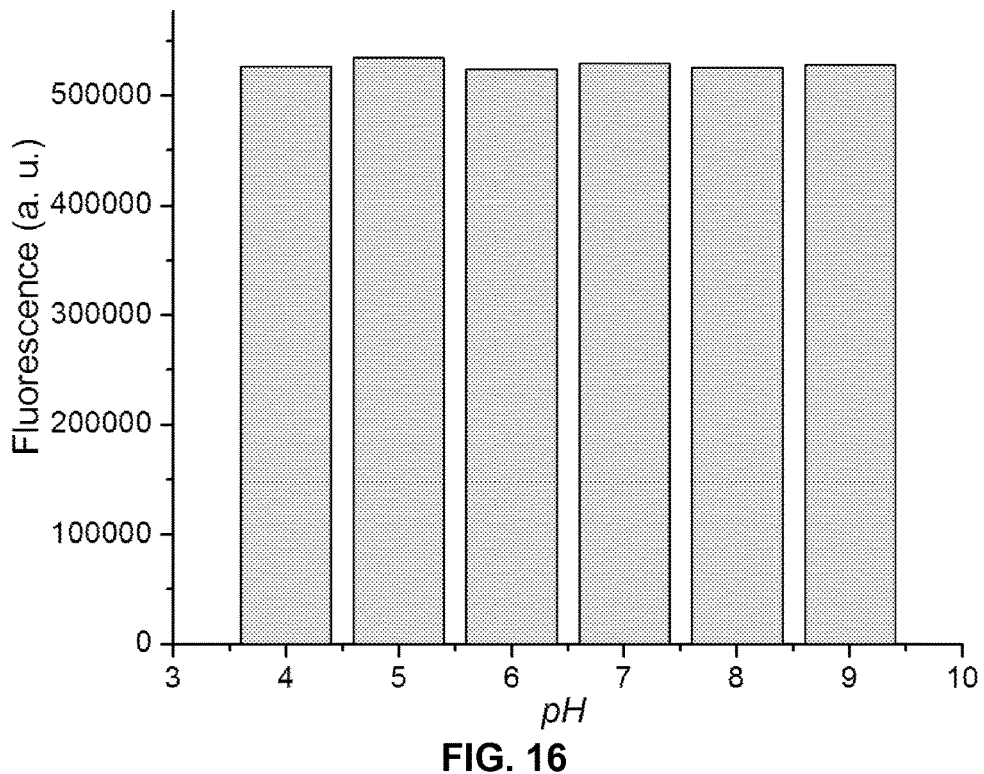
FIG. 16 The fluorescence intensity of PFBT Pdots in HEPES buffer with pH ranging from 4 to 9. No obvious change was observed.

The pH and ion sensitivity of Pdot fluorescence in biological applications was analyzed, particularly the copper-catalyzed click chemistry. It was found that the fluorescence of Pdots was not affected by most biologically relevant ions, including iron, zinc, and copper, three of the most abundant ions in biological organisms. The Pdot fluorescence is also independent of pH in the range of 4 to 9 (FIG. 16). This fact can be attributed to the hydrophobic organic nature of Pdots, which tend not to have any chemical interaction with ionic species. In contrast, inorganic Qdots are significantly quenched by copper and iron ions (H. Y. Xie, H. G. Liang, Z. L. Zhang, Y. Liu, Z. K. He, D. W. Pang, Spectrochimica Acta Part A 2004, 60, 2527). As shown in FIG. 17a, PFBT dots remained highly fluorescent in MilliQ water containing a high $Cu^+$ concentration of 1 mM, whereas Qdots were completely quenched at a much lower $Cu^+$ concentration of 1 μM (S. Han, N. K. Devaraj, J. Lee, S. A. Hilderbrand, R. Weissleder, M. G. Bawendi, J. Am. Chem. Soc. 2010, 132, 7838). This property provides a significant advantage for applying Pdots in various studies based on copper (I)-catalyzed click reactions. To prevent self aggregation of Pdots in the copper solution, we added PEG into the solution.

Example 20: Reactivity of Clickable Pdots

FIG. 17d shows a fluorescence assay examining the reactivity of azido-Pdots towards a terminal alkyne group via copper (I)-catalyzed click reaction. When mixed with a copper solution, the azido-Pdots exhibited an emission intensity similar to that of the pure Pdots, confirming that their fluorescence is insensitive to copper ions. A slight decrease in intensity was observed in the mixture of Pdots and alkyne-Alexa 594 (no Cu (I)), but this was primarily due to the inner filter effect rather than direct quenching caused by fluorescence resonance energy transfer (FRET). In contrast, when directly linked to alkyne-Alexa 594 in the presence of Cu (I), the azido-Pdots showed remarkable fluorescence quenching accompanied by an emission peak from the Alexa dye. This spectroscopic change was a direct result of efficient FRET from the PFBT dots to the Alexa dye in close proximity and indicated the effective azide-alkyne click reaction. In addition, we also clicked the azido-Pdots onto alkyne-functionalized silica nanoparticles to convert the optically inert silica particles into highly fluorescent probes. The Pdot-silica conjugates were clearly visible at the single-particle level even on a mercury lamp-illuminated, low-magnification (4×) fluorescent microscope (FIG. 17e).

Alkyne-Alexa 594 dye was purchased from Invitrogen (Eugene, Oreg., USA) for click reactions with azido-Pdots. In a typical reaction, 50 nM azido-Pdots in MilliQ water containing 1% BSA were mixed with 5 μM alkyne-Alexa 594 dye in the presence of 1 mM $CuSO_4$ and 5 mM sodium ascorbate for 30 minutes before spectroscopic measurements. For click reaction of azido-Pdots to alkyne-silica particles, silica colloids (~200 nm in diameter) were prepared according to the standard Stöber method. Alkyne functionalization to silica particles was performed as follows: 80 mg of silica particles was washed with anhydrous ethanol, dried, and resuspended in 4 mL anhydrous dimethylformamide (DMF). 80 μL of O-(Propargyloxy)-N-(Trimethoxysilylpropyl)Urethane was added to the silica in DMF suspension, and the mixture was magnetically stirred on a 90° C. hotplate for 24 hours. The alkyne-functionalized silica nanoparticles were washed thoroughly with ethanol, and resuspended in MilliQ water. For a typical click reaction, 0.5 mL of 50 nM azido-Pdots in MilliQ water containing 1% BSA was mixed with 0.1 mL of alkyne-silica particles (20 mg/mL) in the presence of 1 mM $CuSO_4$ and 5 mM sodium ascorbate for 2 hours. The Pdot-decorated silica particles were then washed thoroughly with MilliQ water. A drop of the dilute solution of Pdot-decorated silica particles was placed on a coverslip and viewed on an upright microscope with an AZ-Plan Apo 4× objective (Nikon AZ100, Melville, N.Y., USA) and with a mercury lamp as the excitation source.

Example 21: Metabolic Labeling with Clickable Pdots

To demonstrate cellular labeling with Pdots and click chemistry, newly synthesized proteins modified by bioorthogonal non-canonical amino-acid tagging (BONCAT) were visualized. In the BONCAT technique, newly synthesized proteins in cells are metabolically labeled with an azido- (or alkyne-)bearing artificial amino acid. The artificial amino acid endows the proteins with unique chemical functionality that subsequently can be tagged with exogenous probes for detection or isolation in a highly selective manner (D. C. Dieterich, A. J. Link, J. Graumann, D. A. Tirrell, E. M. Schuman, Proc. Natl. Acad. Sci. USA 2006, 103, 9482). Azidohomoalanine (AHA) and homopropargylglycine (HPG) are two artificial amino acids commonly used in this method. They are effective surrogates for methionine, an essential amino acid; in the absence of methionine, the cellular synthesis machinery straightforwardly incorporates them into proteins. This approach is operationally similar to the traditional metabolic labeling with radioactive amino acid $^{35}$S-methionine. After incorporation, AHA and HPG are susceptible to tagging with exogenous probes, which in the present example are the highly fluorescent Pdots for in situ imaging.

First, AHA-labeled proteins were targeted using Pdot-alkyne probes. MCF-7 human breast cancer cells were grown to confluence before passage into serum-free medium lacking methionine. After incubation to deplete any residual methionine, cell cultures were supplemented with AHA for four hours. Then the cells were washed and fixed before carrying out the click reaction with alkyne-Pdots in the presence of $CuSO_4$, a reducing agent (sodium ascorbate), and a triazole ligand. The Pdot-tagged cells were viewed immediately on a confocal fluorescence microscope. Identical settings were used to acquire images from the Pdot-labeled cells and the negative controls.

Briefly, for metabolic labeling of newly synthesized proteins, homopropargylglycine (HPG) and BlockAid™ blocking buffer were purchased from Invitrogen (Eugene, Oreg., USA). Azidohomoalanine (AHA) was purchased from Medchem Source LLP (Federal Way, Wash., USA). MCF-7 cells were grown to confluence before passage into serum-free medium lacking methionine. After one hour incubation to deplete any residual methionine, cultures were supplemented with 0.1 mM AHA or HPG for four hours. The cells were washed by 1×PBS, fixed with 4% paraformaldehyde/PBS, and blocked in the BlockAid™ blocking buffer. The AHA- or HPG-labeled cells were incubated for one hour with a mixture of 1 mM $CuSO_4$, 5 mM sodium ascorbate, 0.5 mM tris((1-benzyl-1H-1,2,3-triazol-4-yl)methyl)amine (TBTA, triazole ligand), and 50 nM alkyne-Pdots (for AHA-labeled cells) or azido-Pdots (for HPG-labeled cells). The Pdot-tagged cells were then counterstained with Hoechst 34580 and imaged immediately on a fluorescence confocal microscope (Zeiss LSM 510).

Figure 18:
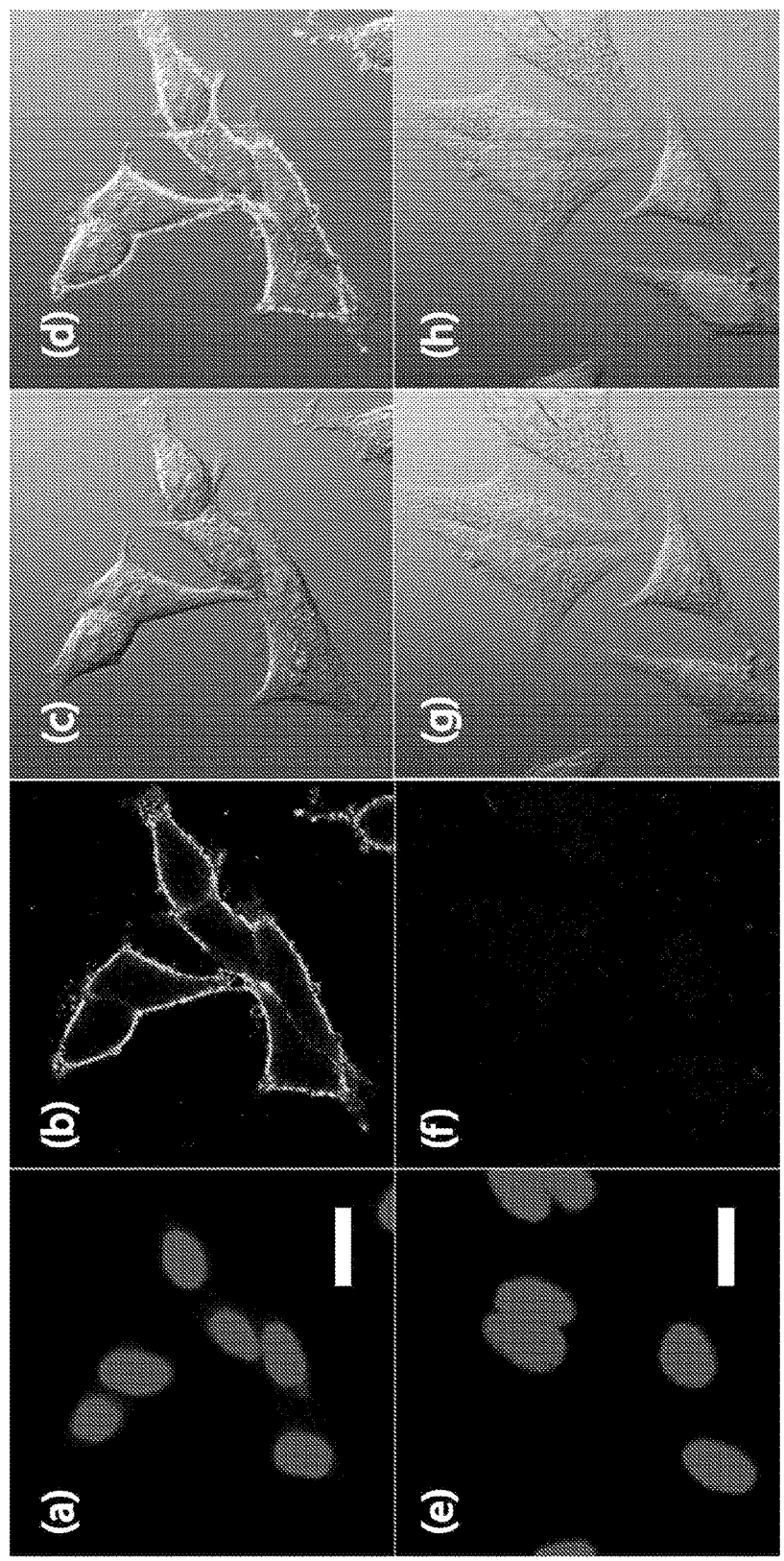
FIG. 18 Fluorescence imaging of newly synthesized proteins in the AHA-treated MCF-7 cells tagged with Pdot-alkyne probes. (a-d) Positive Pdot labeling in the presence of copper (I). (e-h) Pdot labeling in the control sample was carried out under identical conditions as in (a-d) but in the absence of the reducing agent (sodium ascorbate) that generates copper (I) from copper (II). The top row shows fluorescence images; green fluorescence is from Pdots and blue fluorescence is from the nuclear stain Hoechst 34580. The bottom row shows Nomarski (DIC) and combined DIC and fluorescence images. Scale bar represents 20 µm.
Figure 19:
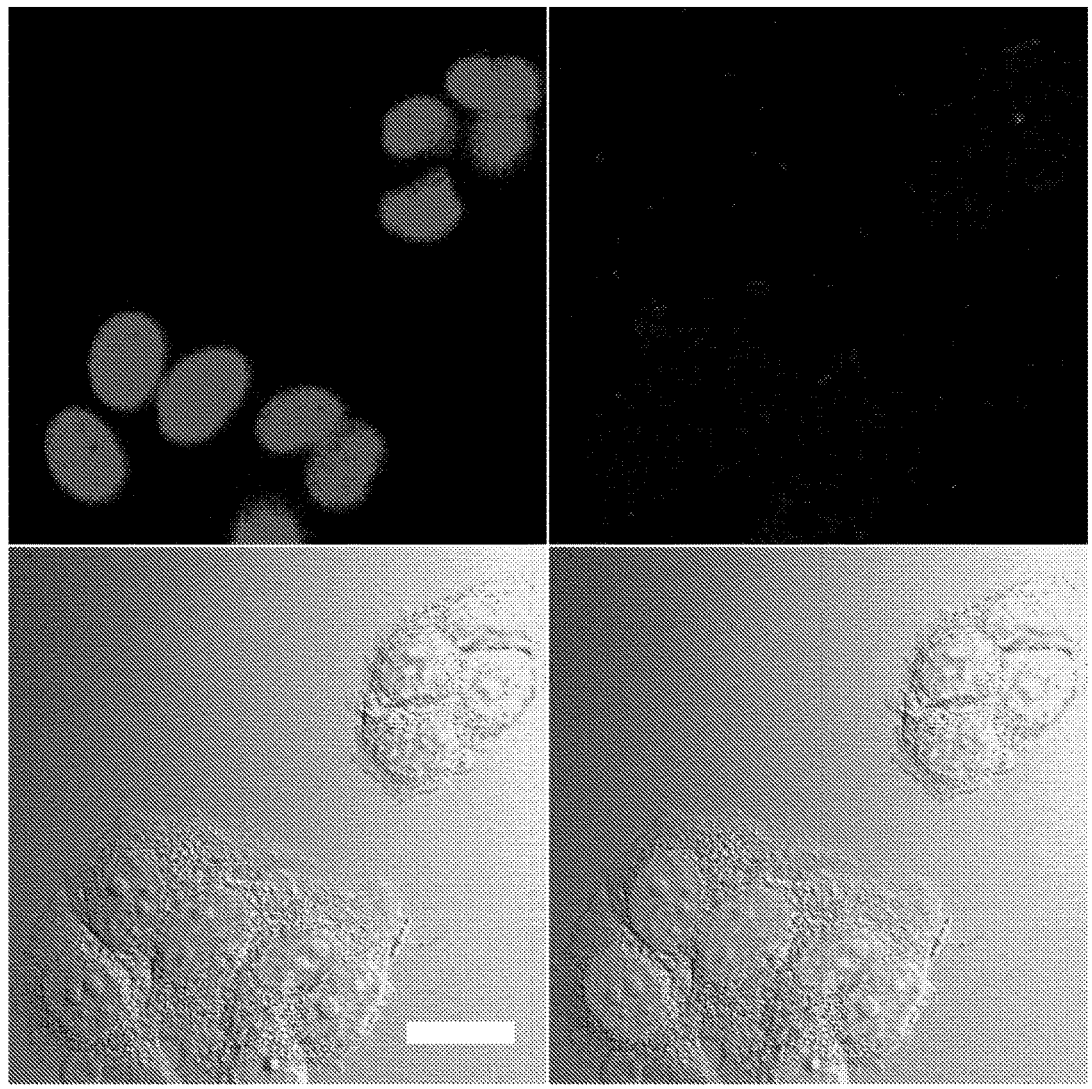
FIG. 19 Copper (I)-catalyzed Pdot-alkyne tagging was performed under identical conditions as those in FIG. 18a-18d but in cells not exposed to AHA. In this control, cell labeling was not observed. The top row shows fluorescence images; blue fluorescence was from the nuclear stain Hoechst 34580; no fluorescence from Pdots was observed (top right panel). The bottom row shows Nomarski (DIC) (lower left panel) and combined DIC and fluorescence (lower right panel) images. Scale bar represents 20 µm.
Figure 20:
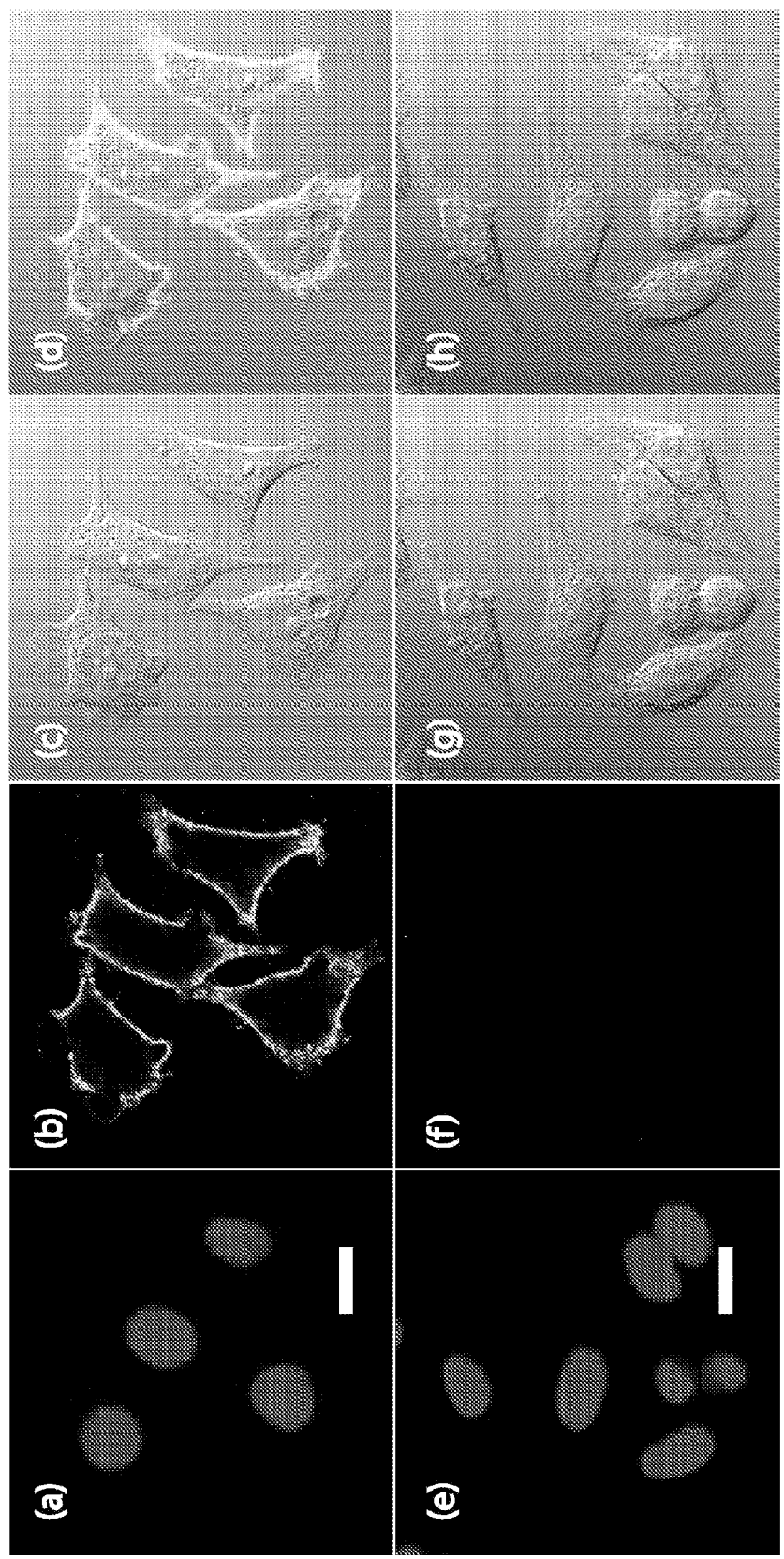
FIG. 20 Fluorescence imaging of newly synthesized proteins in MCF-7 cells tagged with Pdot-azide. (a-d) Copper (I)-catalyzed positive Pdot labeling in the HPG-treated cells. (e-h) Pdot labeling in the control sample was carried out under identical conditions as in (a-d) but in cells not exposed to HPG. The top row shows fluorescence images; green fluorescence is from Pdots and blue fluorescence is from the nuclear stain Hoechst 34580. The bottom row shows Nomarski (DIC) and combined DIC and fluorescence images. Scale bar represents 20 µm.
Figure 21:
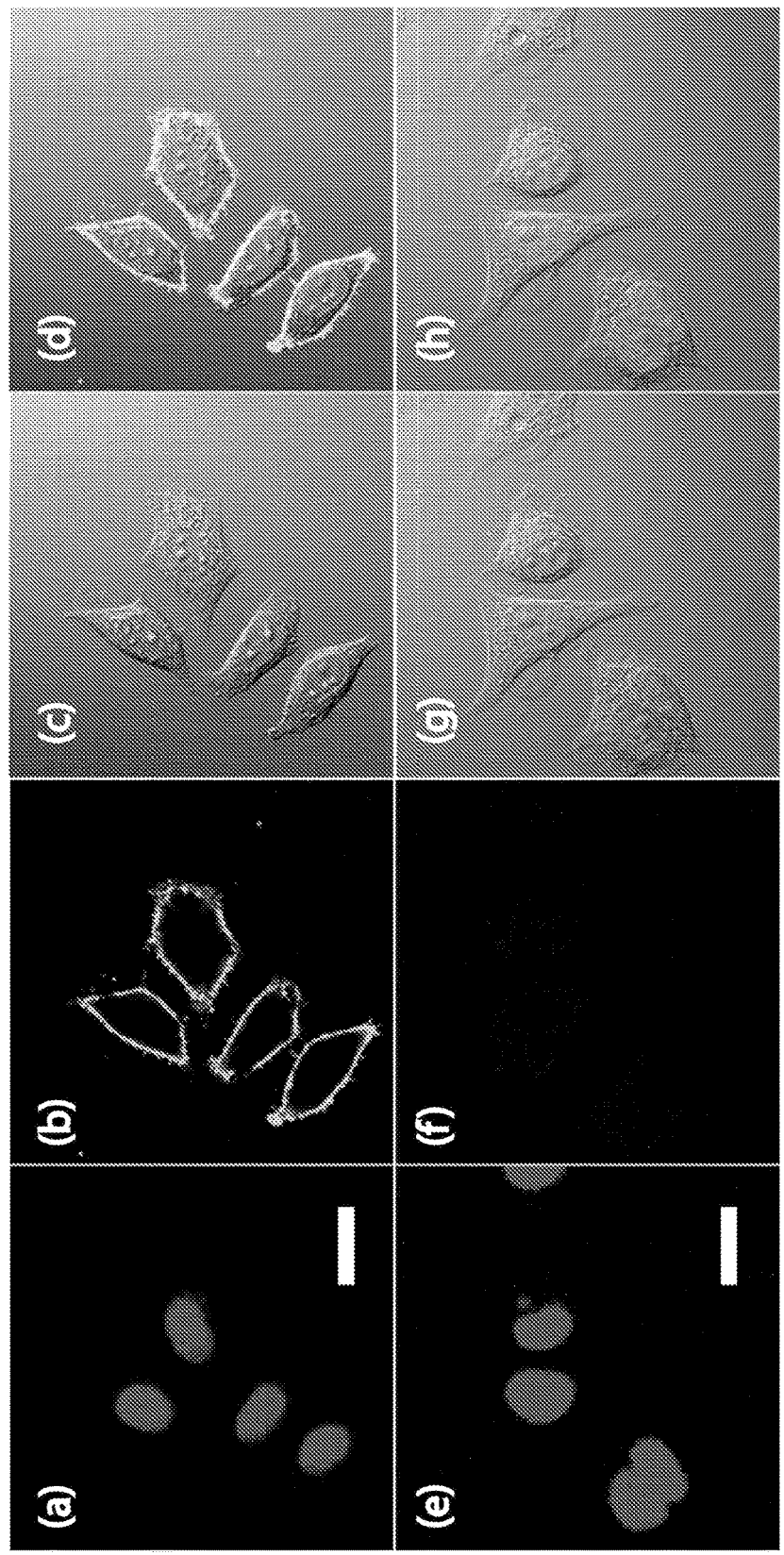
FIG. 21 Fluorescence imaging of glycoproteins in Gal-NAz-treated MCF-7 cells tagged with Pdot-alkyne probes. (a-d) Positive Pdot labeling in the presence of copper (I). (e-h) Pdot labeling in the control sample was carried out under identical conditions as in (a-d) but in the absence of copper (I). The top row shows fluorescence images; green fluorescence is from Pdots and blue fluorescence is from the nuclear stain Hoechst 34580. The bottom row shows Nomarski (DIC) and combined DIC and fluorescence images. Scale bar represents 20 µm.

FIG. 18 shows confocal fluorescence and bright-field images of the Pdot-labeled cells and the control samples. Very bright fluorescence was observed for the AHA-labeled cells tagged with Pdot-alkyne via click reaction (FIG. 18a-18d). When the cells were incubated under identical conditions but in absence of the reducing agent (sodium ascorbate) that forms copper (I) from $CuSO_4$, cell labeling by Pdots was not observed, indicating that Pdot-alkyne was selective for the copper (I)-catalyzed reaction (FIG. 18e-18h). In a different control, copper (I)-catalyzed Pdot-alkyne tagging was performed under identical conditions as those in FIG. 18a-18d but in cells not exposed to AHA. In this control, cell labeling also was not observed (FIG. 19), indicating Pdot-alkyne tagging was highly specific for the cellular targets of interest. In addition, Pdot-azide was used to detect newly synthesized proteins in MCF-7 cells incubated with HPG. In this case, the Pdot-azide also specifically and effectively labeled the targets (FIG. 20). In comparison with the Pdot-alkyne labeling (AHA-treated cells), an obvious difference in the fluorescence brightness of the Pdot-azide labeling (HPG-treated cells) was not observed. This is consistent with the literature results that HPG and AHA show very similar activities in the synthesis of nascent proteins in mammalian cells.

Example 22: Glycoprotein Labeling with Clickable Pdots

Pdot-alkyne was used to selectively target glycoproteins, a subset of proteins extensively involved in various biological functions. The bioorthogonal chemical reaction strategy has been previously developed for probing glycans on cultured cells and in various living organisms (see, for example, J. A. Prescher, D. H. Dube, C. R. Bertozzi, Nature 2004, 430, 873; D. H. Dube, J. A. Prescher, C. N. Quang, C. R. Bertozzi, Proc. Natl. Acad. Sci. USA 2006, 103, 4819; S. T. Laughlin, C. R. Bertozzi, Proc. Natl. Acad. Sci. USA 2009, 106, 12; and M. A. Breidenbach, J. E. G. Gallagher, D. S. King, B. P. Smart, P. Wu, C. R. Bertozzi, Proc. Natl. Acad. Sci. USA 2010, 107, 3988). The method involves metabolic labeling of glycans with a monosaccharide precursor that is functionalized with an azido group, after which the azido sugars are covalently tagged with imaging probes. MCF-7 cells were incubated with N-azidoacetylgalactosamine (GalNAz) for three days in order to enrich O-linked glycoproteins with the azido groups. The GalNAz-treated cells were tagged with Pdot-alkyne via click reaction and subsequently viewed on a confocal microscope. Bright cell-surface labeling was observed for the cells positively tagged with Pdot-alkyne (FIG. 21a-21d). In the negative control, where cells were incubated with Pdot-alkyne in the absence of the reducing agent, cell labeling was not observed (FIG. 21e-21h). As an additional control, Pdot tagging was performed under identical conditions but in cells lacking azides; in this case, cell labeling was not observed, again indicating Pdot labeling was highly specific for the cellular targets of interest.

Briefly, for metabolic labeling of glycoproteins, N-azidoacetylgalactosamine (GalNAz) was purchased from Invitrogen (Eugene, Oreg., USA). MCF-7 cells were cultured using the general EMEM medium containing 50 µM N-azidoacetylgalactosamine (GalNAz) for three days in order to enrich the azido groups in O-linked glycoproteins. The GalNAz-labeled cells were washed by 1×PBS, fixed with 4% paraformaldehyde/PBS, and blocked in the BlockAid™ blocking buffer. Then the GalNaz-labeled cells were incubated for one hour with a mixture of 1 mM $CuSO_4$, 5 mM sodium ascorbate, 0.5 mM tris(1-benzyl-1H-1,2,3-triazol-4-yl)methyl)amine (TBTA, triazole ligand), and 50 nM alkyne-Pdots. The Pdot-tagged cells were then counterstained with Hoechst 34580 and imaged immediately on a fluorescence confocal microscope (Zeiss LSM 510).

Example 23: Preparation and Functionalization of Red-Emitting PBdots

The red-emitting semiconducting polymers PF-0.1TBT and PF-0.1DHTBT were synthesized and characterized as in previous reports (Hou, Q. et al. J. Mater. Chem. 12, 2887-2892 (2002); and Hou, Q. et al. Macromol. 37, 6299-6305 (2004)). The light-harvesting semiconducting polymer poly [{9,9-dioctyl-2,7-divinylene-fluorenylene}-alt-co-{2-methoxy-5-(2-ethylhexyloxy)-1,4-phenylene}] (PFPV, MW 220,000, polydispersity 3.1), and poly[(9,9-dioctylfluorenyl-2,7-diyl)-co-(1,4-benzo-{2,1',3}-thiadiazole)] (PFBT, MW 157,000, polydispersity 3.0) was purchased from ADS Dyes, Inc. (Quebec, Canada). The amphiphilic functional polymer poly(styrene-co-maleic anhydride) (PSMA, cumene terminated, average Mn ~1,700, styrene content 68%) was purchased from Sigma-Aldrich (St. Louis, Mo., USA)). All other reagents for PBdot preparation were purchased from Sigma-Aldrich (St. Louis, Mo., USA).

Functionalized PBdots in aqueous solution were prepared by using a modified nano-precipitation method (Wu, C., Peng, H., Jiang, Y. & McNeill, J. J. Phys. Chem. B 110, 14148-14154 (2006); and Wu, C., Bull, B., Szymanski, C., Christensen, K. & McNeill, J. ACS Nano 2, 2415-2423 (2008)). All experiments were performed at room temperature unless indicated otherwise. In a typical preparation, the light-harvesting polymer PFBT, red-emitting polymer PF-0.1TBT, and amphiphilic functional PSMA were first dissolved in tetrahydrofuran (THF) to make a 1 mg/mL stock solution, respectively. The three polymer solutions were diluted and mixed in THF to produce a solution mixture with a PFBT concentration of 50 µg/mL, a PF-0.1TBT concentration of 30 µg/mL, and a PSMA concentration of 20 µg/mL. The mixture was sonicated to form a homogeneous solution. A 5 mL quantity of the solution mixture was quickly added to 10 mL of MilliQ water in a vigorous bath sonicator. The THF was removed by nitrogen stripping. The solution was concentrated by continuous nitrogen stripping to 5 mL on a 90° C. hotplate followed by filtration through a 0.2 micron filter. During nanoparticle formation, the maleic anhydride units of PSMA molecules were hydrolyzed in the aqueous environment, generating carboxyl groups on PBdots. The PBdot dispersions were clear and stable for months without signs of aggregation.

Example 24: Surface Bioconjugation to Carboxyl Blended Polymer Dots (PBdots)

For biomolecular conjugation, tumor-specific peptide ligand chlorotoxin (CTX) was purchased from Alomone Labs, Ltd. (Jerusalem, Israel). Streptavidin was purchased from Invitrogen (Eugene, Oreg., USA). 1-ethyl-3-(3-dimethylaminopropyl)carbodiimide (EDC), and amine terminated polyethylene glycol(Methyl-$PEG_8$-$NH_2$) was purchased from Thermo Fisher Scientific (Rockford, Ill., U.S.A).

Bioconjugation was performed by utilizing the EDC-catalyzed reaction between carboxyl PBdots and the respective amine-containing biomolecules (Methyl-PEG$_8$-NH$_2$, chlorotoxin, and streptavidin). In a typical conjugation reaction, 60 µL of polyethylene glycol (5% w/v PEG, MW 3350) and 60 µL of concentrated HEPES buffer (1 M) were added to 3 mL of carboxyl PBdot solution (50 µg/mL in MilliQ water), resulting in a PBdot solution in 20 mM HEPES buffer with a pH of 7.3. Then, 30 µL of amine-containing molecules (1 mg/mL) was added to the solution and mixed well on a vortex. Last, 60 µL of freshly-prepared EDC solution (5 mg/mL in MilliQ water) was added to the solution, and the above mixture was magnetically stirred for 4 hours at room temperature. Finally, the resulting PBdot-CTX and PBdot-PEG conjugates were separated from free molecules by Bio-Rad EconoPac® 10DG columns (Hercules, Calif., USA). PBdot-streptavidin bioconjugates were separated by gel filtration using Sephacryl HR-300 gel media.

Example 25: Characterization of Blended Polymer Dots (PBdots)

Single-particle imaging was performed to carry out a side-by-side brightness comparison of the PBdot with the Qdot that emits at 655 nm, the brightest one of different colored Qdot probes. With a 488 nm laser excitation power so that Qdot 655 can be reasonably detected (FIG. 26b), the majority of PBdots actually saturated the detector under identical acquisition and laser conditions. Such a prominent contrast is attributed to the high molar extinction coefficient of PBdots (~3.0×10$^7$ cm$^{-1}$M$^{-1}$ at 488 nm for nanoparticles of ~15 nm diameter). To avoid detector saturation, a neutral density filter (optical density of 1, which blocks 90% of the emitted fluorescence) was placed together with the emission filter to obtain single-particle fluorescence images of PBdots (FIG. 26c). Thousands of particles are collected and their fluorescence intensities were back-calculated according to the attenuation factor. Fluorescence intensity distribution indicated that PBdot were ~15 times brighter than Qdot 655 nanocrystals (FIG. 26d), consistent with the brightness comparison based on the bulk spectra analysis. Fluorescence lifetime of PBdots was determined to be 3.5 ns by a TCSPC setup. It is worth noting that single PBdots contain multiple emitters, which results in photon emission rates that are higher than those predicted from fluorescence lifetime alone.

Example 26: Preparation and Characterization of Conjugated PBdots

Functionalized PBdots in aqueous solution were prepared by using a modified nano-precipitation method (Veiseh, O. et al., Cancer Res. 69, 6200-6207 (2009); and Choi, H. S. et al., Nature Biotechnol. 25, 1165-1170 (2007)). In a typical preparation, light-harvesting polymer PFBT, red-emitting polymer PF-0.1TBT, and functional polymer PSMA were dissolved in tetrahydrofuran (THF) to produce a solution mixture with PFBT concentration of 50 µg/mL, PF-0.1TBT concentration of 30 µg/mL, and PSMA concentration of 20 µg/mL. The mixture was sonicated to form a homogeneous solution. A 5 mL quantity of the solution mixture was quickly added to 10 mL of MilliQ water in a bath sonicator. The THF was removed by nitrogen stripping. The solution was concentrated by continuous nitrogen stripping to 5 mL on a 90° C. hotplate followed by filtration through a 0.2 micron filter.

Chlorotoxin (CTX), a 36-amino acid peptide, was selected as a tumor-targeting ligand because of its strong affinity for tumors of neuroectodermal origin. It has been shown that CTX specifically binds to glioma, medulloblastoma, prostate cancer, sarcoma, and intestinal cancer. First, the PBdots were functionalized by an amphiphilic polymer, poly(styrene-co-maleic anhydride) (PSMA). The hydrophobic polystyrene units of PSMA molecules were anchored inside the PBdot particles, while the maleic anhydride units localized to the PBdot surface and hydrolyzed in the aqueous environment to generate carboxyl groups. The carboxyl groups enabled surface conjugations by the standard carbodiimide chemistry (Hermanson, G. T. Bioconjugate Techniques (Academic Press, San Diego, 2008)).

Figure 29:
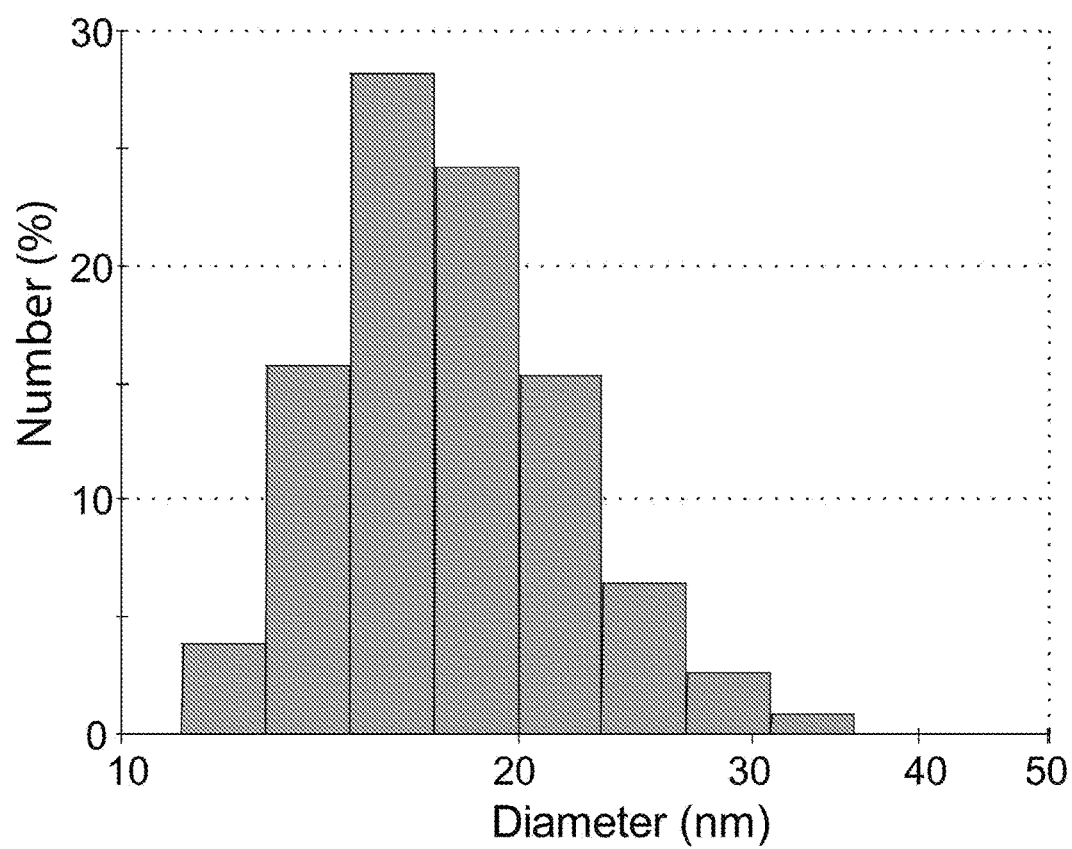
FIG. 29 Particle size distribution of PFBT co PFTBT PBdots measured by dynamic light scattering (Malvern Zetasizer NanoZS).

Besides CTX, polyethylene glycol (PEG) can be conjugated to reduce protein adsorption, limit immune recognition, and thereby increase the nanoparticle serum half-life in vivo. Streptavidin was also used in bioconjugation as a separate control to verify the conjugation strategy by specific cellular labeling. Transmission electron microscopy (TEM) showed that both the bare and the functionalized PBdots had comparable particle sizes (~15 nm in diameter) (FIG. 26d), consistent with the dynamic light scattering results (FIG. 29). After conjugation to different molecules (PEG, CTX, and streptavidin), gel electrophoresis showed shifted migration bands of the PBdot-conjugates in a 0.7% agarose gel due to the changes in surface charge and particle size. These results clearly show successful carboxyl functionalization and surface bioconjugations.

Surface bioconjugation was performed by utilizing the EDC-catalyzed reaction between carboxyl Pdots and the respective amine-containing biomolecules (chlorotoxin, Methyl-PEG$_8$-NH$_2$, or strepavidin). In a typical conjugation reaction, 60 µL of polyethylene glycol (5% w/v PEG, MW 3350) and 60 µL of concentrated HEPES buffer (1 M) were added to 3 mL of carboxyl PBdot solution (50 µg/mL in MilliQ water), resulting in a Pdot solution in 20 mM HEPES buffer with a pH of 7.3. Then, 30 µL of amine-containing biomolecules (1 mg/mL) was added to the solution and mixed well on a vortex. Last, 60 µL of freshly-prepared EDC solution (5 mg/mL in MilliQ water) was added to the solution, and the above mixture was magnetically stirred for 4 hours at room temperature. Finally, the resulting PBdot-CTX and PBdot-PEG conjugates were separated from free molecules by Bio-Rad Econo-Pac® 10DG columns (Hercules, Calif., USA). PBdot-streptavidin bioconjugates were separated by gel filtration using Sephacryl HR-300 gel media.

Figure 30:
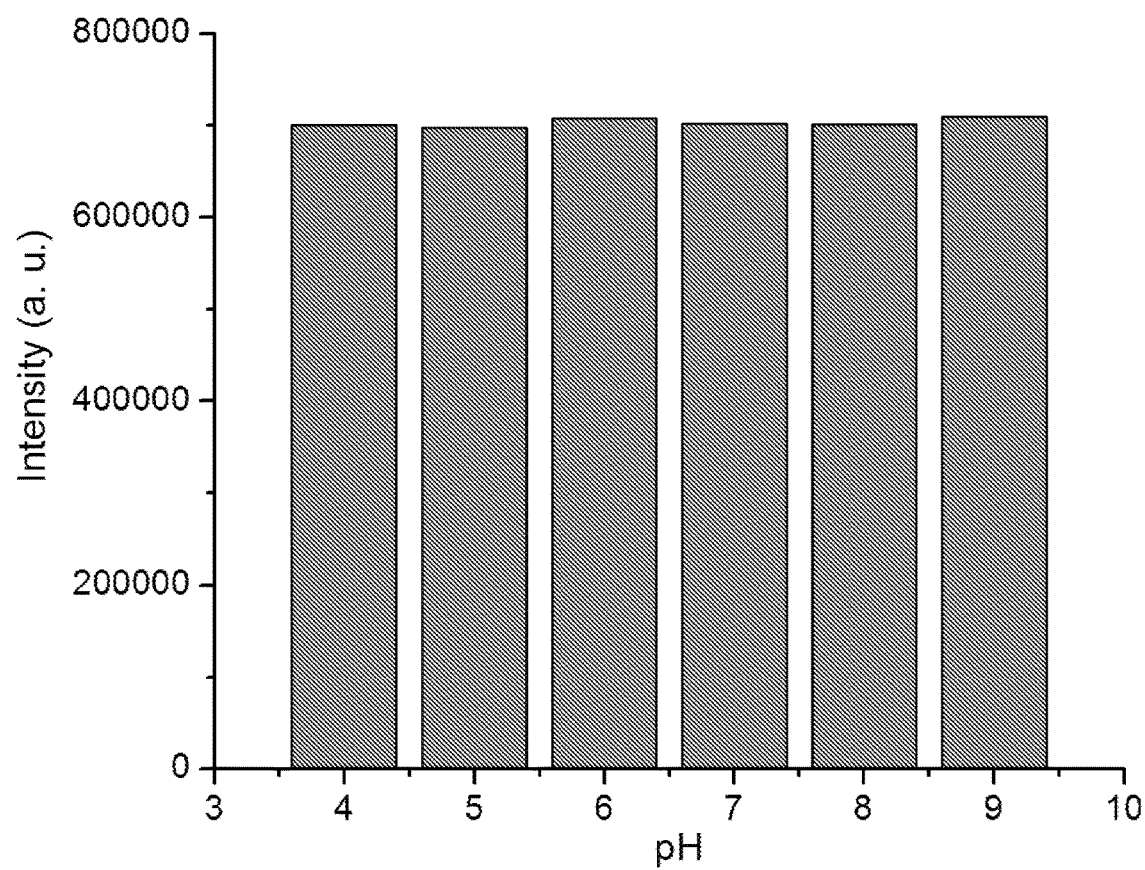
FIG. 30 Fluorescence intensity of PFBT co PFTBT PBdots in HEPES buffer with pH ranging from 4 to 9. No obvious change was observed.
Figure 31:
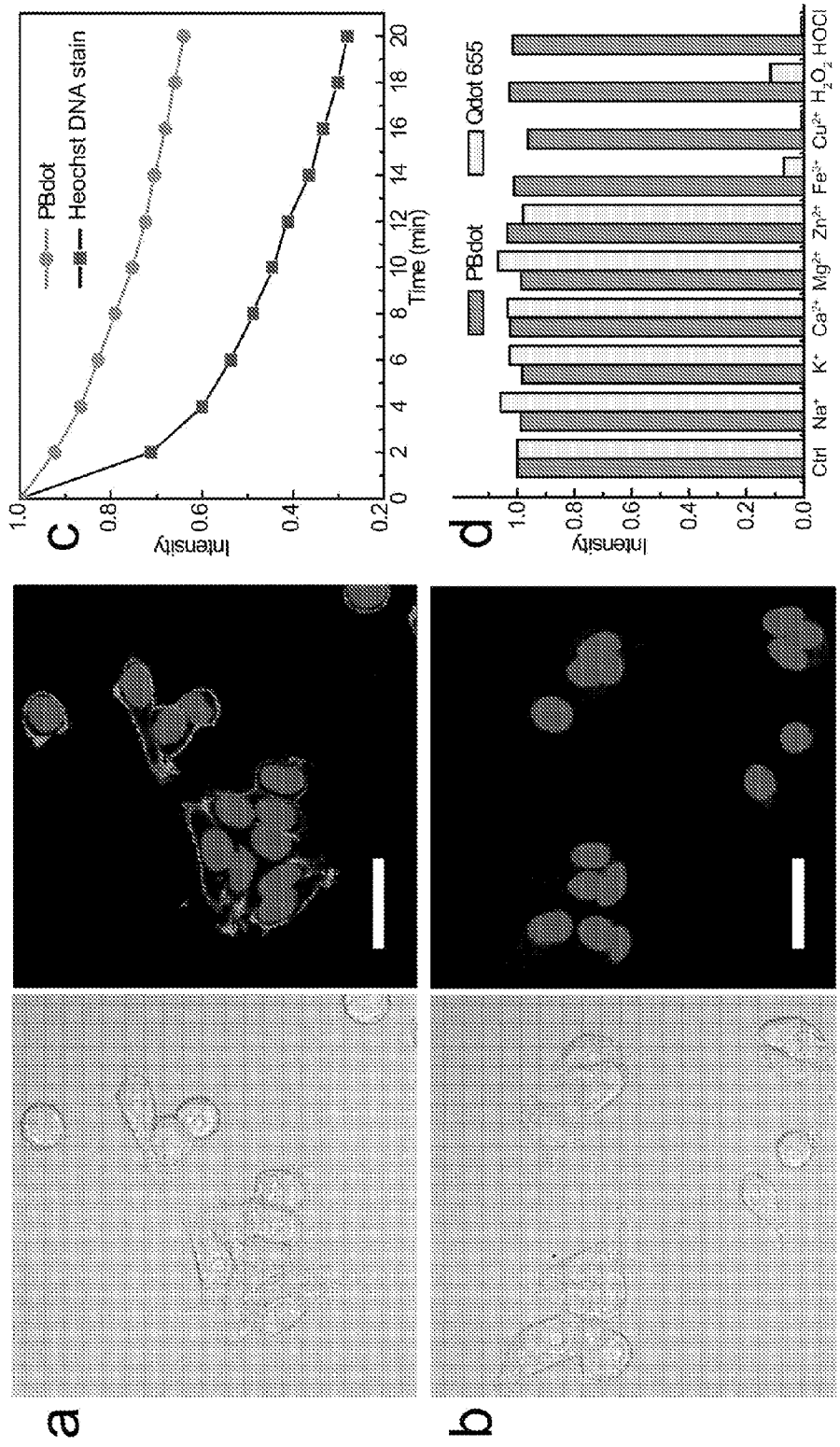
FIG. 31(a) Confocal imaging of live MCF-7 cells incubated sequentially with anti-EpCAM primary antibody, biotinylated goat anti-mouse IgG secondary antibody, and PBdot-streptavidin conjugates. (b) Negative control for PBdot cell labeling where no biotinylated secondary antibody was used. For both a and b are shown phase contrast images (left) and the combined fluorescence images (right). Red fluorescence is from PBdots and blue fluorescence is from the nuclear stain Hoechst 34580. Scale bar, 40 µm. (c) Photobleaching curves extracted from confocal fluorescence images obtained under continuous laser scanning for 20 minutes. (d) Fluorescence stability of PBdots towards biologically relevant ions and ROS in MilliQ water. Qdot 655 nanocrystals were shown for a reference. The concentration for each metal ion is 500 µM. For ROS stability test, the $H_2O_2$ and chlorine concentration is $1\times10^{-3}$, and $4\times10^{-5}$, respectively. To prevent aggregation, the solution contained PEG.

The long-term fate and in vivo stability are of both fundamental and clinical significance for designing in vivo probes. The integrity of nanoprobes is primarily dependent on their chemical reactivity towards ionic species and reactive oxygen species (ROS) in biological environment. For example, Qdots undergo severe chemical degradation due to copper ions and ROS at physiological concentrations, which cause the loss of luminescence and release of toxic Cd ions. The sensitivity of PBdots to pH, biologically relevant ions, and ROS was examined. PBdots showed constant fluorescence in physiological pH range from 4 to 9 (FIG. 30). The fluorescence of PBdots was also not affected by any biologically relevant ions under test (FIG. 31), including iron, zinc, and copper, three of the most abundant ions in biological organisms. Furthermore, the two common and stable ROS in physiological environment, hypochlorous acid (HOCl) and hydrogen peroxide (H$_2$O$_2$), do not show any effect on the fluorescence of PBdots. In contrast, the streptavidin-conjugated, polymer-encapsulated Qdot 655 probes are significantly quenched by $H_2O_2$ and iron ions, and completely quenched by HOCl and copper ions, with the same concentrations as used for PBdots. The stable fluorescence of PBdots can be attributed to their hydrophobic organic polymeric nature, which tends not to have chemical interactions with the metal ions and ROS. This property provides a significant advantage for using PBdots as in vivo probes.

Example 27: Detection of $Cu^{2+}$ and $Fe^{2+}$ Ions by Functionalized Pdots

Typically, 40 μg of PFBT and 8 μg of PSMA were dissolved into 5 mL of THF. This mixture was then quickly injected into 10 mL of water under vigorous sonication. The THF was then removed by purging with nitrogen on a 96° C. hotplate for one hour. The resulting Pdot solution was filtered through a 0.2 μm cellulose acetate membrane filter to remove any aggregates formed during preparation.

Figure 32:
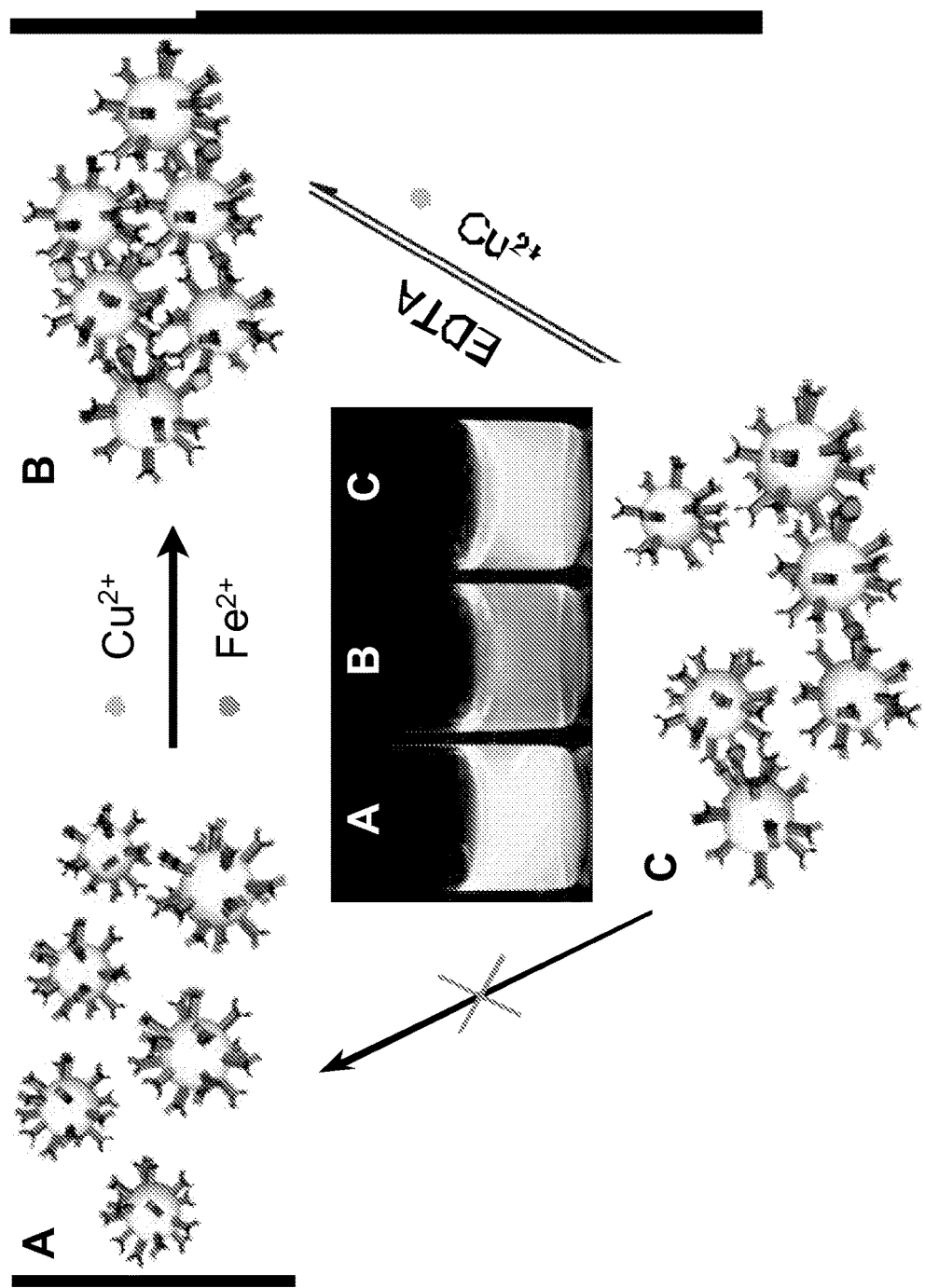
FIG. 32 Schematic showing the sensing of $Cu^{2+}$ and $Fe^{2+}$ using PS-COOH functionalized PFBT Pdots. The PFBT Pdots were first functionalized with PS-COOH, which served as a chelating group (A). The aggregation and quenching of Pdots was induced by adding $Cu^{2+}$ and/or $Fe^{2+}$ (B). The $Cu^{2+}$-induced aggregation could be reversed by introducing EDTA into solution, while the aggregation of Pdots resulting from binding to $Fe^{2+}$ could not be redispersed (C). The inset in the center shows photographs of each corresponding solution under a 365 nm lamp.

A highly fluorescent semiconducting polymer, poly[9,9-dioctylfluorenyl-2,7-diyl)-co-1,4-benzo-{2,1'-3}-thiadiazole)] (PFBT) was employed and the PSMA polymer (20%) was added into the PFBT matrix to form the PS-COOH co PFBT Pdots. The carboxyl groups on the Pdot surface were produced by the hydrolysis of the maleic anhydride units while the polystyrene portions tended to anchor inside the hydrophobic core of the PFBT polymer. These Pdots dispersed well in aqueous solutions and the carboxyl moieties served as selective coordination groups for metal ions without further modification. The fluorescence of the carboxyl-functionalized PFBT Pdots were found to be quenched selectively by $Cu^{2+}$ and $Fe^{2+}$ ions (FIG. 32).

Several different types of polymers, including PFBT and poly[(4-(5-(7-methyl-9,9-dioctyl-9H-fluoren-2-yl)thiophen-2-yl)-7-(5-methylthiophen-2 yl)benzo[c][1,2,5]thiadiazole)] (PFTBT) Pdots (without being blended with PSMA), exhibited excellent stability (no aggregation and quenching) toward various ions in buffer solution (vide infra), which demonstrates that unfunctionalized Pdots can serve as a good control in these methods.

Figures 33A, 33B:
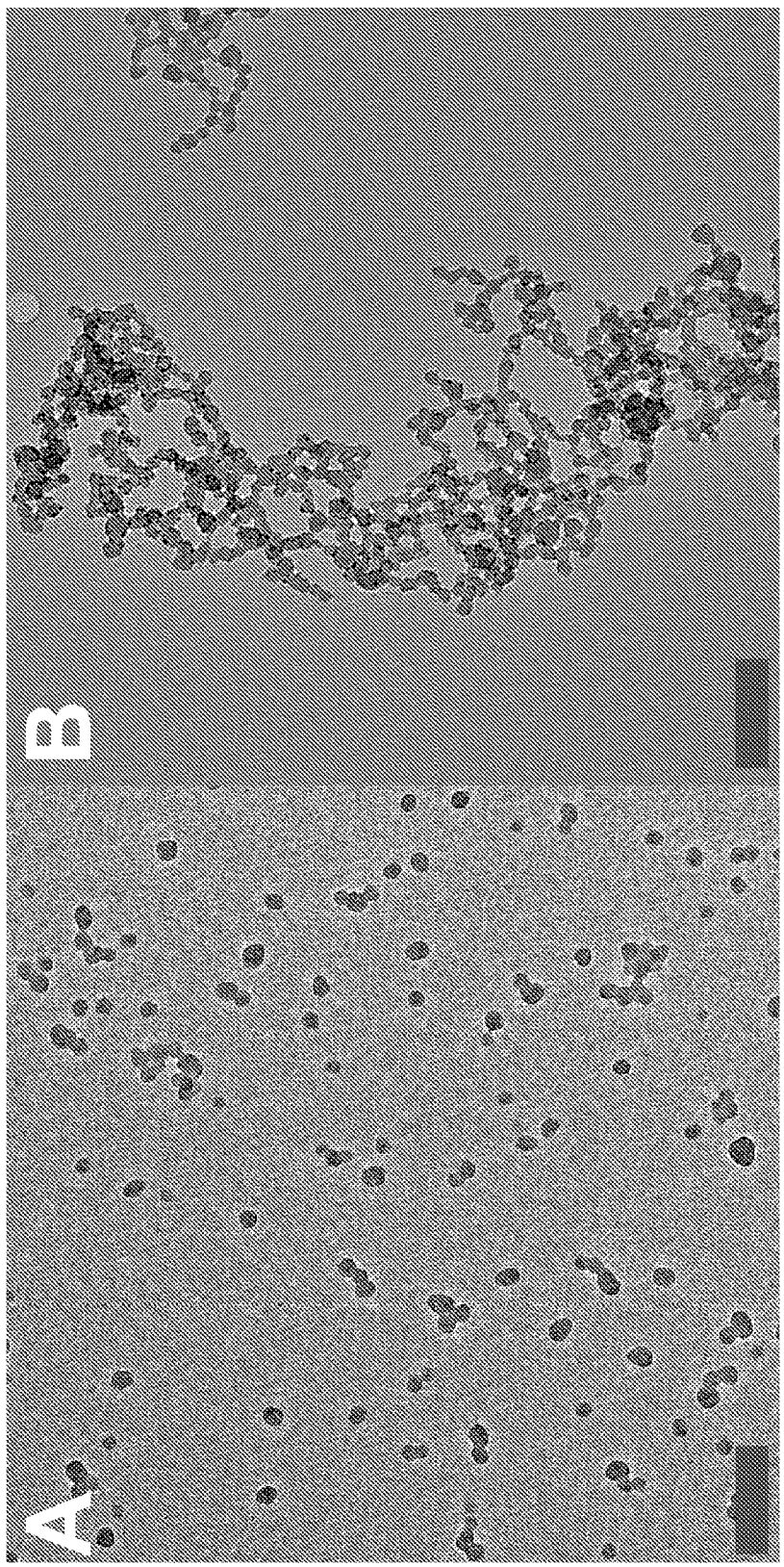
FIG. 33 TEM images of PS-COOH co PFBT Pdots before (A) and after (B) the addition of $Cu^{2+}$, which illustrate $Cu^{2+}$ induced aggregation of the carboxyl functionalized Pdots. The scale bars are 200 nm (C) Dynamic light scattering measurements of Pdots before and after addition of $Cu^{2+}$, as well as after addition of EDTA. Hydrodynamic diameter of PFBT co PS-COOH Pdots measured by DLS in water (grey) and in $Cu^{2+}$ containing solution (black), as well as after the addition of EDTA to the $Cu^{2+}$ containing solution (black).
Figure 33C:
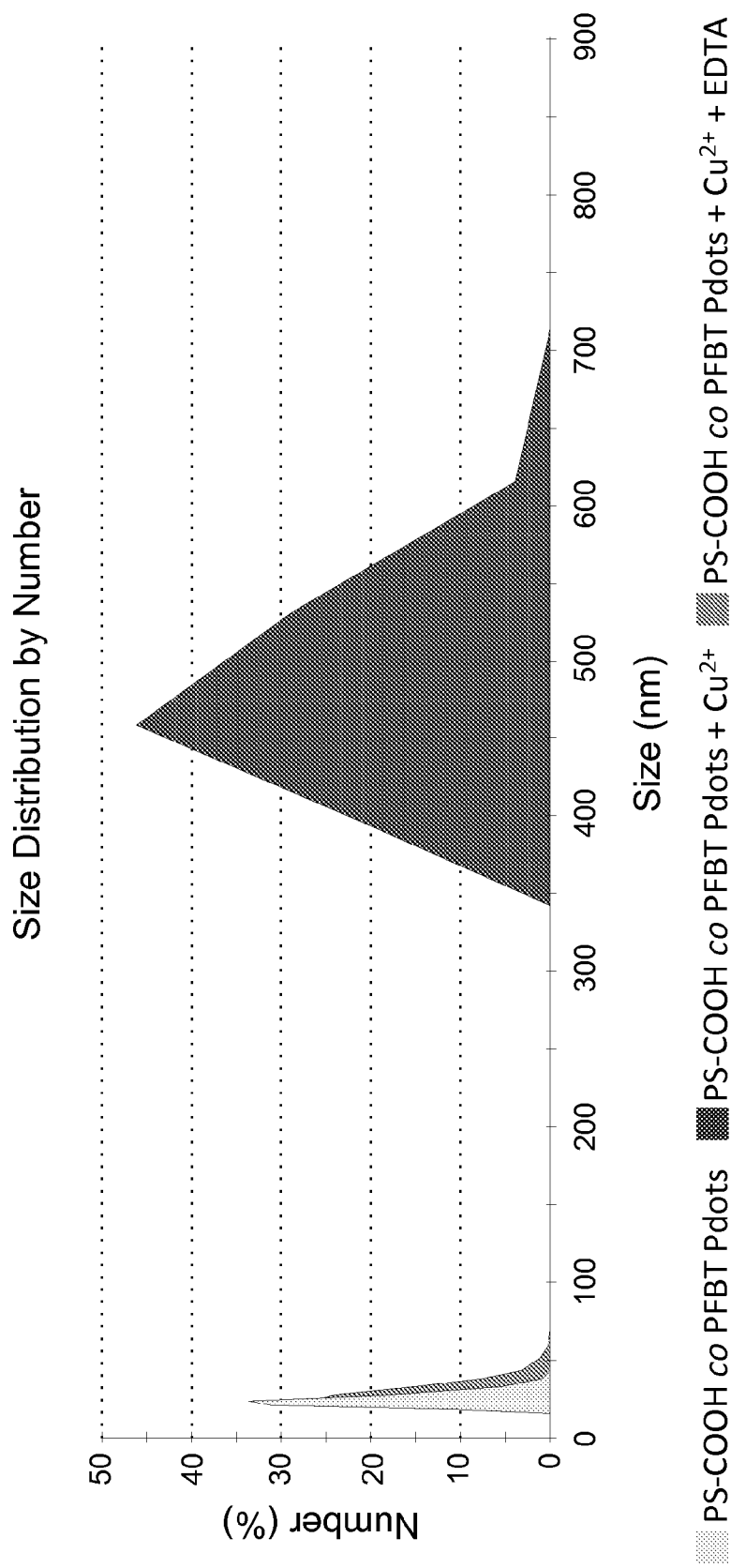

The aggregation and self-quenching behavior of Pdots was attributed to the chelating interactions between the PS-COOH groups on the surface of Pdots with $Cu^{2+}$ and $Fe^{2+}$ in solution. We note we did not add PEG into the solution in the experiments described in this example, because PEG can prevent the aggregation and self-quenching behavior of Pdots. This phenomenon is clearly revealed by transmission electron microscopy (TEM) measurements taken before and after the addition of $Cu^{2+}$ (FIGS. 33A and B). Dynamic light scattering (DLS) measurements also showed that the diameter of the as-prepared Pdots was ~21 nm on average before the addition of $Cu^{2+}$, but increased to ~500 nm after the addition of $Cu^{2+}$ (FIG. 33C).

Figure 34:
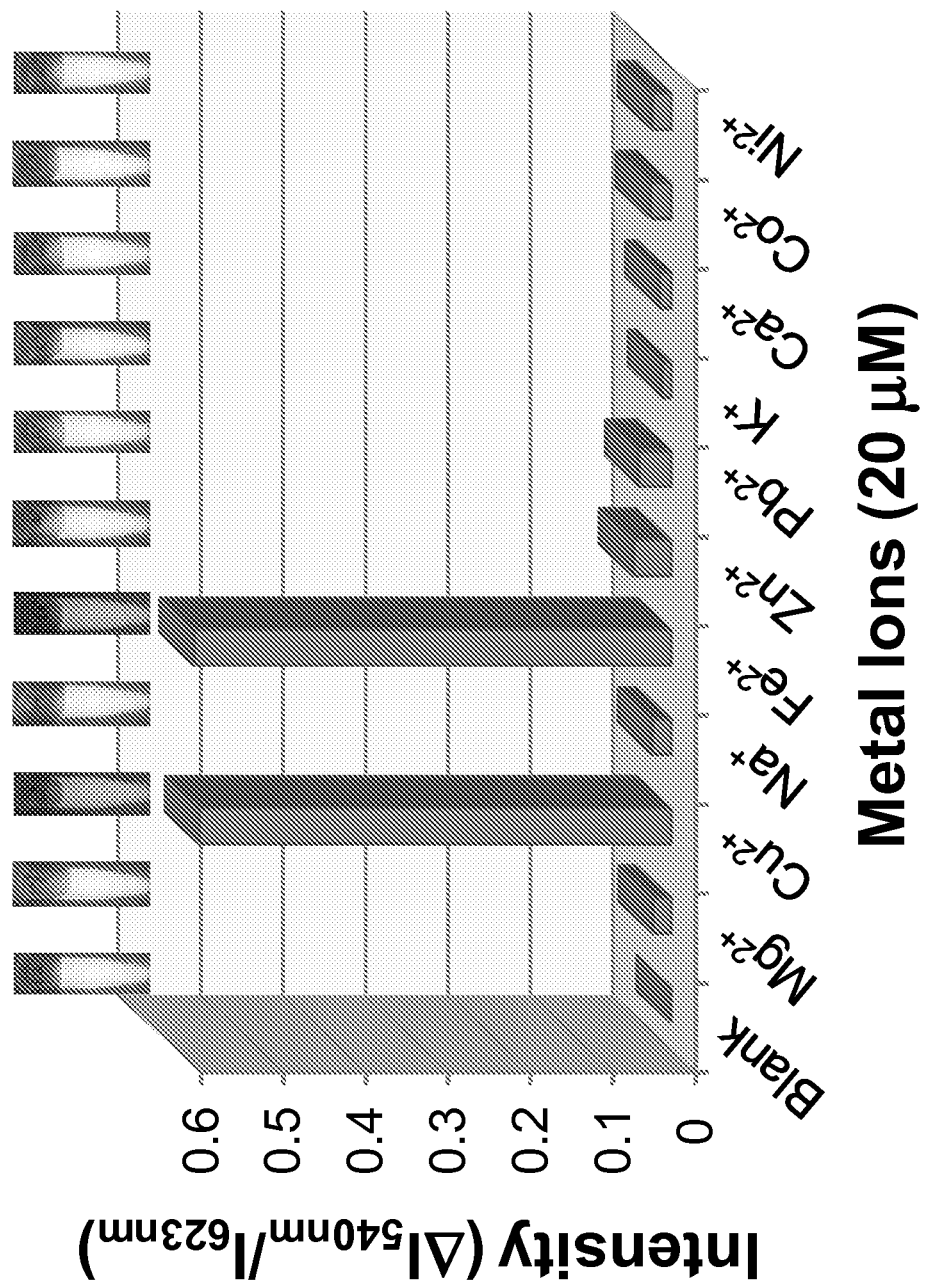
FIG. 34 Effects of different ions (20 μM) on the fluorescence intensity of solutions containing PS-COOH co PFBT Pdots and PFBT co PFTBT Pdots. Images on the top show each sample under a 365 nm lamp.

The effect of various other physiologically important cations on the fluorescence of PS-COOH co PFBT Pdots was also investigated. It was found that their emission intensity was unaffected or minimally affected by other cations, as compared with the emission intensity of PS-COOH co PFBT Pdots in pure water ($I_{blank}$) (FIG. 34).

In this study, non-functionalized PFBT co PFTBT Pdots were used as an internal standard. While PS-COOH co PFBT Pdots emit at 540 nm when excited at wavelengths below 490 nm, PFBT co PFTBT Pdots emit at 623 nm when excited at the same wavelengths. This shift in emission wavelength is caused by the efficient energy transfer from PFBT to PFTBT and subsequent emission from PFTBT. The use of PFBT co PFTBT Pdots as an internal standard allowed the application of ratiometric ion determination based on two fluorescence emission intensities (540 nm/623 nm), thereby eliminating any interference from the environment or drift in the instrument.

Figure 35:
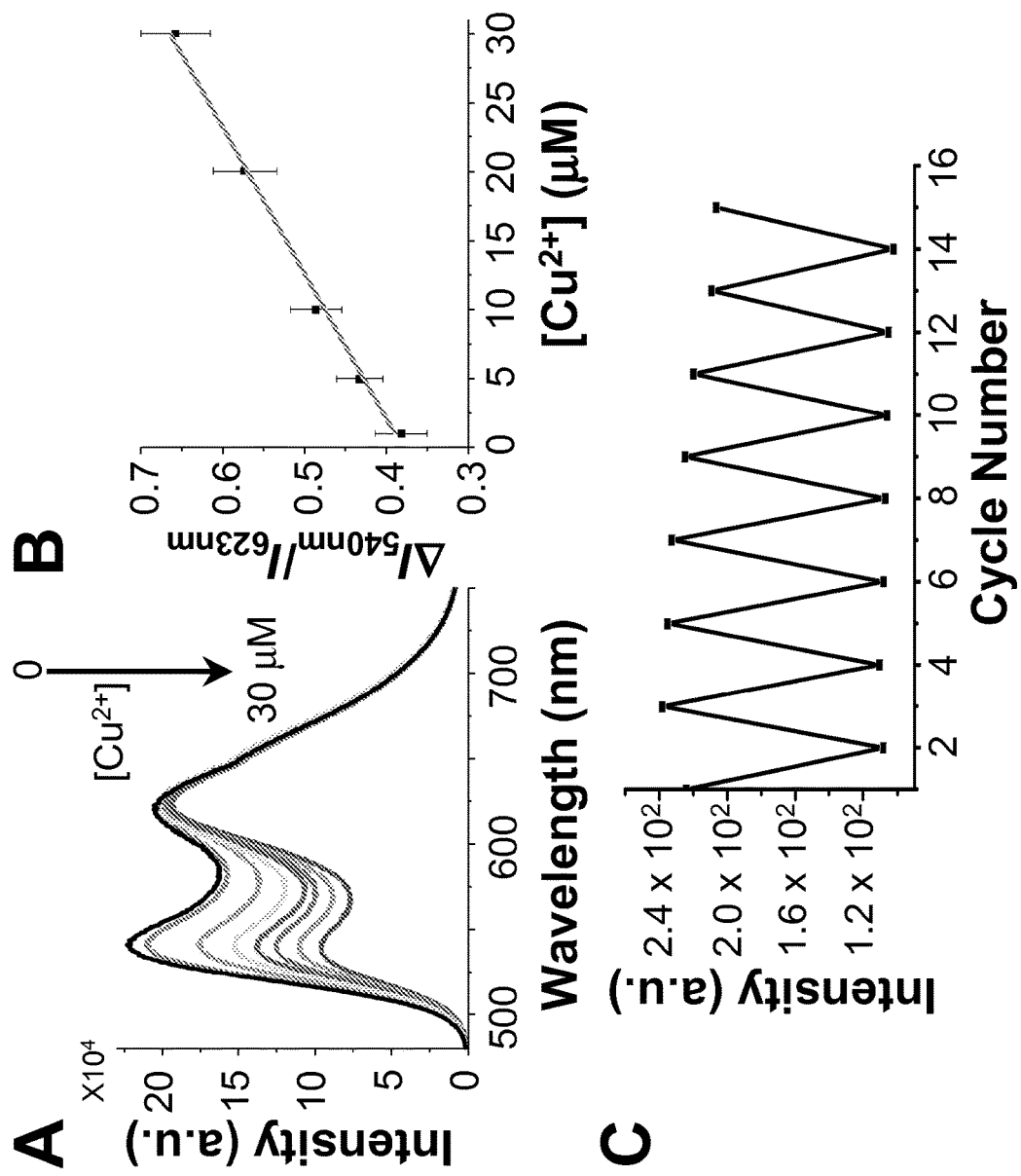
FIG. 35(A) Effect of various concentrations of $Cu^{2+}$ ions on the fluorescence of solutions containing PS-COOH co PFBT Pdots and PFBT co PFTBT Pdots. Concentrations of $Cu^{2+}$ ranged from 0 to 30 μM: black line: 0, red line: 100 nM, pink line: 500 nM, gold line: 1 μM, plum line: 5 μM, green line: 10 μM, orange line: 20 μM, blue line: 30 μM. (B) A plot of the ratio of the 540 nm peak (from PS-COOH co PFBT Pdots) over the 623 nm peak (from PFBT co PFTBT Pdots) as a function of the $Cu^{2+}$ concentration. The red line is a linear fit to the data ($R^2$=0.992). (C) The fluorescence intensity of Pdots after quenching by $Cu^{2+}$ ions (30 μM) can be recovered by the addition of 30 μM EDTA.

FIG. 35A shows the emission spectra of solutions containing PS-COOH co PFBT Pdots and PFBT co PFTBT Pdots as a function of $Cu^{2+}$ concentration. It is evident that while the emission intensity of the PFTBT containing Pdots (623 nm) remained constant, the PS-COOH containing Pdots decreased their intensity (540 nm) with increasing $Cu^{2+}$ concentrations up to 30 μM. No further decrease in fluorescence intensity was observed for concentrations above 30 μM, indicating that all of the carboxyl groups have already been occupied by copper ions. For this set of experiments, the relative standard deviation of blank signal from 10 replicates was 1.1%. A quenching signal of ~6% could be observed at 100 nM of copper ions. FIG. 35B shows a linear correlation between the ratio of $\Delta I_{540\ nm}/I_{623\ nm}$ and $Cu^{2+}$ concentration, which ranged from 1 μM to 30 μM ($R^2$=0.992).

Because the aggregation-induced fluorescence quenching was caused by the formation of 2:1 sandwich complexes between carboxyl moieties on the Pdot surface and $Cu^{2+}$, one might expect that a strong copper ion chelator, ethylenediaminetetraacetic acid (EDTA), might be able to prevail over carboxyl groups and thus redisperse the aggregation. To test this hypothesis, the same molar amount of EDTA as $Cu^{2+}$ ions was added into the aggregated Pdot solution and found that the fluorescence intensity of PS-COOH co PFBT Pdots was completely restored (FIG. 35C).

Moreover, the addition of excessive amounts of EDTA into the solution did not lead to any further increases in emission intensity, which suggests that no additional copper ion could be chelated by EDTA. The DLS experiments also verified that the aggregated Pdots were redispersed after the addition of EDTA (FIG. 33C).

Notably, this process could be repeated many times with minimal relative signal loss, which indicates that this protocol could be reused for many cycles rather than just as a one-time-use assay. This reversibility was not observed on quantum dot-based (e.g. CdSe) $Cu^{2+}$ sensors due to the non-reversible cation-exchange processes between $Cu^{2+}$ and $Cd^{2+}$ (Y.-H. Chan Y. H. et al., Anal. Chem., 2010, 82, 3671-3678; and Sadtler B. et al., J. Am. Chem. Soc., 2009, 131, 5285-5293). It is worth noting that the response time for both the aggregation and redispersion of Pdots was very short (less than 1 min) and the fluorescence intensity remained unchanged for several days after reaction.

Figure 36:
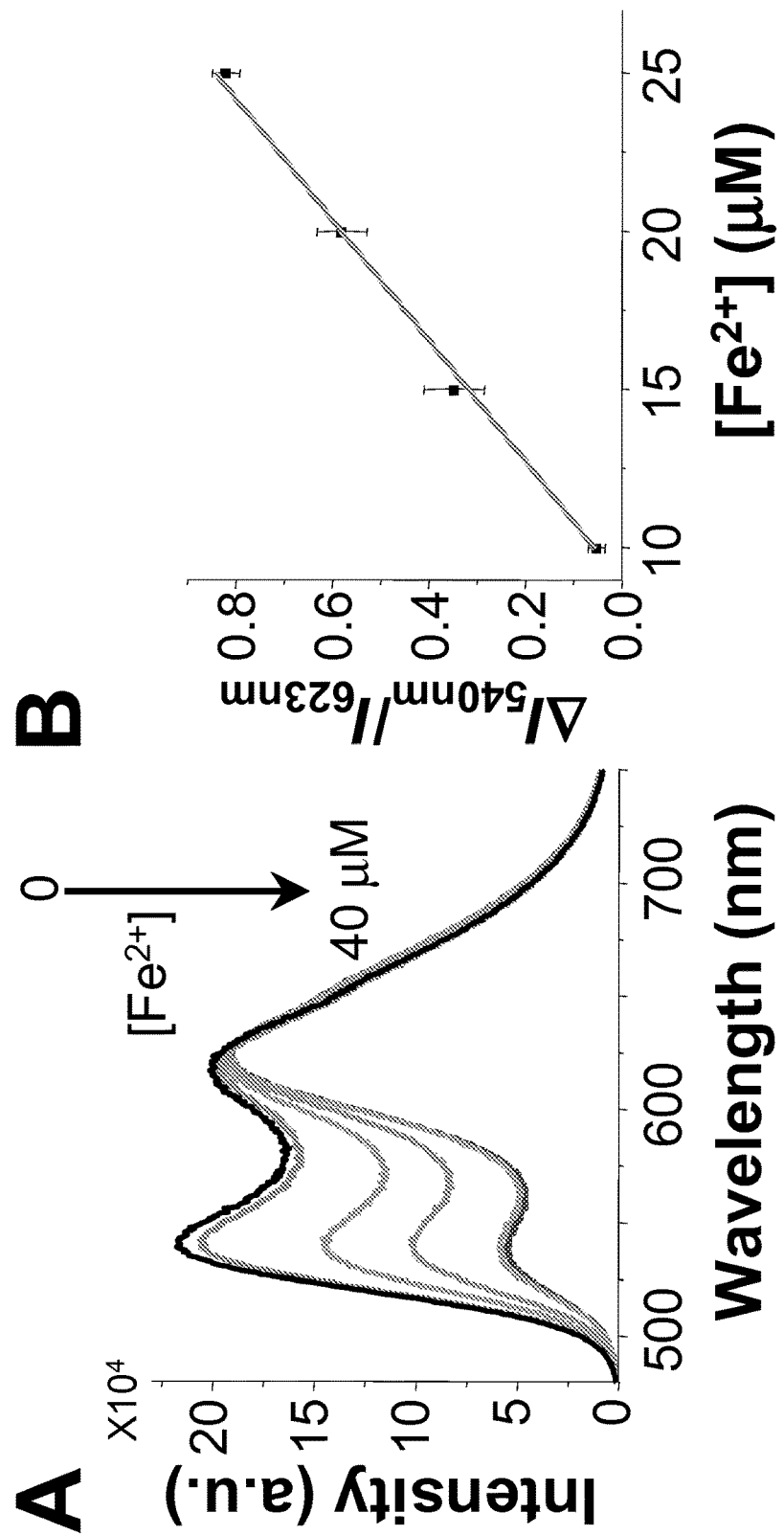
FIG. 36(A) Effect of various concentrations of $Fe^{2+}$ on the fluorescence of PS-COOH co PFBT Pdots at 540 nm; the solution also contained PFBT co PFTBT Pdots (emission centered at 623 nm) as an internal standard. Concentration of $Fe^{2+}$ from 0 to 40 μM: black line: 0, red line: 10 μM, green line: 15 μM, pink line: 20 μM, orange line: 25 μM, blue line: 40 μM. (B) A plot of the ratio of the 540 nm peak (from PS-COOH co PFBT Pdots) over the 623 nm peak (from PFBT co PFTBT Pdots) as a function of the Fe2+ concentrations. The red line is a linear fit to the data ($R^2$=0.996).

The aggregation and self-quenching phenomenon could be observed also for $Fe^{2+}$ sensing with a dynamic range from 10 to 25 μM as shown in FIG. 36 ($R^2$=0.996). The fluorescence intensity of PS-COOH co PFBT Pdots was quenched significantly (by as much as 70%) by $Fe^{2+}$, but this quenching could not be reversed by adding EDTA, which is likely due to the much lower binding constant of EDTA for $Fe^{2+}$ than for $Cu^{2+}$.

We also adjusted the pH value of the Pdot-$Fe^{2+}$ mixture in an effort to protonate the carboxyl groups, and then added excessive amounts of EDTA into the solution. However, no substantial emission intensity (less than 10%) could be recovered even at pH=1. Besides, these Pdots are prone to aggregation at pH below 2. Therefore, the selective recovery of fluorescence, by addition of EDTA, from $Cu^{2+}$-induced self-quenching allowed us to differentiate between copper and iron sensing and to determine their concentrations individually.

Example 28: Simultaneous Detection of Cu2+ and Fe2+ Ions by Functionalized Pdots To demonstrate the application of the detection method outlined in Example 26, cell-culture media was selected because it simulates complex physiological fluids and at the same time also serves as a well controlled solution. Here, the test samples were prepared by spiking 10 µM and 15 µM of copper and iron ions, respectively, into Dulbecco's Modified Eagle Medium (DMEM D-5921) solutions containing the Pdot sensors. Then EDTA was added into the solution so that the concentration of $Cu^{2+}$ could be calculated from the restored emission intensity of Pdots. We then estimated the $Fe^{2+}$ concentration by comparing to the $I_{blank}$. This measurement showed that the concentrations of copper and iron were 10.17±1.34 µM and 16.16±1.82 µM, respectively, which exhibited good accordance with the spiking values. This experiment demonstrates the feasibility of using this Pdot-based sensing system for copper and iron detection in complex samples.

Example 29: Functionalized Chromophoric Polymer Dots with Near Infrared Fluorescence This example provides a demonstration that near infrared (NIR) dyes can be doped into the functionalized chromophoric polymer dot (CPdot or Pdot) to tune the fluorescence properties of the chromophoric polymer dot bioconjugate. We use below CPdots or Pdots interchangeably to describe chromophoric polymer dots.

Preparation and characterization of NIR dye-doped CPdots. In a typical procedure, a THF solution containing 50 µg/mL of PFBT, 50 µg/mL of PS-PEG-COOH, and 0.2 µg/mL of a NIR dye, silicon 2,3-naphthalocyanine bis(trihexylsilyloxide) (NIR775) was prepared. A 5 mL aliquot of the mixture was then quickly dispersed into 10 mL of water under vigorous sonication. The extra THF was evaporated at an elevated temperature (lower than 100° C.) with the protection of nitrogen gas. The THF-free CPdot solution was filtrated through a 0.2 µm cellulose membrane filter and adjusted to the appropriate concentration. The size and the morphology of the CPdots were investigated using a transmission electron microscope (PEI Tecnai F20, 200 kV). The size of the CPdots was also measured in aqueous solution using a dynamic light scattering instrument (Malvern Zetasizer NanoZS). UV-Vis absorption spectra of CPdots and NIR dyes were recorded with a DU 720 scanning spectrophotometer (Beckman Coulter, Inc., Calif. USA) in water. The carboxyl surface of CPdots was verified by testing the Zeta potential using Malvern Zetasizer NanoZS. CPdots with and without carboxyl surface were both tested in a gel electrophoresis experiment. The gel was prepared using 0.7% of normal melting agarose, 0.2% of PEG (MW 3350) and 20 mM HEPES buffer. The CPdot samples were loaded to electrophoresis channels with the help of 30% glycerol, and run in 20 mM HEPES buffer (pH 7.4) under an electrophoresis force of 10 V/cm for 15 min using a Mupid®-exU submarine electrophoresis system. The gel was then developed using a Kodak image station 440CF system. Fluorescence spectra of CPdots and NIR dyes were measured using a Fluorolog-3 fluorospectrometer (HORIBA Jobin Yvon, N.J. USA). Fluorescence lifetime data of NIR dye-doped CPdots and PFBT dots were obtained using a time-correlated single-photon counting instrument (TC-SPC). Fluorescence quantum yields of PFBT dots and NIR dye-doped CPdots were collected by an integrating sphere (Model C9920-02, Hamamatsu Photonics) with a 457 nm excitation from a 150W CW Xenon lamp.

Figure 37:
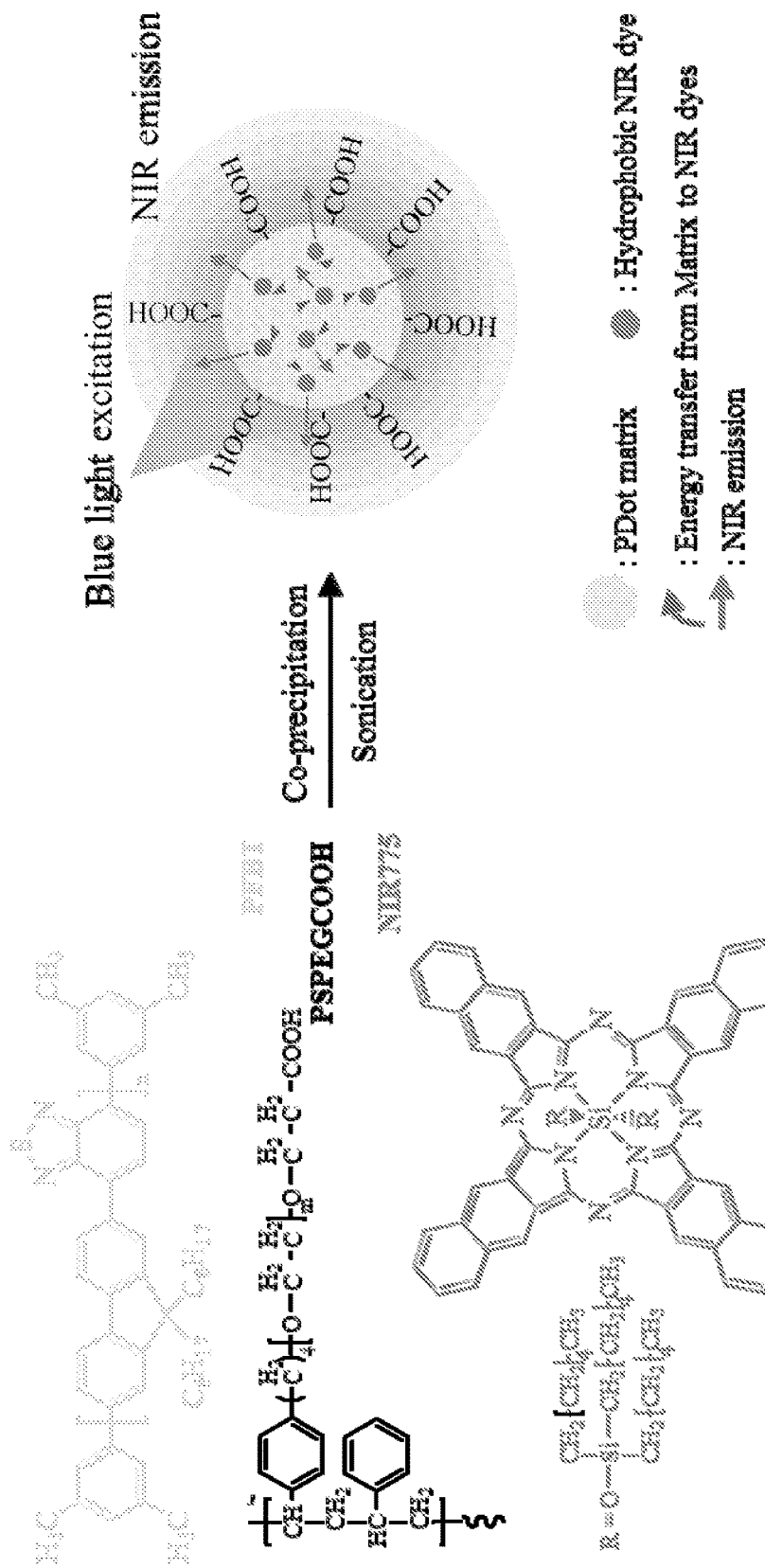
FIG. 37 Preparation of near-IR (NIR) dye-doped and functionalized CPdots (interchangeably called Pdots). Chromophoric polymer PFBT, amphiphilic polymer PS-PEG-COOH, and NIR dyes were mixed together in THF and co-precipitated in water under sonication to form NIR dye-doped Pdots. The Pdot matrix can absorb blue light and transfer the energy to the doped NIR dyes (indicated by green arrows), which then generate strong NIR fluorescence (indicated by red arrows).

Functionalized CPdots with NIR emission. We formulated the NIR dye-doped CPdots using three components of different functions: green semiconducting polymer (PFBT), NIR dye (NIR775), and amphiphilic polymer (PSPEG-COOH) (FIG. 37). As the essential part of CPdots, the semiconducting polymer formed the hydrophobic matrix of Pdot and served as a host for the NIR dyes. NIR775 dyes are highly fluorescent in hydrophobic solvents while they are significantly less so in physiological environments due to self-aggregation. The aggregation was avoided or significantly reduced when these dyes were doped inside Pdot matrices. Inside the CPdots, the NIR dyes serve as an acceptor receiving energy from the semiconducting polymer matrix, and generate strong NIR fluorescence. For the purpose of fluorescence imaging, the surface of CPdots was modified with carboxyl groups using amphiphilic polymer, PS-PEG-COOH. Here, the hydrophobic part of the polymer entangled with Pdot matrix and the hydrophilic part stretched out into the physiological environment. The NIR dye-doped CPdots were synthesized using the nano-precipitation method because of its simplicity and high efficiency for Pdot fabrication and hydrophobic dye doping (FIG. 37). All the components of CPdots were first dissolved and mixed in anhydrous THF, and then quickly precipitated in water under sonication. The sudden change of solvent environment and the strong sonicating force produced a nanometer-sized semiconducting polymer particle and simultaneously trapped the hydrophobic NIR dye (NIR775) in the CPdot matrix. The carboxylate surface was also generated as the amphiphilic polymer assembled at the interface of CPdots and water.

Figure 38:
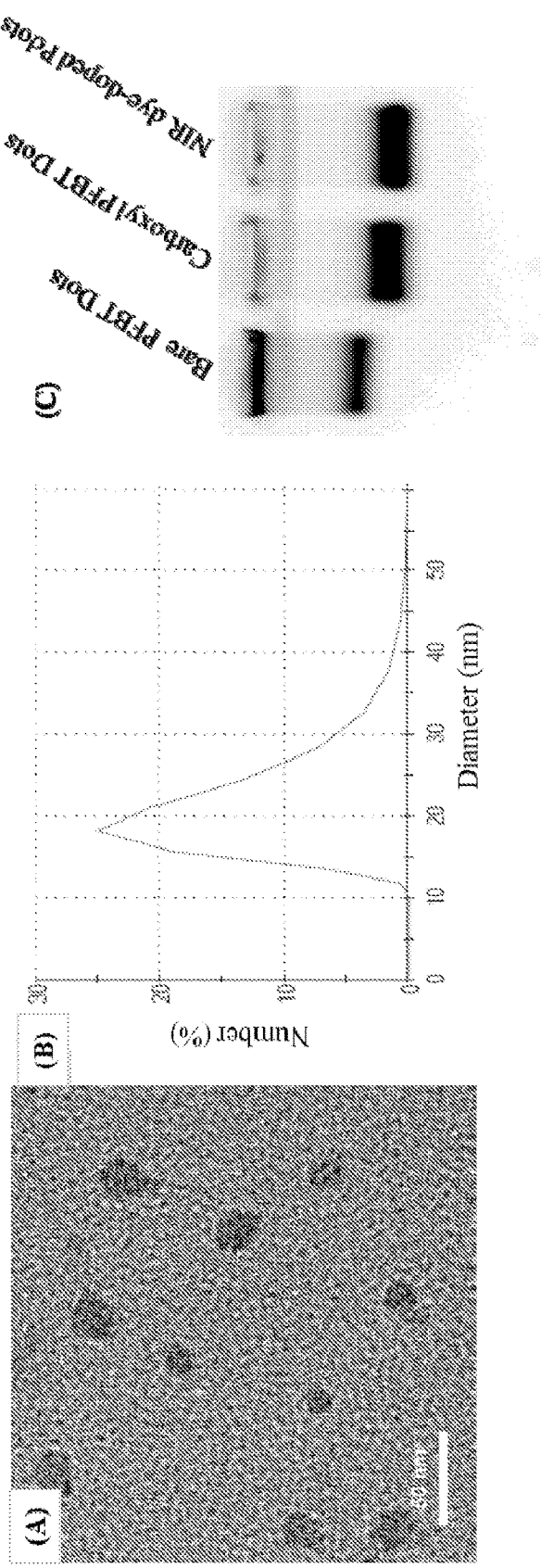
FIG. 38 Characterization of NIR dye-doped and functionalized CPdots (interchangeably called Pdots). (A) TEM image of NIR dye-doped Pdots. The diameter of the CPdots was 18 nm. Scale bar: 50 nm. (B) Number average diameter of NIR dye-doped CPdots measured by DLS. (C) Agarose gel electrophoresis. Bare PFBT dots, Carboxyl PFBT dots and NIR dye-doped CPdots were loaded in an agarose gel containing 0.7% of agarose and 0.2% of PEG, and run at a force of 10 V/cm in 20 mM HEPES for 15 min. Bare PFBT dots run slower due to lacking of carboxyl surface. Carboxyl PFBT dots and NIR dye-doped CPdots both contain carboxyl groups on their surfaces and run faster.

Both the TEM image and the DLS results show that the NIR dye-doped CPdots were monodispersed particles with an average diameter of 18 nm (FIGS. 38A and 38B). In these particles, NIR dyes were successfully encapsulated as proven by the following experiments. First, the Pdot solution was filtrated using a 100K molecular weight cutoff centrifugal membrane, which only allows free NIR dyes to pass through but not the doped ones. The filtrate did not contain NIR dye as monitored by UV-Vis spectrometer, while the absorbance of NIR dye was observed in the solution of the NIR dye-doped CPdots after the filtration. This result shows NIR dyes were completely doped in the CPdots. The surface of CPdots was functionalized with carboxylate groups using the amphiphilic polymer PSPEG-COOH. This surface functionalization significantly decreased the zeta potential of the CPdots from −35.4 mV (bare PFBT Dots) to −46.0 mV (CPdots of PS-PEG-COOH coating). Gel electrophoresis also showed the carboxylate CPdots moved much faster than the bare PFBT Dots of similar size towards the positive electrode (FIG. 38C). The NIR doping did not affect the surface potential of the carboxylate CPdots, which suggested that NIR dyes were only located inside the CPdots but not on the surface.

Figure 39:
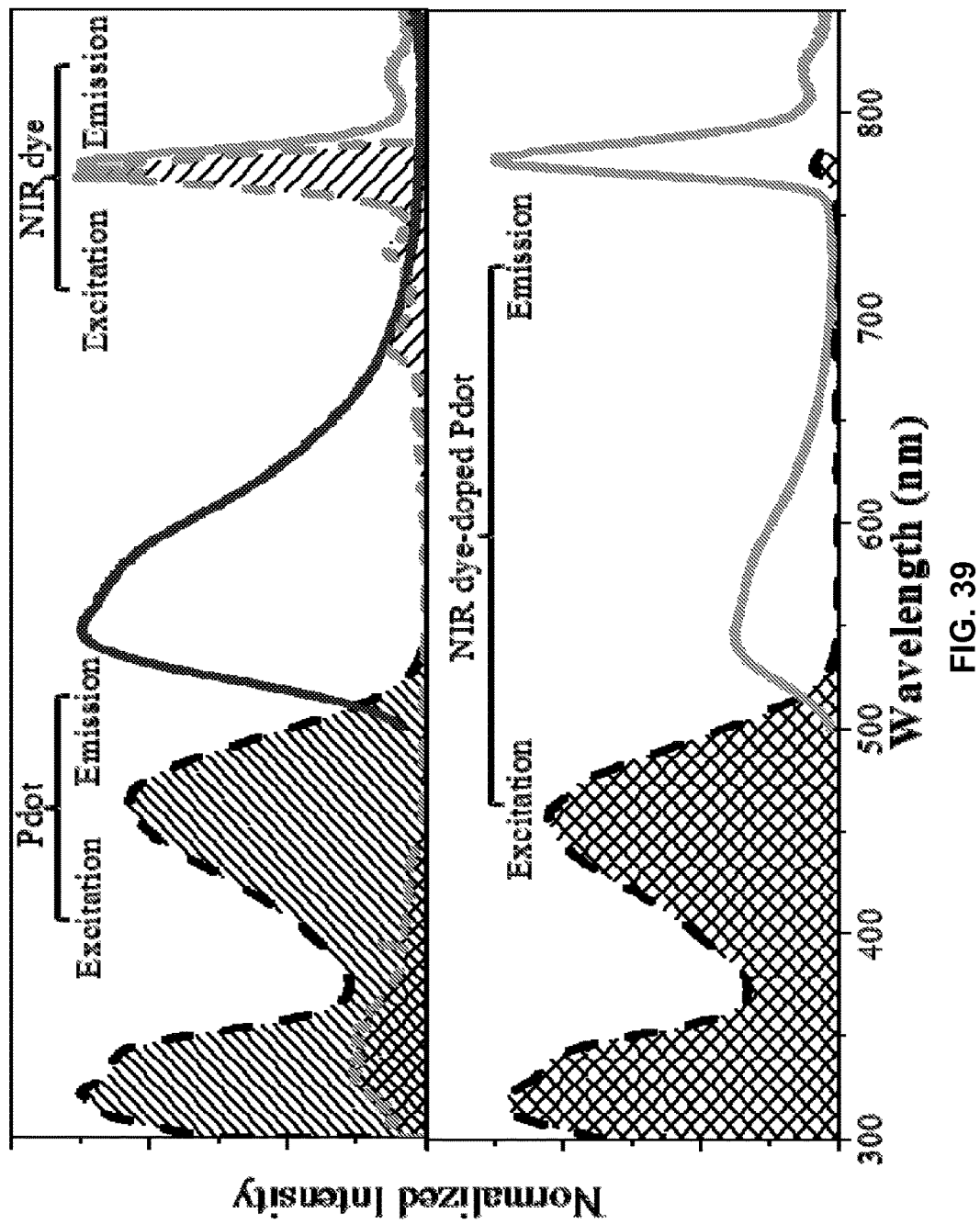
FIG. 39 Excitation and emission spectra of PFBT dots, NIR dyes, and NIR dye-doped CPdots (interchangeably called Pdots). The upper Figure shows the excitation spectra of PFBT dots (Black dash line with shadow) and NIR dyes (Dark yellow dash line with shadow), and the emission spectra of PFBT dots (Blue solid line) and NIR dyes (Red solid line). The lower figure shows the excitation (Black dash line with shadow) and the emission (Red solid line) of NIR dye-doped CPdots.
Figure 40:
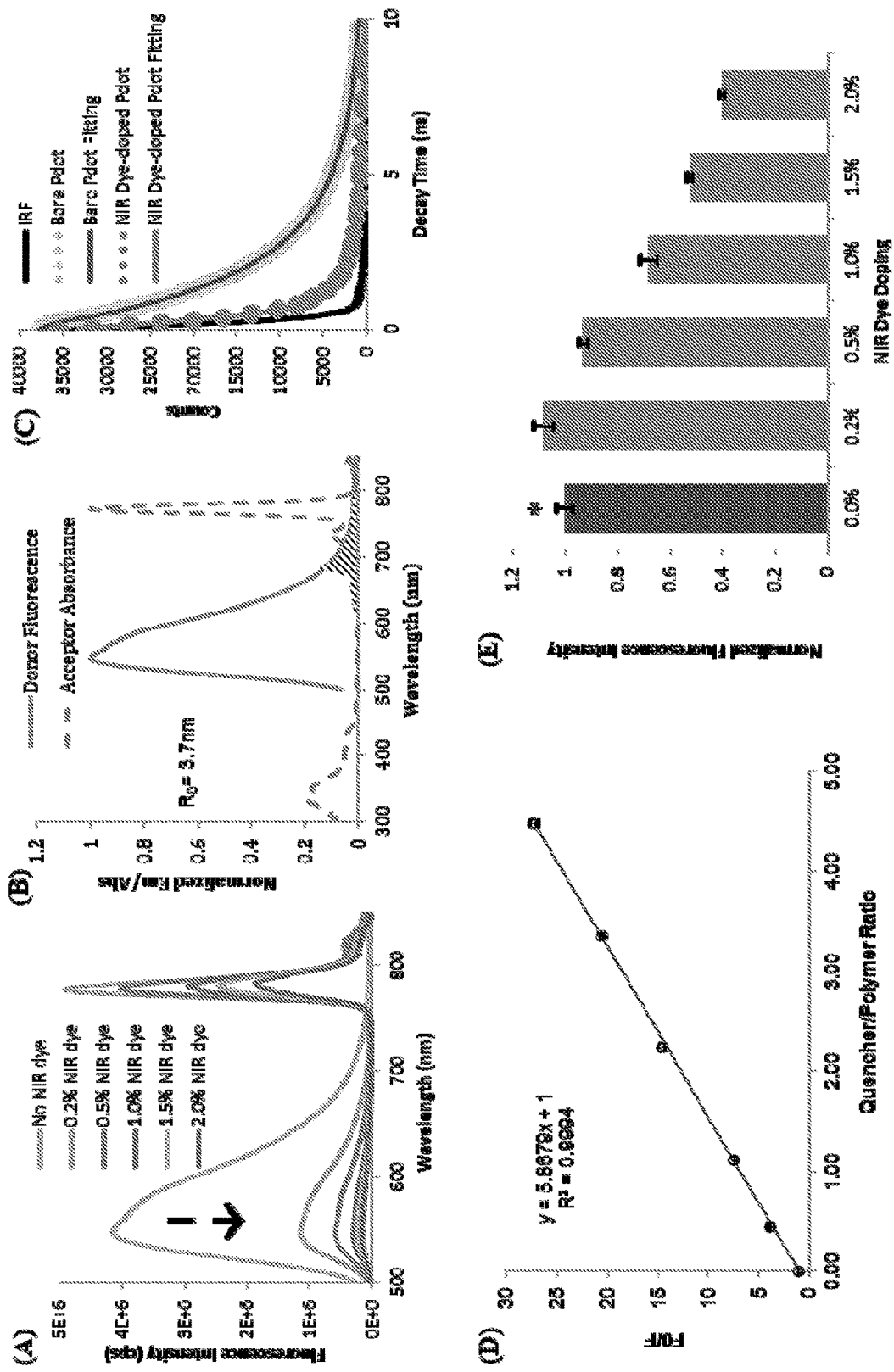
FIG. 40 Fluorescence properties of NIR dye-doped CPdots (interchangeably called Pdots). (A) Fluorescence spectra of NIR dye-doped CPdots with different NW dye doping.
(B) Overlap between the normalized emission spectrum of PFBT dot (donor) and the normalized absorption spectrum of NIR dye (acceptor); the calculated Forster radius between the donor and acceptor pair ($R_0$) is 3.7 nm. (C) Fluorescence lifetime measurement of CPdots. The lifetime of bare CPdots is 2.4 ns (Experimental data: Green dots, Fitting: Blue solid line), and is reduced to 1.2 ns after doping with NIR dyes (Experimental data: Red dots, Fitting: Red solid line). Black solid line represents the internal reference (IRF). (D) Applied quenching effect of NIR dyes in Pdot matrix. The fluorescence intensity ratio of the original CPdots without dye doping ($F_0$) and the NIR dye-doped CPdots (F) is proportional to the concentration of dopants (Hollow dots with error bar). Data were fit with the Stern-Volmer equation (solid line). (E) Manipulating the NIR emission of NIR dye-doped CPdots by controlling the dopant concentration. Increase the dye concentration led to a decrease of NIR emission (Red columns). The black column with asterisk represents the 546 nm emission of CPdots without dye doping.

Energy transfer mediated fluorescence in NIR Dye-Doped CPdots. Excited at 457 nm, the NIR dye-doped CPdots possess two fluorescence emissions: one visible emission from the polymer matrix and one NIR emission from the doped NIR dyes (FIG. 39). The two fluorescence emissions were modulated by manipulating the NIR dye concentration inside the Pdot. NIR dye can efficiently quench the CPdot fluorescence even at a low concentration; the reduction of the polymer fluorescence was achieved by increasing the NIR dye concentration in the range from 0.2% to 2% (FIG. 40A). The NIR emission of the CPdot was also modulated by controlling the concentration of dye doping. Doping more NIR dyes into CPdot matrix lead to a drop of the NIR fluorescence because NIR dyes may self quench in CPdots at high concentrations (FIG. 40E). Therefore, there is an optimal doping concentration for maximizing the fluorescence in the NIR region.

Figure 41:
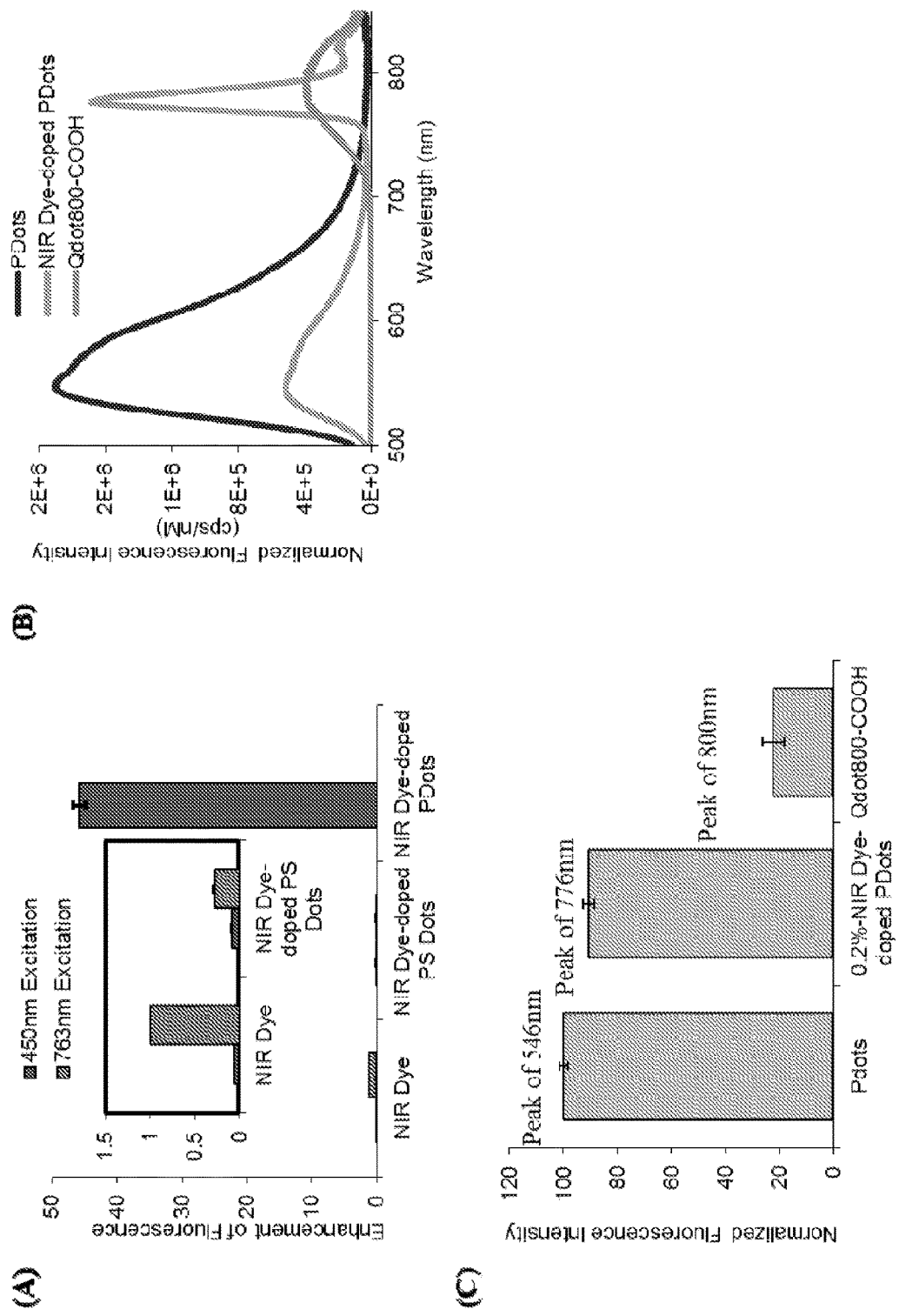
FIG. 41 Fluorescence enhancement of NIR dyes inside CPdot matrix (interchangeably called Pdots). (A) Normalized fluorescence peak intensities of free NIR dyes and the doped NIR dyes excited at 450 nm (Blue columns) and at 763 nm (black patterned columns). The fluorescence of free NIR dyes was measured in THF, others were measured in 20 mM HEPES buffer (pH 7.4). (B) Fluorescence emissions of fluorescent nanomaterials at same particle concentration. (C) The peak intensity of fluorescent nanomaterials normalized by the particle concentration.

There is efficient intra-particle energy transfer from PFBT polymer to NIR dyes. Even a small amount of NIR dye (0.2% w/w) was adequate to quench the polymer fluorescence by 75 percent. More than 95 percent of the polymer fluorescence was quenched when 2% of NIR dye was doped. The quenching results were well described by Stern-Volmer relationship (FIG. 40D). The quenching of Pdot matrix was also evident by the change of the fluorescence lifetime of the CPdots before and after NIR dye doping. The lifetime of the PFBT dots, which was originally 2.4 ns, decreased to 1.2 ns after doping 0.2% of NIR dye into Pdot matrix. The fluorescence quantum yield of the 540 nm emission also dropped from 0.368 to 0.08 according to the NIR dye doping. The NIR dye-doped CPdots can efficiently convert the received energy to NIR emission by transferring energy from the matrix to the NIR dyes. For example, the 0.2% NIR dye-doped CPdots exhibited a strong NIR emission, which is comparable to the 540 nm peak of the CPdots without dye doping. The quantum yield of this NIR emission was around 0.11, which indicates an efficient energy conversion. The fluorescence intensity of the NIR dye was greatly enhanced by the doping strategy. Excited at 457 nm in the aqueous solution, the doped NIR dye exhibited 40 times stronger fluorescence over the equivalent amount of free NIR dye excited at 763 nm in THF (FIG. 41A).

The light harvesting efficiency is one key parameter that determines the fluorescence brightness of nanoparticles. Doping NIR dyes into CPdot extensively improved the light harvesting capability of the doped dyes. The brightness of the NIR dye-doped CPdots is compared with NIR quantum dots (Qdot800 from Invitrogen Inc.). At the same particle concentration, NIR dye-doped CPdots are about 4 times more intense and have much narrower fluorescence emission than Qdot800 (FIGS. 41B and 41C).

Figure 42:
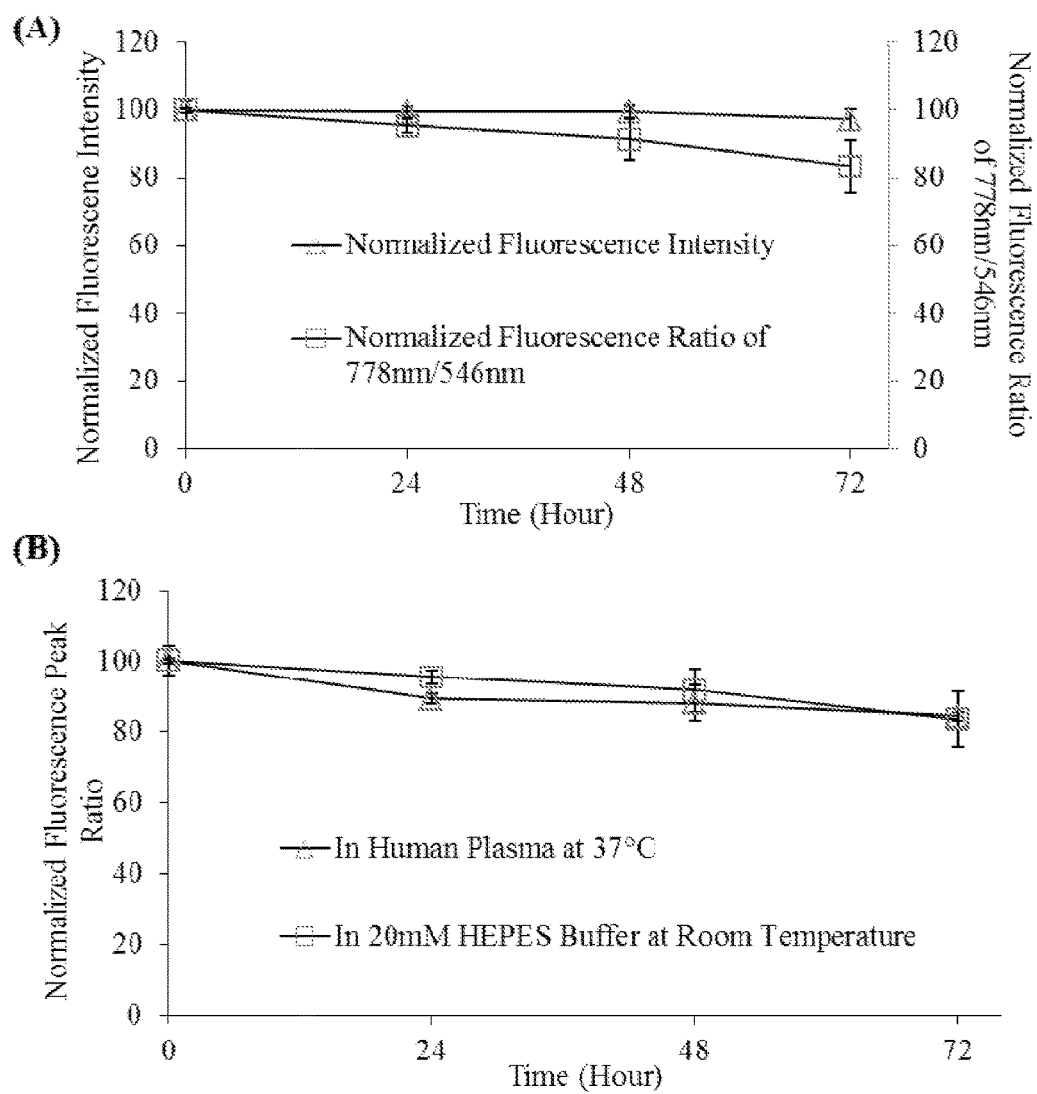
FIG. 42 Leaking test of NIR dye-doped CPdots. NIR dye leakage can be monitored by the change of peak ratio between the fluorescence emissions of 778 nm (acceptor) and 546 nm (donor). (A) Dye leakage tested at room temperature in 20 mM HEPES buffer (pH 7.4). The NIR emission kept unchanged in 72 hours (Blue hollow triangle), the acceptor-to-donor ratio slightly decreased after 72 hours (Red hollow square). (B) Dye leakage tested at 37° C. in human plasma. Data measured in plasma (Blue hollow triangle) are comparable to the data in 20 mM HEPES buffer (Red hollow square).

Dye-leakage. To exam the dye leakage, the acceptor-to-donor fluorescence ratio of the NIR dye-doped CPdots was monitored in 20 mM HEPES buffer for 72 hours. The results show that the acceptor-to-donor ratio only slightly decreased to 85% after 72 hours, and the NIR fluorescence did not change (FIG. 42A). This result indicates that the hydrophobic NIR dyes are unlikely to leak out to aqueous solutions and the NIR dye-doped CPdots can sustain their fluorescence properties for at least 72 hours and likely much longer. Because the NIR dye-doped CPdots are desirable for the in vivo applications, the leaking test was also carried out in human plasma at 37° C. The result shows similar data to the former test at room temperature, which suggests that the change of the solution conditions does not compromise the performance of the NIR dye-doped CPdots in 72 hours (FIG. 42B). To completely overcome dye leakage, we can covalently link the dye molecules to the chromophoric polymer matrix to form CPdots.

Example 30: Functionalized Chromophoric Polymer Dots for Ratiometric Temperature Sensors This example provides a demonstration that functionalized chromophoric dots can be used to form ratiometric nanoparticle temperature sensors. We use below CPdots or Pdots interchangeably to describe chromophoric polymer dots.

Figure 43:
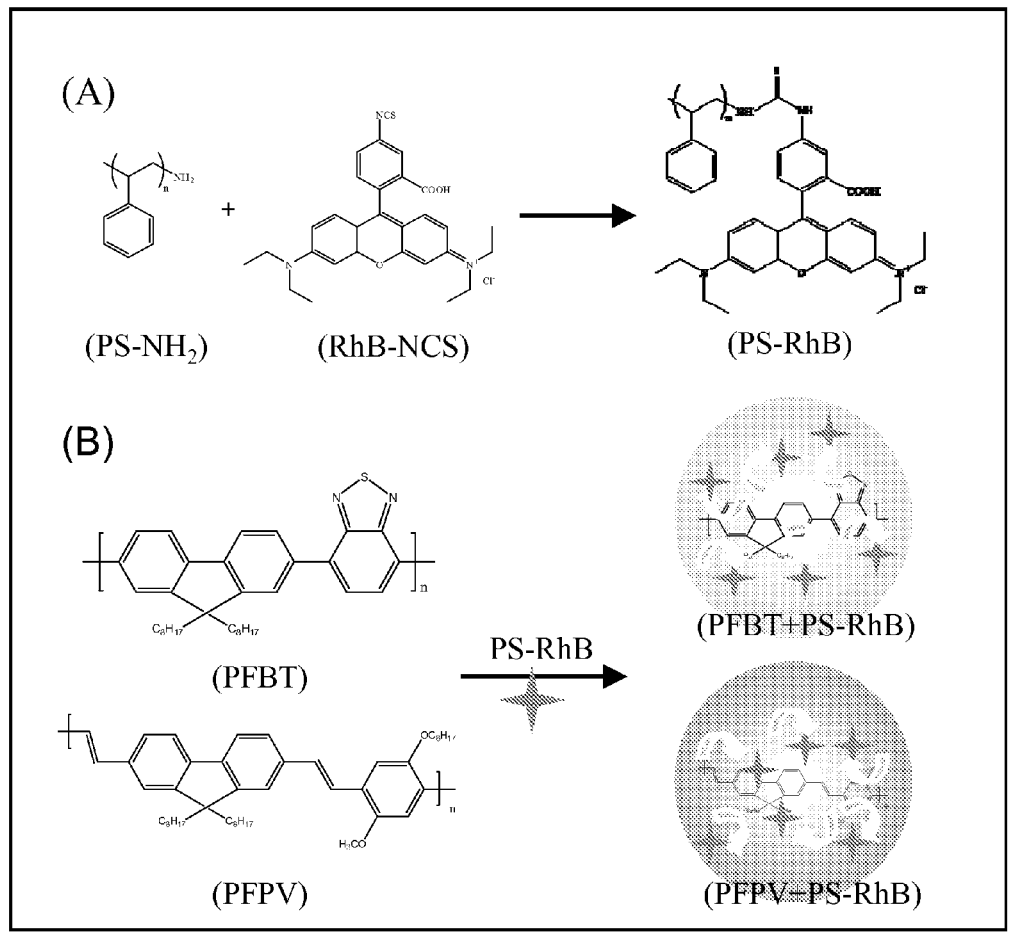
FIG. 43 Scheme for preparing CPdots temperature sensors.

Preparation of CPdot temperature sensor. First, we use functional polymer such as amine-terminated polystyrene polymer to react with a temperature sensing dye Rhodamine B (RhB). Because Rhodamine B is a water-soluble dye, the reaction with a functional hydrophobic polymer can make the dye hydrophobic, therefore it can be entrapped inside the hydrophobic CPdots. In a 10 mL round-bottom flask, 200 μL of 10 mg/mL Rhodamine B-isothiocyanate in DMF (anhydrous) and 1 mg $NaHCO_3$ were added into 2 mL 1 mg/mL (in DMF) amine-terminated polystyrene (PS-$NH_2$, MW 1000, polydispersity 1.1) to perform $NH_2$-isothiocyanate reaction as shown in FIG. 43A. The mixture was gently stirred overnight under the protection of $N_2$. DMF was removed by rotary evaporation at 75° C. The resulting red solid was then dissolved in 1 mL THF (anhydrous). $NaHCO_3$ was filtered off with 200 nm membrane filter since it did not dissolve in THF. The obtained PS-RhB in THF was then doped into chromophoric polymer to make CPdot.

The copolymers poly[{9,9-dioctyl-2,7-divinylene-fluorenylene}-alt-co-{2 methoxy-5-(2-ethylhexyloxy)-1,4-phenylene}] (PFPV, MW 220 000, polydispersity 3.1), and poly[(9,9 dioctylfluorenyl-2,7-diyl)-co-(1,4-benzo-{2,1',3}-thiadiazole)] (PFBT, MW 150 000, polydispersity 3.0), were used for preparation of CPdot temperature sensors. 10 mg of the above polymer was dissolved in 10 mL THF by stirring overnight under inert atmosphere. Rhodamine B doped CPdots were prepared by first mixing 200 μL of 1 mg/mL (in THF) PFPV or PFBT and 10 μL of 2 mg/mL (in THF) PS-RhB in 5 mL THF and then by injecting the mixed polymer in THF solutions into 10 mL of MilliQ water under sonication. THF was then removed by partial vacuum evaporation, and a small fraction of aggregates was removed by filtration through a 0.2 μm membrane filter. Free Rhodamine B is removed by Bio-Rad Econo-Pac® 10DG columns (Hercules, Calif., USA). FIG. 43B shows the illustration of CPdot preparation and the energy transfer between the chromophoric polymer and RhB within the nanoparticles.

Figure 44:
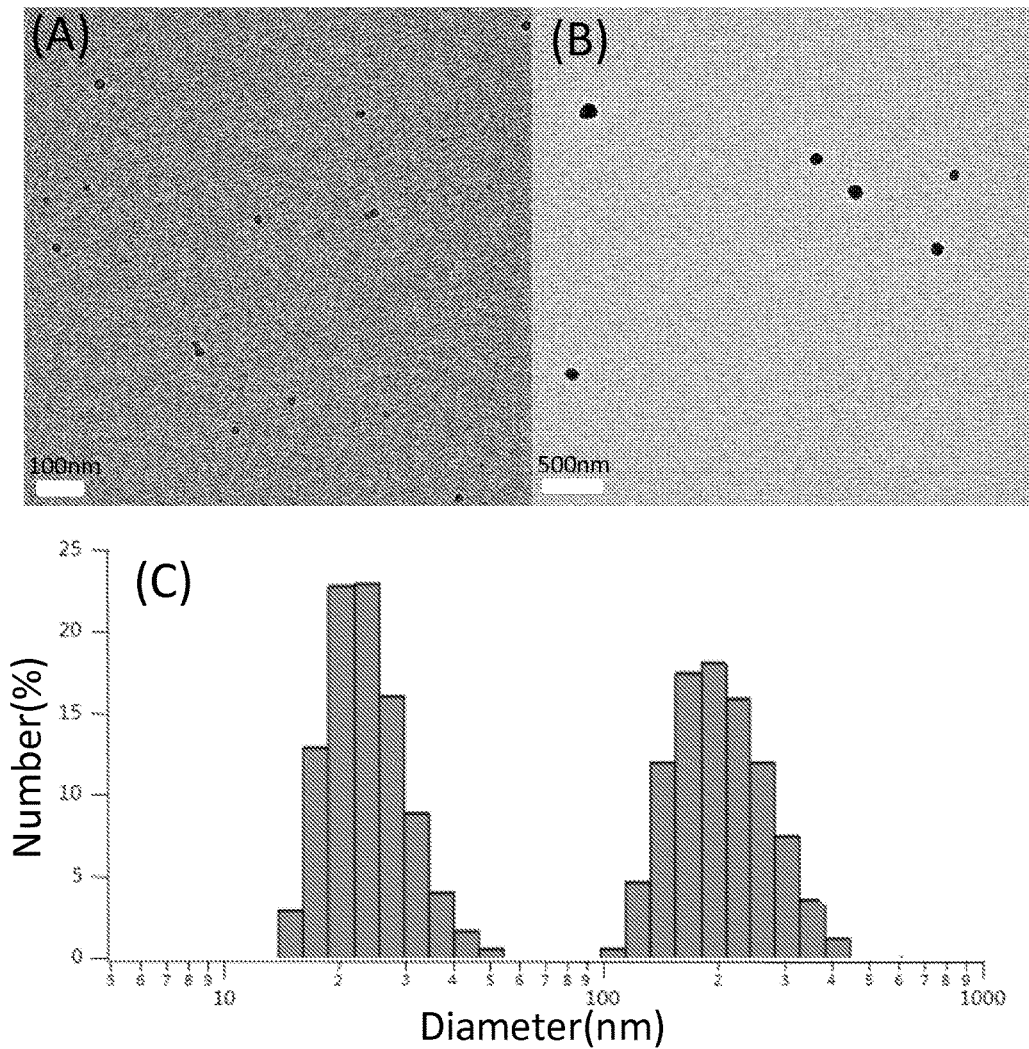
FIG. 44 TEM and dynamic light scattering of CPdot temperature sensors. (A) TEM of CPdot PFPV-RhB. (B) TEM of CPdot PFBT-RhB. (C) Dynamic light scattering of CPdot temperature sensors.

Characterizations of CPdot temperature sensors. The particle size of Pdots in bulk solution was characterized by dynamic light scattering (DLS, Malvern Zetasizer NanoZS). FIG. 44 shows the DLS data for the Pdots. The resulting PFPV-RhB dots are about 26 nm in diameter while PFBT-RhB dots are 160 nm in average diameter. The CPdot size is highly dependent on the molecular weight of polymer, polymer backbone structure and the concentration ratio of PS-RhB to the chromophoric polymer. In PFBT-RhB system, 20 wt % or higher PS-RhB concentration results in the aggregation of nanoparticles. We found 10% PS-RhB in PFBT Pdot showed the best sensitivity and relatively small size. In PFPV-RhB system, very small Pdots were obtained. 10% PS-RhB is also confirmed to be the best doping amount based on the fluorescence intensity and sensitivity.

Figure 45:
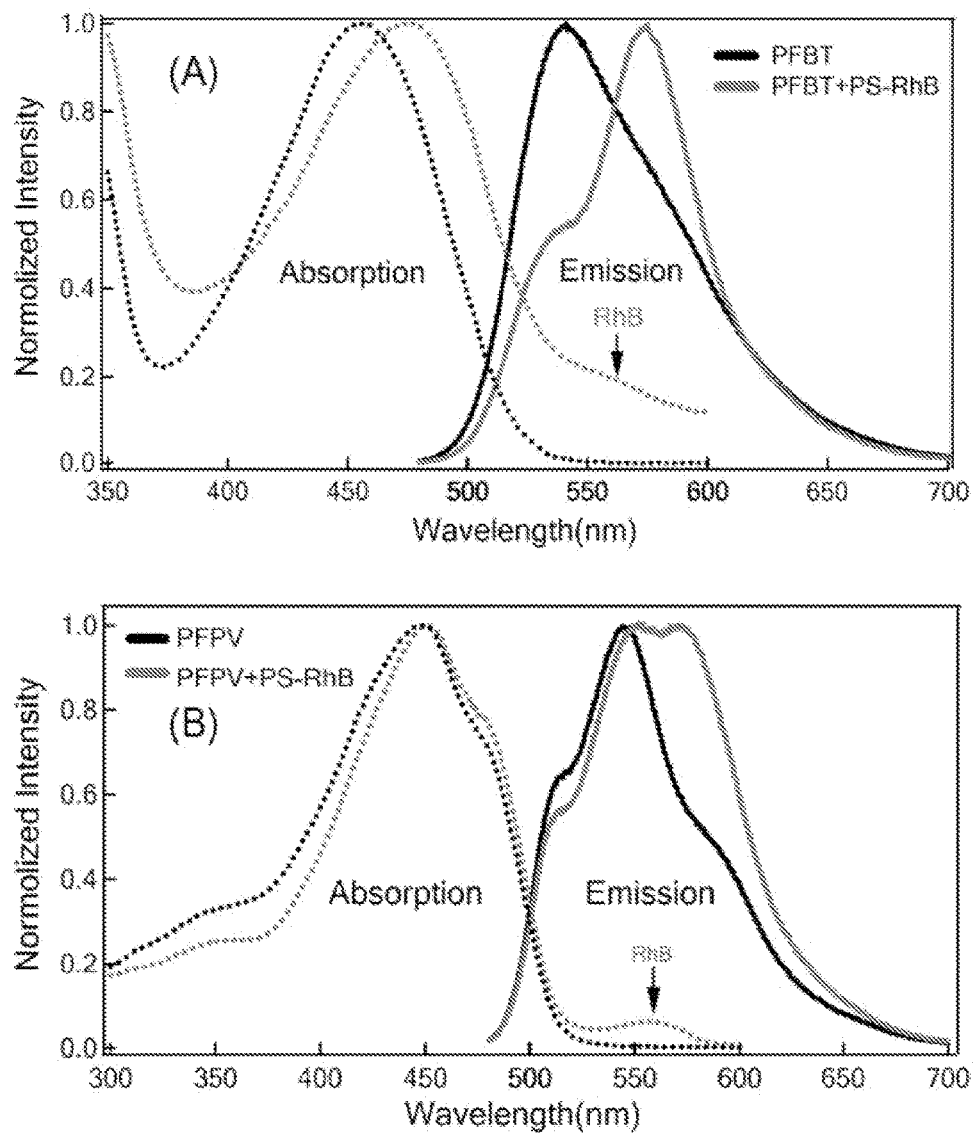
FIG. 45 Absorption and emission spectra of CPdot temperature sensors.

UV-Vis absorption spectra were recorded with a DU 720 spectrophotometer. Fluorescence spectra were collected with a Fluorolog-3 fluorometer. All CPdots were excited at 450 nm because both PFPV and PFBT showed their adsorption peaks around 450 nm. FIG. 45A shows the absorption (dashed) and emission (solid) spectra of PFBT (black) and PFBT-RhB (red) dots at room temperature. In the absorption spectrum, an additional small absorption peak at 540 nm appeared, accompanied by a 10 nm red shift from 450 nm to 460 nm for PFBT absorption peak. The 540 nm peak corresponds to the absorption of RhB, while the red-shift of PFBT is due to the size increase from ~20 nm of pure PFBT dot to ~160 nm PFBT-RhB dots. PFBT-RhB dots shows two emission peaks, a relatively weak emission peak at 540 nm and a strong emission peak at 573 nm. The latter peak corresponds to the emission of RhB. Because of the good overlap between the emission of PFBT (peak at 540 nm) and the adsorption of RhB (peak at 540 nm) as well as the close proximity between PFBT polymer chain and Rhodamine B molecule, efficient energy transfer resulted in strong fluorescence of RhB, whereas pure RhB dye was poorly excited by 450 nm.

FIG. 45B shows the absorption and emission spectra of PFPV and PFPV-RhB dots at room temperature. In the absorption spectrum, PFPV-RhB dots show a small absorption peak at 540 nm for Rhodamine B, while there was no noticeable shift for PFPV peak at 450 nm. The emission spectrum shows two peaks at 510 nm and 540 nm for PFPV dots, while PFPV-RhB dot shows an additional RhB peak at 573 nm. Similar to PFBT-RhB, there is strong FRET between PFPV and RhB due to the good spectral overlap between the emission of PFPV (peak at 540 nm) and the adsorption of RhB (peak at 540 nm) and the compact packing of polymer chain and RhB inside the nanoparticle.

Figure 46:
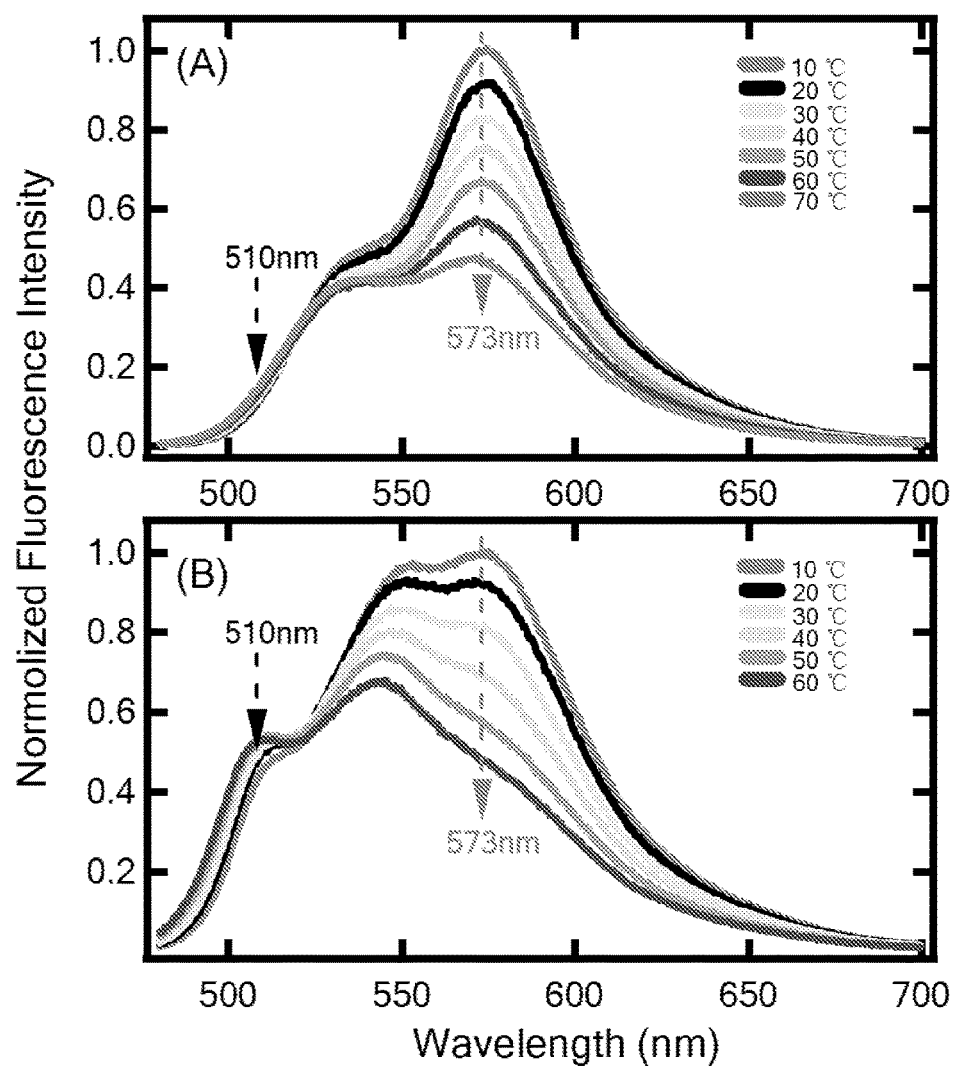
FIG. 46 Emission spectra of CPdot PFBT-RhB (A) and PFPV-RhB (B) sensors at different temperatures.
Figure 47:
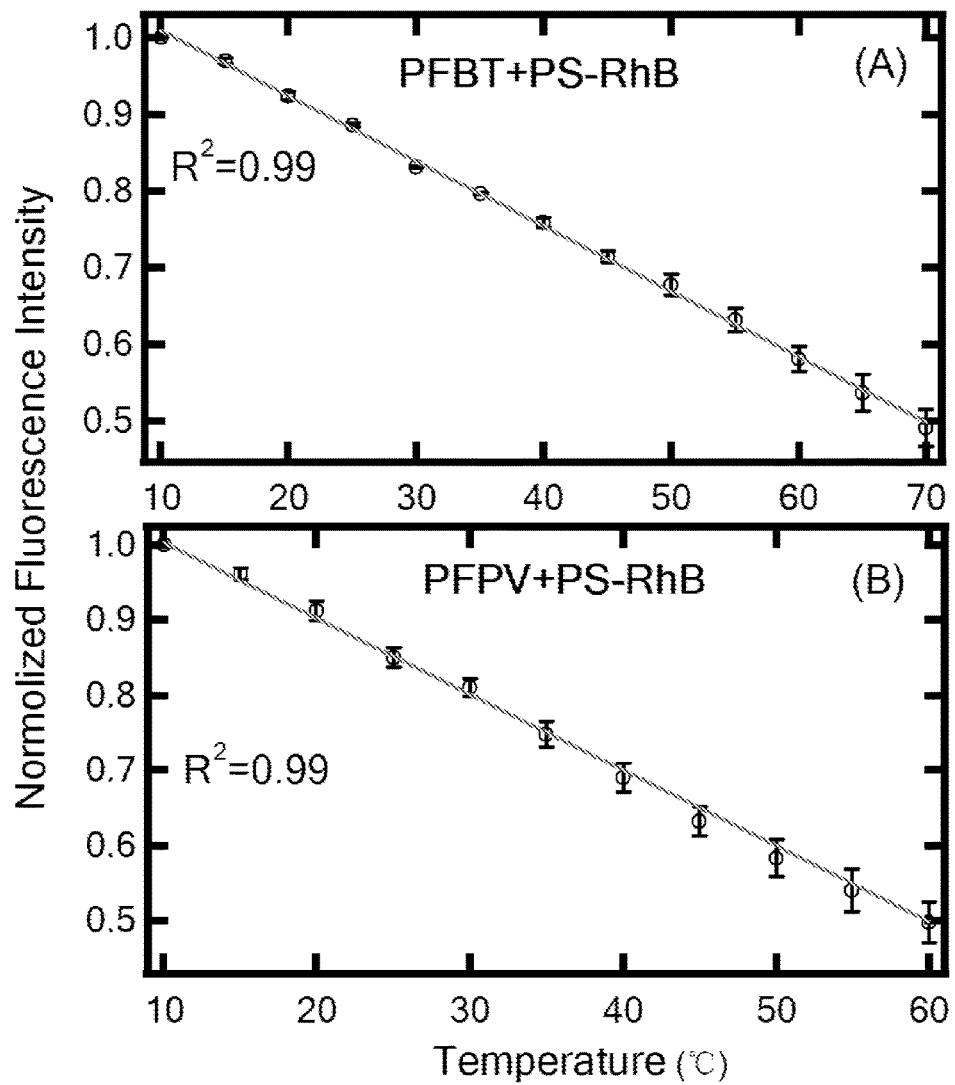
FIG. 47 Intensity-temperature plot and their linear fittings for CPdot temperature sensors.
Figure 48:
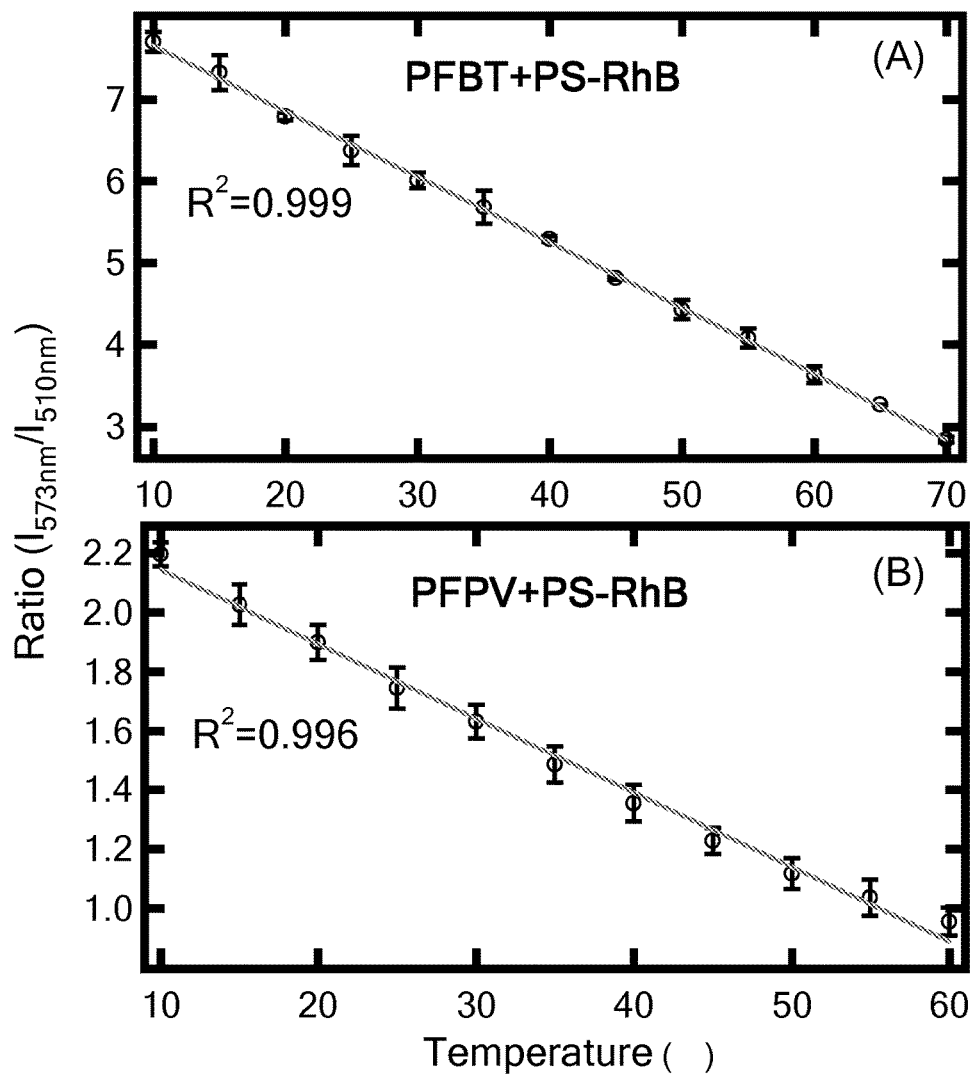
FIG. 48 Intensity ratio vs. temperature and the linear fittings for CPdot temperature sensors.

Fluorescent CPdot temperature sensing. The temperature-dependent fluorescence of Pdots was measured in a Fluorolog-3 fluorometer coupling with a heating/cooling system. The absolute temperature of Pdot solutions was measured by digital thermometer TM902C by inserting a temperature probe into the solution. The solution is stirred gently to yield homogeneous cooling and heating during the experiment. FIG. 46 shows the fluorescence spectra of PFBT-RhB (A) and PFPV-RhB (B) towards temperature rising from 10° C. to 70° C. and 10° C. to 60° C., respectively. The right dashed line (red) shows the emission peak of RhB at 573 nm, while the left one is 510 nm which is selected as internal reference for the ratiometric calculation. FIG. 47 shows the fluorescence intensity as a function of temperature for both Pdots. The fluorescence intensity decreases for PFBT-RhB dot as temperature increases. More importantly, the intensity shows a linear relationship relative to temperature change. The unique characteristics of these CPdot sensors over free Rhodamine B or other nanoparticles as temperature probe are the ratiometric measurements. FIG. 48 shows ratiometric plots of $I_{573\ nm}/I_{510\ nm}$ as a function of temperature for PFBT-RhB dot (A) and PFPV-RhB dot (B). Linear fittings well described the sensing behavior, so the temperature can be determined from a given fluorescence intensity ratio obtained in experiment.

Example 31: Functionalized Chromophoric Polymer Dots for Ratiometric pH Sensors

This example provides a demonstration that functionalized chromophoric dots can be used to form ratiometric nanoparticle pH sensors. We use below CPdots or Pdots interchangeably to describe chromophoric polymer dots.

Preparation of CPdot pH sensors. We used a chromophoric polymer poly(2,5-di(3',7'-dimethyloctyl)phenylene-1,4-ethynylene (PPE) as the polymer donor and a pH sensitive dye fluorescein as a acceptor to form ratiometric CPdot pH sensors. Thiol-terminated polystyrene (PS-SH) or amino-terminated polystyrene ($PS-NH_2$) were used to covalently linked the dye to CPdots.

Preparation of Thiol Functionalized PPE dots. Typically, 40 μg of PPE and 12 μg of PS-SH were dissolved into 5 mL of THF. This mixture was then quickly injected into 10 mL of water under vigorous sonication. The THF was then removed by purging with nitrogen on a 96° C. hotplate for one hour. The resulting Pdot solution was filtered through a 0.2 μm cellulose acetate membrane filter to remove any aggregates formed during preparation.

Figure 49:
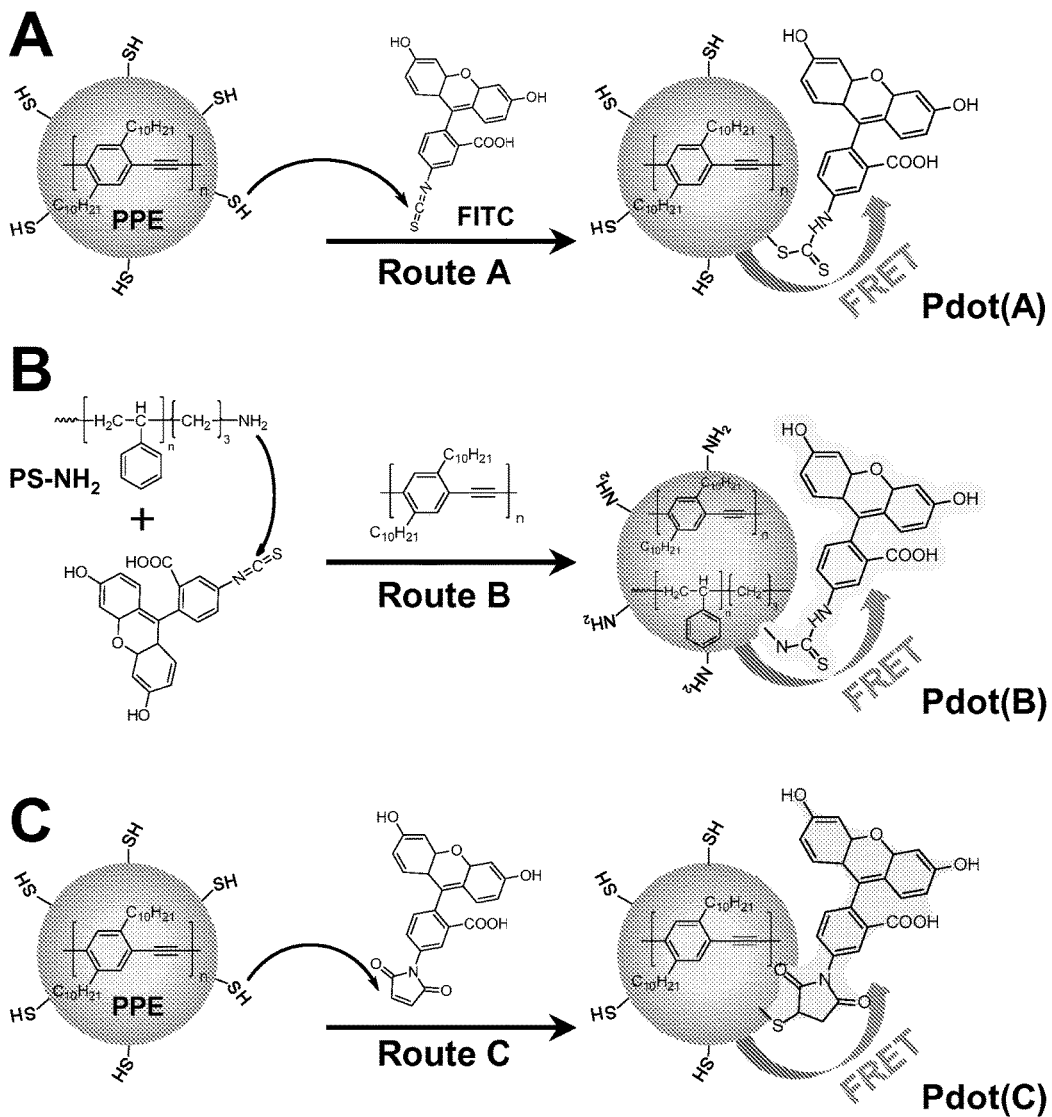
FIG. 49 Schematic showing three routes for the preparation of PPE Pdot-based pH sensor. (A) PS-SH co PPE Pdots in water were first prepared and then reacted with the isothiocyanate moieties on the FITC molecules. (B) FITC was first conjugated to $PS-NH_2$ polymers through the amine-isothiocyanate reaction, and the resulting fluorescein-labeled PS polymers were blended with PPE polymers to form the $PS-NH_2$-FITC co PPE Pdots. (C) PS-SH co PPE Pdots were first prepared in the same way as (A), but were subsequently coupled to fluorescein-5-maleimide. PPE: poly (2,5-di(3',7'-dimethyloctyl)phenylene-1,4-ethynylene; PS: polystyrene polymer; FITC: fluorescein isothiocyanate.

Preparation of Fluorescein Conjugated PPE dots (Pdot (A), Pdot(B), and Pdot(C)) (FIG. 49). For Pdot(A), 0.2 mg of fluorescein isothiocyanate (FITC) dissolved in anhydrous DMSO was added to a 4 mL of PS-SH co PPE Pdot (20 μg/mL) aqueous solution in a glass vial. The mixture was stirred for 12 h at room temperature and then was purified through a Bio-Rad EconoPac® 10DG column (Hercules, Calif., USA) to separate from the free FITC molecules. For the preparation of Pdot(B), 5 mg FITC and 20 mg $PS-NH_2$ were dissolved and mixed in 1 mL DMF. Then 5 mL triethylamine was added to the solution. The mixture was left on a rotary shaker overnight. 0.2 mL of PPE (1 mg/1 mL) in THF and 27 μL of $PS-NH_2$-FITC conjugate solution were mixed into 5 mL of THF. This mixture was then quickly injected into 10 mL of water under vigorous sonication. The THF was then removed by purging with nitrogen on a 96° C. hotplate for one hour. The resulting Pdot(B) solution was first filtered through a 0.2 μm cellulose acetate membrane filter to remove any aggregates formed during preparation, and then purified through a Bio-Rad EconoPac® 10DG column to separate from the free FITC molecules. For the preparation of Pdot(C), 15 μg of fluorescein-5-maleimide in anhydrous DMSO, and 60 μL of concentrated HEPES buffer (1 M) were added into a freshly prepared 4 mL of PS-SH co PPE Pdot (20 μg/mL) aqueous solution in a glass vial. The mixture was stirred for 12 h at room temperature and was then purified through a Bio-Rad Econo-Pac® 10DG column to separate from the free FITC molecules.

Selection and Optimization of chromophoric polymer-Fluorescein Pair. To fabricate a ratiometric sensing platform based on FRET and excited under a single wavelength, the first step is to select a suitable donor-acceptor pair. Herein the fluorescein was chosen as the FRET acceptor because its absorption profile and emission intensity is highly dependent on the pH. The changes in absorption profile of fluorescein at different pH allow us to modulate the FRET efficiency between the donor (chromophoric polymer matrix) and the acceptor (fluorescein molecules), whereas the response of fluorescence intensity to pH provides a feedback of proton activity. In order to optimize the FRET efficiency, it is important to select an ideal donor polymer based on its spectroscopic properties. We found the PPE polymer dots exhibited a great energy transfer to fluorescein in several conjugation routes. This phenomenon can be interpreted by the substantial spectral overlap between the emission spectrum of PPE polymer and the excitation spectrum of fluorescein as shown in FIG. 50A.

Conjugation of fluorescein to PPE Pdots. The PPE Pdots were used as the polymer matrix while the fluorescein dyes were immobilized onto PPE Pdots by virtue of three different routes as depicted in FIG. 49. For routes A and C, we first prepared the thiol-functionalized PPE Pdots by blending the thiol-terminated polystyrene into the PPE polymer, forming the PS-SH co PPE Pdots in aqueous solution by the precipitation method. Subsequently, the PS-SH co PPE Pdots were reacted with fluorescein isothiocyanate (route A) or fluorescein-5-maleimide (route C), generating the pH-sensitive Pdot-dye complex. Because we found amino-functionalized PPE Pdots to be unstable, we devised route B, where fluorescein isothiocyanate was first coupled to the amino-terminated polystyrene ($PS-NH_2$) under organic phase and was then blended with the PPE polymer followed by the nanoparticle precipitation in aqueous solution. We then investigated the ratiometric sensing capability of each system by manipulating the ratio of polymer to dye. For example, in route A and C, we examined different blending percentage of PS-SH in the PPE polymer and found a high sensitivity with a low standard deviation could be obtained at 30% of PS-SH doping level. Similar results were also observed in the route B system, in which 60% of PS-NH$_2$-fluorescein blending led to the best ratiometric pH sensitivity.

Figure 50:
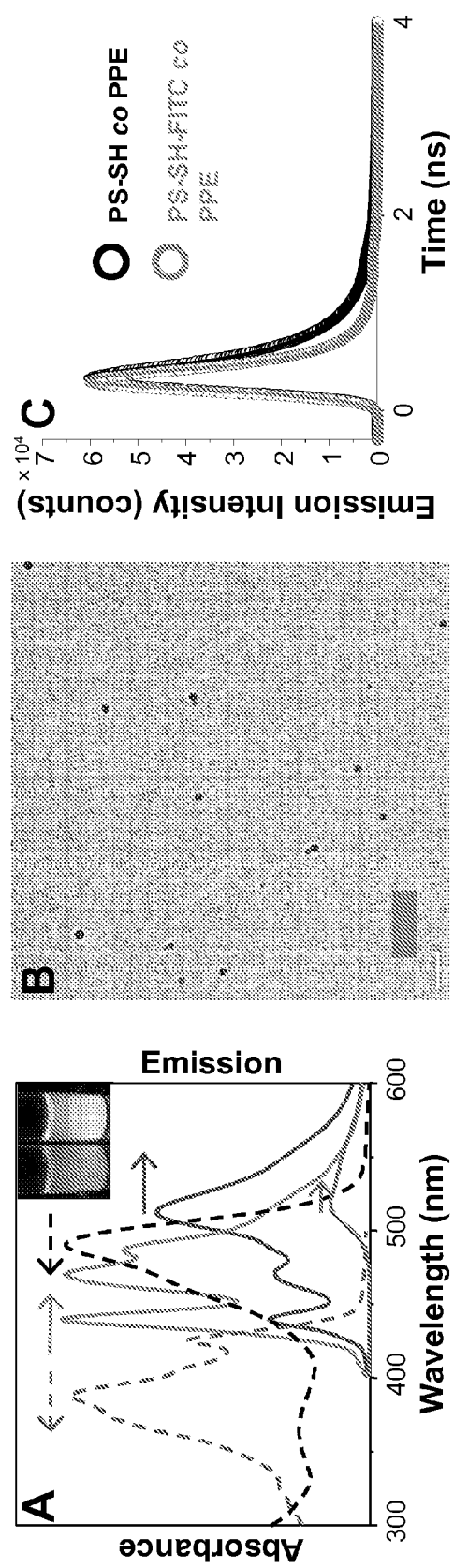
FIG. 50(A) UV-visible spectra of PPE Pdots (dashed plum line) and FITC (dashed black line) in water; and emission spectra of PS-SH co PPE (solid red line), PS-SH-FITC co PPE (solid blue line), and $PS-NH_2$-FITC co PPE Pdots in pH=7 HEPES buffer solutions. The inset in the upper-right corner shows the photographs of PS-SH co PPE (left) and PS-SH-FITC co PPE pdot solutions (right) under a 365 nm UV lamp. (B) Transmission electron microscopy images of the CPdot pH sensors. (C) Comparison of lifetime of CPdots.
Figure 51:
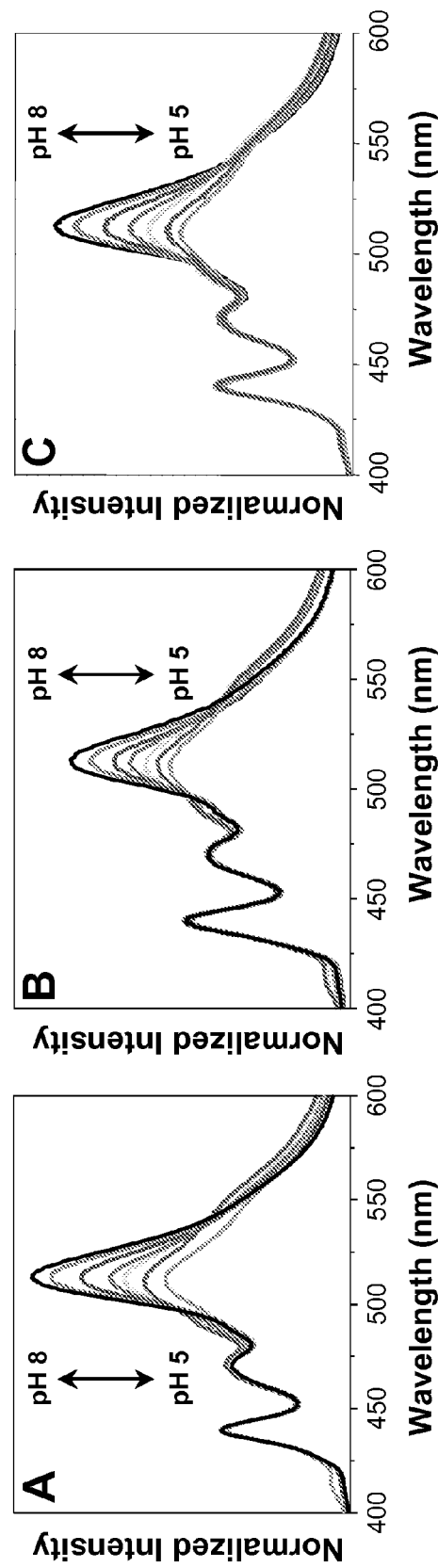
FIG. 51 Fluorescence spectra of (A) Pdot(A), (B) Pdot (B), and (C) Pdot(C) at different pH, ranging from 5 to 8 (black line: pH=8, red line: pH=7.5, blue line: pH=7, green line: pH=6.5, gold line: pH=6, brown line: pH=5.5, pink line: pH=5). Excitation wavelength was 390 nm.
Figure 52:
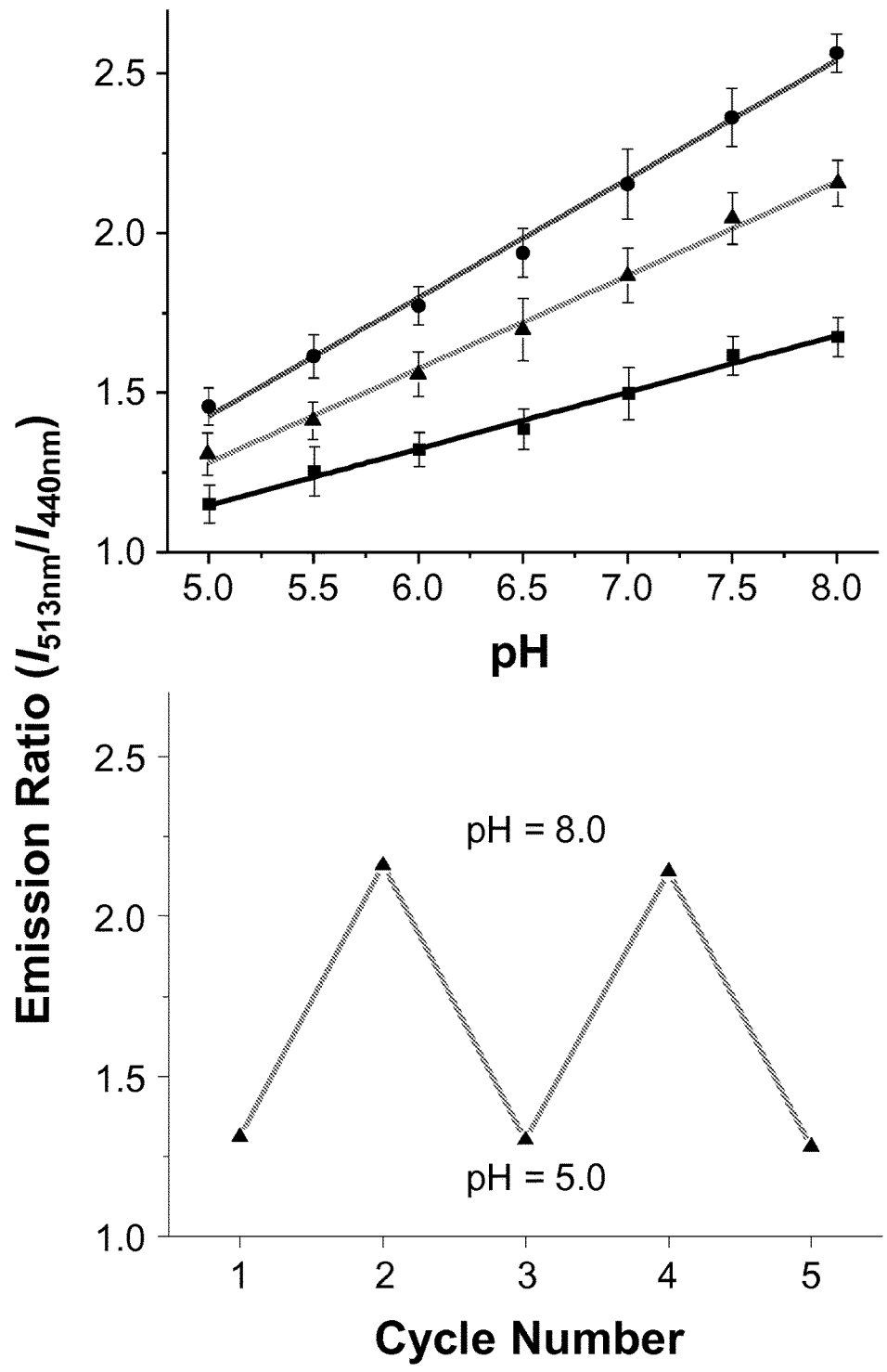
FIG. 52 PH sensitivity and reversibility of the three fluorescein conjugated Pdots. (A) Ratiometric pH calibration plot of the emission ratio ($I_{513\ nm}/I_{440\ nm}$) of Pdot(A) (●), Pdot(B) (■), and Pdot(C) (▲) as a function of pH. The blue, black, and red lines are linear fit to the data of Pdot(A) ($R^2$=0.995), Pdot(B) ($R^2$=0.991), and Pdot(C) ($R^2$=0.994), respectively. The slopes for Pdot(A), Pdot(B), and Pdot(C) are 0.37, 0.18, and 0.29, respectively. (B) The intensity ratio ($I_{513\ nm}, I_{440\ nm}$) of Pdot(C) when the pH was toggled between 5.0 and 8.0 repeatedly, illustrating the reversibility and reproducibility of pH sensing.

FRET between PPE and fluorescein. Once the fluorescein molecules were attached onto the PPE Pdots, an efficient energy transfer from PPE to fluorescein could be readily observed. This effective FRET is partially attributed to the considerable spectral overlap between the emission spectrum of PS-SH co PPE Pdots (red solid line) and the excitation spectrum of fluorescein (black dashed line) as shown in FIG. 50A. Take Pdot(A) for example, as compared to the fluorescence spectrum of bare PS-SH co PPE Pdots of the same concentration (without dye conjugation, red solid line), the increase of the emission of the dye ($\lambda=513$ nm, blue solid line) with concomitant suppression of the PPE Pdot emission ($\lambda=420$-490 nm, blue solid line) clearly demonstrated that the FRET happened from the Pdot to the dye. It should be noticed that the emission intensity of unbound fluorescein at the same concentration was very weak when excited by the same wavelength of 390 nm, meaning that most of the emission intensity of fluorescein arose from the energy transfer rather than the fluorescence itself. To further confirm the FRET phenomenon, time resolved fluorescence decay curves of PPE Pdots (440±20 nm) were measured for the control, PS-SH co PPE Pdots and the Pdot-dye complex, Pdot(A). The fluorescence lifetime of Pdot control was 0.30 ns, while the lifetime of Pdot(A) was shortened to be 0.21 ns, indicating the occurrence of FRET from the PPE Pdot to the fluorescein. To better understand the spectroscopic behaviors of the Pdot-dye complexes, we conducted additional studies of the calculation of FRET efficiency at different pH as described below. In addition to the spectral overlap, to ensure an efficient FRET behavior, the size of the Pdot plays an important role in that the FRET depends on the inverse sixth power of the intermolecular separation. The resulting hydrodynamic diameters of the Pdot-dye complexes measured by dynamic light scattering (DLS) are 26 nm, 25 nm, and 26 nm on average for route A, B, and C, respectively. A typical transmission electron microscopy (TEM) image of Pdot(C) is as shown in FIG. 50, which is consistent with the DLS measurements.

pH-sensitivity and reversibility measurements. Fluorescence spectroscopy measurements were performed in each system to study the ratiometric response to pH in HEPES buffer solutions. As shown in FIG. 51, the emission peak of fluorescein increased with increasing pH, while the fluorescence intensity of PPE Pdots remained constant in all of the three systems. We also examined the pH response of PPE Pdots alone and the result again suggests that the PPE Pdot is pH non-responsive from pH=5.0 to 8.0, rendering it a good reference for the ratiometric pH detection. FIG. 52 shows that the emission intensity ratio of fluorescein ($\lambda=513$ nm) to PPE ($\lambda=440$ nm) changes linearly as a function of pH ranging from 5.0 to 8.0 for these three complexes. Among them, Pdot(A) reveals the highest detection sensitivity with $I_{513\,nm}/I_{440\,nm}$ varying by 0.37 per unit change in pH. This high sensitivity might originate from the shortest separation between the Pdot and the dye, adding an efficient energy transfer from PPE to fluorescein. Nevertheless, it is known that thiocarbamoyl unit between thiol and isothiocyanate is prone to gradual degradation in the presence of excess free thiols, making Pdot(A) less feasible in more complicated biological applications. On the contrary, Pdot(B) provides a stable amine-isothiocyanate adduct between the Pdot and the dye but the long side chain of PS-NH$_2$ results in a relatively low pH sensitivity of 0.18 variation per unit change in pH on account of the less efficient energy transfer. To overcome the above mentioned obstacles, Pdot(C) was aimed to offer a complementary system with good pH sensitivity and high bonding stability. The ratio of $I_{513\,nm}/I_{440\,nm}$ varied by 0.29 per unit change in pH for Pdot(C) system.

Figure 53:
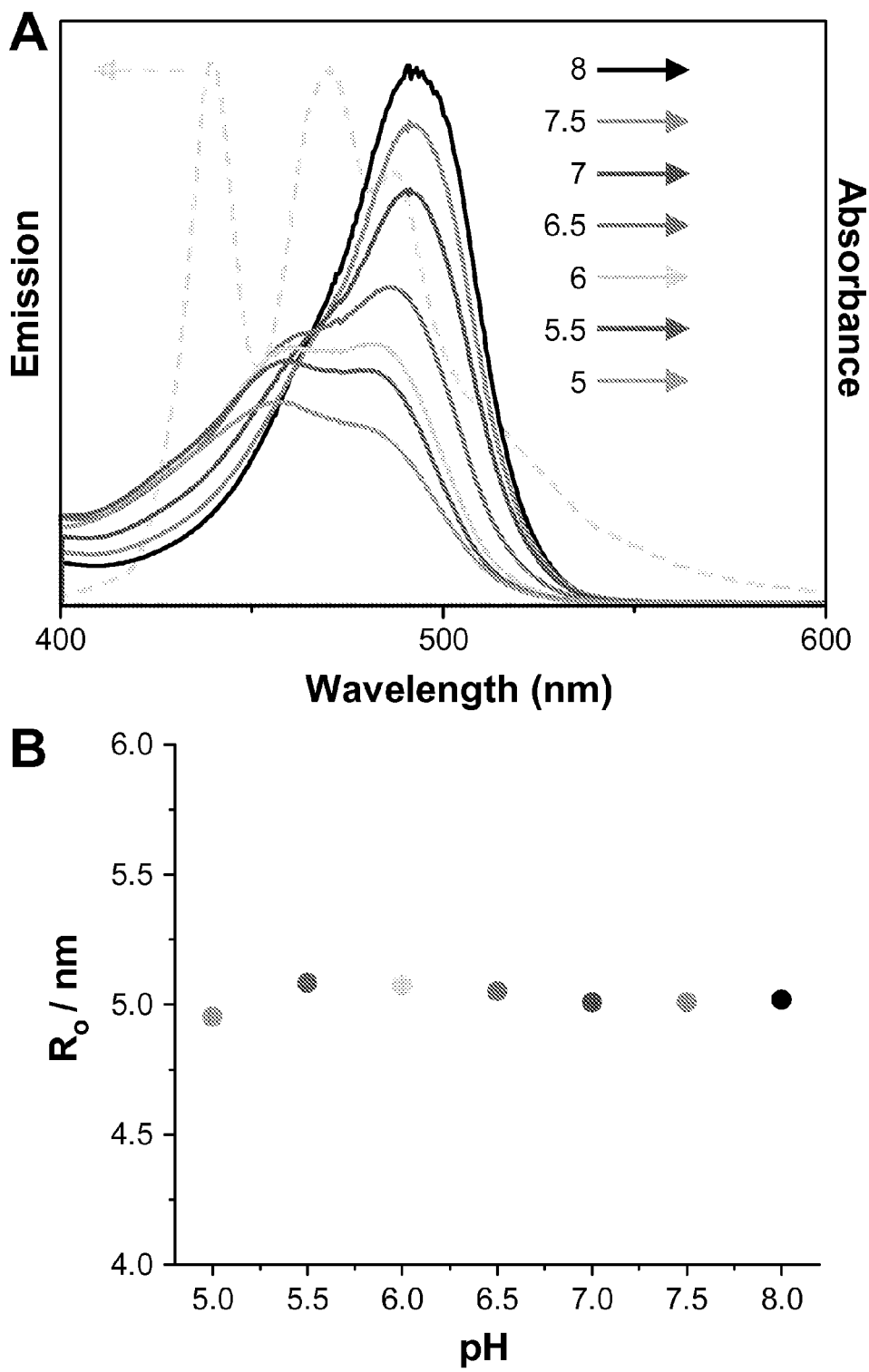
FIG. 53 Illustration of spectral overlap between the emission of donor (i.e., PPE) and the absorption of acceptor (i.e., FITC); and their calculated Forster distance, Ro. (A) Emission spectrum of PS-SH-FITC co PPE Pdots (dashed light green line) and excitation spectra of FITC at pH ranging from 5 to 8. The areas under curves were filled with color for easier observation of spectral overlap. (B) The corresponding Forster distance of PPE-FITC at different pH was plotted based on the overlap integral as shown in (A).

All of these three nanosensors showed good pH reversibility. Take Pdot(C) for example, the pH of solution containing Pdot(C) nanosensors was varied between p=5 and pH=8. The good reproducibility of the fluorescein to PPE fluorescence emission ratio is indicative of the great reversibility and robustness for this Pdot-based pH sensor (FIG. 52). Additionally, the pH response time of the sensor is too fast to be measured by a conventional fluorescence spectrometer owing to the small size (i.e., large surface-to-volume ratio) of the Pdots. FIG. 53 shows the spectral overlap between PPE and fluorescein as well as the calculated Forster distance as a function of solution pH.

Figure 54:
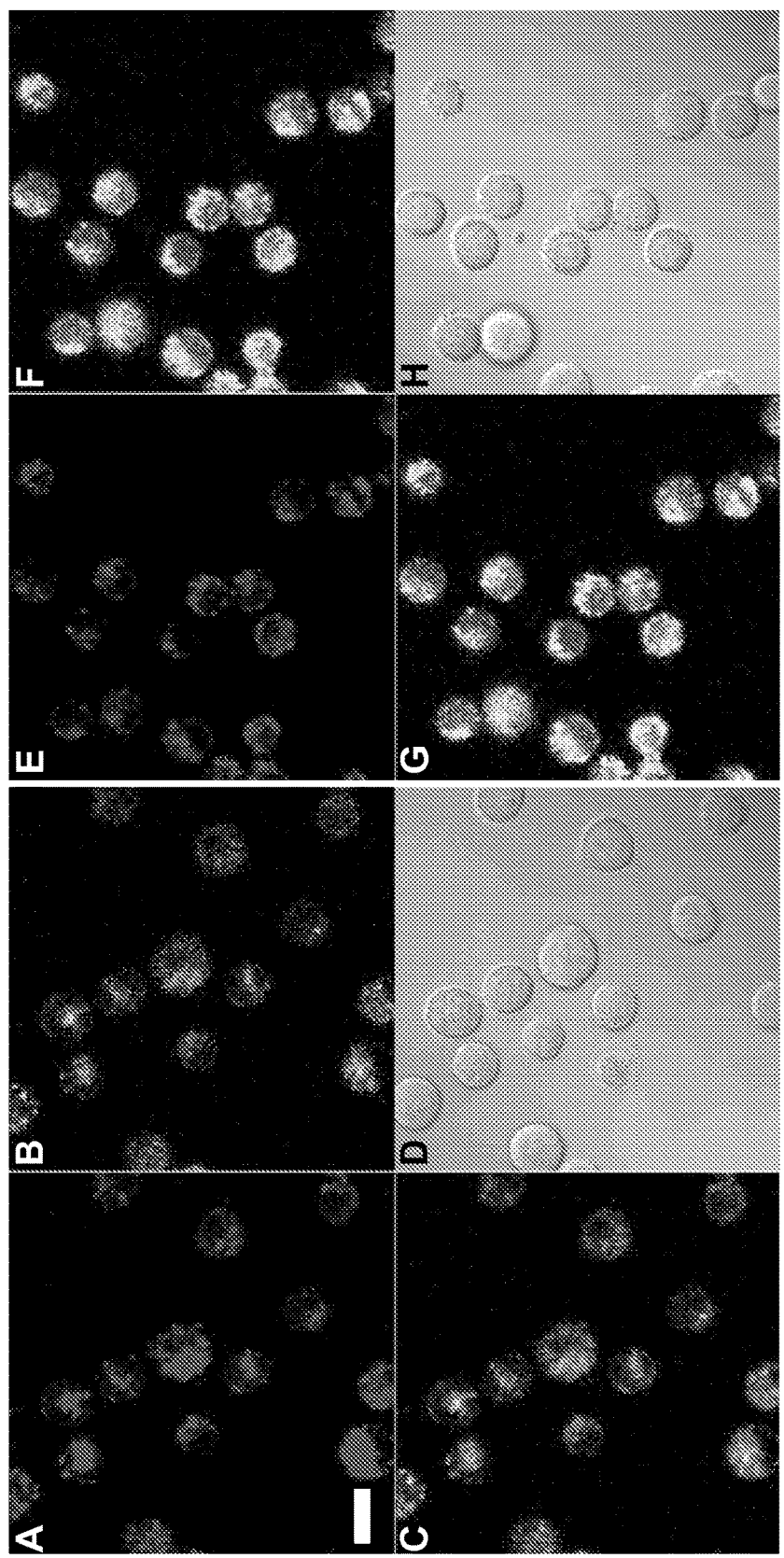
FIG. 54 Confocal scanning microscopy images of HeLa cells labeled by PPE Pdots (A-C) and PS-SH-FITC co PPE Pdots (E-G); and their corresponding bright-field images shown in (D) and (H), respectively. The blue fluorescence shown in (A) and (E) was produced by integrating the spectral region of Pdots from 433-444 nm, while the green fluorescence shown in (B) and (F) was integrated from 507-518 nm. The images (C) and (G) are the overlay of blue and green fluorescence.
Figure 55:
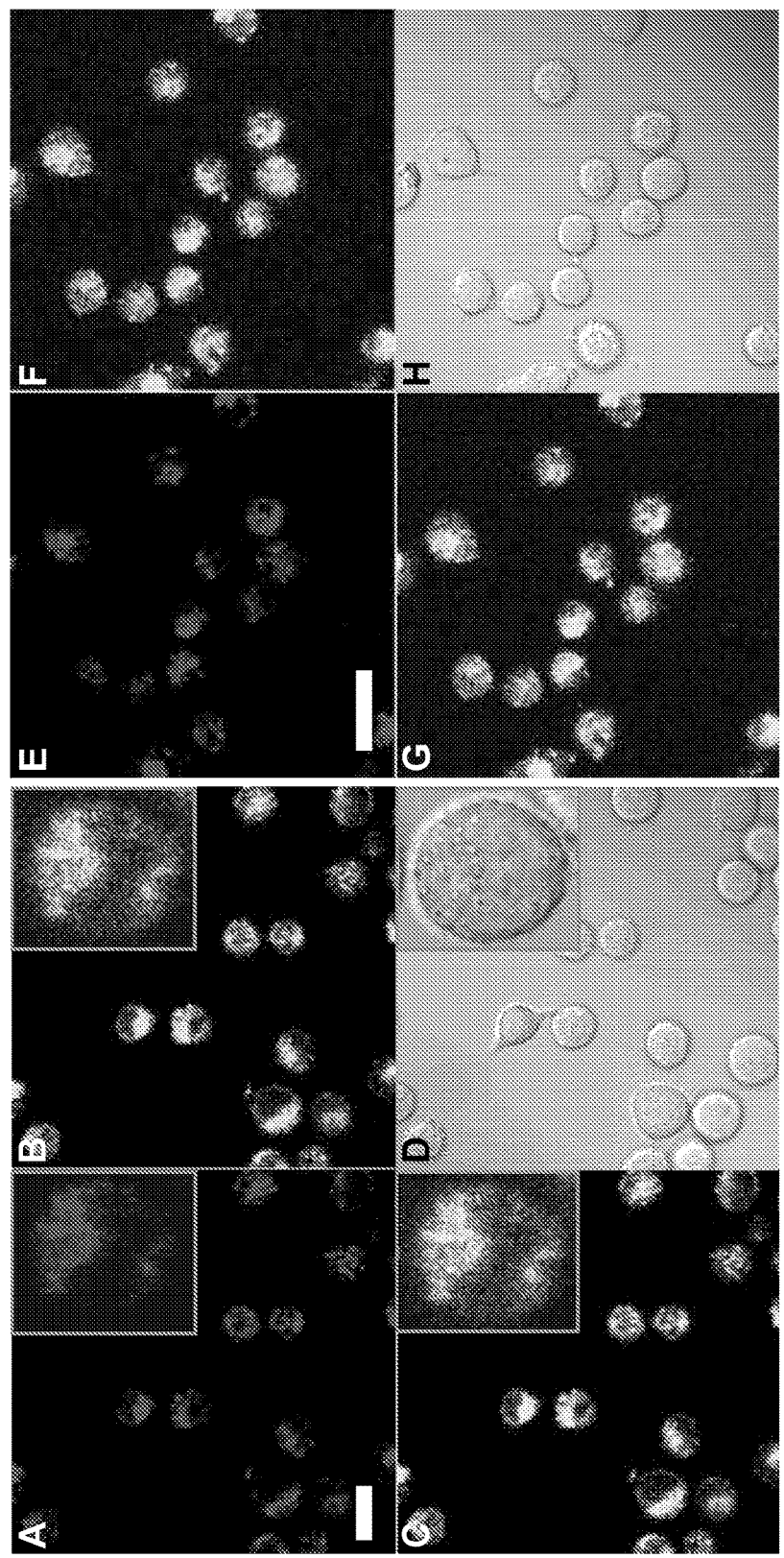
FIG. 55 Confocal microscopy images of HeLa cells labeled by Pdot(B) (A-C) and Pdot(C) (E-G) at $\lambda_{exc}$=405 nm; their corresponding bright-field images are shown in (D) and (H), respectively. The blue channel shown in (A) and (E) was produced by integrating the spectral region from 433-444 nm, while the green channel shown in (B) and (F) was from 507-518 nm. The images in (C) and (G) are the overlay of the blue and green channels. The insets show a magnified view of a single HeLa cell. The scale bars are 20 μm.

Intracellular pH Measurements. To demonstrate the applicability of this FRET-based ratiometric Pdot-nanosensors for intracellular pH measurements, the Pdot-fluorescein nanoparticles were introduced into living HeLa cells through endocytic processes without any additional agents. After particle uptake, the non-incorporated particles were removed by extensive washing with PBS buffer. FIG. 54 shows the confocal fluorescence microscopy images of HeLa cells after Pdot(A) ingestion (E-G), while the bare PPE Pdots in cells is served as a negative control (A-C). The blue channels (A&E) were obtained by integrating the spectral region from 433-444 nm and green channels (B&F) were acquired by integrating the fluorescence signals from 507-518 nm. The intracellular pH was determined by comparing the ratio between the average fluorescence signal from 507-518 nm and the average fluorescence from 433-444 nm to the pH calibration curve. The average pH value based on at least 50 cells using the Pdot(A) system was estimated to be 4.95±0.70, which is in good agreement with the reported pH ranges for the acidic pathways of endocytosis, as in the case of early endosome (pH~6.5) and lysosomal compartment (pH=4.5-5.0). The pH values measured by using the Pdot(B) and Pdot(C) probe were found to be 4.81±0.86 and 4.92±0.64, respectively (FIG. 55), which again demonstrated the feasibility of these Pdot-based nanosensors for the intracellular pH measurements. More importantly, from the amplified and overlay images as shown in the top-right insets of FIG. 55A-C, it clearly reveals a perfect co-localization of both the fluorescence of PPE and fluorescein. This co-localization suggests a simultaneous uptake of PPE and fluorescein by HeLa cells rather than the individual fluorophore uptake as a result of unstable bond breakage.

While this invention has been described with an emphasis on preferred embodiments, it will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being defined by the following claims.

What is claimed is:

1. A functionalized chromophoric polymer dot (Pdot) comprising:
a core and a cap, wherein said core comprises a chromophoric polymer, and said cap comprises a functionalization agent bearing one or more reactive functional groups, with the proviso that less than 100% of the cap is an organo silicate and the proviso that said cap does not encapsulate said core.

2. The functionalized chromophoric polymer dot (Pdot) of claim 1, having a hydrophobic core and a hydrophilic cap, the Pdot comprising:
(a) the chromophoric polymer; and
(b) an amphiphilic molecule, having a hydrophobic moiety and a hydrophilic moiety, the hydrophilic moiety attached to the one or more reactive functional groups,
wherein:
the chromophoric polymer is embedded within the hydrophobic core of the Pdot;
a hydrophobic portion of the amphiphilic molecule is embedded within the hydrophobic core of the Pdot;
the hydrophilic cap comprises a hydrophilic portion of the amphiphilic molecule; and
the reactive functional group is located in the hydrophilic cap.

3. The functionalized chromophoric polymer dot of claim 1, wherein the polymer dot comprises a blend of chromophoric polymers.

4. The functionalized chromophoric polymer dot of claim 1, wherein the chromophoric polymer is a semiconducting polymer.

5. The functionalized chromophoric polymer dot of claim 4, wherein the polymer dot comprises a blend of semiconducting polymers.

6. The functionalized chromophoric polymer dot of claim 5, wherein the blend of semiconducting polymers includes a fluorene-benzothiadiazole-thiophen semiconducting polymer.

7. The functionalized chromophoric polymer dot of claim 2, wherein the weight ratio of the amphiphilic molecule to chromophoric polymer is from about 1% to about 50%.

8. The functionalized chromophoric polymer dot of claim 7, wherein the weight ratio of the amphiphilic molecule to chromophoric polymer is from about 5% to about 25%.

9. The functionalized chromophoric polymer dot of claim 2, wherein the hydrophilic moiety of the amphiphilic molecule comprises a polyalkylene glycol.

10. The functionalized chromophoric polymer dot of claim 9, wherein the polyalkylene glycol is a polyethylene glycol.

11. The functionalized chromophoric polymer dot of claim 2, wherein the amphiphilic molecule is an amphiphilic polymer.

12. The functionalized chromophoric polymer dot of claim 11, wherein the amphiphilic polymer is an amphiphilic, comb-like polymer.

13. The functionalized chromophoric polymer dot of claim 11, wherein the amphiphilic polymer is a polyethylene glycol-grafted polystyrene.

14. The functionalized chromophoric polymer dot of claim 13, wherein the polyethylene glycol moiety of the amphiphilic polymer is attached to one or more carboxyl groups.

15. The functionalized chromophoric polymer dot of claim 11, wherein the amphiphilic polymer is a poly(styrene-co-maleic anhydride).

16. The functionalized chromophoric polymer dot of claim 11, wherein the amphiphilic polymer is a semiconducting polymer.

17. The functionalized chromophoric polymer dot of claim 11, wherein the amphiphilic polymer is a non-semiconducting polymer.

18. The functionalized chromophoric polymer dot of claim 2, wherein the hydrophilic moiety of the amphiphilic polymer is attached to more than one reactive functional group.

19. The functionalized chromophoric polymer dot of claim 1, wherein the one or more reactive functional group is selected from the group consisting of a carboxyl, amino, mercapto, azido, alkyne, aldehyde, hydroxyl, carbonyl, sulfate, sulfonate, phosphate, cyanate, succinimidyl ester, strained alkyne, azide, diene, alkene, tetrazine, strained alkene, cyclooctyne, phosphine groups, and any derivative thereof.

20. The functionalized chromophoric polymer dot of claim 19, wherein the one or more reactive functional group is an alkyne, azido, strained alkyne, diene, alkene, tetrazine, strained alkene, cyclooctyne, phosphine or other moiety capable of being conjugated to a molecule via a bioorthogonal reaction.

21. The functionalized chromophoric polymer dot of claim 20, wherein the bioorthogonal reaction is a click chemistry reaction.

22. The functionalized chromophoric polymer dot of claim 1, wherein a biological molecule is conjugated to a reactive functional group on the surface of the polymer dot.

23. The functionalized chromophoric polymer dot of claim 22, wherein the biological molecule comprises a molecule selected from the group consisting of a synthetic or naturally occurring protein, a glycoprotein, a polypeptide, an amino acid, a nucleic acid, a carbohydrate, a lipid, a fatty acid, and any combination thereof.

24. The functionalized chromophoric polymer dot of claim 23, wherein the biological molecule is a polypeptide, an antibody, an aptamer, or a nucleic acid.

25. The functionalized chromophoric polymer dot of claim 1, wherein the polymer dot is further conjugated to one or more non-reactive chemical groups.

26. The functionalized chromophoric polymer dot of claim 25, wherein the non-reactive chemical group is a water soluble polymer.

27. The functionalized chromophoric polymer dot of claim 26, wherein the water soluble polymer is polyethylene glycol.

28. The functionalized chromophoric polymer dot of claim 1, further comprising an optically inactive polymer chemically cross-linked to the core.

29. The functionalized chromophoric polymer dot of claim 1, further comprising a second chromophoric polymer chemically cross-linked to the core.

30. The functionalized chromophoric polymer dot of claim 28, comprising an optically inactive polymer chemically cross-linked to the chromophoric polymer, wherein the chromophoric polymer is a semiconducting polymer.

31. The functionalized chromophoric polymer dot of claim 28, wherein the optically inactive polymer is an amphiphilic polymer.

32. The functionalized chromophoric polymer dot of claim 28, wherein the optically inactive polymer comprises a functional group suitable for conjugation to a biological molecule.

33. The functionalized chromophoric polymer dot of claim 32, further comprising a biological molecule conjugated to the chromophoric polymer dot, wherein:
the biological molecule comprises an amine group;
the functional group is a carboxyl group; and
the amine group is cross-linked to the carboxyl group.

34. The functionalized chromophoric polymer dot of claim 31, wherein the amphiphilic polymer is a semiconducting polymer.

35. The functionalized chromophoric polymer dot of claim 31, wherein the amphiphilic polymer comprises a hydrophilic moiety, and wherein the hydrophilic moiety of the amphiphilic polymer is attached to more than one reactive functional group.

36. A functionalized chromophoric polymer dot (Pdot) comprising:
a hydrophobic core comprising a chromophoric polymer; and
a hydrophilic cap, comprising a functionalization agent bearing one or more reactive functional groups,
wherein at least a portion of an exterior surface of the functionalized chromophoric polymer dot is a surface of said hydrophobic core, with the proviso that less than 100% of the cap is an organo silicate.

37. The functionalized chromophoric polymer dot (Pdot) of claim 36, the Pdot comprising an amphiphilic molecule having a hydrophobic moiety and a hydrophilic moiety, the hydrophilic moiety attached to the one or more reactive functional groups, wherein:
a hydrophobic portion of the amphiphilic molecule is embedded within the hydrophobic core of the Pdot;
the hydrophilic cap comprises a hydrophilic portion of the amphiphilic molecule; and
the one or more reactive functional groups are located in the hydrophilic cap.

38. The functionalized chromophoric polymer dot of claim 36, wherein the polymer dot comprises a blend of chromophoric polymers.

39. The functionalized chromophoric polymer dot of claim 36, wherein the chromophoric polymer is a semiconducting polymer.

40. The functionalized chromophoric polymer dot of claim 39, wherein the polymer dot comprises a blend of semiconducting polymers.

41. The functionalized chromophoric polymer dot of claim 40, wherein the blend of semiconducting polymers includes a fluorene-benzothiadiazole-thiophen semiconducting polymer.

42. The functionalized chromophoric polymer dot of claim 37, wherein the weight ratio of the amphiphilic molecule to chromophoric polymer is from about 1% to about 50%.

43. The functionalized chromophoric polymer dot of claim 42, wherein the weight ratio of the amphiphilic molecule to chromophoric polymer is from about 5% to about 25%.

44. The functionalized chromophoric polymer dot of claim 37, wherein the hydrophilic moiety of the amphiphilic molecule comprises a polyalkylene glycol.

45. The functionalized chromophoric polymer dot of claim 44, wherein the polyalkylene glycol is a polyethylene glycol.

46. The functionalized chromophoric polymer dot of claim 37, wherein the amphiphilic molecule is an amphiphilic polymer.

47. The functionalized chromophoric polymer dot of claim 46, wherein the amphiphilic polymer is an amphiphilic, comb-like polymer.

48. The functionalized chromophoric polymer dot of claim 46, wherein the amphiphilic polymer is a polyethylene glycol-grafted polystyrene.

49. The functionalized chromophoric polymer dot of claim 48, wherein the polyethylene glycol moiety of the amphiphilic polymer is attached to one or more carboxyl groups.

50. The functionalized chromophoric polymer dot of claim 46, wherein the amphiphilic polymer is a poly(styrene-co-maleic anhydride).

51. The functionalized chromophoric polymer dot of claim 46, wherein the amphiphilic polymer is a semiconducting polymer.

52. The functionalized chromophoric polymer dot of claim 46, wherein the amphiphilic polymer is a non-semiconducting polymer.

53. The functionalized chromophoric polymer dot of claim 37, wherein the hydrophilic moiety of the amphiphilic polymer is attached to more than one reactive functional group.

54. The functionalized chromophoric polymer dot of claim 36, wherein the one or more reactive functional group is selected from the group consisting of a carboxyl, amino, mercapto, azido, alkyne, aldehyde, hydroxyl, carbonyl, sulfate, sulfonate, phosphate, cyanate, succinimidyl ester, strained alkyne, azide, diene, alkene, tetrazine, strained alkene, cyclooctyne, phosphine groups, and any derivative thereof.

55. The functionalized chromophoric polymer dot of claim 54, wherein the one or more reactive functional group is an alkyne, azido, strained alkyne, diene, alkene, tetrazine, strained alkene, cyclooctyne, phosphine or other moiety capable of being conjugated to a molecule via a bioorthogonal reaction.

56. The functionalized chromophoric polymer dot of claim 55, wherein the bioorthogonal reaction is a click chemistry reaction.

57. The functionalized chromophoric polymer dot of claim 36, wherein a biological molecule is conjugated to a reactive functional group on the surface of the polymer dot.

58. The functionalized chromophoric polymer dot of claim 57, wherein the biological molecule comprises a molecule selected from the group consisting of a synthetic or naturally occurring protein, a glycoprotein, a polypeptide, an amino acid, a nucleic acid, a carbohydrate, a lipid, a fatty acid, and any combination thereof.

59. The functionalized chromophoric polymer dot of claim 58, wherein the biological molecule is a polypeptide, an antibody, an aptamer, or a nucleic acid.

60. The functionalized chromophoric polymer dot of claim 36, wherein the polymer dot is further conjugated to one or more non-reactive chemical groups.

61. The functionalized chromophoric polymer dot of claim 60, wherein the non-reactive chemical group is a water soluble polymer.

62. The functionalized chromophoric polymer dot of claim 61, wherein the water soluble polymer is polyethylene glycol.

63. The functionalized chromophoric polymer dot of claim 36, further comprising an optically inactive polymer chemically cross-linked to the core.

64. The functionalized chromophoric polymer dot of claim 36, further comprising a second chromophoric polymer chemically cross-linked to the core.

65. The functionalized chromophoric polymer dot of claim 63, comprising an optically inactive polymer chemically cross-linked to the chromophoric polymer, wherein the chromophoric polymer is a semiconducting polymer.

66. The functionalized chromophoric polymer dot of claim 63, wherein the optically inactive polymer is an amphiphilic polymer.

67. The functionalized chromophoric polymer dot of claim 63, wherein the optically inactive polymer comprises a functional group suitable for conjugation to a biological molecule.

68. The functionalized chromophoric polymer dot of claim 67, further comprising a biological molecule conjugated to the chromophoric polymer dot, wherein:
   the biological molecule comprises an amine group;
   the functional group is a carboxyl group; and
   the amine group is cross-linked to the carboxyl group.

69. The functionalized chromophoric polymer dot of claim 66, wherein the amphiphilic polymer is a semiconducting polymer.

70. The functionalized chromophoric polymer dot of claim 66, wherein the amphiphilic polymer comprises a hydrophilic moiety, and wherein the hydrophilic moiety of the amphiphilic polymer is attached to more than one reactive functional group.

* * * * *